US012589104B2

(12) United States Patent
Fahy et al.

(10) Patent No.: US 12,589,104 B2
(45) Date of Patent: Mar. 31, 2026

(54) THIOSACCHARIDES FOR USE IN TREATING CORONAVIRUS INFECTION

(71) Applicants: The Regents of the University of California, Oakland, CA (US); University College Dublin, Dublin (IE)

(72) Inventors: John Vincent Fahy, San Francisco, CA (US); Irina Gitlin, San Francisco, CA (US); Wilfred Raymond, San Francisco, CA (US); Stefan Oscarson, Dublin (IE)

(73) Assignees: THE REGENTS OF THE UNIVERSITY OF CALIFORNIA, Oakland, CA (US); UNIVERSITY COLLEGE DUBLIN, Dublin (IE)

( * ) Notice: Subject to any disclaimer, the term of this patent is extended or adjusted under 35 U.S.C. 154(b) by 561 days.

(21) Appl. No.: 17/924,662

(22) PCT Filed: May 11, 2021

(86) PCT No.: PCT/US2021/031734

§ 371 (c)(1),
(2) Date: Nov. 10, 2022

(87) PCT Pub. No.: WO2021/231397

PCT Pub. Date: Nov. 18, 2021

(65) Prior Publication Data

US 2023/0181607 A1 Jun. 15, 2023

Related U.S. Application Data

(60) Provisional application No. 63/024,107, filed on May 13, 2020.

(51) Int. Cl.

| | |
|---|---|
| ***A61K 31/7016*** | (2006.01) |
| ***A61K 9/00*** | (2006.01) |
| ***A61P 11/00*** | (2006.01) |
| ***A61P 29/00*** | (2006.01) |
| ***A61P 31/14*** | (2006.01) |

(52) U.S. Cl.
CPC ........ *A61K 31/7016* (2013.01); *A61K 9/0073* (2013.01); *A61P 11/00* (2018.01); *A61P 29/00* (2018.01); *A61P 31/14* (2018.01)

(58) Field of Classification Search
CPC .................................................. A61K 31/7016
See application file for complete search history.

(56) References Cited

U.S. PATENT DOCUMENTS

| | | | | |
|---|---|---|---|---|
| 9,856,283 | B2 * | 1/2018 | Oscarson ................ | A61P 11/06 |
| 9,963,427 | B2 | 5/2018 | Johnson et al. | |
| 10,106,551 | B2 | 10/2018 | Johnson et al. | |
| 10,526,283 | B2 | 1/2020 | Johnson et al. | |
| 2005/0267172 | A1 | 12/2005 | Franklin et al. | |
| 2006/0189542 | A1 | 8/2006 | Furukawa et al. | |
| 2009/0068142 | A1 | 3/2009 | Blatt | |
| 2009/0156473 | A1 | 6/2009 | Schubert | |
| 2011/0218241 | A1 | 9/2011 | Preston et al. | |
| 2016/0060284 | A1 | 3/2016 | Oscarson et al. | |
| 2017/0056347 | A1 | 3/2017 | Glick et al. | |
| 2018/0344751 | A1 | 12/2018 | Walker et al. | |
| 2023/0172885 | A1 | 6/2023 | Fahy et al. | |
| 2023/0285441 | A1 * | 9/2023 | Kumar .................... | A61P 31/14 |

FOREIGN PATENT DOCUMENTS

| | | | |
|---|---|---|---|
| WO | WO-2017/197360 | A1 | 11/2017 |
| WO | WO-2020/055916 | A1 | 3/2020 |
| WO | WO-2021/217221 | A1 | 11/2021 |
| WO | WO-2021/231421 | A1 | 11/2021 |

OTHER PUBLICATIONS

Brady, Bernadette et al., Carbohydrate Research, "Bisthiocyclomalto-oligosaccharides with trehalosyl and octyl links: their synthesis for dual-cavity inclusion", 1998, vol. 309, pp. 237-241 (Year: 1998).*
Khanna, K. et al. (Dec. 8, 2020). "Binding of SARS-CoV-2 spike protein to ACE2 is disabled by thiol-based drugs; evidence from in vitro SARS-CoV-2 infection studies," *bioRxiv* 22 pages.
Khanna, K. et al. (Nov. 11, 2021). "Thiol drugs decrease SARS-CoV-2 lung injury in vivo and disrupt SARS-CoV-2 spike complex binding to ACE2 in vitro," *bioRxiv* 59 pages.
Partial European Search Report mailed on May 10, 2024, for EP Patent Application No. 21802893.4, 18 pages.
Rothan, H. A. et al. (Aug. 2020). "The FDA-approved gold drug auranofin inhibits novel coronavirus (SARS-CoV-2) replication and attenuates inflammation in human cells," *Virology* 547:7-11.
Shi, Y. et al. (Feb. 8, 2022). "Thiol-based chemical probes exhibit antiviral activity against SARS-CoV-2 via allosteric disulfide disruption in the spike glycoprotein," *PNAS USA* 119(6):e2120419119.
Abell, B.A. et al. (Sep. 1993). "Sindbis virus membrane fusion is mediated by reduction of glycoprotein disulfide bridges at the cell surface," *J Virol* 67(9):5496-5501.
Akerlund, B. et al. (1996). "Effect of N-acetylcysteine(NAC) treatment on HIV-1 infection: a double-blind placebo-controlled trial," *Eur. J. Clin. Pharmacol.* 50(6):457-461.
Ali, F. et al. (Jun. 2021, e-published Mar. 2, 2021). "The new SARS-CoV-2 strain shows a stronger binding affinity to ACE2 due to N501Y mutant," *Med. Drug Discov.* 10:100086.
Bouazza, N. et al. (Dec. 2011). "Population pharmacokinetics and pharmacodynamics of cysteamine in nephropathic cystinosis patients," *Orphanet J. Rare Dis.* 6:86.
Chan, J. F. W. et al. (Dec. 3, 2020). "Simulation of the Clinical and Pathological Manifestations of Coronavirus Disease 2019 (COVID-19) in a Golden Syrian Hamster Model: Implications for Disease Pathogenesis and Transmissibility," *Clin. Infect. Dis.* 71(9):2428-2446.
Gallagher, T.M. (Jul. 1996). "Murine coronavirus membrane fusion is blocked by modification of thiols buried within the spike protein," *J. Virol.* 70(7):4683-4690.

(Continued)

*Primary Examiner* — Bahar Craigo
(74) *Attorney, Agent, or Firm* — Mintz, Levin, Cohn, Ferris, Glovsky and Popeo, P.C.

(57) ABSTRACT

Disclosed herein, inter alia, are methods of using thiosaccharide compounds for treating coronavirus infection.

12 Claims, 22 Drawing Sheets

Specification includes a Sequence Listing.

(56) References Cited

OTHER PUBLICATIONS

Gallina, A. et al. (Dec. 27, 2002). "Inhibitors of protein-disulfide isomerase prevent cleavage of disulfide bonds in receptor-bound glycoprotein 120 and prevent HIV-1 entry," *J. Biol. Chem.* 277(52):50579-50588.
Hati, S. et al. (Jun. 23, 2020). "Impact of Thiol-Disulfide Balance on the Binding of Covid-19 Spike Protein with Angiotensin-Converting Enzyme 2 Receptor," *ACS Omega* 5(26):16292-16298.
Horowitz, R.I. et al. (Apr. 21, 2020). "Efficacy of glutathione therapy in relieving dyspnea associated with COVID-19 pneumonia: A report of 2 cases," *Respir. Med. Case Reports* 30:101063.
Imai, M. et al. (Jul. 14, 2020, e-published Jun. 22, 2020). "Syrian hamsters as a small animal model for SARS-CoV-2 infection and countermeasure development," *PNAS USA* 117(28):16587-16595.
International Search Report mailed on Sep. 8, 2021, for PCT Application PCT/US2021/031772, filed May 11, 2021, 2 pages.
International Search Report mailed on Sep. 8, 2021, for PCT Application PCT/US2021/031734, filed May 11, 2021, 3 pages.
Lan, J. et al. (May 2020). "Structure of the SARS-CoV-2 spike receptor-binding domain bound to the ACE2 receptor," *Nature* 581(7807):215-220.
Lavillette, D. et al. (Apr. 7, 2006, e-published Jan. 17, 2006). "Significant redox insensitivity of the functions of the SARS-CoV spike glycoprotein: comparison with HIV envelope," *J. Biol. Chem.* 281(14):9200-9204.
Lobo-Galo, N. et al. (Jun. 2021). "FDA-approved thiol-reacting drugs that potentially bind into the SARS-CoV-2 main protease, essential for viral replication," *J Biomol. Struct. Dyn.* 39(9):3419-3427.
Luan, B. et al. (Mar. 17, 2021). "Enhanced binding of the N501Y-mutated SARS-CoV-2 spike protein to the human ACE2 receptor: insights from molecular dynamics simulations," *FEBS Lett.* 1873-3468.14076.
Roberts, A. et al. (Jan. 2005). "Severe acute respiratory syndrome coronavirus infection of golden Syrian hamsters," *J Virol.* 79(1):503-511.
Ryser, H.J. et al. (May 10, 1994). "Inhibition of human immunodeficiency virus infection by agents that interfere with thiol-disulfide interchange upon virus-receptor interaction," *PNAS USA* 91(10):4559-4563.
Sia, S. F. et al. (Jul. 2020, e-published May 14, 2020). "Pathogenesis and transmission of SARS-CoV-2 in golden hamsters," *Nature* 583(7818):834-838.
Tian, F. et al. (2021). "Mutation N501Y in RBD of Spike Protein Strengthens the Interaction between COVID-19 and its Receptor ACE2," *bioRxiv* 2021.02.14.431117.
Wallin, M. et al. (Jan. 14, 2004, e-published Dec. 11, 2003). "Isomerization of the intersubunit disulphide-bond in Env controls retrovirus fusion," *EMBO J.* 23(1):54-65.
Wang, Q. et al. (May 14, 2020, e-published Apr. 9, 2020). "Structural and Functional Basis of SARS-CoV-2 Entry by Using Human ACE2," *Cell* 181(4):894-904.e9.
Whitt, M.A. (Nov. 2010, e-published Aug. 13, 2010). "Generation of VSV pseudotypes using recombinant ΔG-VSV for studies on virus entry, identification of entry inhibitors, and immune responses to vaccines," *J Virol Methods* 169(2):365-374.
Wong, S.K. et al. (Jan. 30, 2004, e-published Dec. 11, 2003). "A 193-amino acid fragment of the SARS coronavirus S protein efficiently binds angiotensin-converting enzyme 2," *J. Biol. Chem.* 279(5):3197-3201.
Written Opinion mailed on Sep. 8, 2021, for PCT Application PCT/US2021/031772, filed May 11, 2021, 6 pages.
Written Opinion mailed on Sep. 8, 2021, for PCT Application PCT/US2021/031734, filed May 11, 2021, 9 pages.
Yuan, S. et al. (Feb. 25, 2015). "Oxidation increases mucin polymer cross-links to stiffen airway mucus gels," *Sci. TransL Med.* 7(276):276ra27.
Extended European Search Report mailed on Apr. 18, 2024, for EP Patent Application No. 21804356.0, 9 pages.

* cited by examiner

NAC

MUC

319 RVQPTESIVRFPNITNLCPFGEVFNATRFASVYAWNRKRISNCVADYSVLYNSASFSTFK

379 CYGVSPTKLNDLCFTNVYADSFVIRGDEVRQIAPGQTGKIADYNYKLPDDFTGCVIAWNS
N (P.1, B.1.351)

439 NNLDSKVGGNYNYLYRLFRKSNLKPFERDISTEIYQAGSTPCNGVEGFNCYFPLQSYGFQ
R (B.1.427, B.1.429) K (P.1, P.2, B.1.351, B.1.525)

499 PTNGVGYQPYRVVVLSFELLHAPATVCGPKKSTNLVKNKCVNF (SEQ ID NO:1)
Y (P.1, B.1.1.7, B.1.351)

SEQUENCE LISTING

<160> NUMBER OF SEQ ID NOS: 5

<210> SEQ ID NO 1
<211> LENGTH: 223
<212> TYPE: PRT
<213> ORGANISM: Artificial Sequence
<220> FEATURE:
<223> OTHER INFORMATION: Synthetic polypeptide

<400> SEQUENCE: 1

```
Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe
    210                 215                 220
```

<210> SEQ ID NO 2
<211> LENGTH: 222
<212> TYPE: PRT
<213> ORGANISM: Artificial Sequence
<220> FEATURE:
<223> OTHER INFORMATION: Synthetic polypeptide

<400> SEQUENCE: 2

```
Arg Val Val Pro Ser Gly Asp Val Val Arg Phe Pro Asn Ile Thr Asn
1               5                   10                  15

Leu Cys Pro Phe Gly Glu Val Phe Asn Ala Thr Lys Phe Pro Ser Val
            20                  25                  30

Tyr Ala Trp Glu Arg Lys Lys Ile Ser Asn Cys Val Ala Asp Tyr Ser
        35                  40                  45

Val Leu Tyr Asn Ser Thr Phe Phe Ser Thr Phe Lys Cys Tyr Gly Val
    50                  55                  60

Ser Ala Thr Lys Leu Asn Asp Leu Cys Phe Ser Asn Val Tyr Ala Asp
65                  70                  75                  80
```

-continued

```
Ser Phe Val Val Lys Gly Asp Asp Val Arg Gln Ile Ala Pro Gly Gln
                85                  90                  95

Thr Gly Val Ile Ala Asp Tyr Asn Tyr Lys Leu Pro Asp Asp Phe Met
            100                 105                 110

Gly Cys Val Leu Ala Trp Asn Thr Arg Asn Ile Asp Ala Thr Ser Thr
        115                 120                 125

Gly Asn Tyr Asn Tyr Lys Tyr Arg Phe Leu Arg His Gly Lys Leu Arg
    130                 135                 140

Pro Phe Glu Arg Asp Ile Ser Asn Val Pro Phe Ser Pro Asp Gly Lys
145                 150                 155                 160

Pro Cys Thr Pro Pro Ala Leu Asn Cys Tyr Trp Pro Leu Asn Asp Tyr
                165                 170                 175

Gly Phe Tyr Thr Thr Thr Gly Ile Gly Tyr Gln Pro Tyr Arg Val Val
            180                 185                 190

Val Leu Ser Phe Glu Leu Leu Asn Ala Pro Ala Thr Val Cys Gly Pro
        195                 200                 205

Lys Leu Ser Thr Asp Leu Ile Lys Asn Gln Cys Val Asn Phe
    210                 215                 220


<210> SEQ ID NO 3
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 3

ttacaaacat tggccgcaaa                                                  20


<210> SEQ ID NO 4
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 4

gcgcgacatt ccgaagaa                                                    18


<210> SEQ ID NO 5
<211> LENGTH: 23
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: 6-FAM labeled
<220> FEATURE:
<221> NAME/KEY: misc_feature
<222> LOCATION: (23)..(23)
<223> OTHER INFORMATION: BHQ-1 labeled

<400> SEQUENCE: 5

acaatttgcc cccagcgctt cag                                              23
```

THIOSACCHARIDES FOR USE IN TREATING CORONAVIRUS INFECTION

CROSS-REFERENCES TO RELATED APPLICATIONS

This application is the national stage filing under 35 U.S.C. § 371 of International Application No. PCT/US2021/031734 filed May 11, 2021, which claims the benefit of U.S. Provisional Application No. 63/024,107, filed May 13, 2020, which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under grant nos. P01 HL128191 and R01 HL080414, awarded by the National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 048536-689N01US_Sequence_Listing_ST25.txt, created Nov. 3, 2022, 5,206 bytes, machine format IBM-PC, MS Windows operating system, is hereby incorporated by reference.

BACKGROUND

Coronaviruses are enveloped RNA viruses that cause respiratory tract infections. The novel 2019 strain of coronavirus (SARS-CoV-2) causes Coronavirus Disease 2019 (COVID-19), characterized by severe systemic inflammation and pneumonia. COVID-19 has rapidly become a source of profound morbidity and mortality worldwide. Disclosed herein, inter alia, are solutions to these and other problems in the art.

BRIEF SUMMARY

In an aspect is provided a method of treating a coronavirus infection in a subject in need thereof, the method including administering to the subject in need thereof an effective amount of a thiosaccharide compound, or a pharmaceutically acceptable salt thereof.

In an aspect is provided a pharmaceutical composition including a pharmaceutically acceptable excipient and a thiosaccharide compound, or a pharmaceutically acceptable salt thereof.

BRIEF DESCRIPTION OF THE DRAWINGS

FIG. 1A: a graph illustrating that 6,6'-dithiotrehalose ("MUC") and N-acetyl-L-cysteine (NAC) inhibit binding of SARS-CoV-2 spike protein (SARS-2-S) to ACE2. FIG. 1B: Chemical structures of N-acetyl-L-cysteine (NAC) and 6,6'-dithiotrehalose ("MUC").

FIG. 5A: Cystine map for SARS-2-S domain S1, amino acids 15-685, comprising the sequence from the mature N-terminus to the first TMPRSS2 proteolytic site R685 (UniProt Entry: P0DTC2). Ten cystine linkages are denoted by dashed lines with amino acid residue number above. The dark gray region is the receptor binding domain (RBD), and the lighter gray box highlights the ACE2 binding motif, a cluster of amino acids that make contact with ACE2. FIG. 5B: Amino acid alignment of SARS-2-S RBD domain (SEQ ID NO:1, aa 319-541, PDB Entry 6M0J) and SARS-1-S RBD domain (SEQ ID NO:2, aa 306-517, PDB Entry 3SCI). Residues that are shared are highlighted by black boxes and residues that represent a similar amino acid class replacement are bound by gray boxes. The solid lines link cystine-forming cysteines. The solid line and numbers 480-488 and 467-474 highlight the conserved cystine bridge in the RBDs for both viruses. Asterisks denote amino acids that are within 4 angstroms of ACE2 in their respective solved structures. FIG. 5C: A surface rendering of SARS-2-RBD (PDB Entry 6M0J) generated with UCSF Chimera software oriented with the ACE2 binding region facing forward. FIG. 5D: Amino acid sequence of SAR-2-S RBD (SEQ ID NO:1, aa 319-541, PDB Entry 6M0J) highlighting the RBD mutations identified in the circulating SARS CoV2 variants B.1.1.7, B.1.351, P.1, P.2 and B.1.525. Amino acids are noted with single letter code and sequence number. The conserved RBD cystine formed by C480 and C488 is highlighted.

FIG. 6A: Schematic representation of a SARS CoV-2 RBD to ACE2 binding assay. RBD was covalently coupled to plates functionalized with primary amine-reactive maleic anhydride. ACE2 binding was then evaluated after RBD exposure to thiol-based drugs for 60 minutes. FIG. 6B shows percent of binding of $RBD^{original}$ to ACE2 in the presence of the drugs (n=4-6). Without drug treatment, the binding was 100%, whereas treatment with the thiol-based drugs showed a decrease in the binding % relative to no drug control. The X axis is scaled to log 2. At the highest illustrated concentrations, points in the graph from top to bottom correspond to carbocysteine, amifostine, tiopronin, and NAC, respectively. FIG. 6C shows area under the curve (AUC) analysis for effects of the thiol-based drugs on $RBD^{original}$ to ACE2 binding. Reference AUC was calculated from $RBD^{original}$ to ACE2 binding with no drug control; dashed line represents 50% of reference AUC. FIG. 6D shows binding of $RBD^{original}$ to ACE2 at one and two hours post TM21, WR-1065, cysteamine, Mesna or bucillamine exposure and washout (n=4-5). At two hours, points from top to bottom correspond to MESNA, TS21, bucillamine, cysteamine, and WR-1065, respectively. FIG. 6E shows the fold change in the binding of $RBDN^{N501Y}$ to ACE2 with respect to $RBD^{original}$ (n=7). FIG. 6F shows percent of binding of $RBD^{N501Y}$ to ACE2 in the presence of TS21, cysteamine and carbocysteine (n=4-6). The X axis is scaled to log 2. Compounds noted in the legend correspond to the plots, from top to bottom, respectively. FIG. 6G shows area under the curve (AUC) analysis for effects of TS21, cysteamine and carbocysteine on $RBD^{N501Y}$ to ACE2 binding. Reference AUC was calculated from $RBD^{N501Y}$ to ACE2 binding with no drug control; dashed line represents 50% of reference AUC. FIG. 6H shows schematic representation of a BODIPY assay. FIG. 6I shows the change in fluorescence with respect to time when thiol-based drugs react with BODIPY FL cystine. Dotted lines indicate SEM for the graph. Beginning with the most vertical plot at the left, plots in clockwise order are as follows: WR-1065, cysteamine, TS21, bucillamine, tiopronin, MESNA, NAC, amifostine, carbocysteine. FIG. 6J shows maximum slope (Max V) for the fluorescence vs time graph in FIG. 6I for the thiol-based drugs-BODIPY cystine reaction. Data are mean±SEM. Statistical significance for FIGS. 6C, 6G, and 6J was analyzed by one-way ANOVA followed by Dunnett's post-hoc analysis. Significance indicates differences from reference AUC. Statistical significance for FIG. 6E inset was analyzed by two tailed unpaired t-test. $p\leq0.01$, *$p\leq0.005$, ****, $p\leq0.0001$.

FIG. 8A shows the study design for assessing the effect of thiol-based drugs in Syrian hamster model of COVID-19. TS21 (0.5 mg/kg lung deposited dose) was given to hamsters via nose-only inhalation exposure for 3 days (Days 0-2). Cysteamine hydrochloride (147 mg/kg) was administered to hamsters via intraperitoneal injection for 5 days (Days 0-4). Both drugs were given twice daily, with the first dose given 2 hours prior to the virus inoculation on Day 0. SARS CoV2 virus inoculation was carried out by intranasal administration at 1E+05$TCID_{50}$/animal. All animals were sacrificed on Day5. FIG. 8B shows viral RNA levels in the lungs of animals treated with TS21 and cysteamine relative to the respective vehicle control groups. FIG. 8C shows the lung weights, normalized to the terminal body weights, of the animals. FIG. 8D shows total leukocyte counts in the BAL fluid of hamsters treated with TS21 and cysteamine with respected to the vehicle controls. FIGS. 8E-8H: Differential leukocyte counts in the BAL fluid of animals, with FIG. 8E showing neutrophil, FIG. 8F showing macrophage, FIG. 8G showing lymphocyte and FIG. 8H showing eosinophil counts in treated and vehicle control groups. Aero control—aerosol vehicle control group; IP control—intraperitoneal vehicle control group. Each group had N=10 animals (5 Males, 5 females). One animal in the aero control group died during inhalation exposure. 2 BAL samples from the cysteamine group were not analyzed because of a technical error. Data are mean±SEM. Statistical significance was analyzed by two tailed, unpaired t-test between treated and respective control groups (aero control vs TS21; IP control vs cysteamine). *$p\leq0.05$, $p\leq0.01$ *$p\leq0.005$, ****$p\leq0.0001$.

DETAILED DESCRIPTION

I. Definitions

Figure 1A:
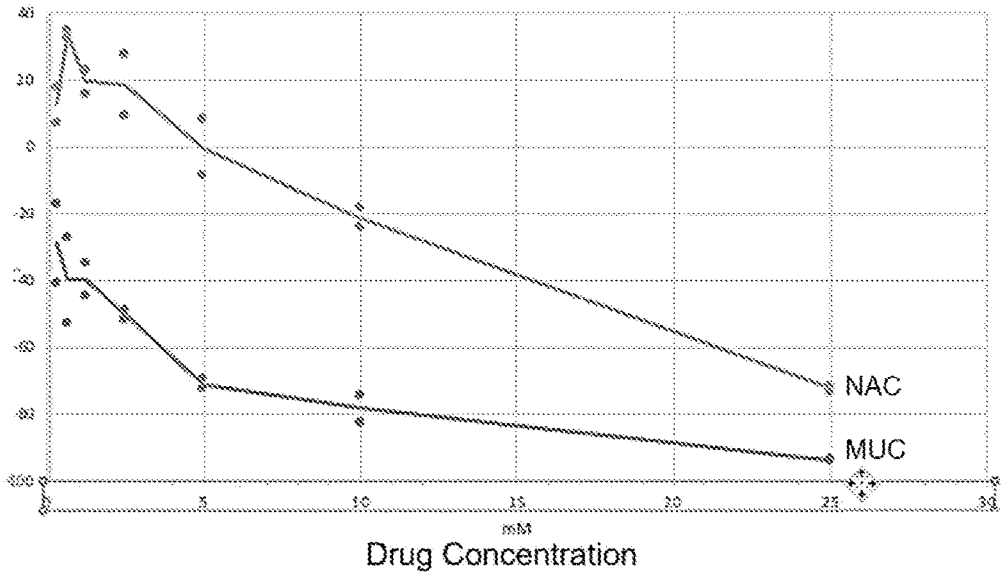
FIGS. 1A-1B.

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., $—CH_2O—$ is equivalent to $—OCH_2—$.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di-, and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds. In embodiments, the alkyl is fully saturated. In embodiments, the alkyl is monounsaturated. In embodiments, the alkyl is polyunsaturated.

The term "alkylene," by itself or as part of another substituent, means, unless otherwise stated, a divalent radical derived from an alkyl, as exemplified, but not limited by, $—CH_2CH_2CH_2CH_2—$. Typically, an alkyl (or alkylene) group will have from 1 to 24 carbon atoms, with those groups having 10 or fewer carbon atoms being preferred herein. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from an alkene. The term "alkynylene" by itself or as part of another substituent, means, unless otherwise stated, a divalent radical derived from an alkyne. In embodiments, the alkylene is fully saturated. In embodiments, the alkylene is monounsaturated. In embodiments, the alkylene is polyunsaturated. In embodiments, an alkenylene includes one or more double bonds. In embodiments, an alkynylene includes one or more triple bonds.

The term "heteroalkyl," by itself or in combination with another term, means, unless otherwise stated, a stable straight or branched chain, or combinations thereof, including at least one carbon atom and at least one heteroatom (e.g., O, N, P, Si, and S), and wherein the nitrogen and sulfur atoms may optionally be oxidized, and the nitrogen heteroatom may optionally be quaternized. The heteroatom(s) (e.g., O, N, S, Si, or P) may be placed at any interior position of the heteroalkyl group or at the position at which the alkyl group is attached to the remainder of the molecule. Heteroalkyl is an uncyclized chain. Examples include, but are not limited to: $—CH_2—CH_2—O—CH_3$, $—CH_2—CH_2—NH—CH_3$, $—CH_2—CH_2—N(CH_3)—CH_3$, $—CH_2—S—CH_2—CH_3$, $—CH_2—S—CH_2$, $—S(O)—CH_3$, $—CH_2—CH_2—S(O)_2—CH_3$, $—CH═CH—O—CH_3$, $—Si(CH_3)_3$, $—CH_2—CH═N—OCH_3$, $—CH═CH—N(CH_3)—CH_3$, $—O—CH_3$, $—O—CH_2—CH_3$, and —CN. Up to two or three heteroatoms may be consecutive, such as, for example, $—CH_2—NH—OCH_3$ and $—CH_2—O—Si(CH_3)_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P). The term "heteroalkenyl," by itself or in combination with another term, means, unless otherwise stated, a heteroalkyl including at least one double bond. A heteroalkenyl may optionally include more than one double bond and/or one or more triple bonds in additional to the one or more double bonds. The term "heteroalkynyl," by itself or in combination with another term, means, unless otherwise stated, a heteroalkyl including at least one triple bond. A heteroalkynyl may optionally include more than one triple bond and/or one or more double bonds in additional to the one or more triple bonds. In embodiments, the heteroalkyl is fully saturated. In embodiments, the heteroalkyl is monounsaturated. In embodiments, the heteroalkyl is polyunsaturated. A "thiol-alkyl" (e.g., $C_1$-$C_{10}$ thiol-alkyl) is an alkyl having a thiol substituent. A "thiol-heteroalkyl" (e.g., 2 to 10 membered thiol-heteroalkyl) is a heteroalkyl having a thiol substituent. A "thiol-unsaturated alkyl" (e.g., $C_1$-$C_{10}$ thiol-unsaturated alkyl) is an alkyl having a thiol substituent and having a double bond or a triple bond.

Similarly, the term "heteroalkylene," by itself or as part of another substituent, means, unless otherwise stated, a divalent radical derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $—C(O)_2R'—$ represents both $—C(O)_2R'—$ and $—R'C(O)_2—$. As described above, heteroalkyl groups, as used herein, include those groups that are attached to the remainder of the molecule through a heteroatom, such as —C(O)R', —C(O)NR', —NR'R", —OR', —SR', and/or $—SO_2R'$. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as NR'R or the like. The term "heteroalkenylene," by itself or as part of another substituent, means, unless otherwise stated, a divalent radical derived from a heteroalkene. The term "heteroalkynylene" by itself or as part of another substituent, means, unless otherwise stated, a divalent radical derived from a heteroalkyne. In embodiments, the heteroalkylene is fully saturated. In embodiments, the heteroalkylene is monounsaturated. In embodiments, the heteroalkylene is polyunsaturated. In embodiments, a heteroalkenylene includes one or more double bonds. In embodiments, a heteroalkynylene includes one or more triple bonds.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. In embodiments, the cycloalkyl is fully saturated. In embodiments, the cycloalkyl is monounsaturated. In embodiments, the cycloalkyl is polyunsaturated. In embodiments, the heterocycloalkyl is fully saturated. In embodiments, the heterocycloalkyl is monounsaturated. In embodiments, the heterocycloalkyl is polyunsaturated.

In embodiments, the term "cycloalkyl" means a monocyclic, bicyclic, or a multicyclic cycloalkyl ring system. In embodiments, monocyclic ring systems are cyclic hydrocarbon groups containing from 3 to 8 carbon atoms, where such groups can be saturated or unsaturated, but not aromatic. In embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. In embodiments, bridged monocyclic rings contain a monocyclic cycloalkyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. In embodiments, fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkyl is attached to the parent molecular moiety through any carbon atom contained within the monocyclic cycloalkyl ring. In embodiments, cycloalkyl groups are optionally substituted with one or two groups which are independently oxo or thia. In embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkyl is attached to the parent molecular moiety through any carbon atom contained within the base ring. In embodiments, multicyclic cycloalkyl ring systems are a monocyclic cycloalkyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic cycloalkyl groups include, but are not limited to tetradecahydrophenanthrenyl, perhydrophenothiazin-1-yl, and perhydrophenoxazin-1-yl.

In embodiments, a cycloalkyl is a cycloalkenyl. The term "cycloalkenyl" is used in accordance with its plain ordinary meaning. In embodiments, a cycloalkenyl is a monocyclic, bicyclic, or a multicyclic cycloalkenyl ring system. In embodiments, monocyclic cycloalkenyl ring systems are cyclic hydrocarbon groups containing from 3 to 8 carbon atoms, where such groups are unsaturated (i.e., containing at least one annular carbon carbon double bond), but not aromatic. Examples of monocyclic cycloalkenyl ring systems include cyclopentenyl and cyclohexenyl. In embodiments, bicyclic cycloalkenyl rings are bridged monocyclic rings or a fused bicyclic rings. In embodiments, bridged monocyclic rings contain a monocyclic cycloalkenyl ring where two non adjacent carbon atoms of the monocyclic ring are linked by an alkylene bridge of between one and three additional carbon atoms (i.e., a bridging group of the form $(CH_2)_w$, where w is 1, 2, or 3). Representative examples of bicyclic cycloalkenyls include, but are not limited to, norbornenyl and bicyclo[2.2.2]oct 2 enyl. In embodiments, fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. In embodiments, the bridged or fused bicyclic cycloalkenyl is attached to the parent molecular moiety through any carbon atom contained within the monocyclic cycloalkenyl ring. In embodiments, cycloalkenyl groups are optionally substituted with one or two groups which are independently oxo or thia. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. In embodiments, the multicyclic cycloalkenyl is attached to the parent molecular moiety through any carbon atom contained within the base ring. In embodiments, multicyclic cycloalkenyl rings contain a monocyclic cycloalkenyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two ring systems independently selected from the group consisting of a phenyl, a monocyclic heteroaryl, a monocyclic cycloalkyl, a monocyclic cycloalkenyl, and a monocyclic heterocyclyl.

In embodiments, a heterocycloalkyl is a heterocyclyl. In embodiments, the term "heterocycloalkyl" means a monocyclic, bicyclic, or a multicyclic heterocycloalkyl ring system. In embodiments, heterocycloalkyl groups are fully saturated. A bicyclic or multicyclic heterocycloalkyl ring system refers to multiple rings fused together wherein at least one of the fused rings is a heterocycloalkyl ring and wherein the multiple rings are attached to the parent molecular moiety through any atom contained within a heterocycloalkyl ring of the multiple rings. The term "heterocyclyl" as used herein, means a monocyclic, bicyclic, or multicyclic heterocycle. The heterocyclyl monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N, and S. The 5 membered ring can contain zero or one double bond and one, two or three heteroatoms selected from the group consisting of O, N, and S. The 6 or 7 membered ring contains zero, one or two double bonds and one, two or three heteroatoms selected from the group consisting of O, N, and S. The heterocyclyl monocyclic heterocycle is connected to the parent molecular moiety through any carbon atom or any nitrogen atom contained within the heterocyclyl monocyclic heterocycle. Representative examples of heterocyclyl monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The heterocyclyl bicyclic heterocycle is a monocyclic heterocycle fused to either a phenyl, a monocyclic cycloalkyl, a monocyclic cycloalkenyl, a monocyclic heterocycle, or a monocyclic heteroaryl. The heterocyclyl bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. In embodiments, heterocyclyl groups are optionally substituted with one or two groups which are independently oxo or thia. In certain embodiments, the bicyclic heterocyclyl is a 5 or 6 membered monocyclic heterocyclyl ring fused to a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia. Multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a bicyclic aryl, a monocyclic or bicyclic heteroaryl, a monocyclic or bicyclic cycloalkyl, a monocyclic or bicyclic cycloalkenyl, and a monocyclic or bicyclic heterocyclyl. The multicyclic heterocyclyl is attached to the parent molecular moiety through any carbon atom or nitrogen atom contained within the base ring. In embodiments, multicyclic heterocyclyl ring systems are a monocyclic heterocyclyl ring (base ring) fused to either (i) one ring system selected from the group consisting of a bicyclic aryl, a bicyclic heteroaryl, a bicyclic cycloalkyl, a bicyclic cycloalkenyl, and a bicyclic heterocyclyl; or (ii) two other ring systems independently selected from the group consisting of a phenyl, a monocyclic heteroaryl, a monocyclic cycloalkyl, a monocyclic cycloalkenyl, and a monocyclic heterocyclyl. Examples of multicyclic heterocyclyl groups include, but are not limited to 10H-phenothiazin-10-yl, 9,10-dihydroacridin-9-yl, 9,10-dihydroacridin-10-yl, 10H-phenoxazin-10-yl, 10,11-dihydro-5H-dibenzo[b,f]azepin-5-yl, 1,2,3,4-tetrahydropyrido[4,3-g]isoquinolin-2-yl, 12H-benzo[b]phenoxazin-12-yl, and dodecahydro-1H-carbazol-9-yl.

The terms “halo” or “halogen,” by themselves or as part of another substituent, mean, unless otherwise stated, a fluorine, chlorine, bromine, or iodine atom. Additionally, terms such as “haloalkyl” are meant to include monohaloalkyl and polyhaloalkyl. For example, the term “halo($C_1$-$C_4$) alkyl” includes, but is not limited to, fluoromethyl, difluoromethyl, trifluoromethyl, 2,2,2-trifluoroethyl, 4-chlorobutyl, 3-bromopropyl, and the like.

The term “acyl” means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term “aryl” means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring and wherein the multiple rings are attached to the parent molecular moiety through any carbon atom contained within an aryl ring of the multiple rings. The term “heteroaryl” refers to aryl groups (or rings) that contain at least one heteroatom such as N, O, or S, wherein the nitrogen and sulfur atoms are optionally oxidized, and the nitrogen atom(s) are optionally quaternized. Thus, the term “heteroaryl” includes fused ring heteroaryl groups (i.e., multiple rings fused together wherein at least one of the fused rings is a heteroaromatic ring and wherein the multiple rings are attached to the parent molecular moiety through any atom contained within a heteroaromatic ring of the multiple rings). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, naphthyl, pyrrolyl, pyrazolyl, pyridazinyl, triazinyl, pyrimidinyl, imidazolyl, pyrazinyl, purinyl, oxazolyl, isoxazolyl, thiazolyl, furyl, thienyl, pyridyl, pyrimidyl, benzothiazolyl, benzoxazoyl benzimidazolyl, benzofuran, isobenzofuranyl, indolyl, isoindolyl, benzothiophenyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An “arylene” and a “heteroarylene,” alone or as part of another substituent, mean a divalent radical derived from an aryl and heteroaryl, respectively. A heteroaryl group substituent may be —O— bonded to a ring heteroatom nitrogen.

A fused ring heterocyloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substituents described herein.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g., substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g., all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol “ ” denotes the point of attachment of a chemical moiety to the remainder of a molecule or chemical formula.

The term “oxo,” as used herein, means an oxygen that is double bonded to a carbon atom.

The term “alkylarylene” as an arylene moiety covalently bonded to an alkylene moiety (also referred to herein as an alkylene linker). In embodiments, the alkylarylene group has the formula:

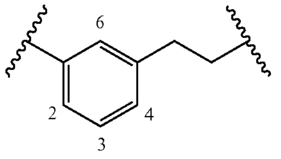

or

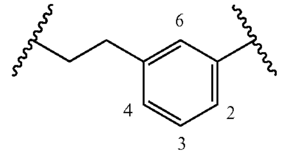

.

An alkylarylene moiety may be substituted (e.g., with a substituent group) on the alkylene moiety or the arylene linker (e.g., at carbons 2, 3, 4, or 6) with halogen, oxo, —$N_3$, —$CF_3$, —$CCl_3$, —$CBr_3$, —$CI_3$, —CN, —CHO, —OH, —$NH_2$, —COOH, —$CONH_2$, —$NO_2$, —SH, —$SO_2CH_3$, —$SO_3H$, —$OSO_3H$, —$SO_2NH_2$, —$NHNH_2$, —$ONH_2$, —NHC(O)$NHNH_2$, substituted or unsubstituted $C_1$-$C_5$ alkyl or substituted or unsubstituted 2 to 5 membered heteroalkyl). In embodiments, the alkylarylene is unsubstituted.

The term “alkylsulfonyl,” as used herein, means a moiety having the formula —S($O_2$)—R', where R' is a substituted or unsubstituted alkyl group as defined above. R' may have a specified number of carbons (e.g., “$C_1$-$C_4$ alkylsulfonyl”).

Each of the above terms (e.g., “alkyl,” “heteroalkyl,” “cycloalkyl,” “heterocycloalkyl,” “aryl,” and “heteroaryl”) includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'C(O)NR"R'", —NR"C$(O)_2$R', —NRC(NR'R"R'")=NR"", —NRC(NR'R")=NR'", —S(O)R', —S$(O)_2$', —S$(O)_2$NR'R", —NR$SO_2$R', —NR'NR"R'", —ONR'R", —NR'C(O)NR"NR'R'", —CN, —$NO_2$, —NR'$SO_2$R", —NR'C(O)R", —NR'C(O)OR", —NR'OR", —$N_3$, in a number ranging from zero to (2m'+1), where m' is the total number of carbon atoms in such radical. R, R', R", R'", and R'" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R includes, but is not limited to, 1-pyrrolidinyl and 4-morpholinyl. From the above discussion of substituents, one of skill in the art will understand that the term “alkyl” is meant to include groups including carbon atoms bound to groups other than hydrogen groups, such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC(O)NR'R", —NR"C(O)R', —NR'C(O)NR"R'", —NR"C$(O)_2$R', —NRC(NR'R"R'")=NR"", —NRC(NR'R")=NR'", —S(O)R', —S$(O)_2$R', —S$(O)_2$NR'R", —NR$SO_2$R', —NR'NR"R'", —ONR'R", —NR'C(O)NR"NR'R'", —CN, —$NO_2$, —R', —$N_3$, —CH$(Ph)_2$, fluoro($C_1$-$C_4$)alkoxy, and fluoro($C_1$-$C_4$alkyl, —NR'$SO_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g., cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g., a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, fund attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'— (C"R"R')$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) oxo, halogen, —CCl$_3$, —CBr$_3$, —CF$_3$, —C$_3$, —CHCl$_2$, —CHBr$_2$, —CHF$_2$, —CHI$_2$, —CH$_2$Cl, —CH$_2$Br, —CH$_2$F, —CH$_2$I, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC (O)OH, —NHOH, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (B) alkyl (e.g., C$_1$-C$_{20}$, C$_1$-C$_{12}$, C$_1$-C$_8$, C$_1$-C$_6$, C$_1$-C$_4$, or C$_1$-C$_2$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., C$_3$-C$_{10}$, C$_3$-C$_8$, C$_3$-C$_6$, C$_4$-C$_6$, or C$_5$-C$_6$), heterocycloalkyl (e.g., 3 to 10 membered, 3 to 8 membered, 3 to 6 membered, 4 to 6 membered, 4 to 5 membered, or 5 to 6 membered), aryl (e.g., C$_6$-C$_{12}$, C$_6$-C$_{10}$, or phenyl), or heteroaryl (e.g., 5 to 12 membered, 5 to 10 membered, 5 to 9 membered, or 5 to 6 membered), substituted with at least one substituent selected from:

(i) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., C$_6$-C$_{10}$ aryl, C$_{10}$ aryl, or phenyl), or unsubstituted heteroaryl (e.g., 5 to 10 membered heteroaryl, 5 to 9 membered heteroaryl, or 5 to 6 membered heteroaryl), and (ii) alkyl (e.g., C$_1$-C$_{20}$, C$_1$-C$_{12}$, C$_1$-C$_8$, C$_1$-C$_6$, C$_1$-C$_4$, or C$_1$-C$_2$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., C$_3$-C$_{10}$, C$_3$-C$_8$, C$_3$-C$_6$, C$_4$-C$_6$, or C$_5$-C$_6$), heterocycloalkyl (e.g., 3 to 10 membered, 3 to 8 membered, 3 to 6 membered, 4 to 6 membered, 4 to 5 membered, or 5 to 6 membered), aryl (e.g., C$_6$-C$_{12}$, C$_6$-C$_{10}$, or phenyl), or heteroaryl (e.g., 5 to 12 membered, 5 to 10 membered, 5 to 9 membered, or 5 to 6 membered), substituted with at least one substituent selected from:

(a) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$I, —OCH$_2$F, —CN, —OH, —NH$_2$, —COOH, —CONH$_2$, —NO$_2$, —SH, —SO$_3$H, —OSO$_3$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —N$_3$, unsubstituted alkyl (e.g., C$_1$-C$_8$ alkyl, C$_1$-C$_6$ alkyl, or C$_1$-C$_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., C$_3$-C$_8$ cycloalkyl, C$_3$-C$_6$ cycloalkyl, or C$_5$-C$_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl), and (b) alkyl (e.g., $C_1$-$C_{20}$, $C_1$-$C_{12}$, $C_1$-$C_8$, $C_1$-$C_6$, $C_1$-$C_4$, or $C_1$-$C_2$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., $C_3$-$C_{10}$, $C_3$-$C_8$, $C_3$-$C_6$, $C_4$-$C_6$, or $C_5$-$C_6$), heterocycloalkyl (e.g., 3 to 10 membered, 3 to 8 membered, 3 to 6 membered, 4 to 6 membered, 4 to 5 membered, or 5 to 6 membered), aryl (e.g., $C_6$-$C_{12}$, $C_6$-$C_{10}$, or phenyl), or heteroaryl (e.g., 5 to 12 membered, 5 to 10 membered, 5 to 9 membered, or 5 to 6 membered), substituted with at least one substituent selected from: oxo, halogen, $-CCl_3$, $-CBr_3$, $-CF_3$, $-CI_3$, $-CHCl_2$, $-CHBr_2$, $-CHF_2$, $-CHI_2$, $-CH_2Cl$, $-CH_2Br$, $-CH_2F$, $-CH_2I$, $-OCCl_3$, $-OCF_3$, $-OCBr_3$, $-OCI_3$, $-OCHCl_2$, $-OCHBr_2$, $-OCHI_2$, $-OCHF_2$, $-OCH_2Cl$, $-OCH_2Br$, $-OCH_2I$, $-OCH_2F$, —CN, —OH, $-NH_2$, —COOH, $-CONH_2$, $-NO_2$, —SH, $-SO_3H$, $-OSO_3H$, $-SO_2NH_2$, $-NHNH_2$, $-ONH_2$, $-NHC(O)NHNH_2$, $-NHC(O)NH_2$, $-NHSO_2H$, —NHC(O)H, —NHC(O)OH, —NHOH, $-N_3$, unsubstituted alkyl (e.g., $C_1$-$C_8$ alkyl, $C_1$-$C_6$ alkyl, or $C_1$-$C_4$ alkyl), unsubstituted heteroalkyl (e.g., 2 to 8 membered heteroalkyl, 2 to 6 membered heteroalkyl, or 2 to 4 membered heteroalkyl), unsubstituted cycloalkyl (e.g., $C_3$-$C_8$ cycloalkyl, $C_3$-$C_6$ cycloalkyl, or $C_5$-$C_6$ cycloalkyl), unsubstituted heterocycloalkyl (e.g., 3 to 8 membered heterocycloalkyl, 3 to 6 membered heterocycloalkyl, or 5 to 6 membered heterocycloalkyl), unsubstituted aryl (e.g., $C_6$-$C_{10}$ aryl, $C_{10}$ aryl, or phenyl), or unsubstituted heteroaryl (e.g., 5 to 10 membered heteroaryl, 5 to 9 membered heteroaryl, or 5 to 6 membered heteroaryl).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and each substituted or unsubstituted heteroaryl is a substituted or unsubstituted 5 to 6 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_5$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted phenyl, and/or each substituted or unsubstituted heteroaryl is a substituted or unsubstituted 5 to 6 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted phenylene, and/or each substituted or unsubstituted heteroarylene is a substituted or unsubstituted 5 to 6 membered heteroarylene. In some embodiments, the compound is a chemical species set forth in the application (e.g., Examples section, claims, embodiments, figures, or tables below).

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

In a recited claim or chemical formula description herein, each R substituent or L linker that is described as being "substituted" without reference as to the identity of any chemical moiety that composes the "substituted" group (also referred to herein as an "open substitution" on an R substituent or L linker or an "openly substituted" R substituent or L linker), the recited R substituent or L linker may, in embodiments, be substituted with one or more first substituent groups as defined below.

The first substituent group is denoted with a corresponding first decimal point numbering system such that, for example, $R^1$ may be substituted with one or more first substituent groups denoted by $R^{1.1}$, $R^2$ may be substituted with one or more first substituent groups denoted by $R^{2.1}$, $R^3$ may be substituted with one or more first substituent groups denoted by $R^{3.1}$, $R^4$ may be substituted with one or more first substituent groups denoted by $R^{4.1}$, $R^5$ may be substituted with one or more first substituent groups denoted by $R^{5.1}$, and the like up to or exceeding an $R^{100}$ that may be substituted with one or more first substituent groups denoted by $R^{100.1}$. As a further example, $R^{1A}$ may be substituted with one or more first substituent groups denoted by $R^{1A.1}$, $R^{2A}$ may be substituted with one or more first substituent groups denoted by $R^{2A.1}$, $R^{3A}$ may be substituted with one or more first substituent groups denoted by $R^{3A.1}$, $R^{4A}$ may be substituted with one or more first substituent groups denoted by $R^{4A.1}$, $R^{5A}$ may be substituted with one or more first substituent groups denoted by $R^{5A.1}$ and the like up to or exceeding an $R^{100A}$ may be substituted with one or more first substituent groups denoted by $R^{100A.1}$. As a further example, $L^1$ may be substituted with one or more first substituent groups denoted by $R^{L1.1}$, $L^2$ may be substituted with one or more first substituent groups denoted by $R^{L2.1}$, $L^3$ may be substituted with one or more first substituent groups denoted by $R^{L3.1}$, $L^4$ may be substituted with one or more first substituent groups denoted by $R^{L4.1}$, $L^5$ may be substituted with one or more first substituent groups denoted by $R^{L5.1}$ and the like up to or exceeding an $L^{100}$ which may be substituted with one or more first substituent groups denoted by $R^{L100.1}$. Thus, each numbered R group or L group (alternatively referred to herein as $R^{WW}$ or $L^{WW}$ wherein "WW" represents the stated superscript number of the subject R group or L group) described herein may be substituted with one or more first substituent groups referred to herein generally as or $R^{LWW.1}$, respectively. In turn, each first substituent group (e.g., $R^{1.1}$, $R^{2.1}$, $R^{3.1}$, $R^{4.1}$, $R^{5.1}$ . . . $R^{100.1}$; $R^{1A.1}$, $R^{2A.1}$, $R^{3A.1}$, $R^{4A.1}$, $R^{5A.1}$ . . . $R^{100A.1}$; $R^{L1.1}$, $R^{L2.1}$, $R^{L3.1}$, $R^{L4.1}$, $R^{L5.1}$ . . . $R^{L100.1}$) may be further substituted with one or more second substituent groups ($R^{1.2}$, $R^{2.2}$, $R^{3.2}$, $R^{4.2}$, $R^{5.2}$ . . . $R^{100.2}$; $R^{1A.2}$, $R^{2A.2}$, $R^{3A.2}$, $R^{4A.2}$, $R^{5A.2}$ . . . $R^{100A.2}$; $R^{L1.2}$, $R^{L2.2}$, $R^{L3.2}$, $R^{L4.2}$, $R^{L5.2}$ . . . $R^{L100.2}$, respectively). Thus, each first substituent group, which may alternatively be represented herein as $R^{WW.1}$ as described above, may be further substituted with one or more second substituent groups, which may alternatively be represented herein as $R^{WW.2}$.

Finally, each second substituent group (e.g., $R^{1.2}$, $R^{2.2}$, $R^{3.2}$, $R^{4.2}$, $R^{5.2}$ . . . $R^{100.2}$; $R^{1A.2}$, $R^{2A.2}$, $R^{3A.2}$, $R^{4.2}$, $R^{5A.2}$ . . . $R^{100A.2}$; $R^{L1.2}$, $R^{L2.2}$, $R^{L3.2}$, $R^{L4.2}$, $R^{L5.2}$ . . . $R^{L100.2}$) may be further substituted with one or more third substituent groups (e.g., $R^{1.3}$, $R^{2.3}$, $R^{3.3}$, $R^{4.3}$, $R^{5.3}$ . . . $R^{100.3}$; $R^{1A.3}$, $R^{2A.3}$, $R^{3A.3}$, $R^{4A.3}$, $R^{5A.3}$ . . . $R^{100A.3}$; $R^{L1.3}$, $R^{L2.3}$, $R^{L3.3}$, $R^{L4.3}$, $R^{L5.3}$ . . . $R^{L100.3}$; respectively). Thus, each second substituent group, which may alternatively be represented herein as $R^{WW.2}$ as described above, may be further substituted with one or more third substituent groups, which may alternatively be represented herein as $R^{WW.3}$. Each of the first substituent groups may be optionally different. Each of the second substituent groups may be optionally different. Each of the third substituent groups may be optionally different.

Thus, as used herein, $R^{WW}$ represents a substituent recited in a claim or chemical formula description herein which is openly substituted. "WW" represents the stated superscript number of the subject R group (1, 2, 3, 1A, 2A, 3A, 1B, 2B, 3B, etc.). Likewise, $L^{WW}$ is a linker recited in a claim or chemical formula description herein which is openly substituted. Again, "WW" represents the stated superscript number of the subject L group (1, 2, 3, 1A, 2A, 3A, 1B, 2B, 3B, etc.). As stated above, in embodiments, each $R^{WW}$ may be unsubstituted or independently substituted with one or more first substituent groups, referred to herein as $R^{WW.1}$; each first substituent group, $R^{WW.1}$, may be unsubstituted or independently substituted with one or more second substituent groups, referred to herein as $R^{WW.2}$; and each second substituent group may be unsubstituted or independently substituted with one or more third substituent groups, referred to herein as $R^{WW.3}$. Similarly, each $L^{WW}$ linker may be unsubstituted or independently substituted with one or more first substituent groups, referred to herein as $R^{LWW.1}$; each first substituent group, $R^{LWW.1}$, may be unsubstituted or independently substituted with one or more second substituent groups, referred to herein as $R^{LWW.2}$; and each second substituent group may be unsubstituted or independently substituted with one or more third substituent groups, referred to herein as $R^{LWW.3}$. Each first substituent group is optionally different. Each second substituent group is optionally different. Each third substituent group is optionally different. For example, if $R^{WW}$ is phenyl, the said phenyl group is optionally substituted by one or more $R^{WW.1}$ groups as defined herein below, e.g., when $R^{WW.1}$ is $R^{WW.2}$-substituted or unsubstituted alkyl, examples of groups so formed include but are not limited to itself optionally substituted by 1 or more $R^{WW.2}$, which $R^{WW.2}$ is optionally substituted by one or more $R^{WW.3}$. By way of example when the $R^{WW}$ group is phenyl substituted by $R^{WW.1}$, which is methyl, the methyl group may be further substituted to form groups including but not limited to:

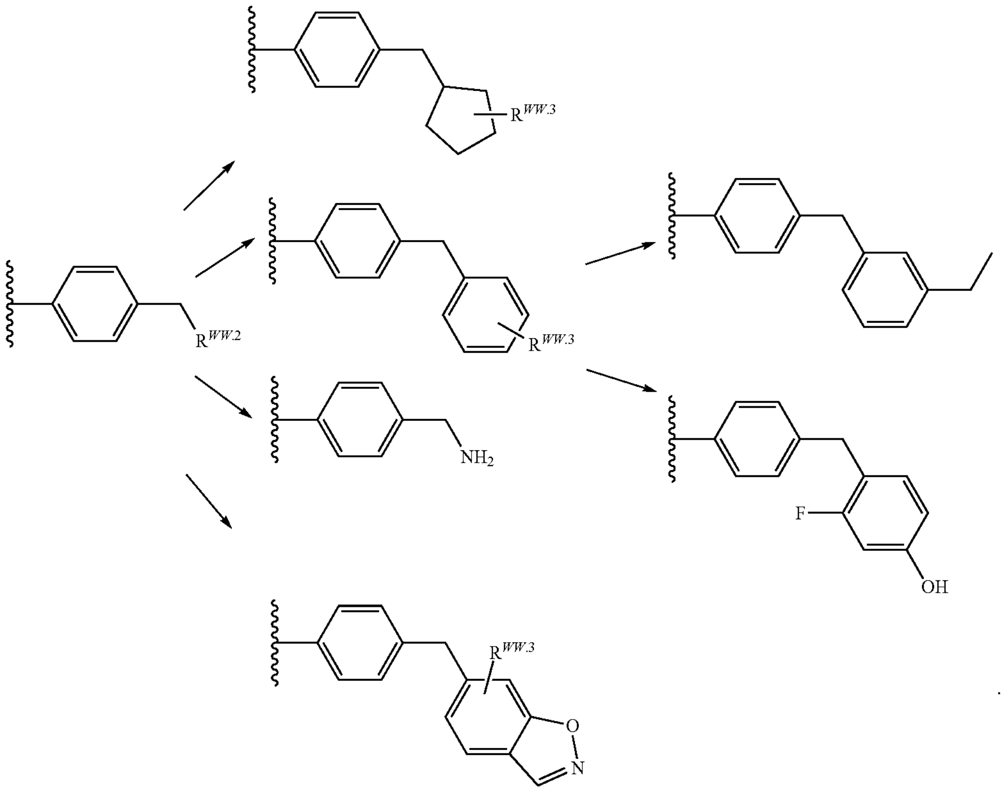

$R^{WW.1}$ is independently oxo, halogen, $—CX^{WW.1}_3$, $—CHX^{WW.1}_2$, $—CH_2X^{WW.1}$, $—OCX^{WW.1}_3$, $—OCH_2X^{WW.1}$, $—OCHX^{WW.1}_2$, —CN, —OH, $—NH_2$, —COOH, $—CONH_2$, $—NO_2$, —SH, $—SO_3H$, $—OSO_3H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $R^{WW.2}$-substituted or unsubstituted alkyl (e.g., $C_1$-$C_8$, $C_1$-$C_6$, $C_1$-$C_4$, or $C_1$-$C_2$), $R^{WW.2}$-substituted or unsubstituted heteroalkyl (e.g., 2 to 8 membered, 2 to 6 membered, 4 to 6 membered, 2 to 3 membered, or 4 to 5 membered), $R^{WW.2}$-substituted or unsubstituted cycloalkyl (e.g., $C_3$-$C_8$, $C_3$-$C_6$, $C_4$-$C_6$, or $C_5$-$C_6$), $R^{WW.2}$-substituted or unsubstituted heterocycloalkyl (e.g., 3 to 8 membered, 3 to 6 membered, 4 to 6 membered, 4 to 5 membered, or 5 to 6 membered), $R^{WW.2}$ substituted or unsubstituted aryl (e.g., $C_6$-$C_{12}$, $C_6$-$C_{10}$, or phenyl), or $R^{WW.2}$-substituted or unsubstituted heteroaryl (e.g., 5 to 12 membered, 5 to 10 membered, 5 to 9 membered, or 5 to 6 membered). In embodiments, $R^{WW.1}$ is independently oxo, halogen, $—CX^{WW.1}_3$, $—CH^{WW.1}_2$, $—CH_2X^{WW.1}$, $—OCX^{WW.1}_3$, $—OCH_2X^{WW.1}$, $—OCHX^{WW.1}_2$, —CN, —OH, $—NH_2$, —COOH, $—CONH_2$, $—NO_2$, —SH, $—SO_3H$, $—OSO_3H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.1}$ is independently —F, —Cl, —Br, or —I.

$R^{WW.2}$ is independently oxo, halogen, $—CX^{WW.2}_3$, $—CHX^{WW.2}_2$, $CH_2X^{WW.2}$, $—OCX^{WW.2}_3$, $—OCH_2X^{WW.2}$, $—OCHX^{WW.2}_2$, —CN, —OH, $—NH_2$, —COOH, $—CONH_2$, $—NO_2$, —SH, $—SO_3H$, $—OSO_3H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $R^{WW.3}$-substituted or unsubstituted alkyl (e.g., $C_1$-$C_8$, $C_1$-$C_6$, $C_1$-$C_4$, or $C_1$-$C_2$), $R^{WW.3}$-substituted or unsubstituted heteroalkyl (e.g., 2 to 8 membered, 2 to 6 membered, 4 to 6 membered, 2 to 3 membered, or 4 to 5 membered), $R^{WW.3}$-substituted or unsubstituted cycloalkyl (e.g., $C_3$-$C_8$, $C_3$-$C_6$, $C_4$-$C_6$, or $C_5$-$C_6$), $R^{WW.3}$-substituted or unsubstituted heterocycloalkyl (e.g., 3 to 8 membered, 3 to 6 membered, 4 to 6 membered, 4 to 5 membered, or 5 to 6 membered), $R^{WW.3}$-substituted or unsubstituted aryl (e.g., $C_6$-$C_{12}$, $C_6$-$C_{10}$, or phenyl), or $R^{WW.3}$-substituted or unsubstituted heteroaryl (e.g., 5 to 12 membered, 5 to 10 membered, 5 to 9 membered, or 5 to 6 membered). In embodiments, $R^{WW.2}$ is independently oxo, halogen, $—CX^{WW.1}_3$, $—CHX^{WW.2}_2$, $—CH_2X^{WW.2}$, $OCX^{WW.1}_3$, $—OCH_2X^{WW.2}$, $—OCHX^{WW.2}$, —CN, —OH, $—NH_2$, —COOH, $—CONH_2$, $—NO_2$, —SH, $—SO_3H$, $—OSO_3H$, $—SO_2NH_2$, $—NHNH_2$, $—ONH_2$, $—NHC(O)NHNH_2$, $—NHC(O)NH_2$, $—NHSO_2H$, —NHC (O)H, —NHC(O)OH, —NHOH, $—N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.2}$ is independently —F, —Cl, —Br, or —I.

$R^{WW.3}$ is independently oxo, halogen, $—CX^{WW.3}_3$, $—CHX^{WW.3}_2$, $—CH_2X^{WW.3}$, $—OCX^{WW.3}_3$, $—OCH_2X^{WW.3}$, $—OCHX^{WW.3}_2$, —CN, —OH, $—NH_2$, —COOH, $—CONH_2$, $—NO_2$, —SH, $—SO_3H$, $—OSO_3H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{WW.3}$ is independently —F, —Cl, —Br, or —I.

Where two different $R^{WW}$ substituents are joined together to form an openly substituted ring (e.g., substituted cycloalkyl, substituted heterocycloalkyl, substituted aryl or substituted heteroaryl), in embodiments the openly substituted ring may be independently substituted with one or more first substituent groups, referred to herein as $R^{WW.1}$; each first substituent group, $R^{WW.1}$, may be unsubstituted or independently substituted with one or more second substituent groups, referred to herein as $R^{WW.2}$; and each second substituent group, $R^{WW.2}$, may be unsubstituted or independently substituted with one or more third substituent groups, referred to herein as $R^{WW.3}$; and each third substituent group, $R^{WW.3}$, is unsubstituted. Each first substituent group is optionally different. Each second substituent group is optionally different. Each third substituent group is optionally different. In the context of two different $R^{WW}$ substituents joined together to form an openly substituted ring, the "WW" symbol in the $R^{WW.1}$, $R^{WW.2}$ and $R^{WW.3}$ refers to the designated number of one of the two different $R^{WW}$ substituents. For example, in embodiments where $R^{100A}$ and $R^{100B}$ are optionally joined together to form an openly substituted ring, $R^{WW.1}$ is $R^{100A.1}$, $R^{WW.2}$ is $R^{100A.2}$, and $R^{WW.3}$ is $R^{100A.3}$. Alternatively, in embodiments where $R^{100A}$ and $R^{100B}$ are optionally joined together to form an openly substituted ring, $R^{WW.1}$ is $R^{100B.1}$, $R^{WW.2}$ is $R^{100B.2}$, and $R^{WW.3}$ is $R^{100B.3}$. $R^{WW.1}$, $R^{WW.2}$ and $R^{WW.3}$ in this paragraph are as defined in the preceding paragraphs.

$R^{LWW.1}$ is independently oxo, halogen, $—CX^{LWW.1}_3$, $—CHX^{LWW.1}_2$, $—CH_2X^{LWW.1}$, $—OCX^{LWW.1}_3$, $—OCH_2X^{LWW.1}$, $—OCHX^{LWW.1}_2$, —CN, —OH, $—NH_2$, —COOH, $—CONH_2$, $—NO_2$, —SH, $—SO_3H$, $—OSO_3H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, $R^{LWW.1}$-substituted or unsubstituted alkyl (e.g., $C_1$-$C_8$, $C_1$-$C_6$, $C_1$-$C_4$, or $C_1$-$C_2$), $R^{LWW.2}$-substituted or unsubstituted heteroalkyl (e.g., 2 to 8 membered, 2 to 6 membered, 4 to 6 membered, 2 to 3 membered, or 4 to 5 membered), $R^{LWW.1}$-substituted or unsubstituted cycloalkyl (e.g., $C_3$-$C_8$, $C_3$-$C_6$, $C_4$-$C_6$, or $C_5$-$C_6$), $R^{LWW.1}$-substituted or unsubstituted heterocycloalkyl (e.g., 3 to 8 membered, 3 to 6 membered, 4 to 6 membered, 4 to 5 membered, or 5 to 6 membered), $R^{LWW.2}$-substituted or unsubstituted aryl (e.g., $C_6$-$C_{12}$, $C_6$-$C_{10}$, or phenyl), or $R^{LWW.2}$-substituted or unsubstituted heteroaryl (e.g., 5 to 12 membered, 5 to 10 membered, 5 to 9 membered, or 5 to 6 membered). In embodiments, $R^{LWW.1}$ is independently oxo, halogen, $—CX^{LWW.1}_3$, $—CHX^{LWW.1}_2$, $—CH_2X^{LWW.1}$, $—OCX^{LWW.1}_3$, $—OCH_2X^{LWW.1}$, $—OCHX^{LWW.1}_2$, —CN, —OH, $—NH_2$, —COOH, $—CONH_2$, $—NO_2$, —SH, $—SO_3H$, $—OSO_3H$, $—SO_2NH_2$, $—NHNH_2$, $—ONH_2$, $—NHC(O)NHNH_2$, $—NHC(O)NH_2$, $—NHSO_2H$, —NHC(O)H, —NHC(O)OH, —NHOH, $—N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.1}$ is independently —F, —Cl, —Br, or —I.

$R^{LWW.2}$ is independently oxo, halogen, —$CX^{LWW.2}_3$, —$CHX^{LWW.2}_2$, —$C_2X^{LWW.2}$, —$OCX^{LWW.2}_3$, —$OCH_2X^{LWW.2}$, —$OCHX^{LWW.2}_2$, —CN, —OH, —$NH_2$, —COOH, —$CONH_2$, —$NO_2$, —SH, —$SO_3H$, —$OSO_3H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$N_3$, $R^{LWW.3}$-substituted or unsubstituted alkyl (e.g., $C_1$-$C_8$, $C_1$-$C_6$, $C_1$-$C_4$, or $C_1$-$C_2$), $R^{LWW.3}$-substituted or unsubstituted heteroalkyl (e.g., 2 to 8 membered, 2 to 6 membered, 4 to 6 membered, 2 to 3 membered, or 4 to 5 membered), $R^{WW.3}$-substituted or unsubstituted cycloalkyl (e.g., $C_3$-$C_8$, $C_3$-$C_6$, $C_4$-$C_6$, or $C_5$-$C_6$), $R^{LWW.3}$-substituted or unsubstituted heterocycloalkyl (e.g., 3 to 8 membered, 3 to 6 membered, 4 to 6 membered, 4 to 5 membered, or 5 to 6 membered), $R^{LWW.3}$-substituted or unsubstituted aryl (e.g., $C_6$-$C_{12}$, $C_6$-$C_{10}$, or phenyl), or $R^{LWW.3}$-substituted or unsubstituted heteroaryl (e.g., 5 to 12 membered, 5 to 10 membered, 5 to 9 membered, or 5 to 6 membered). In embodiments, $R^{LWW.2}$ is independently oxo, halogen, —$CX^{LWW.2}_3$, —$CHX^{LWW.2}_2$, —$CH_{2X}L^{LWW.2}$, —$OCX^{LWW.2}_3$, —$OCH_2X^{LWW.2}$, —$OCHX^{LWW.2}_2$, —CN, —OH, —$NH_2$, —COOH, —$CONH_2$, —$NO_2$, —SH, —$SO_3H$, —$OSO_3H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.2}$ is independently —F, —Cl, —Br, or —I.

$R^{LWW.3}$ is independently oxo, halogen, —$CX^{LWW.3}_3$, —$CHX^{LWW.3}_2$, —$CH_2X^{LWW.3}$, —$OCX^{LWW.3}_3$, —$OCH_2X^{LWW.3}$, $OCHX^{LWW.3}_2$, —CN, —OH, —$NH_2$, —COOH, —$CONH_2$, —$NO_2$, —SH, —$SO_3H$, —$OSO_3H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$N_3$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, 2 to 3 membered, or 4 to 5 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered). $X^{LWW.3}$ is independently —F, —Cl, —Br, or —I.

In the event that any R group recited in a claim or chemical formula description set forth herein ($R^{WW}$ substituent) is not specifically defined in this disclosure, then that R group ($R^{WW}$ group) is hereby defined as independently oxo, halogen, —$CX^{WW}_3$, —$CHX^{WW}_2$, —$CH_2X^{WW}$, —$OCX^{WW}_3$, —$OCH_2X^{WW}$, —$OCHX^{WW}_2$, —CN, —OH, —$NH_2$, —COOH, —$CONH_2$, —$NO_2$, —SH, —$SO_3H$, —$OSO_3H$, —$SO_2NH_2$, —$NHNH_2$, —$ONH_2$, —$NHC(O)NHNH_2$, —$NHC(O)NH_2$, —$NHSO_2H$, —NHC(O)H, —NHC(O)OH, —NHOH, —$N_3$, $R^{WW.1}$-substituted or unsubstituted alkyl (e.g., $C_1$-$C_8$, $C_1$-$C_6$, $C_1$-$C_4$, or $C_1$-$C_2$), $R^{WW.1}$-substituted or unsubstituted heteroalkyl (e.g., 2 to 8 membered, 2 to 6 membered, 4 to 6 membered, 2 to 3 membered, or 4 to 5 membered), $R^{WW.1}$-substituted or unsubstituted cycloalkyl (e.g., $C_3$-$C_8$, $C_3$-$C_6$, $C_4$-$C_6$, or $C_5$-$C_6$), $R^{WW.1}$-substituted or unsubstituted heterocycloalkyl (e.g., 3 to 8 membered, 3 to 6 membered, 4 to 6 membered, 4 to 5 membered, or 5 to 6 membered), $R^{WW.1}$-substituted or unsubstituted aryl (e.g., $C_6$-$C_{12}$, $C_6$-$C_{10}$, or phenyl), or $R^{WW.1}$-substituted or unsubstituted heteroaryl (e.g., 5 to 12 membered, 5 to 10 membered, 5 to 9 membered, or 5 to 6 membered). $X^{WW}$ is independently —F, —Cl, —Br, or —I. Again, "WW" represents the stated superscript number of the subject R group (e.g., 1, 2, 3, 1A, 2A, 3A, 1B, 2B, 3B, etc.). $R^{WW.1}$, $R^{WW.2}$, and $R^{WW.3}$ are as defined above.

In the event that any L linker group recited in a claim or chemical formula description set forth herein (i.e., an $L^{WW}$ substituent) is not explicitly defined, then that L group ($L^{WW}$ group) is herein defined as independently a bond, —O—, —NH—, —C(O)—, —C(O)NH—, —NHC(O)—, —NHC(O)NH—, —C(O)O—, —OC(O)—, —S—, —$SO_2$—, —$SO_2NH$—, $R^{LWW.1}$-substituted or unsubstituted alkylene (e.g., $C_1$-$C_8$, $C_1$-$C_6$, $C_1$-$C_4$, or $C_1$-$C_2$), $R^{LWW.1}$-substituted or unsubstituted heteroalkylene (e.g., 2 to 8 membered, 2 to 6 membered, 4 to 6 membered, 2 to 3 membered, or 4 to 5 membered), $R^{LWW.1}$-substituted or unsubstituted cycloalkylene (e.g., $C_3$-$C_8$, $C_3$-$C_6$, $C_4$-$C_6$, or $C_5$-$C_6$), $R^{LWW.1}$-substituted or unsubstituted heterocycloalkylene (e.g., 3 to 8 membered, 3 to 6 membered, 4 to 6 membered, 4 to 5 membered, or 5 to 6 membered), $R^{LWW.1}$-substituted or unsubstituted arylene (e.g., $C_6$-$C_{12}$, $C_6$-$C_{10}$, or phenyl), or $R^{LWW.1}$-substituted or unsubstituted heteroarylene (e.g., 5 to 12 membered, 5 to 10 membered, 5 to 9 membered, or 5 to 6 membered). Again, "WW" represents the stated superscript number of the subject L group (1, 2, 3, 1A, 2A, 3A, 1B, 2B, 3B, etc.). $R^{LWW.2}$, as well as $R^{LWW.2}$ and $R^{LWW.3}$ are as defined above.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)-or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The compounds of the present disclosure may also contain unnatural proportions of atomic isotopes at one or more of the atoms that constitute such compounds. For example, the compounds may be radiolabeled with radioactive isotopes, such as for example tritium ($^{3}H$), iodine-125 ($^{125}I$), or carbon-14 ($^{14}C$). All isotopic variations of the compounds of the present disclosure, whether radioactive or not, are encompassed within the scope of the present disclosure.

The term "thiosaccharide" as used herein refers to a compound containing at least one tetrahydropyrane ring substituted with at least one thiol (—SH) containing moiety or at least one thioacetyl (—SAc) moiety (and optionally further substituted for example, with hydroxyl moieties or additional tetrahydropyrane rings or tetrahydrofuran rings via ether linkers) or at least one tetrahydrofuran ring substituted with at least one thiol containing moiety (and optionally further substituted for example, with hydroxyl moieties or additional tetrahydropyrane rings or tetrahydrofuran rings via ether linkers). Thus, the term "thiol saccharide" refers to a thiosaccharide with at least one thiol (—SH) moiety, and the term "thioacetyl saccharide" refers to a thiosaccharide with at least one thioacetyl (—SAc) moiety. The tetrahydropyrane ring may be a pyranose ring or pyranoside ring in which one or more hydroxyl groups are replaced with a thiol containing moiety (referred to herein as a "thiol pyranose" or "thiol pyranoside", respectively). The tetrahydropyrane ring may be a pyranose ring or pyranoside ring in which one or more hydroxyl groups are replaced with a thioacetyl containing moiety (referred to herein as a "thioacetyl pyranose" or "thioacetyl pyranoside", respectively). The tetrahydrofuran ring may be a furanose ring or furanoside ring in which one or more hydroxyl groups are replaced with a thiol containing moiety (referred to herein as a "thiol pyranose" or "thiol pyranoside", respectively). The tetrahydrofuran ring may be a furanose ring or furanoside ring in which one or more hydroxyl groups are replaced with a thioacetyl containing moiety (referred to herein as a "thioacetyl pyranose" or "thioacetyl pyranoside", respectively). A "thiol monosaccharide" (e.g., thiol monopyranose, thiol monopyranoside, thiol monofuranose, thiol monofuranoside) as used herein refers to compound containing one tetrahydropyrane ring substituted with at least one thiol (—SH) containing moiety or one tetreahydrofuran ring substituted with at least one thiol (—SH) containing moiety. A "thioacetyl monosaccharide" (e.g., thioacetyl monopyranose, thioacetyl monopyranoside, thioacetyl monofuranose, thioacetyl monofuranoside) as used herein refers to compound containing one tetrahydropyrane ring substituted with at least one thioacetyl (—SAc) containing moiety or one tetreahydrofuran ring substituted with at least one thioacetyl (—SAc) containing moiety. A "thiol disaccharide" (e.g., thiol dipyranoside, thiol dipyranoside, thiol difuranose, thiol difuranoside) as used herein refers to a compound containing two tetrahydropyrane rings substituted with at least one thiol (—SH) containing moiety. A "thioacetyl disaccharide" (e.g., thioacetyl dipyranoside, thioacetyl dipyranoside, thioacetyl difuranose, thioacetyl difuranoside) as used herein refers to compound containing two tetrahydropyrane rings substituted with at least one thioacetyl (—SAc) containing moiety. A "thiol trisaccharide" (e.g., thiol tripyranoside, thiol tripyranoside, thiol trifuranose, thiol trifuranoside) as used herein refers to a compound containing three tetrahydropyrane rings substituted with at least one thiol (—SH) containing moiety. A "thioacetyl trisaccharide" (e.g., thioacetyl tripyranoside, thioacetyl tripyranoside, thioacetyl trifuranose, thioacetyl trifuranoside) as used herein refers to compound containing three tetrahydropyrane rings substituted with at least one thioacetyl (—SAc) containing moiety. A "thiol oligosaccharide" (e.g., thiol oligopyranoside, thiol oligopyranoside, thiol oligofuranose, thiol oligofuranoside) as used herein refers to a compound containing more than three tetrahydropyrane rings substituted with at least one thiol (—SH) containing moiety. A "thioacetyl oligosaccharide" (e.g., thioacetyl oligopyranoside, thioacetyl oligopyranoside, thioacetyl oligofuranose, thioacetyl oligofuranoside) as used herein refers to a compound containing more than three tetrahydropyrane rings substituted with at least one thioacetyl (—SAc) containing moiety.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

As used herein, the term "bioconjugate reactive moiety" and "bioconjugate reactive group" refers to a moiety or group capable of forming a bioconjugate (e.g., covalent linker) as a result of the association between atoms or molecules of bioconjugate reactive groups. The association can be direct or indirect. For example, a conjugate between a first bioconjugate reactive group (e.g., $—NH_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e., the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N-hydroxysuccinimide moiety) is covalently attached to the second bioconjugate reactive group (e.g., an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccinimide moiety) is covalently attached to the second bioconjugate reactive group (e.g., an amine).

Useful bioconjugate reactive moieties used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc.; (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc.; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g., phosphines) to form, for example, phosphate diester bonds; (n) azides coupled to alkynes using copper catalyzed cycloaddition click chemistry, and (o) biotin conjugate can react with avidin or streptavidin to form an avidin-biotin complex or streptavidin-biotin complex.

The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

"Analog" or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound.

The terms "a" or "an", as used in herein means one or more. In addition, the phrase "substituted with a[n]", as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl", the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$, etc., wherein each of $R^{13A}$, $R^{13B}$, $R^{13C}$, $R^{13D}$, etc. is defined within the scope of the definition of $R^{13}$ and optionally differently.

A "detectable agent" or "detectable moiety" is a substance, element, compound, or composition; or moiety thereof, detectable by appropriate means such as spectroscopic, photochemical, biochemical, immunochemical, chemical, magnetic resonance imaging, or other physical means. For example, useful detectable agents include $^{18}F$, $^{32}P$, $^{33}P$, $^{45}Ti$, $^{47}Sc$, $^{52}Fe$, $^{59}Fe$, $^{62}Cu$, $^{67}Cu$, $^{67}Ga$, $^{68}Ga$, $^{77}As$, $^{86}Y$, $^{89}Y$, $^{89}Sr$, $^{89}Zr$, $^{94}Tc$, $^{94}Tc$, $^{99m}Tc$, $^{99}Mo$, $^{105}Pd$, $^{105}Rh$, $^{111}Ag$, $^{111}In$, $^{123}I$, $^{124}I$, $^{125}I$, $^{131}I$, $^{142}Pr$, $^{143}Pr$, $^{149}Pm$, $^{153}Sm$, $^{154-1581}Gd$, $^{161}Tb$, $^{166}Dy$, $^{166}Ho$, $^{169}Er$, $^{175}Lu$, $^{177}Lu$, $^{186}Re$, $^{188}Re$, $^{189}Re$, $^{194}Ir$, $^{198}Au$, $^{199}Au$, $^{211}At$, $^{211}Pb$, $^{212}Bi$, $^{212}Pb$, $^{213}Bi$, $^{223}Ra$, $^{225}Ac$, Cr, V, Mn, Fe, Co, Ni, Cu, La, Ce, Pr, Nd, Pm, Sm, Eu, Gd, Tb, Dy, Ho, Er, Tm, Yb, Lu, $^{32}P$, fluorophore (e.g., fluorescent dyes), electron-dense reagents, enzymes (e.g., as commonly used in an ELISA), biotin, digoxigenin, paramagnetic molecules, paramagnetic nanoparticles, ultrasmall superparamagnetic iron oxide ("USPIO") nanoparticles, USPIO nanoparticle aggregates, superparamagnetic iron oxide ("SPIO") nanoparticles, SPIO nanoparticle aggregates, monochrystalline iron oxide nanoparticles, monochrystalline iron oxide, nanoparticle contrast agents, liposomes or other delivery vehicles containing Gadolinium chelate ("Gd-chelate") molecules, Gadolinium, radioisotopes, radionuclides (e.g., carbon-11, nitrogen-13, oxygen-15, fluorine-18, rubidium-82), fluorodeoxyglucose (e.g., fluorine-18 labeled), any gamma ray emitting radionuclides, positron-emitting radionuclide, radiolabeled glucose, radiolabeled water, radiolabeled ammonia, biocolloids, microbubbles (e.g., including microbubble shells including albumin, galactose, lipid, and/or polymers; microbubble gas core including air, heavy gas(es), perfluorcarbon, nitrogen, octafluoropropane, perflexane lipid microsphere, perflutren, etc.), iodinated contrast agents (e.g., iohexol, iodixanol, ioversol, iopamidol, ioxilan, iopromide, diatrizoate, metrizoate, ioxaglate), barium sulfate, thorium dioxide, gold, gold nanoparticles, gold nanoparticle aggregates, fluorophores, two-photon fluorophores, or haptens and proteins or other entities which can be made detectable, e.g., by incorporating a radiolabel into a peptide specifically reactive with a target peptide. A detectable moiety is a monovalent detectable agent or a detectable agent capable of forming a bond with another composition.

Radioactive substances (e.g., radioisotopes) that may be used as imaging and/or labeling agents in accordance with the embodiments of the disclosure include, but are not limited to, $^{18}F$, $^{23}P$, $^{33}P$, $^{45}Ti$, $^{47}Sc$, $^{52}Fe$, $^{59}Fe$, $^{62}Cu$, $^{64}Cu$, $^{67}Cu$, $^{67}Ga$, $^{77}As$, $^{86}Y$, $^{90}Y$, $^{89}Sr$, $^{89}Zr$, $^{94}Tc$, $^{94}Tc$, $^{99m}Tc$, $^{99}Mo$, $^{105}Pd$, $^{105}Rh$, $^{111}Ag$, $^{111}In$, $^{123}I$, $^{124}I$, $^{125}I$, $^{131}I$, $^{142}Pr$, $^{143}Pr$, $^{149}Pm$, $^{153}Sm$, $^{154-1581}Gd$, $^{161}Tb$, $^{166}Dy$, $^{166}Ho$, $^{169}Er$, $^{175}Lu$, $^{177}Lu$, $^{186}Re$, $^{188}Re$, $^{189}Re$, $^{194}Ir$, $^{198}Au$, $^{199}Au$, $^{211}At$, $^{211}Pb$, $^{212}Pb$, $^{212}Bi$, $^{213}Bi$, $^{223}Ra$, and $^{225}Ac$. Paramagnetic ions that may be used as additional imaging agents in accordance with the embodiments of the disclosure include, but are not limited to, ions of transition and lanthanide metals (e.g., metals having atomic numbers of 21-29,42,43, 44, or 57-71). These metals include ions of Cr, V, Mn, Fe, Co, Ni, Cu, La, Ce, Pr, Nd, Pm, Sm, Eu, Gd, Tb, Dy, Ho, Er, Tm, Yb, and Lu.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

A person of ordinary skill in the art will understand when a variable (e.g., moiety or linker) of a compound or of a compound genus (e.g., a genus described herein) is described by a name or formula of a standalone compound with all valencies filled, the unfilled valence(s) of the variable will be dictated by the context in which the variable is used. For example, when a variable of a compound as described herein is connected (e.g., bonded) to the remainder of the compound through a single bond, that variable is understood to represent a monovalent form (i.e., capable of forming a single bond due to an unfilled valence) of a standalone compound (e.g., if the variable is named "methane" in an embodiment but the variable is known to be attached by a single bond to the remainder of the compound, a person of ordinary skill in the art would understand that the variable is actually a monovalent form of methane, i.e., methyl or $—CH_3$). Likewise, for a linker variable (e.g., $L^1$, $L^2$, or $L^3$ as described herein), a person of ordinary skill in the art will understand that the variable is the divalent form of a standalone compound (e.g., if the variable is assigned to "PEG" or "polyethylene glycol" in an embodiment but the variable is connected by two separate bonds to the remainder of the compound, a person of ordinary skill in the art would understand that the variable is a divalent (i.e., capable of forming two bonds through two unfilled valences) form of PEG instead of the standalone compound PEG).

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present disclosure contain both basic and acidic functionalities that allow the compounds to be converted into either base or acid addition salts.

Thus, the compounds of the present disclosure may exist as salts, such as with pharmaceutically acceptable acids. The present disclosure includes such salts. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g., methyl iodide, ethyl iodide, and the like). These salts may be prepared by methods known to those skilled in the art.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the parent sugar of a thiosaccharide agent as disclosed herein, wherein the thiosaccharide agent lacks a thiol functionality, e.g., D-glucopyranose, D-galactopyranose, D-mannopyranose, D-glucopyranoside, D-galactopyranoside, or D-mannopyranoside. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

"Contacting" is used in accordance with its plain ordinary meaning and refers to the process of allowing at least two distinct species (e.g., chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments, contacting includes allowing a compound described herein to interact with a protein or enzyme that is involved in a signaling pathway.

As defined herein, the term "activation", "activate", "activating", "activator" and the like in reference to a protein-inhibitor interaction means positively affecting (e.g., increasing) the activity or function of the protein relative to the activity or function of the protein in the absence of the activator. In embodiments activation means positively affecting (e.g., increasing) the concentration or levels of the protein relative to the concentration or level of the protein in the absence of the activator. The terms may reference activation, or activating, sensitizing, or up-regulating signal transduction or enzymatic activity or the amount of a protein decreased in a disease. Thus, activation may include, at least in part, partially or totally increasing stimulation, increasing or enabling activation, or activating, sensitizing, or up-regulating signal transduction or enzymatic activity or the amount of a protein associated with a disease (e.g., a protein which is decreased in a disease relative to a non-diseased control). Activation may include, at least in part, partially or totally increasing stimulation, increasing or enabling activation, or activating, sensitizing, or up-regulating signal transduction or enzymatic activity or the amount of a protein.

The terms "agonist", "activator", "upregulator", etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

As defined herein, the term "inhibition", "inhibit", "inhibiting" and the like in reference to a protein-inhibitor interaction means negatively affecting (e.g., decreasing) the activity or function of the protein relative to the activity or function of the protein in the absence of the inhibitor. In embodiments inhibition means negatively affecting (e.g., decreasing) the concentration or levels of the protein relative to the concentration or level of the protein in the absence of the inhibitor. In embodiments, inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g., an inhibitor binds to the target protein). In embodiments, inhibition refers to a reduction of activity of a target protein from an indirect interaction (e.g., an inhibitor binds to a protein that activates the target protein, thereby preventing target protein activation).

The terms "inhibitor", "repressor", "antagonist", or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The term "modulator" refers to a composition that increases or decreases the level of a target molecule or the function of a target molecule or the physical state of the target of the molecule relative to the absence of the modulator. The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "associated" or "associated with" in the context of a substance or substance activity or function associated with a disease means that the disease is caused by (in whole or in part), or a symptom of the disease is caused by (in whole or in part) the substance or substance activity or function.

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g., by administering a compound or using a method as described herein), results in reduction of the disease or one or more disease symptoms.

The term "signaling pathway" as used herein refers to a series of interactions between cellular and optionally extra-cellular components (e.g., proteins, nucleic acids, small molecules, ions, lipids) that conveys a change in one component to one or more other components, which in turn may convey a change to additional components, which is optionally propogated to other signaling pathway components. For example, binding of a thioredoxin protein with a compound as described herein may reduce the interactions between the thioredoxin protein and downstream effectors or signaling pathway components, resulting in changes in cell growth, proliferation, or survival.

In this disclosure, "comprises", "comprising", "containing", and "having" and the like can have the meaning ascribed to them in U.S. Patent law and can mean "includes", "including", and the like. "Consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

The terms "disease" or "condition" refer to a state of being or health status of a patient or subject capable of being treated with a compound, pharmaceutical composition, or method provided herein. In embodiments, the disease is a coronavirus infection. In embodiments, the disease is coronavirus disease 2019 (COVID-19).

The term "coronavirus" is used in accordance with its plain ordinary meaning and refers to an RNA virus that in humans causes respiratory tract infections. Coronaviruses constitute the subfamily Orthocoronavirinae, in the family Coronaviridae, order Nidovirales, and realm Riboviria. In embodiments, the coronavirus is an enveloped viruses with a positive-sense single-stranded RNA genome.

The term "severe acute respiratory syndrome coronavirus" or "SARS-CoV-1" refers to the strain of coronavirus that causes severe acute respiratory syndrome (SARS). In embodiments, SARS-CoV-1 is an enveloped, positive-sense, single-stranded RNA virus that infects the epithelial cells within the lungs. In embodiments, the virus enters the host cell by binding to the angiotensin-converting enzyme 2 (ACE2) receptor.

The term "severe acute respiratory syndrome coronavirus 2" or "SARS-CoV-2" refers to the strain of coronavirus that causes coronavirus disease 2019 (COVID-19). In embodiments, SARS-CoV-2 is a positive-sense single-stranded RNA virus.

The terms "treating" or "treatment" refer to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing. In embodiments, treating refers to treating a subject having a disease.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms, fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof.

It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is not prophylactic treatment.

The term "prevent" refers to a decrease in the occurrence of a disease or disease symptoms in a patient. As indicated above, the prevention may be complete (no detectable symptoms) or partial, such that fewer symptoms are observed than would likely occur absent treatment.

As used herein, a "symptom" of a disease includes any clinical or laboratory manifestation associated with the disease, and is not limited to what a subject can feel or observe. In embodiments, the symptoms include, but are not limited to, cough, shortness of breath or difficulty breathing, fever, chills, repeated shaking with chills, muscle pain, headache, sore throat, and new loss of taste or smell.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

An "effective amount" is an amount sufficient for a compound to accomplish a stated purpose relative to the absence of the compound (e.g., achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

For any compound described herein, the therapeutically effective amount can be initially determined from binding assays or cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as an aerosol, dry powder, nasal spray, suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

"Co-administer" it is meant that a composition described herein is administered at the same time, just prior to, or just after the administration of one or more additional therapies. The compounds provided herein can be administered alone or can be coadministered to the patient. Co-administration is meant to include simultaneous or sequential administration of the compounds individually or in combination (more than one compound). Thus, the preparations can also be combined, when desired, with other active substances (e.g., to reduce metabolic degradation). The compositions of the present disclosure can be delivered transdermally, by a topical route, or formulated as applicator sticks, solutions, suspensions, emulsions, gels, creams, ointments, pastes, jellies, paints, powders, and aerosols. The preparations may also be combined with inhaled mucolytics (e.g., rhDNase, as known in the art) or with inhaled bronchodilators (short or long acting beta agonists, short or long acting anticholinergics), inhaled corticosteroids, or inhaled antibiotics to improve the efficacy of these drugs by providing additive or synergistic effects. The compositions of the present invention can be delivered transdermally, by a topical route, formulated as applicator sticks, solutions, suspensions, emulsions, gels, creams, ointments, nanoparticles, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., *spodoptera*) and human cells. Cells may be useful when they are naturally nonadherent or have been treated not to adhere to surfaces, for example by trypsinization.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The terms "bind" and "bound" as used herein is used in accordance with its plain and ordinary meaning and refers to the association between atoms or molecules. The association can be covalent (e.g., by a covalent bond or linker) or non-covalent (e.g., electrostatic interactions (e.g., ionic bond, hydrogen bond, or halogen bond), van der Waals interactions (e.g., dipole-dipole, dipole-induced dipole, or London dispersion), ring stacking (pi effects), hydrophobic interactions, and the like).

As used herein, the term "conjugated" when referring to two moieties means the two moieties are bonded, wherein the bond or bonds connecting the two moieties may be covalent or non-covalent. In embodiments, the two moieties are covalently bonded to each other (e.g., directly or through a covalently bonded intermediary). In embodiments, the two moieties are non-covalently bonded (e.g., through ionic bond(s), van der Waals bond(s)/interactions, hydrogen bond(s), polar bond(s), or combinations or mixtures thereof).

The term "thiol" is used in accordance with its ordinary meaning in the art and refers to the moiety

II. Methods

In an aspect is provided a method of treating a coronavirus infection in a subject in need thereof, the method including administering to the subject in need thereof an effective amount of a thiosaccharide compound, or a pharmaceutically acceptable salt thereof.

In an aspect is provided a method of treating inflammation in a subject in need thereof, the method including administering to the subject in need thereof an effective amount of a thiosaccharide compound, or a pharmaceutically acceptable salt thereof. In embodiments, the inflammation is in the lung. In embodiments, the inflammation is a symptom of infection, such as coronavirus infection. In embodiments, the inflammation is a consequence of infection, such as coronavirus infection.

In embodiments, the coronavirus infection is a SARS-CoV-1 infection. In embodiments, the coronavirus infection is Severe Acute Respiratory Disease (SARS). In embodiments, the coronavirus infection is a SARS-CoV-2 infection. In embodiments, the coronavirus infection is coronavirus disease 2019 (COVID-19). In embodiments, the subject in need thereof has or is suspected of having COVID-19. In embodiments, the subject in need thereof has post acute COVID syndrome (e.g., COVID long haul syndrome) and treatment is administered because the syndrome may be caused by persistent viral infection in the airways and lungs. In embodiments, the coronavirus infection is an HCoV-NL63 coronavirus infection. In embodiments, HCoV-NL63 coronavirus infection is a cause of the common cold. In embodiments, HCoV-NL63 coronavirus infection is a cause of pneumonia. In embodiments, the coronavirus infection is an HCoV-229E coronavirus infection. In embodiments, HCoV-229E coronavirus infection is a cause of the common cold. In embodiments, HCoV-229E coronavirus infection is a cause of pneumonia. In embodiments, the coronavirus infection is an HCoV-OC43 coronavirus infection. In embodiments, HCoV-OC43 coronavirus infection is a cause of the common cold. In embodiments, HCoV-OC43 coronavirus infection is a cause of pneumonia. In embodiments, the coronavirus infection is an HCoV-HKU1 coronavirus infection. In embodiments, HCoV-HKU1 coronavirus infection is a cause of the common cold. In embodiments, HCoV-HKU1 coronavirus infection is a cause of pneumonia.

In embodiments, the effective amount is administered within 12 to 96 hours of the onset of one or more symptoms of the infection. In embodiments, the effective amount is administered within 18 to 96 hours of the onset of one or more symptoms of the infection. In embodiments, the effective amount is administered within 24 to 96 hours of the onset of one or more symptoms of the infection. In embodiments, the effective amount is administered within 36 to 96 hours of the onset of one or more symptoms of the infection. In embodiments, the effective amount is administered within 48 to 96 hours of the onset of one or more symptoms of the infection. In embodiments, the effective amount is administered within 12 hours of the onset of the one or more symptoms. In embodiments, the effective amount is administered within 18 hours of the onset of the one or more symptoms. In embodiments, the effective amount is administered within 24 hours of the onset of the one or more symptoms. In embodiments, the effective amount is administered within 36 hours of the onset of the one or more symptoms. In embodiments, the effective amount is administered within 48 hours of the onset of the one or more symptoms. In embodiments, the effective amount is administered within 60 hours of the onset of the one or more symptoms. In embodiments, the effective amount is administered within 72 hours of the onset of the one or more symptoms.

In embodiments, the symptoms include, but are not limited to, cough, shortness of breath or difficulty breathing, fever, chills, repeated shaking with chills, muscle pain, headache, sore throat, and new loss of taste or smell.

In embodiments, the subject in need thereof is not hospitalized. In embodiments, the subject in need thereof is hospitalized. In embodiments, the subject in need thereof is in an intensive care unit.

In embodiments, the thiosaccharide compound is a thiol saccharide compound. In embodiments, the thiosaccharide compound is a thioacetyl saccharide compound. In embodiments, the thiosaccharide compound is a thiol monosaccharide compound, a thiol disaccharide compound, or a thiol trisaccharide compound. In embodiments, the thiosaccharide compound includes D-glucopyranose, D-galactopyranose, D-mannopyranose, D-glucopyranoside, D-galactopyranoside, or D-mannopyranoside moieties.

In embodiments, the thiosaccharide compound has the formula:

(I)

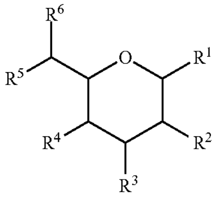

.

$R^1$ is —$SR^{1A}$, —$OR^{1A}$, —$NR^{1B}R^{1C}$, —$NR^{1B}C(O)R^{1C}$, —$NR^{1B}C(O)OR^{1C}$, substituted or unsubstituted alkyl (e.g., $C_1$-$C_{10}$, $C_1$-$C_6$, $C_1$-$C_4$, or $C_1$-$C_2$), or substituted or unsubstituted heteroalkyl (e.g., 2 to 10 membered, 2 to 6 membered, 4 to 6 membered, or 2 to 3 membered). $R^2$ is —$SR^{2A}$, —$OR^{2A}$, —$NR^{2B}R^{2C}$, —$NR^{2B}C(O)R^{2C}$, —$NR^{2B}C(O)OR^{2C}$, substituted or unsubstituted alkyl (e.g., $C_1$-$C_{10}$, $C_1$-$C_6$, $C_1$-$C_4$, or $C_1$-$C_2$), or substituted or unsubstituted heteroalkyl (e.g., 2 to 10 membered, 2 to 6 membered, 4 to 6 membered, or 2 to 3 membered). $R^3$ is —$SR^{3A}$, —$OR^{3A}$, —$NR^{3B}R^{3C}$, —$NR^{3B}C(O)R^{3C}$, —$NR^{3B}C(O)OR^{3C}$, substituted or unsubstituted alkyl (e.g., $C_1$-$C_{10}$, $C_1$-$C_6$, $C_1$-$C_4$, or $C_1$-$C_2$), or substituted or unsubstituted heteroalkyl (e.g., 2 to 10 membered, 2 to 6 membered, 4 to 6 membered, or 2 to 3 membered). $R^4$ is —$SR^{4A}$, —$SC(O)R^{4A}$, —$OR^{4A}$, —$NR^{4B}R^{4C}$, —$NR^{4B}C(O)R^{4C}$, —$NR^{4B}C(O)OR^{4C}$, substituted or unsubstituted alkyl (e.g., $C_1$-$C_{10}$, $C_1$-$C_6$, $C_1$-$C_4$, or $C_1$-$C_2$), or substituted or unsubstituted heteroalkyl (e.g., 2 to 10 membered, 2 to 6 membered, 4 to 6 membered, or 2 to 3 membered). $R^5$ is hydrogen, —$SR^{5A}$, —$SC(O)R^{5A}$, —$OR^{5A}$, —$NR^{5B}R^{5C}$, —$NR^{5B}C(O)R^{5C}$, —$NR^{5B}C(O)OR^{5C}$, or substituted or unsubstituted alkyl (e.g., $C_1$-$C_{10}$, $C_1$-$C_6$, $C_1$-$C_4$, or $C_1$-$C_2$), or substituted or unsubstituted heteroalkyl (e.g., 2 to 10 membered, 2 to 6 membered, 4 to 6 membered, or 2 to 3 membered). $R^6$ is hydrogen, —$SR^{6A}$, —$OR^{6A}$, —$NR^{6B}R^{6C}$, —$NR^{6B}C(O)R^{6C}$, —$NR^{6B}C(O)OR^{6C}$, substituted or unsubstituted alkyl (e.g., $C_1$-$C_{10}$, $C_1$-$C_4$, $C_1$-$C_4$, or $C_1$-$C_2$), or substituted or unsubstituted heteroalkyl (e.g., 2 to 10 membered, 2 to 6 membered, 4 to 6 membered, or 2 to 3 membered). $R^{1A}$, $R^{1B}$, $R^{1C}$, $R^{2A}$, $R^{2B}$, $R^{2C}$, $R^{3A}$, $R^{3B}$, $R^{3C}$, $R^{4A}$, $R^{4B}$, $R^{4C}$, $R^{5A}$, $R^{5B}$, $R^{5C}$, $R^{6A}$, $R^{6B}$, and $R^{6C}$ are each independently hydrogen, substituted or unsubstituted alkyl (e.g., $C_1$-$C_{10}$, $C_1$-$C_6$, $C_1$-$C_4$, or $C_1$-$C_2$), or substituted or unsubstituted heteroalkyl (e.g., 2 to 10 membered, 2 to 6 membered, 4 to 6 membered, or 2 to 3 membered).

In embodiments, the thiosaccharide compound comprises at least two thiol moieties. In embodiments, the thiosaccharide compound includes at a maximum two thiol moieties.

In embodiments, $R^1$ is —$SR^{1A}$. In embodiments, $R^1$ is —$OR^{1A}$. In embodiments, $R^1$ is —$NR^{1B}R^{1C}$. In embodiments, $R^1$ is —$NR^{1B}C(O)R^{1C}$. In embodiments, $R^1$ is —$NR^{1B}C(O)OR^{1C}$. In embodiments, $R^1$ is —SH. In embodiments, $R^1$ is —OH. In embodiments, $R^1$ is —$NH_2$. In embodiments, $R^1$ is —NHC(O)H. In embodiments, $R^1$ is —NHC(O)OH. In embodiments, $R^1$ is substituted or unsubstituted $C_1$-$C_{10}$ alkyl. In embodiments, $R^1$ is unsubstituted $C_1$-$C_5$ alkyl. In embodiments, $R^1$ is unsubstituted methyl. In embodiments, $R^1$ is unsubstituted ethyl. In embodiments, $R^1$ is unsubstituted propyl. In embodiments, $R^1$ is unsubstituted n-propyl. In embodiments, $R^1$ is unsubstituted isopropyl. In embodiments, $R^1$ is unsubstituted butyl. In embodiments, $R^1$ is unsubstituted n-butyl. In embodiments, $R^1$ is unsubstituted tert-butyl. In embodiments, $R^1$ is substituted or unsubstituted 2 to 10 membered heteroalkyl. In embodiments, $R^1$ is substituted or unsubstituted $C_1$-$C_{10}$ thiol-alkyl or substituted or unsubstituted 2 to 10 membered thiol-heteroalkyl. In embodiments, $R^1$ is unsubstituted $C_1$-$C_{10}$ thiol-alkyl or unsubstituted 2 to 10 membered thiol-heteroalkyl. In embodiments, $R^1$ is unsubstituted thiomethyl (e.g., —$CH_2SH$), unsubstituted thioethyl (e.g., —$(CH_2)_2SH$), unsubstituted thiopropyl (e.g., —$(CH_2)_3SH$), unsubstituted thiobutyl (e.g., —$(CH_2)_4SH$), unsubstituted thiopentyl (e.g., —$(CH_2)_5SH$), unsubstituted thiohexyl (e.g., —$(CH_2)_6SH$), unsubstituted thioheptyl (e.g., —$(CH_2)_7SH$), unsubstituted thiooctyl (e.g., —$(CH_2)_8SH$), unsubstituted thiononyl (e.g., —$(CH_2)_9SH$), or unsubstituted thiodecyl (e.g., —$(CH_2)_{10}SH$). In embodiments, $R^1$ is unsubstituted thioethyl. In embodiments, $R^1$ is unsubstituted thiopropyl. In embodiments, $R^1$ is unsubstituted thiobutyl. In embodiments, $R^1$ is unsubstituted thiopentyl. In embodiments, $R^1$ is unsubstituted thioethyloxyethyl. In embodiments, $R^1$ is unsubstituted alkoxy. In embodiments, $R^1$ is —O-(unsubstituted $C_1$-$C_4$ alkyl). In embodiments, $R^1$ is unsubstituted methoxy. In embodiments, $R^1$ is unsubstituted ethoxy. In embodiments, $R^1$ is unsubstituted propoxy. In embodiments, $R^1$ is unsubstituted n-propoxy. In embodiments, $R^1$ is unsubstituted isopropoxy. In embodiments, $R^1$ is unsubstituted butoxy. In embodiments, $R^1$ is unsubstituted n-butoxy. In embodiments, $R^1$ is unsubstituted tert-butoxy.

In embodiments, a substituted $R^1$ (e.g., substituted alkyl and/or substituted heteroalkyl) is substituted with at least one substituent group, size-limited substituent group, or lower substituent group; wherein if the substituted $R^1$ is substituted with a plurality of groups selected from substituent groups, size-limited substituent groups, and lower substituent groups; each substituent group, size-limited substituent group, and/or lower substituent group may optionally be different. In embodiments, when $R^1$ is substituted, it is substituted with at least one substituent group. In embodiments, when $R^1$ is substituted, it is substituted with at least one size-limited substituent group. In embodiments, when $R^1$ is substituted, it is substituted with at least one lower substituent group.

In embodiments, $R^{1A}$ is hydrogen. In embodiments, $R^{1A}$ is substituted or unsubstituted $C_1$-$C_{10}$ alkyl. In embodiments, $R^{1A}$ is unsubstituted $C_1$-$C_{10}$ alkyl. In embodiments, $R^{1A}$ is unsubstituted $C_1$-$C_5$ alkyl. In embodiments, $R^{1A}$ is unsubstituted methyl. In embodiments, $R^{1A}$ is unsubstituted ethyl. In embodiments, $R^{1A}$ is unsubstituted propyl. In embodiments, $R^{1A}$ is unsubstituted n-propyl. In embodiments, $R^{1A}$ is unsubstituted isopropyl. In embodiments, $R^{1A}$ is unsubstituted butyl. In embodiments, $R^{1A}$ is unsubstituted n-butyl. In embodiments, $R^{1A}$ is unsubstituted tert-butyl. In embodiments, $R^{1A}$ is substituted or unsubstituted 2 to 10 membered heteroalkyl. In embodiments, $R^{1A}$ is unsubstituted 2 to 6 membered heteroalkyl. In embodiments, $R^{1A}$ is substituted or unsubstituted $C_1$-$C_{10}$ thiol-alkyl or substituted or unsubstituted 2 to 10 membered thiol-heteroalkyl. In embodiments, $R^{1A}$ is unsubstituted $C_1$-$C_{10}$ thiol-alkyl or unsubstituted 2 to 10 membered thiol-heteroalkyl. In embodiments, $R^{1A}$ is unsubstituted thiomethyl (e.g., $—CH_2SH$), unsubstituted thioethyl (e.g., $—(CH_2)_2SH$), unsubstituted thiopropyl (e.g., $—(CH_2)_3SH$), unsubstituted thiobutyl (e.g., $—(CH_2)_4SH$), unsubstituted thiopentyl (e.g., $—(CH_2)_5SH$), unsubstituted thiohexyl (e.g., $—(CH_2)_6SH$), unsubstituted thioheptyl (e.g., $—(CH_2)_7SH$), unsubstituted thiooctyl (e.g., $—(CH_2)_8SH$), unsubstituted thiononyl (e.g., $—(CH_2)_9SH$), or unsubstituted thiodecyl (e.g., $—(CH_2)_{10}SH$). In embodiments, $R^{1A}$ is unsubstituted thioethyl. In embodiments, $R^{1A}$ is unsubstituted thiopropyl. In embodiments, $R^{1A}$ is unsubstituted thiobutyl. In embodiments, $R^{1A}$ is unsubstituted thiopentyl. In embodiments, $R^{1A}$ is unsubstituted thioethyloxyethyl.

In embodiments, a substituted $R^{1A}$ (e.g., substituted alkyl and/or substituted heteroalkyl) is substituted with at least one substituent group, size-limited substituent group, or lower substituent group; wherein if the substituted $R^{1A}$ is substituted with a plurality of groups selected from substituent groups, size-limited substituent groups, and lower substituent groups; each substituent group, size-limited substituent group, and/or lower substituent group may optionally be different. In embodiments, when $R^{1A}$ is substituted, it is substituted with at least one substituent group. In embodiments, when $R^{1A}$ is substituted, it is substituted with at least one size-limited substituent group. In embodiments, when $R^{1A}$ is substituted, it is substituted with at least one lower substituent group.

In embodiments, $R^{1A}$ is

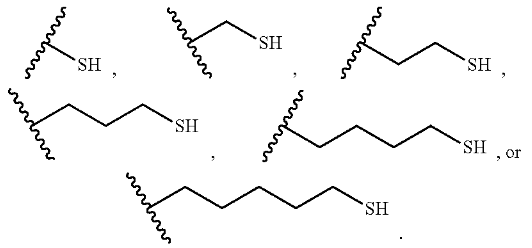

In embodiments, $R^{1B}$ is hydrogen. In embodiments, $R^{1B}$ is substituted or unsubstituted $C_1$-$C_{10}$ alkyl. In embodiments, $R^{1B}$ is substituted or unsubstituted 2 to 10 membered heteroalkyl. In embodiments, $R^{1B}$ is substituted or unsubstituted $C_1$-$C_{10}$ thiol-alkyl or substituted or unsubstituted 2 to 10 membered thiol-heteroalkyl. In embodiments, $R^{1B}$ is unsubstituted $C_1$-$C_{10}$ thiol-alkyl or unsubstituted 2 to 10 membered thiol-heteroalkyl. In embodiments, $R^{1B}$ is —C(O)-(substituted or unsubstituted $C_1$-$C_{10}$ alkyl). In embodiments, $R^{1B}$ is —C(O)-(substituted or unsubstituted $C_1$-$C_{10}$ thiol-alkyl). In embodiments, $R^{1B}$ is —C(O)-(substituted or unsubstituted 2 to 10 membered thiol-heteroalkyl).

In embodiments, a substituted $R^{1B}$ (e.g., Substituted alkyl and/or substituted heteroalkyl) is substituted with at least one substituent group, size-limited substituent group, or lower substituent group; wherein if the substituted $R^{1B}$ is substituted with a plurality of groups selected from substituent groups, size-limited substituent groups, and lower substituent groups; each substituent group, size-limited substituent group, and/or lower substituent group may optionally be different. In embodiments, when $R^{1B}$ is substituted, it is substituted with at least one substituent group. In embodiments, when $R^{1B}$ is substituted, it is substituted with at least one size-limited substituent group. In embodiments, when $R^{1B}$ is substituted, it is substituted with at least one lower substituent group.

In embodiments, $R^{1C}$ is hydrogen. In embodiments, $R^{1C}$ is substituted or unsubstituted $C_1$-$C_{10}$ alkyl. In embodiments, $R^{1C}$ is substituted or unsubstituted 2 to 10 membered heteroalkyl. In embodiments, $R^{1C}$ is substituted or unsubstituted $C_1$-$C_{10}$ thiol-alkyl or substituted or unsubstituted 2 to 10 membered thiol-heteroalkyl. In embodiments, $R^{1C}$ is unsubstituted $C_1$-$C_{10}$ thiol-alkyl or unsubstituted 2 to 10 membered thiol-heteroalkyl.

In embodiments, a substituted $R^{1C}$ (e.g., substituted alkyl and/or substituted heteroalkyl) is substituted with at least one substituent group, size-limited substituent group, or lower substituent group; wherein if the substituted $R^{1C}$ is substituted with a plurality of groups selected from substituent groups, size-limited substituent groups, and lower substituent groups; each substituent group, size-limited substituent group, and/or lower substituent group may optionally be different. In embodiments, when $R^{1C}$ is substituted, it is substituted with at least one substituent group. In embodiments, when $R^{1C}$ is substituted, it is substituted with at least one size-limited substituent group. In embodiments, when $R^{1C}$ is substituted, it is substituted with at least one lower substituent group.

In embodiments, $R^2$ is —$SR^{2A}$. In embodiments, $R^2$ is —$OR^{2A}$. In embodiments, $R^2$ is —$NR^{2B}R^{2C}$. In embodiments, $R^2$ is —$NR^{2B}C(O)R^{2C}$. In embodiments, $R^2$ is —$NR^{2B}C(O)OR^{2C}$. In embodiments, $R^2$ is —SH. In embodiments, $R^2$ is —OH. In embodiments, $R^2$ is —$NH_2$. In embodiments, $R^2$ is —NHC(O)H. In embodiments, $R^2$ is —$NHC(O)CH_3$. In embodiments, $R^2$ is —NHC(O)OH. In embodiments, $R^2$ is substituted or unsubstituted $C_1$-$C_{10}$ alkyl. In embodiments, $R^2$ is unsubstituted $C_1$-$C_5$ alkyl. In embodiments, $R^2$ is unsubstituted methyl. In embodiments, $R^2$ is unsubstituted ethyl. In embodiments, $R^2$ is unsubstituted propyl. In embodiments, $R^2$ is unsubstituted n-propyl. In embodiments, $R^2$ is unsubstituted isopropyl. In embodiments, $R^2$ is unsubstituted butyl. In embodiments, $R^2$ is unsubstituted n-butyl. In embodiments, $R^2$ is unsubstituted tert-butyl. In embodiments, $R^2$ is substituted or unsubstituted 2 to 10 membered heteroalkyl. In embodiments, $R^2$ is substituted or unsubstituted $C_1$-$C_{10}$ thiol-alkyl or substituted or unsubstituted 2 to 10 membered thiol-heteroalkyl. In embodiments, $R^2$ is unsubstituted $C_1$-$C_{10}$ thiol-alkyl or unsubstituted 2 to 10 membered thiol-heteroalkyl. In embodiments, $R^2$ is unsubstituted thiomethyl (e.g., —$CH_2SH$), unsubstituted thioethyl (e.g., —$(CH_2)_2SH$), unsubstituted thiopropyl (e.g., —$(CH_2)_3SH$), unsubstituted thiobutyl (e.g., —$(CH_2)_4SH$), unsubstituted thiopentyl (e.g., —$(CH_2)_5SH$), unsubstituted thiohexyl (e.g., —$(CH_2)_6SH$), unsubstituted thioheptyl (e.g., —$(CH_2)_7SH$), unsubstituted thiooctyl (e.g., —$(CH_2)_8SH$), unsubstituted thiononyl (e.g., —$(CH_2)_9SH$), or unsubstituted thiodecyl (e.g., —$(CH_2)_{10}SH$). In embodiments, $R^2$ is unsubstituted thioethyl. In embodiments, $R^2$ is unsubstituted thiopropyl. In embodiments, $R^2$ is unsubstituted thiobutyl. In embodiments, $R^2$ is unsubstituted thiopentyl. In embodiments, $R^2$ is unsubstituted alkoxy. In embodiments, $R^2$ is —O-(unsubstituted $C_1$-$C_4$ alkyl). In embodiments, $R^2$ is unsubstituted methoxy. In embodiments, $R^2$ is unsubstituted ethoxy. In embodiments, $R^2$ is unsubstituted propoxy. In embodiments, $R^2$ is unsubstituted n-propoxy. In embodiments, $R^2$ is unsubstituted isopropoxy. In embodiments, $R^2$ is unsubstituted butoxy. In embodiments, $R^2$ is unsubstituted n-butoxy. In embodiments, $R^2$ is unsubstituted tert-butoxy.

In embodiments, a substituted $R^2$ (e.g., substituted alkyl and/or substituted heteroalkyl) is substituted with at least one substituent group, size-limited substituent group, or lower substituent group; wherein if the substituted $R^2$ is substituted with a plurality of groups selected from substituent groups, size-limited substituent groups, and lower substituent groups; each substituent group, size-limited substituent group, and/or lower substituent group may optionally be different. In embodiments, when $R^2$ is substituted, it is substituted with at least one substituent group. In embodiments, when $R^2$ is substituted, it is substituted with at least one size-limited substituent group. In embodiments, when $R^2$ is substituted, it is substituted with at least one lower substituent group.

In embodiments, $R^{2A}$ is hydrogen. In embodiments, $R^{2A}$ is substituted or unsubstituted $C_1$-$C_{10}$ alkyl. In embodiments, $R^{2A}$ is substituted or unsubstituted 2 to 10 membered heteroalkyl. In embodiments, $R^{2A}$ is substituted or unsubstituted $C_1$-$C_{10}$ thiol-alkyl or substituted or unsubstituted 2 to 10 membered thiol-heteroalkyl. In embodiments, $R^{2A}$ is unsubstituted $C_1$-$C_{10}$ thiol-alkyl or unsubstituted 2 to 10 membered thiol-heteroalkyl.

In embodiments, a substituted $R^{2A}$ (e.g., substituted alkyl and/or substituted heteroalkyl) is substituted with at least one substituent group, size-limited substituent group, or lower substituent group; wherein if the substituted $R^{2A}$ is substituted with a plurality of groups selected from substituent groups, size-limited substituent groups, and lower substituent groups; each substituent group, size-limited substituent group, and/or lower substituent group may optionally be different. In embodiments, when $R^{2A}$ is substituted, it is substituted with at least one substituent group. In embodiments, when $R^{2A}$ is substituted, it is substituted with at least one size-limited substituent group. In embodiments, when $R^{2A}$ is substituted, it is substituted with at least one lower substituent group.

In embodiments, $R^{2A}$ is

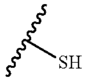 , 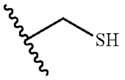 , 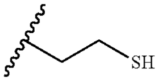 , 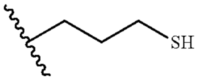 , 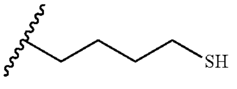 , or 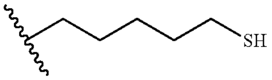 .

In embodiments, $R^{2B}$ is hydrogen. In embodiments, $R^{2B}$ is substituted or unsubstituted $C_1$-$C_{10}$ alkyl. In embodiments, $R^{2B}$ is substituted or unsubstituted 2 to 10 membered heteroalkyl. In embodiments, $R^{2B}$ is substituted or unsubstituted $C_1$-$C_{10}$ thiol-alkyl or substituted or unsubstituted 2 to 10 membered thiol-heteroalkyl. In embodiments, $R^2$ is unsubstituted $C_1$-$C_{10}$ thiol-alkyl or unsubstituted 2 to 10 membered thiol-heteroalkyl. In embodiments, $R^{2B}$ is —C(O)-(substituted or unsubstituted $C_1$-$C_{10}$ alkyl). In embodiments, $R^{2B}$ is —C(O)-(substituted or unsubstituted $C_1$-$C_{10}$ thiol-alkyl). In embodiments, $R^{2B}$ is —C(O)-(substituted or unsubstituted 2 to 10 membered thiol-heteroalkyl).

In embodiments, a substituted $R^{2B}$ (e.g., substituted alkyl and/or substituted heteroalkyl) is substituted with at least one substituent group, size-limited substituent group, or lower substituent group; wherein if the substituted $R^{2B}$ is substituted with a plurality of groups selected from substituent groups, size-limited substituent groups, and lower substituent groups; each substituent group, size-limited substituent group, and/or lower substituent group may optionally be different. In embodiments, when $R^{2B}$ is substituted, it is substituted with at least one substituent group. In embodiments, when $R^{2B}$ is substituted, it is substituted with at least one size-limited substituent group. In embodiments, when $R^{2B}$ is substituted, it is substituted with at least one lower substituent group.

In embodiments, $R^{2C}$ is hydrogen. In embodiments, $R^{2C}$ is substituted or unsubstituted $C_1$-$C_{10}$ alkyl. In embodiments, $R^{2C}$ is substituted or unsubstituted 2 to 10 membered heteroalkyl. In embodiments, $R^{2C}$ is substituted or unsubstituted $C_1$-$C_{10}$ thiol-alkyl or substituted or unsubstituted 2 to 10 membered thiol-heteroalkyl. In embodiments, $R^{2C}$ is unsubstituted $C_1$-$C_{10}$ thiol-alkyl or unsubstituted 2 to 10 membered thiol-heteroalkyl.

In embodiments, a substituted $R^{2C}$ (e.g., substituted alkyl and/or substituted heteroalkyl) is substituted with at least one substituent group, size-limited substituent group, or lower substituent group; wherein if the substituted $R^{2C}$ is substituted with a plurality of groups selected from substituent groups, size-limited substituent groups, and lower substituent groups; each substituent group, size-limited substituent group, and/or lower substituent group may optionally be different. In embodiments, when $R^{2C}$ is substituted, it is substituted with at least one substituent group. In embodiments, when $R^{2C}$ is substituted, it is substituted with at least one size-limited substituent group. In embodiments, when $R^{2C}$ is substituted, it is substituted with at least one lower substituent group.

In embodiments, $R^3$ is —$SR^{3A}$. In embodiments, $R^3$ is —$OR^{3A}$. In embodiments, $R^3$ is —$NR^{3B}R^{3C}$. In embodiments, $R^3$ is —$NR^{3B}C(O)R^{3C}$. In embodiments, $R^3$ is —$NR^{3B}C(O)OR^{3C}$. In embodiments, $R^3$ is —SH. In embodiments, $R^3$ is —OH. In embodiments, $R^3$ is —$NH_2$. In embodiments, $R^3$ is —NHC(O)H. In embodiments, $R^3$ is —NHC(O)OH. In embodiments, $R^3$ is substituted or unsubstituted $C_1$-$C_{10}$ alkyl. In embodiments, $R^3$ is unsubstituted $C_1$-$C_5$ alkyl. In embodiments, $R^3$ is unsubstituted methyl. In embodiments, $R^3$ is unsubstituted ethyl. In embodiments, $R^3$ is unsubstituted propyl. In embodiments, $R^3$ is unsubstituted n-propyl. In embodiments, $R^3$ is unsubstituted isopropyl. In embodiments, $R^3$ is unsubstituted butyl. In embodiments, $R^3$ is unsubstituted n-butyl. In embodiments, $R^3$ is unsubstituted tert-butyl. In embodiments, $R^1$ is substituted or unsubstituted 2 to 10 membered heteroalkyl. In embodiments, $R^3$ is substituted or unsubstituted $C_1$-$C_{10}$ thiol-alkyl or substituted or unsubstituted 2 to 10 membered thiol-heteroalkyl. In embodiments, $R^3$ is unsubstituted $C_1$-$C_{10}$ thiol-alkyl or unsubstituted 2 to 10 membered thiol-heteroalkyl. In embodiments, $R^3$ is unsubstituted thiomethyl (e.g., —$CH_2SH$), unsubstituted thioethyl (e.g., —$(CH_2)_2SH$), unsubstituted thiopropyl (e.g., —$(CH_2)_3SH$), unsubstituted thiobutyl (e.g., —$(CH_2)_4SH$), unsubstituted thiopentyl (e.g., —$(CH_2)_5SH$), unsubstituted thiohexyl (e.g., —$(CH_2)_6SH$), unsubstituted thioheptyl (e.g., —$(CH_2)_7SH$), unsubstituted thiooctyl (e.g., —$(CH_2)_8SH$), unsubstituted thiononyl (e.g., —$(CH_2)_9SH$), or unsubstituted thiodecyl (e.g., —$(CH_2)_{10}SH$). In embodiments, $R^3$ is unsubstituted thioethyl. In embodiments, $R^3$ is unsubstituted thiopropyl. In embodiments, $R^3$ is unsubstituted thiobutyl. In embodiments, $R^3$ is unsubstituted thiopentyl. In embodiments, $R^3$ is unsubstituted alkoxy. In embodiments, $R^3$ is —O-(unsubstituted $C_1$-$C_4$ alkyl). In embodiments, $R^3$ is unsubstituted methoxy. In embodiments, $R^3$ is unsubstituted ethoxy. In embodiments, $R^3$ is unsubstituted propoxy. In embodiments, $R^3$ is unsubstituted n-propoxy. In embodiments, $R^3$ is unsubstituted isopropoxy. In embodiments, $R^3$ is unsubstituted butoxy. In embodiments, $R^3$ is unsubstituted n-butoxy. In embodiments, $R^3$ is unsubstituted tert-butoxy.

In embodiments, a substituted $R^3$ (e.g., substituted alkyl and/or substituted heteroalkyl) is substituted with at least one substituent group, size-limited substituent group, or lower substituent group; wherein if the substituted $R^3$ is substituted with a plurality of groups selected from substituent groups, size-limited substituent groups, and lower substituent groups; each substituent group, size-limited substituent group, and/or lower substituent group may optionally be different. In embodiments, when $R^3$ is substituted, it is substituted with at least one substituent group. In embodiments, when $R^3$ is substituted, it is substituted with at least one size-limited substituent group. In embodiments, when $R^3$ is substituted, it is substituted with at least one lower substituent group.

In embodiments, $R^{3A}$ is hydrogen. In embodiments, $R^{3A}$ is substituted or unsubstituted $C_1$-$C_{10}$ alkyl. In embodiments, $R^{3A}$ is substituted or unsubstituted 2 to 10 membered heteroalkyl. In embodiments, $R^{3A}$ is substituted or unsubstituted $C_1$-$C_{10}$ thiol-alkyl or substituted or unsubstituted 2 to 10 membered thiol-heteroalkyl. In embodiments, $R^{3A}$ is unsubstituted $C_1$-$C_{10}$ thiol-alkyl or unsubstituted 2 to 10 membered thiol-heteroalkyl.

In embodiments, a substituted $R^{3A}$ (e.g., substituted alkyl and/or substituted heteroalkyl) is substituted with at least one substituent group, size-limited substituent group, or lower substituent group; wherein if the substituted $R^{3A}$ is substituted with a plurality of groups selected from substituent groups, size-limited substituent groups, and lower substituent groups; each substituent group, size-limited substituent group, and/or lower substituent group may optionally be different. In embodiments, when $R^{3A}$ is substituted, it is substituted with at least one substituent group. In embodiments, when $R^{3A}$ is substituted, it is substituted with at least one size-limited substituent group. In embodiments, when $R^{3A}$ is substituted, it is substituted with at least one lower substituent group.

In embodiments, $R^{3A}$ is

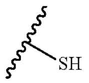,
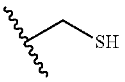,
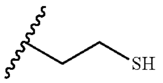,
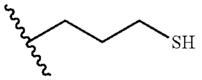,
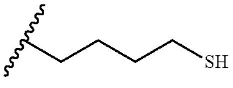, or
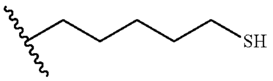.

In embodiments, $R^{3B}$ is hydrogen. In embodiments, $R^{3B}$ is substituted or unsubstituted $C_1$-$C_{10}$ alkyl. In embodiments, $R^{3B}$ is substituted or unsubstituted 2 to 10 membered heteroalkyl. In embodiments, $R^{3B}$ is substituted or unsubstituted $C_1$-$C_{10}$ thiol-alkyl or substituted or unsubstituted 2 to 10 membered thiol-heteroalkyl. In embodiments, $R^{3B}$ is unsubstituted $C_1$-$C_{10}$ thiol-alkyl or unsubstituted 2 to 10 membered thiol-heteroalkyl. In embodiments, $R^{3B}$ is —C(O)-(substituted or unsubstituted $C_1$-$C_{10}$ alkyl). In embodiments, $R^{3B}$ is —C(O)-(substituted or unsubstituted $C_1$-$C_{10}$ thiol-alkyl). In embodiments, $R^{3B}$ is —C(O)-(substituted or unsubstituted 2 to 10 membered thiol-heteroalkyl).

In embodiments, a substituted $R^{3B}$ (e.g., substituted alkyl and/or substituted heteroalkyl) is substituted with at least one substituent group, size-limited substituent group, or lower substituent group; wherein if the substituted $R^{3B}$ is substituted with a plurality of groups selected from substituent groups, size-limited substituent groups, and lower substituent groups; each substituent group, size-limited substituent group, and/or lower substituent group may optionally be different. In embodiments, when $R^{3B}$ is substituted, it is substituted with at least one substituent group. In embodiments, when $R^{3B}$ is substituted, itis substituted with at least one size-limited substituent group. In embodiments, when $R^{3B}$ is substituted, it is substituted with at least one lower substituent group.

In embodiments, $R^{3C}$ is hydrogen. In embodiments, $R^{3C}$ is substituted or unsubstituted $C_1$-$C_{10}$ alkyl. In embodiments, $R^{3C}$ is substituted or unsubstituted 2 to 10 membered heteroalkyl. In embodiments, $R^{3C}$ is substituted or unsubstituted $C_1$-$C_{10}$ thiol-alkyl or substituted or unsubstituted 2 to 10 membered thiol-heteroalkyl. In embodiments, $R^{3C}$ is unsubstituted $C_1$-$C_{10}$ thiol-alkyl or unsubstituted 2 to 10 membered thiol-heteroalkyl.

In embodiments, a substituted $R^{3C}$ (e.g., substituted alkyl and/or substituted heteroalkyl) is substituted with at least one substituent group, size-limited substituent group, or lower substituent group; wherein if the substituted $R^{3C}$ is substituted with a plurality of groups selected from substituent groups, size-limited substituent groups, and lower substituent groups; each substituent group, size-limited substituent group, and/or lower substituent group may optionally be different. In embodiments, when $R^{3C}$ is substituted, it is substituted with at least one substituent group. In embodiments, when $R^{3C}$ is substituted, it is substituted with at least one size-limited substituent group. In embodiments, when $R^{3C}$ is substituted, it is substituted with at least one lower substituent group.

In embodiments, $R^4$ is —$SR^{4A}$. In embodiments, $R^4$ is —$SC(O)R^{4A}$. In embodiments, $R^4$ is —$OR^{4A}$. In embodiments, $R^4$ is —$NR^{4B}R^{4C}$. In embodiments, $R^4$ is —$NR^{4B}C(O)R^{4C}$. In embodiments, $R^4$ is —$NR^{4B}C(O)OR^{4C}$. In embodiments, $R^4$ is —SH. In embodiments, $R^4$ is —$SC(O)CH_3$. In embodiments, $R^4$ is —OH. In embodiments, $R^4$ is —$NH_2$. In embodiments, $R^4$ is —NHC(O)H. In embodiments, $R^4$ is —NHC(O)OH. In embodiments, $R^4$ is substituted or unsubstituted $C_1$-$C_{10}$ alkyl. In embodiments, $R^4$ is unsubstituted $C_1$-$C_5$ alkyl. In embodiments, $R^4$ is unsubstituted methyl. In embodiments, $R^4$ is unsubstituted ethyl. In embodiments, $R^4$ is unsubstituted propyl. In embodiments, $R^4$ is unsubstituted n-propyl. In embodiments, $R^4$ is unsubstituted isopropyl. In embodiments, $R^4$ is unsubstituted butyl. In embodiments, $R^4$ is unsubstituted n-butyl. In embodiments, $R^4$ is unsubstituted tert-butyl. In embodiments, $R^4$ is substituted or unsubstituted 2 to 10 membered heteroalkyl. In embodiments, $R^4$ is substituted or unsubstituted $C_1$-$C_{10}$ thiol-alkyl or substituted or unsubstituted 2 to 10 membered thiol-heteroalkyl. In embodiments, $R^4$ is unsubstituted $C_1$-$C_{10}$ thiol-alkyl or unsubstituted 2 to 10 membered thiol-heteroalkyl. In embodiments, $R^4$ is unsubstituted thiomethyl (e.g., —$CH_2SH$), unsubstituted thioethyl (e.g., —$(CH_2)_2SH$), unsubstituted thiopropyl (e.g., —$(CH_2)_3$ SH), unsubstituted thiobutyl (e.g., —$(CH_2)_4SH$), unsubstituted thiopentyl (e.g., —$(CH_2)_5SH$), unsubstituted thiohexyl (e.g., —$(CH_2)_6SH$), unsubstituted thioheptyl (e.g., —$(CH_2)_7SH$), unsubstituted thiooctyl (e.g., —$(CH_2)_8SH$), unsubstituted thiononyl (e.g., —$(CH_2)_9SH$), or unsubstituted thiodecyl (e.g., —$(CH_2)_{10}SH$). In embodiments, $R^4$ is unsubstituted thioethyl. In embodiments, $R^4$ is unsubstituted thiopropyl. In embodiments, $R^4$ is unsubstituted thiobutyl. In embodiments, $R^4$ is unsubstituted thiopentyl. In embodiments, $R^4$ is unsubstituted alkoxy. In embodiments, $R^4$ is —O-(unsubstituted $C_1$-$C_4$ alkyl). In embodiments, $R^4$ is unsubstituted methoxy. In embodiments, $R^4$ is unsubstituted ethoxy. In embodiments, $R^4$ is unsubstituted propoxy. In embodiments, $R^4$ is unsubstituted n-propoxy. In embodiments, $R^4$ is unsubstituted isopropoxy. In embodiments, $R^4$ is unsubstituted butoxy. In embodiments, $R^4$ is unsubstituted n-butoxy. In embodiments, $R^4$ is unsubstituted tert-butoxy.

In embodiments, a substituted $R^4$ (e.g., substituted alkyl and/or substituted heteroalkyl) is substituted with at least one substituent group, size-limited substituent group, or lower substituent group; wherein if the substituted $R^4$ is substituted with a plurality of groups selected from substituent groups, size-limited substituent groups, and lower substituent groups; each substituent group, size-limited substituent group, and/or lower substituent group may optionally be different. In embodiments, when $R^4$ is substituted, it is substituted with at least one substituent group. In embodiments, when $R^4$ is substituted, it is substituted with at least one size-limited substituent group. In embodiments, when $R^4$ is substituted, it is substituted with at least one lower substituent group.

In embodiments, $R^{4A}$ is hydrogen. In embodiments, $R^{4A}$ is substituted or unsubstituted $C_1$-$C_{10}$ alkyl. In embodiments, $R^{4A}$ is substituted or unsubstituted 2 to 10 membered heteroalkyl. In embodiments, $R^{4A}$ is substituted or unsubstituted $C_1$-$C_{10}$ thiol-alkyl or substituted or unsubstituted 2 to 10 membered thiol-heteroalkyl. In embodiments, $R^{4A}$ is unsubstituted $C_1$-$C_{10}$ thiol-alkyl or unsubstituted 2 to 10 membered thiol-heteroalkyl.

In embodiments, a substituted $R^{4A}$ (e.g., substituted alkyl and/or substituted heteroalkyl) is substituted with at least one substituent group, size-limited substituent group, or lower substituent group; wherein if the substituted $R^{4A}$ is substituted with a plurality of groups selected from substituent groups, size-limited substituent groups, and lower substituent groups; each substituent group, size-limited substituent group, and/or lower substituent group may optionally be different. In embodiments, when $R^{4A}$ is substituted, it is substituted with at least one substituent group. In embodiments, when $R^{4A}$ is substituted, it is substituted with at least one size-limited substituent group. In embodiments, when $R^{4A}$ is substituted, it is substituted with at least one lower substituent group.

In embodiments, $R^{4A}$ is

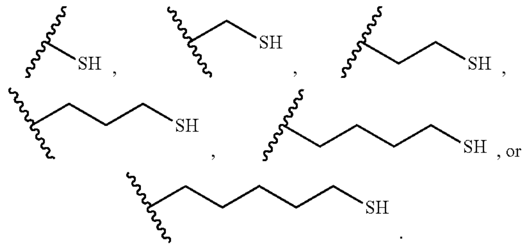

In embodiments, $R^{4B}$ is hydrogen. In embodiments, $R^{4B}$ is substituted or unsubstituted $C_1$-$C_{10}$ alkyl. In embodiments, $R^{4B}$ is substituted or unsubstituted 2 to 10 membered heteroalkyl. In embodiments, $R^{4B}$ is substituted or unsubstituted $C_1$-$C_{10}$ thiol-alkyl or substituted or unsubstituted 2 to 10 membered thiol-heteroalkyl. In embodiments, $R^{4B}$ is unsubstituted $C_1$-$C_{10}$ thiol-alkyl or unsubstituted 2 to 10 membered thiol-heteroalkyl. In embodiments, $R^{4B}$ is —C(O)-(substituted or unsubstituted $C_1$-$C_{10}$ alkyl). In embodiments, $R^{4B}$ is —C(O)-(substituted or unsubstituted $C_1$-$C_{10}$ thiol-alkyl). In embodiments, $R^{4B}$ is —C(O)-(substituted or unsubstituted 2 to 10 membered thiol-heteroalkyl).

In embodiments, a substituted $R^4$ (e.g., substituted alkyl and/or substituted heteroalkyl) is substituted with at least one substituent group, size-limited substituent group, or lower substituent group; wherein if the substituted $R^{4B}$ is substituted with a plurality of groups selected from substituent groups, size-limited substituent groups, and lower substituent groups; each substituent group, size-limited substituent group, and/or lower substituent group may optionally be different. In embodiments, when $R^{4B}$ is substituted, it is substituted with at least one substituent group. In embodiments, when $R^{4B}$ is substituted, it is substituted with at least one size-limited substituent group. In embodiments, when $R^{4B}$ is substituted, it is substituted with at least one lower substituent group.

In embodiments, $R^{4C}$ is hydrogen. In embodiments, $R^{4C}$ is substituted or unsubstituted $C_1$-$C_{10}$ alkyl. In embodiments, $R^{4C}$ is substituted or unsubstituted 2 to 10 membered heteroalkyl. In embodiments, $R^{4C}$ is substituted or unsubstituted $C_1$-$C_{10}$ thiol-alkyl or substituted or unsubstituted 2 to 10 membered thiol-heteroalkyl. In embodiments, $R^{4C}$ is unsubstituted $C_1$-$C_{10}$ thiol-alkyl or unsubstituted 2 to 10 membered thiol-heteroalkyl.

In embodiments, a substituted $R^4$ (e.g., substituted alkyl and/or substituted heteroalkyl) is substituted with at least one substituent group, size-limited substituent group, or lower substituent group; wherein if the substituted $R^4$ is substituted with a plurality of groups selected from substituent groups, size-limited substituent groups, and lower substituent groups; each substituent group, size-limited substituent group, and/or lower substituent group may optionally be different. In embodiments, when $R^4$ is substituted, it is substituted with at least one substituent group. In embodiments, when $R^4$ is substituted, it is substituted with at least one size-limited substituent group. In embodiments, when $R^4$ is substituted, it is substituted with at least one lower substituent group.

In embodiments, $R^5$ is hydrogen. In embodiments, $R^5$ is —$SR^{5A}$. In embodiments, $R^5$ is —$SC(O)R^{5A}$. In embodiments, $R^5$ is —$OR^{5A}$. In embodiments, $R^5$ is —$NR^{5B}R^{5C}$. In embodiments, $R^5$ is —$NR^{5B}C(O)R^{5C}$. In embodiments, $R^5$ is —$NR^{5B}C(O)OR^{5C}$. In embodiments, $R^5$ is —SH. In embodiments, $R^5$ is —$SC(O)CH_3$. In embodiments, $R^5$ is —OH. In embodiments, $R^5$ is —$NH_2$. In embodiments, $R^5$ is —NHC(O)H. In embodiments, $R^5$ is —NHC(O)OH. In embodiments, $R^5$ is substituted or unsubstituted $C_1$-$C_{10}$ alkyl. In embodiments, $R^5$ is unsubstituted $C_1$-$C_5$ alkyl. In embodiments, $R^5$ is unsubstituted methyl. In embodiments, $R^5$ is unsubstituted ethyl. In embodiments, $R^5$ is unsubstituted propyl. In embodiments, $R^5$ is unsubstituted n-propyl. In embodiments, $R^5$ is unsubstituted isopropyl. In embodiments, $R^5$ is unsubstituted butyl. In embodiments, $R^5$ is unsubstituted n-butyl. In embodiments, $R^5$ is unsubstituted tert-butyl. In embodiments, $R^5$ is substituted or unsubstituted 2 to 10 membered heteroalkyl. In embodiments, $R^5$ is substituted or unsubstituted $C_1$-$C_{10}$ thiol-alkyl or substituted or unsubstituted 2 to 10 membered thiol-heteroalkyl. In embodiments, $R^5$ is unsubstituted $C_1$-$C_{10}$ thiol-alkyl or unsubstituted 2 to 10 membered thiol-heteroalkyl. In embodiments, $R^5$ is unsubstituted thiomethyl (e.g., —$CH_2SH$), unsubstituted thioethyl (e.g., —$(CH_2)_2SH$), unsubstituted thiopropyl (e.g., —$(CH_2)_3SH$), unsubstituted thiobutyl (e.g., —$(CH_2)_4SH$), unsubstituted thiopentyl (e.g., —$(CH_2)_5SH$), unsubstituted thiohexyl (e.g., —$(CH_2)_6SH$), unsubstituted thioheptyl (e.g., —$(CH_2)_7SH$), unsubstituted thiooctyl (e.g., —$(CH_2)_8SH$), unsubstituted thiononyl (e.g., —$(CH_2)_9SH$), or unsubstituted thiodecyl (e.g., —$(CH_2)_{10}SH$). In embodiments, $R^5$ is unsubstituted thioethyl. In embodiments, $R^5$ is unsubstituted thiopropyl. In embodiments, $R^5$ is unsubstituted thiobutyl. In embodiments, $R^5$ is unsubstituted thiopentyl. In embodiments, $R^5$ is unsubstituted alkoxy. In embodiments, $R^5$ is —O-(unsubstituted $C_1$-$C_4$ alkyl). In embodiments, $R^5$ is unsubstituted methoxy. In embodiments, $R^5$ is unsubstituted ethoxy. In embodiments, $R^5$ is unsubstituted propoxy. In embodiments, $R^5$ is unsubstituted n-propoxy. In embodiments, $R^5$ is unsubstituted isopropoxy. In embodiments, $R^5$ is unsubstituted butoxy. In embodiments, $R^5$ is unsubstituted n-butoxy. In embodiments, $R^5$ is unsubstituted tert-butoxy.

In embodiments, a substituted $R^5$ (e.g., substituted alkyl and/or substituted heteroalkyl) is substituted with at least one substituent group, size-limited substituent group, or lower substituent group; wherein if the substituted $R^1$ is substituted with a plurality of groups selected from substituent groups, size-limited substituent groups, and lower substituent groups; each substituent group, size-limited substituent group, and/or lower substituent group may optionally be different. In embodiments, when $R^5$ is substituted, it is substituted with at least one substituent group. In embodiments, when $R^5$ is substituted, it is substituted with at least one size-limited substituent group. In embodiments, when $R^5$ is substituted, it is substituted with at least one lower substituent group.

In embodiments, $R^{5A}$ is hydrogen. In embodiments, $R^{5A}$ is substituted or unsubstituted $C_1$-$C_{10}$ alkyl. In embodiments, $R^{5A}$ is unsubstituted $C_1$-$C_{10}$ alkyl. In embodiments, $R^{5A}$ is unsubstituted methyl. In embodiments, $R^{5A}$ is unsubstituted ethyl. In embodiments, $R^{5A}$ is unsubstituted propyl. In embodiments, $R^{5A}$ is unsubstituted n-propyl. In embodiments, $R^{5A}$ is unsubstituted isopropyl. In embodiments, $R^{5A}$ is unsubstituted butyl. In embodiments, $R^{5A}$ is unsubstituted n-butyl. In embodiments, $R^{5A}$ is unsubstituted tert-butyl. In embodiments, $R^{5A}$ is substituted or unsubstituted 2 to 10 membered heteroalkyl. In embodiments, $R^{5A}$ is substituted or unsubstituted $C_1$-$C_{10}$ thiol-alkyl or substituted or unsubstituted 2 to 10 membered thiol-heteroalkyl. In embodiments, $R^{5A}$ is unsubstituted $C_1$-$C_{10}$ thiol-alkyl or unsubstituted 2 to 10 membered thiol-heteroalkyl. In embodiments, $R^{5A}$ is unsubstituted thiomethyl (e.g., —$CH_2SH$), unsubstituted thioethyl (e.g., —$(CH_2)_2SH$), unsubstituted thiopropyl (e.g., —$(CH_2)_3SH$), unsubstituted thiobutyl (e.g., —$(CH_2)_4SH$), unsubstituted thiopentyl (e.g., —$(CH_2)_5SH$), unsubstituted thiohexyl (e.g., —$(CH_2)_6SH$), unsubstituted thioheptyl (e.g., —$(CH_2)_7SH$), unsubstituted thiooctyl (e.g., —$(CH_2)_8SH$), unsubstituted thiononyl (e.g., —$(CH_2)_9SH$), or unsubstituted thiodecyl (e.g., —$(CH_2)_{10}SH$). In embodiments, $R^{5A}$ is unsubstituted thioethyl. In embodiments, $R^{5A}$ is unsubstituted thiopropyl. In embodiments, $R^{5A}$ is unsubstituted thiobutyl. In embodiments, $R^{5A}$ is unsubstituted thiopentyl.

In embodiments, a substituted $R^{5A}$ (e.g., substituted alkyl and/or substituted heteroalkyl) is substituted with at least one substituent group, size-limited substituent group, or lower substituent group; wherein if the substituted $R^{5A}$ is substituted with a plurality of groups selected from substituent groups, size-limited substituent groups, and lower substituent groups; each substituent group, size-limited substituent group, and/or lower substituent group may optionally be different. In embodiments, when $R^{5A}$ is substituted, it is substituted with at least one substituent group. In embodiments, when $R^{5A}$ is substituted, it is substituted with at least one size-limited substituent group. In embodiments, when $R^{5A}$ is substituted, it is substituted with at least one lower substituent group.

In embodiments, $R^{5A}$ is

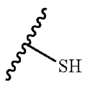 , 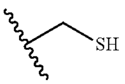 , 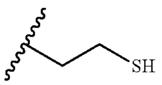 ,

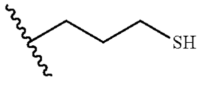 , 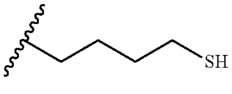 , or

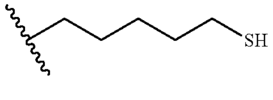 .

In embodiments, $R^{5B}$ is hydrogen. In embodiments, $R^{5B}$ is substituted or unsubstituted $C_1$-$C_{10}$ alkyl. In embodiments, $R^{5B}$ is substituted or unsubstituted 2 to 10 membered heteroalkyl. In embodiments, $R^{5B}$ is substituted or unsubstituted $C_1$-$C_{10}$ thiol-alkyl or substituted or unsubstituted 2 to 10 membered thiol-heteroalkyl. In embodiments, $R^{5B}$ is unsubstituted $C_1$-$C_{10}$ thiol-alkyl or unsubstituted 2 to 10 membered thiol-heteroalkyl. In embodiments, $R^{5B}$ is —C(O)-(substituted or unsubstituted $C_1$-$C_{10}$ alkyl). In embodiments, $R^{5B}$ is —C(O)-(substituted or unsubstituted $C_1$-$C_{10}$ thiol-alkyl). In embodiments, $R^{B}$ is —C(O)-(substituted or unsubstituted 2 to 10 membered thiol-heteroalkyl).

In embodiments, a substituted $R^{5B}$ (e.g., substituted alkyl and/or substituted heteroalkyl) is substituted with at least one substituent group, size-limited substituent group, or lower substituent group; wherein if the substituted $R^{5B}$ is substituted with a plurality of groups selected from substituent groups, size-limited substituent groups, and lower substituent groups; each substituent group, size-limited substituent group, and/or lower substituent group may optionally be different. In embodiments, when $R^{5B}$ is substituted, it is substituted with at least one substituent group. In embodiments, when $R^{5B}$ is substituted, it is substituted with at least one size-limited substituent group. In embodiments, when $R^{5B}$ is substituted, it is substituted with at least one lower substituent group.

In embodiments, $R^{5C}$ is hydrogen. In embodiments, $R^{5C}$ is substituted or unsubstituted $C_1$-$C_{10}$ alkyl. In embodiments, $R^{5C}$ is substituted or unsubstituted 2 to 10 membered heteroalkyl. In embodiments, $R^{5C}$ is substituted or unsubstituted $C_1$-$C_{10}$ thiol-alkyl or substituted or unsubstituted 2 to 10 membered thiol-heteroalkyl. In embodiments, $R^{5C}$ is unsubstituted $C_1$-$C_{10}$ thiol-alkyl or unsubstituted 2 to 10 membered thiol-heteroalkyl.

In embodiments, a substituted $R^{5C}$ (e.g., substituted alkyl and/or substituted heteroalkyl) is substituted with at least one substituent group, size-limited substituent group, or lower substituent group; wherein if the substituted $R^{5C}$ is substituted with a plurality of groups selected from substituent groups, size-limited substituent groups, and lower substituent groups; each substituent group, size-limited substituent group, and/or lower substituent group may optionally be different. In embodiments, when $R^{5C}$ is substituted, it is substituted with at least one substituent group. In embodiments, when $R^{5C}$ is substituted, it is substituted with at least one size-limited substituent group. In embodiments, when $R^{5C}$ is substituted, it is substituted with at least one lower substituent group.

In embodiments, $R^6$ is hydrogen. In embodiments, $R^6$ is —$SR^{6A}$. In embodiments, $R^6$ is —$OR^{6A}$. In embodiments, $R^6$ is —$NR^{6B}R^{6C}$. In embodiments, $R^6$ is —$NR^{6B}C(O)R^{6C}$. In embodiments, $R^6$ is —$NR^{6B}C(O)OR^{6C}$. In embodiments, $R^6$ is —SH. In embodiments, $R^6$ is —OH. In embodiments, $R^6$ is —$NH_2$. In embodiments, $R^6$ is —NHC(O)H. In embodiments, $R^6$ is —NHC(O)OH. In embodiments, $R^6$ is substituted or unsubstituted $C_1$-$C_{10}$ alkyl. In embodiments, $R^6$ is unsubstituted $C_1$-$C_5$ alkyl. In embodiments, $R^6$ is unsubstituted methyl. In embodiments, $R^6$ is unsubstituted ethyl. In embodiments, $R^6$ is unsubstituted propyl. In embodiments, $R^6$ is unsubstituted n-propyl. In embodiments, $R^6$ is unsubstituted isopropyl. In embodiments, $R^6$ is unsubstituted butyl. In embodiments, $R^6$ is unsubstituted n-butyl. In embodiments, $R^6$ is unsubstituted tert-butyl. In embodiments, $R^6$ is substituted or unsubstituted 2 to 10 membered heteroalkyl. In embodiments, $R^6$ is substituted or unsubstituted $C_1$-$C_{10}$ thiol-alkyl or substituted or unsubstituted 2 to 10 membered thiol-heteroalkyl. In embodiments, $R^6$ is unsubstituted $C_1$-$C_{10}$ thiol-alkyl or unsubstituted 2 to 10 membered thiol-heteroalkyl. In embodiments, $R^6$ is unsubstituted thiomethyl (e.g., —$CH_2SH$), unsubstituted thioethyl (e.g., —$(CH_2)_2SH$), unsubstituted thiopropyl (e.g., —$(CH_2)_3SH$), unsubstituted thiobutyl (e.g., —$(CH_2)_4SH$), unsubstituted thiopentyl (e.g., —$(CH_2)_5SH$), unsubstituted thiohexyl (e.g., —$(CH_2)_6SH$), unsubstituted thioheptyl (e.g., —$(CH_2)_7SH$), unsubstituted thiooctyl (e.g., —$(CH_2)_8SH$), unsubstituted thiononyl (e.g., —$(CH_2)_9SH$), or unsubstituted thiodecyl (e.g., —$(CH_2)_{10}SH$). In embodiments, $R^6$ is unsubstituted thioethyl. In embodiments, $R^6$ is unsubstituted thiopropyl. In embodiments, $R^6$ is unsubstituted thiobutyl. In embodiments, $R^6$ is unsubstituted thiopentyl. In embodiments, $R^6$ is unsubstituted alkoxy. In embodiments, $R^6$ is —O-(unsubstituted $C_1$-$C_4$ alkyl). In embodiments, $R^6$ is unsubstituted methoxy. In embodiments, $R^6$ is unsubstituted ethoxy. In embodiments, $R^6$ is unsubstituted propoxy. In embodiments, $R^6$ is unsubstituted n-propoxy. In embodiments, $R^6$ is unsubstituted isopropoxy. In embodiments, $R^6$ is unsubstituted butoxy. In embodiments, $R^6$ is unsubstituted n-butoxy. In embodiments, $R^6$ is unsubstituted tert-butoxy.

In embodiments, a substituted $R^6$ (e.g., substituted alkyl and/or substituted heteroalkyl) is substituted with at least one substituent group, size-limited substituent group, or lower substituent group; wherein if the substituted $R^6$ is substituted with a plurality of groups selected from substituent groups, size-limited substituent groups, and lower substituent groups; each substituent group, size-limited substituent group, and/or lower substituent group may optionally be different. In embodiments, when $R^6$ is substituted, it is substituted with at least one substituent group. In embodiments, when $R^6$ is substituted, it is substituted with at least one size-limited substituent group. In embodiments, when $R^6$ is substituted, it is substituted with at least one lower substituent group.

In embodiments, $R^{6A}$ is hydrogen. In embodiments, $R^{6A}$ is substituted or unsubstituted $C_1$-$C_{10}$ alkyl. In embodiments, $R^{6A}$ is unsubstituted $C_1$-$C_{10}$ alkyl. IIn embodiments, $R^{6A}$ is unsubstituted methyl. In embodiments, $R^{6A}$ is unsubstituted ethyl. In embodiments, $R^{6A}$ is unsubstituted propyl. In embodiments, $R^{6A}$ is unsubstituted n-propyl. In embodiments, $R^{6A}$ is unsubstituted isopropyl. In embodiments, $R^{6A}$ is unsubstituted butyl. In embodiments, $R^{6A}$ is unsubstituted n-butyl. In embodiments, $R^{6A}$ is unsubstituted tert-butyl. In embodiments, $R^{6A}$ is substituted or unsubstituted 2 to 10 membered heteroalkyl. In embodiments, $R^{6A}$ is substituted or unsubstituted $C_1$-$C_{10}$ thiol-alkyl or substituted or unsubstituted 2 to 10 membered thiol-heteroalkyl. In embodiments, $R^{6A}$ is unsubstituted $C_1$-$C_{10}$ thiol-alkyl or unsubstituted 2 to 10 membered thiol-heteroalkyl. In embodiments, $R^{6A}$ is unsubstituted thiomethyl (e.g., —$CH_2SH$), unsubstituted thioethyl (e.g., —$(CH_2)_2SH$), unsubstituted thiopropyl (e.g., —$(CH_2)_3SH$), unsubstituted thiobutyl (e.g., —$(CH_2)_4$ SH), unsubstituted thiopentyl (e.g., —$(CH_2)_5SH$), unsubstituted thiohexyl (e.g., —$(CH_2)_6SH$), unsubstituted thioheptyl (e.g., —$(CH_2)_7SH$), unsubstituted thiooctyl (e.g., —$(CH_2)_8$ SH), unsubstituted thiononyl (e.g., —$(CH_2)_9SH$), or unsubstituted thiodecyl (e.g., —$(CH_2)_{10}SH$). In embodiments, $R^{6A}$ is unsubstituted thioethyl. In embodiments, $R^{6A}$ is unsubstituted thiopropyl. In embodiments, $R^{6A}$ is unsubstituted thiobutyl. In embodiments, $R^{6A}$ is unsubstituted thiopentyl.

In embodiments, a substituted $R^{6A}$(e.g., substituted alkyl and/or substituted heteroalkyl) is substituted with at least one substituent group, size-limited substituent group, or lower substituent group; wherein if the substituted $R^{6A}$ is substituted with a plurality of groups selected from substituent groups, size-limited substituent groups, and lower substituent groups; each substituent group, size-limited substituent group, and/or lower substituent group may optionally be different. In embodiments, when $R^{6A}$ is substituted, it is substituted with at least one substituent group. In embodiments, when $R^{6A}$ is substituted, it is substituted with at least one size-limited substituent group. In embodiments, when $R^{6A}$ is substituted, it is substituted with at least one lower substituent group.

In embodiments, $R^{6A}$ is

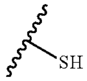 , 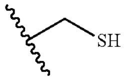 , 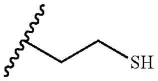 , 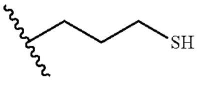 , 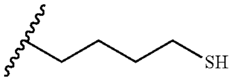 , or 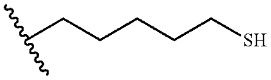 .

In embodiments, $R^{6B}$ is hydrogen. In embodiments, $R^{6B}$ is substituted or unsubstituted $C_1$-$C_{10}$ alkyl. In embodiments, $R^{6B}$ is substituted or unsubstituted 2 to 10 membered heteroalkyl. In embodiments, $R^{6B}$ is substituted or unsubstituted $C_1$-$C_{10}$ thiol-alkyl or substituted or unsubstituted 2 to 10 membered thiol-heteroalkyl. In embodiments, $R^{6B}$ is unsubstituted $C_1$-$C_{10}$ thiol-alkyl or unsubstituted 2 to 10 membered thiol-heteroalkyl. In embodiments, $R^{6B}$ is —C(O)-(substituted or unsubstituted $C_1$-$C_{10}$ alkyl). In embodiments, $R^{6B}$ is —C(O)-(substituted or unsubstituted $C_1$-$C_{10}$ thiol-alkyl). In embodiments, $R^{6B}$ is —C(O)-(substituted or unsubstituted 2 to 10 membered thiol-heteroalkyl).

In embodiments, a substituted $R^{6B}$ (e.g., substituted alkyl and/or substituted heteroalkyl) is substituted with at least one substituent group, size-limited substituent group, or lower substituent group; wherein if the substituted $R^6$ is substituted with a plurality of groups selected from substituent groups, size-limited substituent groups, and lower substituent groups; each substituent group, size-limited substituent group, and/or lower substituent group may optionally be different. In embodiments, when $R^{6B}$ is substituted, it is substituted with at least one substituent group. In embodiments, when $R^{6B}$ is substituted, it is substituted with at least one size-limited substituent group. In embodiments, when $R^{6B}$ is substituted, it is substituted with at least one lower substituent group.

In embodiments, $R^{6C}$ is hydrogen. In embodiments, $R^{6C}$ is substituted or unsubstituted $C_1$-$C_{10}$ alkyl. In embodiments, $R^C$ is substituted or unsubstituted 2 to 10 membered heteroalkyl. In embodiments, $R^{6C}$ is substituted or unsubstituted $C_1$-$C_{10}$ thiol-alkyl or substituted or unsubstituted 2 to 10 membered thiol-heteroalkyl. In embodiments, $R^{6C}$ is unsubstituted $C_1$-$C_{10}$ thiol-alkyl or unsubstituted 2 to 10 membered thiol-heteroalkyl.

In embodiments, a substituted $R^{6C}$ (e.g., substituted alkyl and/or substituted heteroalkyl) is substituted with at least one substituent group, size-limited substituent group, or lower substituent group; wherein if the substituted $R^{6C}$ is substituted with a plurality of groups selected from substituent groups, size-limited substituent groups, and lower substituent groups; each substituent group, size-limited substituent group, and/or lower substituent group may optionally be different. In embodiments, when $R^{6C}$ is substituted, it is substituted with at least one substituent group. In embodiments, when $R^{6C}$ is substituted, it is substituted with at least one size-limited substituent group. In embodiments, when $R^{6C}$ is substituted, it is substituted with at least one lower substituent group.

In embodiments, the thiosaccharide compound has the formula:

(I-1)

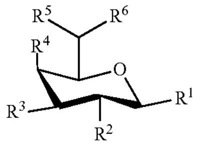 .

$R^1$, $R^2$, $R^3$, $R^4$, $R^5$, and $R^6$ are as described herein, including in embodiments.

In embodiments, the thiosaccharide compound has the formula:

(I-2)

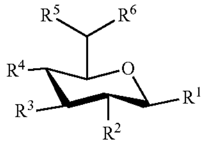 .

$R^1$, $R^2$, $R^3$, $R^4$, $R^5$, and $R^6$ are as described herein, including in embodiments.

In embodiments, the thiosaccharide compound has the formula:

(I-3)

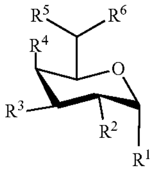 .

$R^1$, $R^2$, $R^3$, $R^4$, $R^5$, and $R^6$ are as described herein, including in embodiments.

In embodiments, the thiosaccharide compound has the formula:

(I-4)

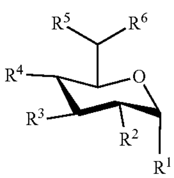 .

$R^1$, $R^2$, $R^3$, $R^4$, $R^5$, and $R^6$ are as described herein, including in embodiments.

In embodiments, $R^2$ is —$SR^{2A}$, —$OR^{2A}$, substituted or unsubstituted $C_1$-$C_{10}$ alkyl, or substituted or unsubstituted 2 to 10 membered heteroalkyl; $R^3$ is —$SR^{3A}$, —$OR^{3A}$, substituted or unsubstituted $C_1$-$C_{10}$ alkyl, or substituted or unsubstituted 2 to 10 membered heteroalkyl; $R^4$ is —$SR^{4A}$, —$OR^{4A}$, substituted or unsubstituted $C_1$-$C_{10}$ alkyl, or substituted or unsubstituted 2 to 10 membered heteroalkyl; $R^5$ is hydrogen, —$SR^{5A}$, —$OR^{5A}$, substituted or unsubstituted $C_1$-$C_{10}$ alkyl, or substituted or unsubstituted 2 to 10 membered heteroalkyl; and $R^6$ is —$SR^{6A}$, —$OR^{6A}$, substituted or unsubstituted $C_1$-$C_{10}$ alkyl, or substituted or unsubstituted 2 to 10 membered heteroalkyl.

In embodiments, $R^2$ is —$SR^{2A}$, —$OR^{2A}$, substituted or unsubstituted $C_1$-$C_{10}$ thiol-alkyl, or substituted or unsubstituted 2 to 10 membered thiol-heteroalkyl; $R^3$ is —$SR^{3A}$, —$OR^{3A}$, substituted or unsubstituted $C_1$-$C_{10}$ thiol-alkyl, or substituted or unsubstituted 2 to 10 membered thiol-heteroalkyl; $R^4$ is —$SR^4$, —$OR^{4A}$, substituted or unsubstituted $C_1$-$C_{10}$ thiol-alkyl, or substituted or unsubstituted 2 to 10 membered thiol-heteroalkyl; $R^5$ is hydrogen, —$SR^{5A}$, —$OR^{5A}$, substituted or unsubstituted $C_1$-$C_{10}$ thiol-alkyl, or substituted or unsubstituted 2 to 10 membered thiol-heteroalkyl; and $R^6$ is —$SR^{6A}$, —$OR^{6A}$, substituted or unsubstituted $C_1$-$C_{10}$ thiol-alkyl, or substituted or unsubstituted 2 to 10 membered thiol-heteroalkyl.

In embodiments, $R^2$ is —$SR^{2A}$ or —$OR^{2A}$; $R^3$ is —$SR^{3A}$ or —$OR^{3A}$; $R^4$ is —$SR^{4A}$ or —$OR^{4A}$; and $R^6$ is —$SR^{6A}$ or —$OR^{6A}$. In embodiments, $R^2$ is —SH or —OH; $R^3$ is —SH or —OH; $R^4$ is —SH or —OH; and $R^6$ is —SH or —OH.

In embodiments, $R^1$, $R^3$, $R^4$, and $R^5$ are independently —OH, and $R^6$ is hydrogen. In embodiments, the thiosaccharide compound has the formula:

(Ia)

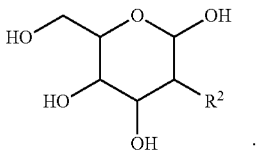

$R^2$ is as described herein, including in embodiments.

In embodiments, the thiosaccharide compound has the formula:

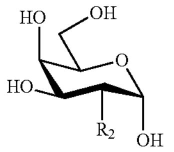

or

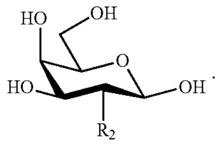

$R^2$ is as described herein, including in embodiments.

In embodiments, $R^2$ is —N(H)—C(O)—CH(NHC(O)$CH_3$)—$CH_{2A}$—SH.

In embodiments, $R^2$, $R^3$, $R^4$ are independently —OH. In embodiments, the thiosaccharide compound has the formula:

(Ib)

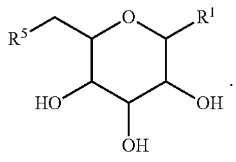

$R^1$ and $R^5$ are as described herein, including in embodiments.

In embodiments, the thiosaccharide compound has the formula:

(Ib′)

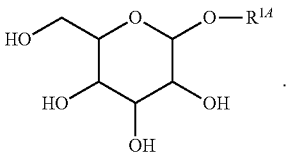

$R^{1A}$ is as described herein, including in embodiments.

In embodiments, the thiosaccharide compound has the formula:

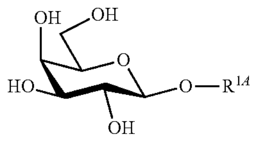

or

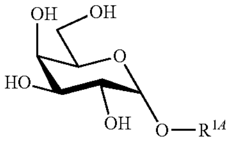

$R^{1A}$ is as described herein, including in embodiments.

In embodiments, the thiosaccharide compound has the formula:

(Ib″)

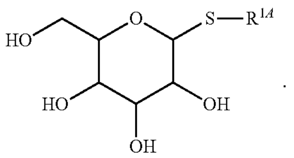

$R^{1A}$ is as described herein, including in embodiments.

In embodiments, the thiosaccharide compound has the formula:

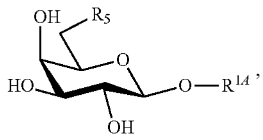

,

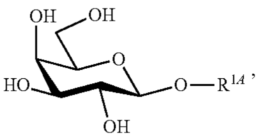

,

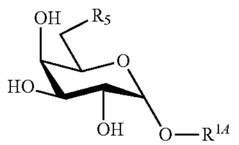

, or

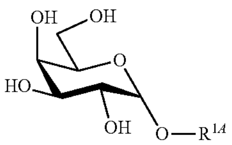

In embodiments, $R^{1A}$ is substituted or unsubstituted $C_1$-$C_{10}$ thiol-alkenyl, or substituted or unsubstituted $C_1$-$C_{10}$ thiol-alkynyl. In embodiments, $R^{1A}$ is unsubstituted $C_1$-$C_{10}$ thiol-alkenyl, or unsubstituted $C_1$-$C_{10}$ thiol-alkynyl.

In embodiments, the thiosaccharide compound has the formula:

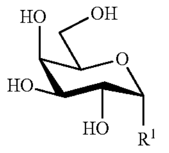
or
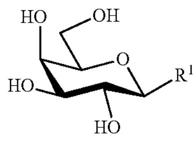

$R^1$ is as described herein, including in embodiments.

In embodiments, the thiosaccharide compound has the formula:

(Ic)
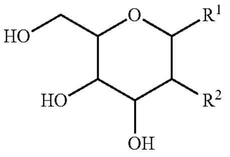

$R^1$ and $R^2$ are as described herein, including in embodiments.

In embodiments, the thiosaccharide compound has the formula:

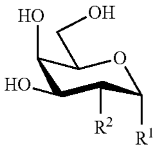
or
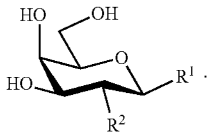

$R^1$ and $R^2$ are as described herein, including in embodiments.

In embodiments, the thiosaccharide compound has the formula:

(Id)
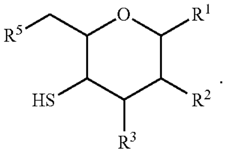

$R^1$, $R^2$, $R^3$, and $R^5$ are as described herein, including in embodiments.

In embodiments, the thiosaccharide compound has the formula:

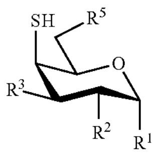
or
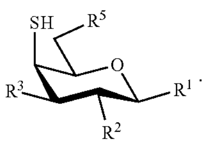

$R^1$, $R^2$, $R^3$, and $R^5$ are as described herein, including in embodiments.

In embodiments, the thiosaccharide compound has the formula:

(Ie)
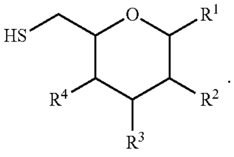

$R^1$, $R^2$, $R^3$, and $R^4$ are as described herein, including in embodiments.

In embodiments, the thiosaccharide compound has the formula:

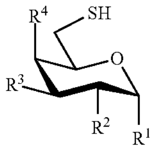
or
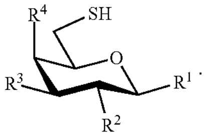

$R^1$, $R^2$, $R^3$, and $R^4$ are as described herein, including in embodiments.

In embodiments, the thiosaccharide compound has the formula:

(Ie')
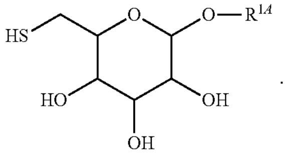

$R^{1A}$ is as described herein, including in embodiments.

In embodiments, the thiosaccharide compound has the formula:

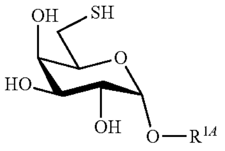
or
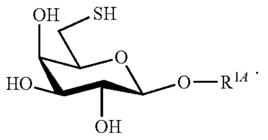

$R^{1A}$ is as described herein, including in embodiments.

In embodiments, the thiosaccharide compound has the formula:

(If)
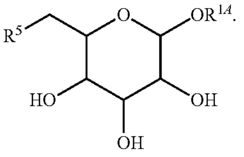

$R^{1A}$ and $R^5$ are as described herein, including in embodiments.

In embodiments, the thiosaccharide compound has the formula:

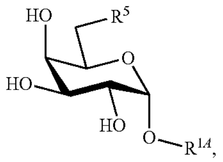
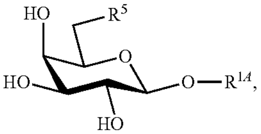
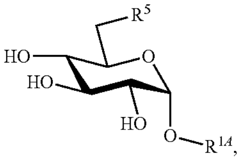
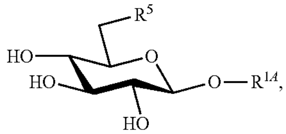
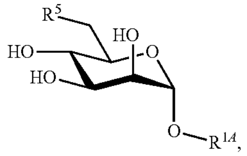
or
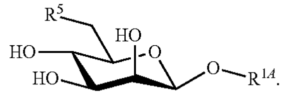

$R^5$ are as described herein, including in embodiments.

In embodiments, the thiosaccharide compound has the formula:

(Ig)

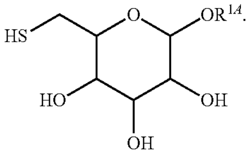

$R^{1A}$ is as described herein, including in embodiments.

In embodiments, the thiosaccharide compound has the formula:

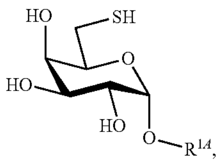
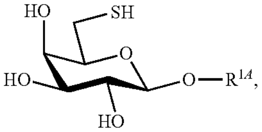

-continued

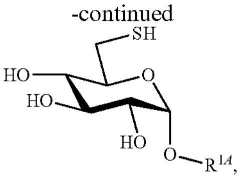
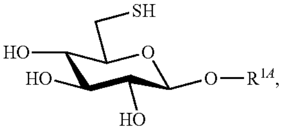
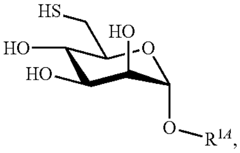
or
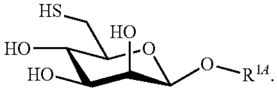

$R^{1A}$ is as described herein, including in embodiments.

In embodiments, the thiosaccharide compound has the formula:

(Ih)

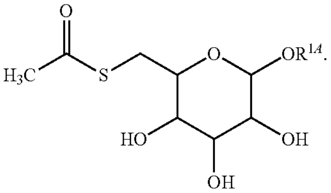

$R^{1A}$ is as described herein, including in embodiments.

In embodiments, the thiosaccharide compound has the formula:

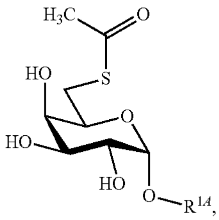
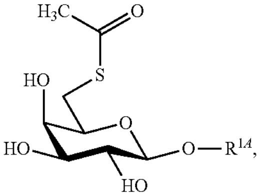
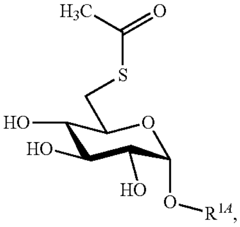

-continued

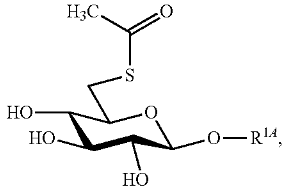

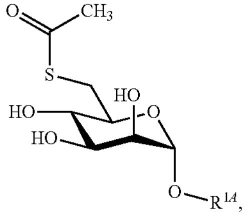

or

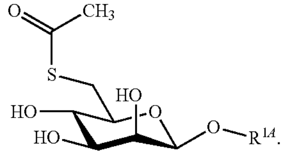

$R^{1A}$ is as described herein, including in embodiments.

In embodiments, the thiosaccharide compound has the formula:

(Ii)

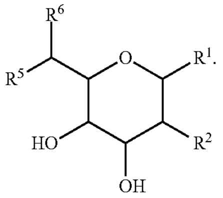

$R^1$, $R^2$, $R^5$, and $R^6$ are as described herein, including in embodiments.

In embodiments, the thiosaccharide compound has the formula:

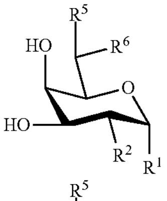

,

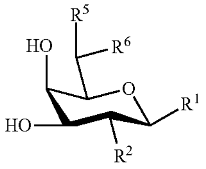

,

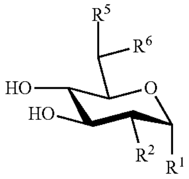

,

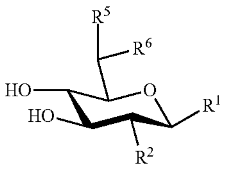

,

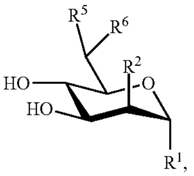

or

-continued

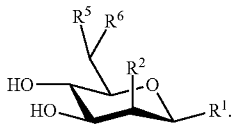

$R^1$, $R^2$, $R^5$, and $R^6$ are as described herein, including in embodiments.

In embodiments, the thiosaccharide compound has the formula:

(II)

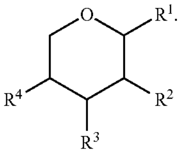

$R^1$, $R^2$, $R^3$, and R are as described herein, including in embodiments.

In embodiments, the thiosaccharide compound has the formula:

(IIa)

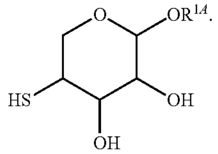

$R^{1A}$ is as described herein, including in embodiments.

In embodiments, the thiosaccharide compound has the formula:

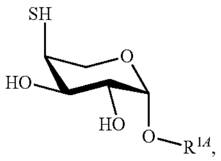

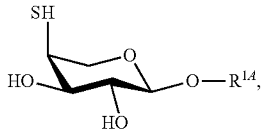

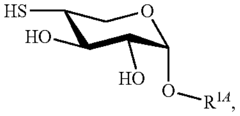

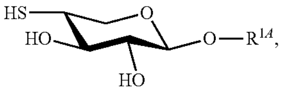

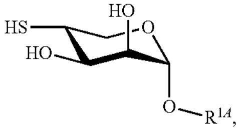

or

-continued

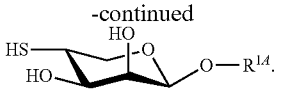

$R^{1A}$ is as described herein, including in embodiments.

In embodiments, the thiosaccharide compound has the formula:

(IIb)

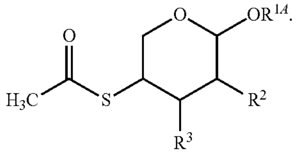

$R^{1A}$, $R^2$, and $R^3$ are as described herein, including in embodiments.

In embodiments, the thiosaccharide compound has the formula:

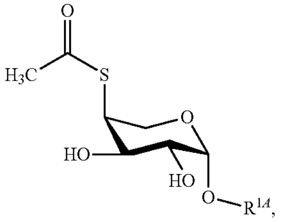

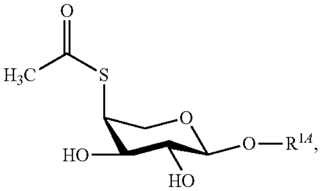

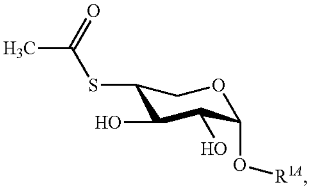

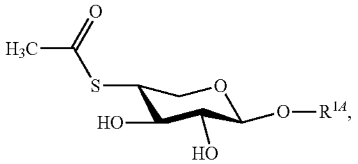

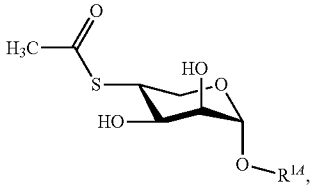

or

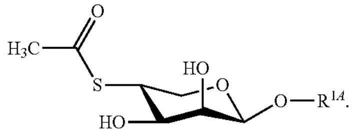

$R^{1A}$ is as described herein, including in embodiments.

In embodiments, the thiosaccharide compound has the formula.

(III)

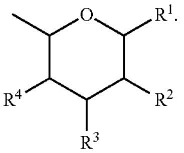

$R^1$, $R^2$, $R^3$, and $R^4$ are as described herein, including in embodiments.

In embodiments, the thiosaccharide compound has the formula:

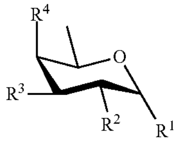

,

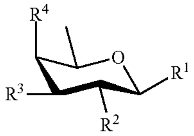

,

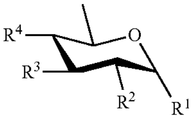

,

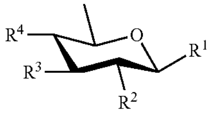

,

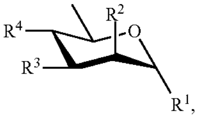

or

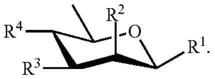

$R^1$, $R^2$, $R^3$, and $R^4$ areas described herein, including in embodiments.

In embodiments, the thiosaccharide compound has the formula:

(VIIa)

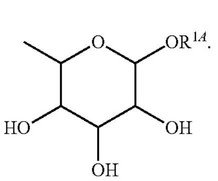

$R^{1A}$ is as described herein, including in embodiments.

In embodiments, the thiosaccharide compound has the formula:

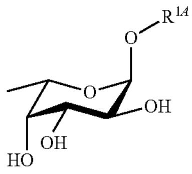

or

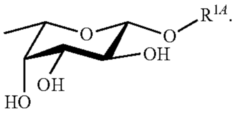

$R^{1A}$ is as described herein, including in embodiments.

In embodiments, the thiosaccharide compound has the formula:

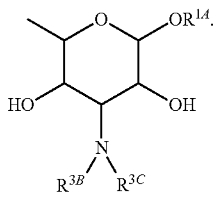

$R^{1A}$, $R^{3B}$, and $R^{3C}$ are as described herein, including in embodiments.

In embodiments, the thiosaccharide compound has the formula:

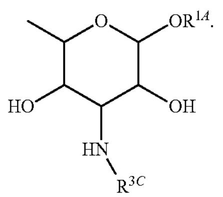

$R^{1A}$ and $R^{3C}$ are as described herein, including in embodiments.

In embodiments, the thiosaccharide compound has the formula:

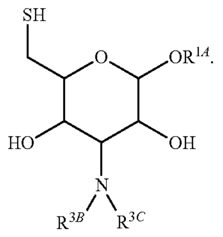

$R^{1A}$, $R^{3B}$, and $R^{3C}$ are as described herein, including in embodiments.

In embodiments, the thiosaccharide compound has the formula:

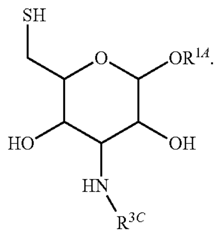

$R^{1A}$ and $R^{3C}$ are as described herein, including in embodiments.

In embodiments, the thiosaccharide compound has the formula:

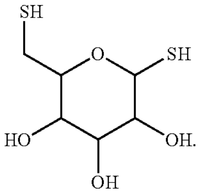 [SMILES: OC1C(S)OC(CS)C(O)C1O]

In embodiments, the thiosaccharide compound has the formula:

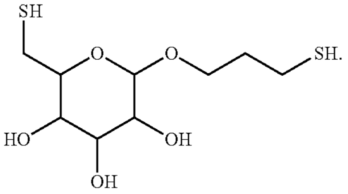

In embodiments, the thiosaccharide compound has the formula:

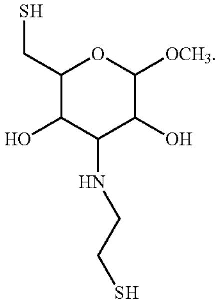 [SMILES: COC1OC(CS)C(O)C(NCCS)C1O]

In embodiments, the thiosaccharide compound has the formula:

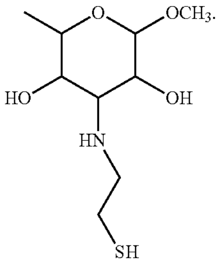

In embodiments, the thiosaccharide compound has the formula:

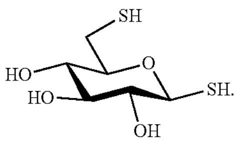

In embodiments, the thiosaccharide compound has the formula:

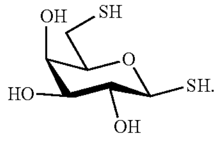

In embodiments, the thiosaccharide compound has the formula:

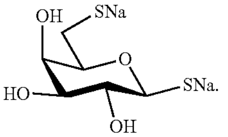

A person having skill in the art will recognize that this salt form is within the scope of formula I and embodiments thereof. In embodiments, the thiosaccharide compound has the formula:

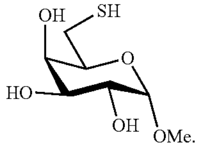

In embodiments, the thiosaccharide compound has the formula:

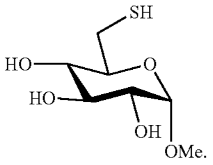

In embodiments, the thiosaccharide compound has the formula:

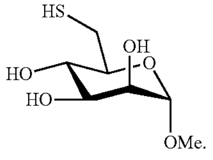

In embodiments, the thiosaccharide compound has the formula:

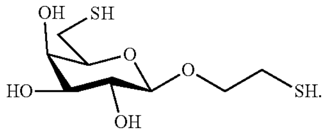

In embodiments, the thiosaccharide compound has the formula:

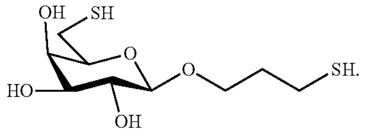

In embodiments, the thiosaccharide compound has the formula:

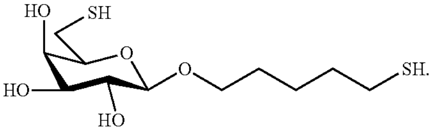

In embodiments, the thiosaccharide compound has the formula:

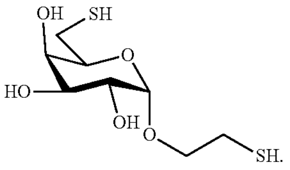

In embodiments, the thiosaccharide compound has the formula:

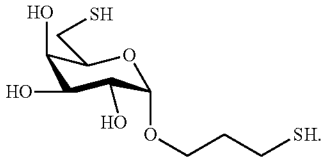

In embodiments, the thiosaccharide compound has the formula:

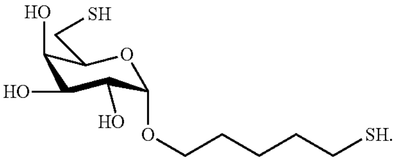

In embodiments, the thiosaccharide compound has the formula:

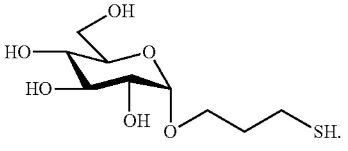

In embodiments, the thiosaccharide compound has the formula:

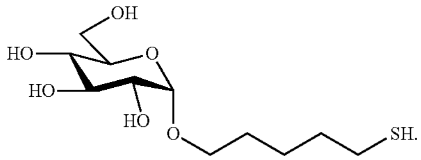

In embodiments, the thiosaccharide compound has the formula:

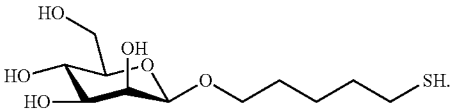

In embodiments, the thiosaccharide compound has the formula:

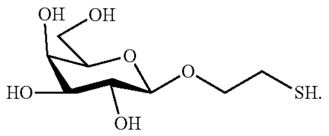

In embodiments, the thiosaccharide compound has the formula:

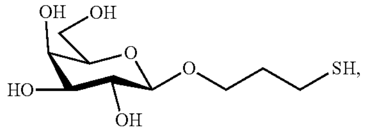

In embodiments, the thiosaccharide compound has the formula:

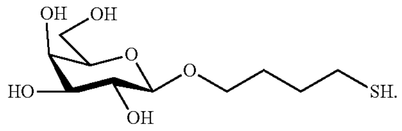

In embodiments, the thiosaccharide compound has the formula:

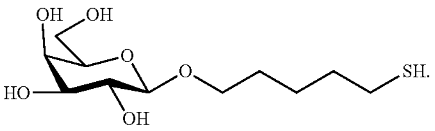

In embodiments, the thiosaccharide compound has the formula:

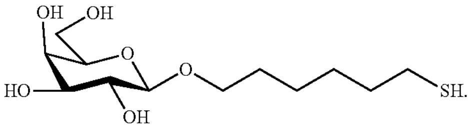

In embodiments, the thiosaccharide compound has the formula:

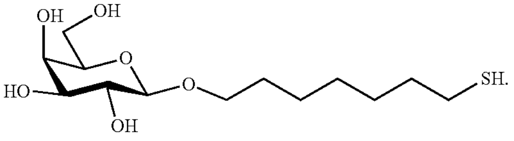

In embodiments, the thiosaccharide compound has the formula:

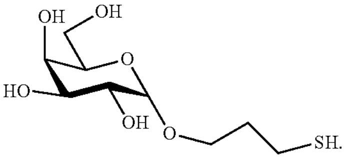

In embodiments, the thiosaccharide compound has the formula:

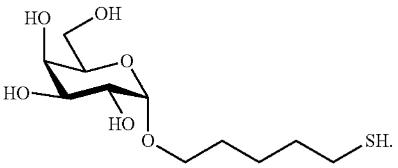

In embodiments, the thiosaccharide compound has the formula:

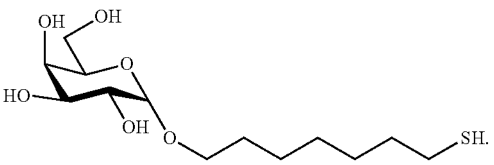

In embodiments, the thiosaccharide compound has the formula:

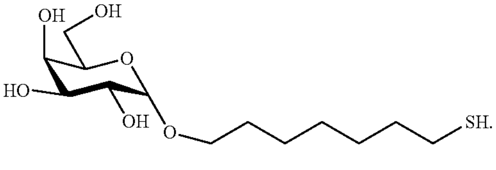

In embodiments, the thiosaccharide compound has the formula:

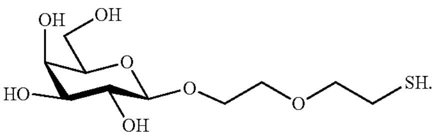

In embodiments, the thiosaccharide compound has the formula:

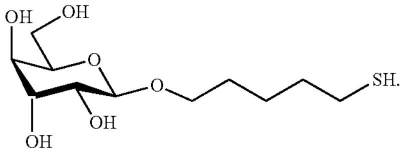

In embodiments, the thiosaccharide compound has the formula:

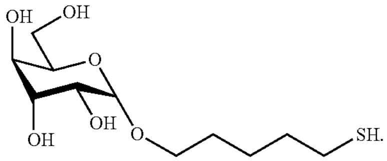

In embodiments, the thiosaccharide compound has the formula:

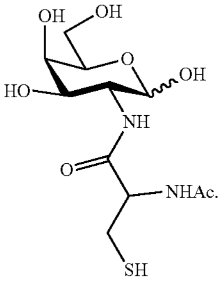

In embodiments, the thiosaccharide compound has the formula:

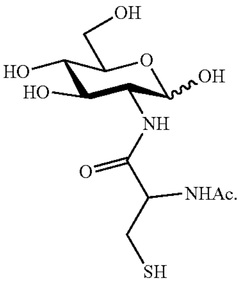

In embodiments, the thiosaccharide compound has the formula:

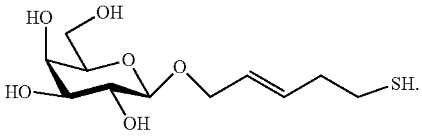

In embodiments, the thiosaccharide compound has the formula:

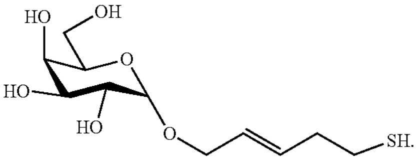

In embodiments, the thiosaccharide compound has the formula:

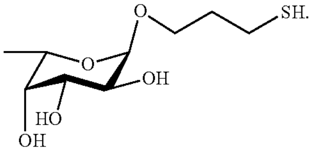

In embodiments, the thiosaccharide compound has the formula:

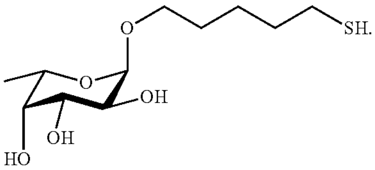

In embodiments, the thiosaccharide compound has the formula:

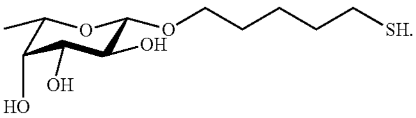

In embodiments, the thiosaccharide compound has the formula:

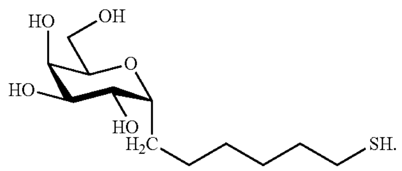

In embodiments, the thiosaccharide compound has the formula:

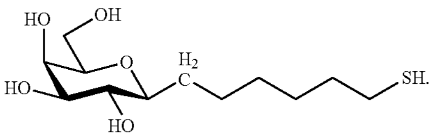

In embodiments, the thiosaccharide compound has the formula:

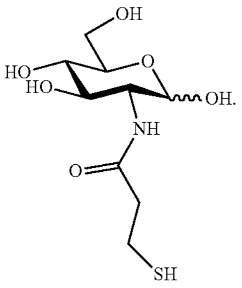

In embodiments, the thiosaccharide compound has the formula:

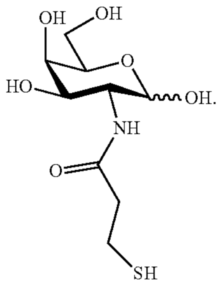

In embodiments, the thiosaccharide compound has the formula:

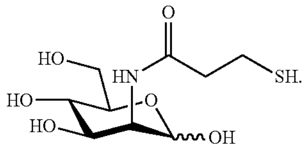

In embodiments, the thiosaccharide compound has the formula:

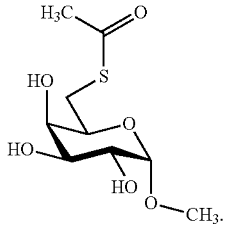

In embodiments, the thiosaccharide compound has the formula:

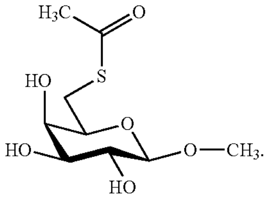

In embodiments, the thiosaccharide compound has the formula:

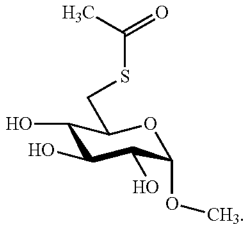

In embodiments, the thiosaccharide compound has the formula:

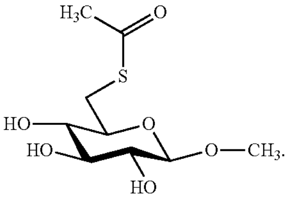

In embodiments, the thiosaccharide compound has the formula:

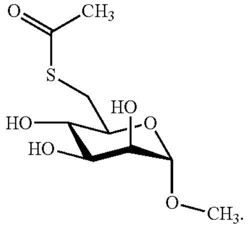

In embodiments, the thiosaccharide compound has the formula:

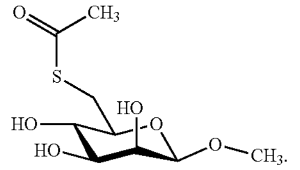

In embodiments, the thiosaccharide compound has the formula:

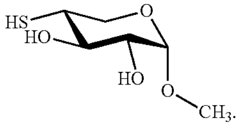

In embodiments, the thiosaccharide compound has the formula:

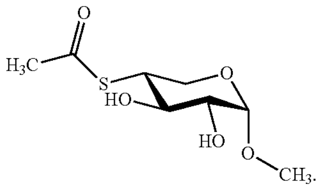

In embodiments, the thiosaccharide compound has the formula:

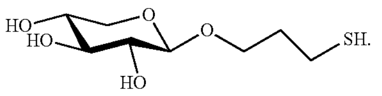

In embodiments, the thiosaccharide compound has the formula:

(IV)

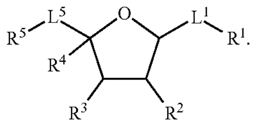

$R^1$, $R^2$, $R^3$, $R^4$, and $R^5$ are as described herein, including in embodiments. $L^1$ and $L^5$ are independently a bond or unsubstituted methylene.

In embodiments, the thiosaccharide compound has the formula:

(V)

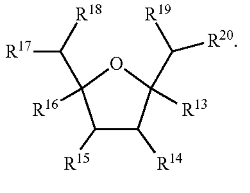

$R^{13}$ is hydrogen, —$SR^{13A}$, —$OR^{13A}$, —$NR^{13B}R^{13C}$, —$NR^{13B}C(O)R^{13C}$, —$NR^{13B}C(O)OR^{13C}$, substituted or unsubstituted alkyl (e.g., $C_1$-$C_{10}$, $C_1$-$C_6$, $C_1$-$C_4$, or $C_1$-$C_2$), or substituted or unsubstituted heteroalkyl (e.g., 2 to 10 membered, 2 to 6 membered, 4 to 6 membered, or 2 to 3 membered). $R^{14}$ is —$SR^{14A}$, —$OR^{14A}$, —$NR^{14B}R^{14C}$, —$NR^{14B}C(O)R^{14C}$, —$NR^{14B}C(O)OR^{14C}$, substituted or unsubstituted alkyl (e.g., $C_1$-$C_{10}$, $C_1$-$C_6$, $C_1$-$C_4$, or $C_1$-$C_2$), or substituted or unsubstituted heteroalkyl (e.g., 2 to 10 membered, 2 to 6 membered, 4 to 6 membered, or 2 to 3 membered). $R^{15}$ is —$SR^{15A}$, —$OR^{15A}$, —$NR^{15B}R^{15C}$, —$NR^{15B}C(O)R^{15C}$, —$NR^{15B}C(O)OR^{15C}$, substituted or unsubstituted alkyl (e.g., $C_1$-$C_{10}$, $C_1$-$C_6$, $C_1$-$C_4$, or $C_1$-$C_2$), or substituted or unsubstituted heteroalkyl (e.g., 2 to 10 membered, 2 to 6 membered, 4 to 6 membered, or 2 to 3 membered). $R^{16}$ is hydrogen, —$SR^{16A}$, —$OR^{16A}$, —$NR^{16B}R^{16C}$, —$NR^{16B}C(O)R^{16C}$, —$NR^{16B}C(O)OR^{16C}$, substituted or unsubstituted alkyl (e.g., $C_1$-$C_{10}$, $C_1$-$C_6$, $C_1$-$C_4$, or $C_1$-$C_2$), or substituted or unsubstituted heteroalkyl (e.g., 2 to 10 membered, 2 to 6 membered, 4 to 6 membered, or 2 to 3 membered). $R^{17}$ is hydrogen, —$SR^{17A}$, —$OR^{17A}$, —$NR^{17B}R^{17C}$, —$NR^{17B}C(O)R^{17C}$, —$NR^{17B}C(O)OR^{17C}$, or substituted or unsubstituted alkyl (e.g., $C_1$-$C_{10}$, $C_1$-$C_6$, $C_1$-$C_4$, or $C_1$-$C_2$), or substituted or unsubstituted heteroalkyl (e.g., 2 to 10 membered, 2 to 6 membered, 4 to 6 membered, or 2 to 3 membered). $R^{18}$ is —$SR^{18A}$, —$OR^{18A}$, —$NR^{18B}R^{18C}$, —$NR^{18B}C(O)R^{18C}$, —$NR^{18B}C(O)OR^{18C}$, substituted or unsubstituted alkyl (e.g., $C_1$-$C_{10}$, $C_1$-$C_6$, $C_1$-$C_4$, or $C_1$-$C_2$), or substituted or unsubstituted heteroalkyl (e.g., 2 to 10 membered, 2 to 6 membered, 4 to 6 membered, or 2 to 3 membered). $R^{19}$ is hydrogen, —$SR^{19A}$, —$OR^{19A}$, —$NR^{19B}R^{19C}$, —$NR^{19B}C(O)R^{19C}$, —$NR^{19B}C(O)OR^{19C}$, substituted or unsubstituted alkyl (e.g., $C_1$-$C_{10}$, $C_1$-$C_6$, $C_1$-$C_4$, or $C_1$-$C_2$), or substituted or unsubstituted heteroalkyl (e.g., 2 to 10 membered, 2 to 6 membered, 4 to 6 membered, or 2 to 3 membered). $R^{20}$ is —$SR^{20A}$, —$OR^{20A}$, —$NR^{20B}R^{20C}$, —$NR^{20B}C(O)R^{20C}$, —$NR^{20B}C(O)OR^{20C}$, or substituted or unsubstituted alkyl (e.g., $C_1$-$C_{10}$, $C_1$-$C_6$, $C_1$-$C_4$, or $C_1$-$C_2$), or substituted or unsubstituted heteroalkyl (e.g., 2 to 10 membered, 2 to 6 membered, 4 to 6 membered, or 2 to 3 membered). $R^{13A}$, $R^{13B}$, $R^{13C}$, $R^{14A}$, $R^{14B}$, $R^{14C}$, $R^{15A}$, $R^{15B}$, $R^{15C}$, $R^{16A}$, $R^{16B}$, $R^{16C}$, $R^{17A}$, $R^{17B}$, $R^{17C}$, $R^{18A}$, $R^{18B}$, $R^{18C}$, $R^{19A}$, $R^{19B}$, $R^{19C}$, $R^{20A}$, $R^{20B}$, and $R^{20C}$ are each independently hydrogen, substituted or unsubstituted alkyl (e.g., $C_1$-$C_{10}$, $C_1$-$C_6$, $C_1$-$C_4$, or $C_1$-$C_2$), or substituted or unsubstituted heteroalkyl (e.g., 2 to 10 membered, 2 to 6 membered, 4 to 6 membered, or 2 to 3 membered); wherein the thiosaccharide compound includes at least two thiol moieties.

In embodiments, $R^{13}$ is hydrogen. In embodiments, $R^{13}$ is —$SR^{13A}$. In embodiments, $R^{13}$ is —$OR^{13A}$. In embodiments, $R^{13}$ is —$NR^{13B}R^{13C}$. In embodiments, $R^{13}$ is —$NR^{13B}C(O)R^{13C}$. In embodiments, $R^{13}$ is —$NR^{13B}C(O)OR^{13C}$. In embodiments, $R^{13}$ is —SH. In embodiments, $R^{13}$ is —OH. In embodiments, $R^{13}$ is —$NH_2$. In embodiments, $R^{13}$ is —NHC(O)H. In embodiments, $R^{13}$ is —$NHC(O)CH_3$. In embodiments, $R^{13}$ is —NHC(O)OH. In embodiments, $R^{13}$ is substituted or unsubstituted $C_1$-$C_{10}$ alkyl. In embodiments, $R^{13}$ is unsubstituted $C_1$-$C_5$ alkyl. In embodiments, $R^{13}$ is unsubstituted methyl. In embodiments, $R^{13}$ is unsubstituted ethyl. In embodiments, $R^{13}$ is unsubstituted propyl. In embodiments, $R^{13}$ is unsubstituted n-propyl. In embodiments, $R^{13}$ is unsubstituted isopropyl. In embodiments, $R^{13}$ is unsubstituted butyl. In embodiments, $R^{13}$ is unsubstituted n-butyl. In embodiments, $R^{13}$ is unsubstituted tert-butyl. In embodiments, $R^{13}$ is substituted or unsubstituted 2 to 10 membered heteroalkyl. In embodiments, $R^{13}$ is substituted or unsubstituted $C_1$-$C_{10}$ thiol-alkyl or substituted or unsubstituted 2 to 10 membered thiol-heteroalkyl. In embodiments, $R^{13}$ is unsubstituted $C_1$-$C_{10}$ thiol-alkyl or unsubstituted 2 to 10 membered thiol-heteroalkyl. In embodiments, $R^{13}$ is unsubstituted thiomethyl (e.g., —$CH_2SH$), unsubstituted thioethyl (e.g., —$(CH_2)_2SH$), unsubstituted thiopropyl (e.g., —$(CH_2)_3SH$), unsubstituted thiobutyl (e.g., —$(CH_2)_4SH$), unsubstituted thiopentyl (e.g., —$(CH_2)_5SH$), unsubstituted thiohexyl (e.g., —$(CH_2)_6SH$), unsubstituted thioheptyl (e.g., —$(CH_2)_7SH$), unsubstituted thiooctyl (e.g., —$(CH_2)_8SH$), unsubstituted thiononyl (e.g., —$(CH_2)_9SH$), or unsubstituted thiodecyl (e.g., —$(CH_2)_{10}SH$). In embodiments, $R^{13}$ is unsubstituted thioethyl. In embodiments, $R^{13}$ is unsubstituted thiopropyl. In embodiments, $R^{13}$ is unsubstituted thiobutyl. In embodiments, $R^{13}$ is unsubstituted thiopentyl. In embodiments, $R^{13}$ is unsubstituted alkoxy. In embodiments, $R^{13}$ is —O-(unsubstituted $C_1$-$C_4$ alkyl). In embodiments, $R^{13}$ is unsubstituted methoxy. In embodiments, $R^{13}$ is unsubstituted ethoxy. In embodiments, $R^{13}$ is unsubstituted propoxy. In embodiments, $R^{13}$ is unsubstituted n-propoxy. In embodiments, $R^{13}$ is unsubstituted isopropoxy. In embodiments, $R^{13}$ is unsubstituted butoxy. In embodiments, $R^{13}$ is unsubstituted n-butoxy. In embodiments, $R^{13}$ is unsubstituted tert-butoxy.

In embodiments, a substituted $R^{13}$ (e.g., substituted alkyl and/or substituted heteroalkyl) is substituted with at least one substituent group, size-limited substituent group, or lower substituent group; wherein if the substituted $R^{13}$ is substituted with a plurality of groups selected from substituent groups, size-limited substituent groups, and lower substituent groups; each substituent group, size-limited substituent group, and/or lower substituent group may optionally be different. In embodiments, when $R^{13}$ is substituted, it is substituted with at least one substituent group. In embodiments, when $R^{13}$ is substituted, it is substituted with at least one size-limited substituent group. In embodiments, when $R^{13}$ is substituted, it is substituted with at least one lower substituent group.

In embodiments, $R^{13A}$ is hydrogen. In embodiments, $R^{13A}$ is substituted or unsubstituted $C_1$-$C_{10}$ alkyl. In embodiments, $R^{13A}$ is substituted or unsubstituted 2 to 10 membered heteroalkyl. In embodiments, $R^{13A}$ is substituted or unsubstituted $C_1$-$C_{10}$ thiol-alkyl or substituted or unsubstituted 2 to 10 membered thiol-heteroalkyl. In embodiments, $R^{13A}$ is unsubstituted $C_1$-$C_{10}$ thiol-alkyl or unsubstituted 2 to 10 membered thiol-heteroalkyl.

In embodiments, a substituted $R^{13A}$ (e.g., substituted alkyl and/or substituted heteroalkyl) is substituted with at least one substituent group, size-limited substituent group, or lower substituent group; wherein if the substituted $R^{13A}$ is substituted with a plurality of groups selected from substituent groups, size-limited substituent groups, and lower substituent groups; each substituent group, size-limited substituent group, and/or lower substituent group may optionally be different. In embodiments, when $R^{13A}$ is substituted, it is substituted with at least one substituent group. In embodiments, when $R^{13A}$ is substituted, it is substituted with at least one size-limited substituent group. In embodiments, when $R^{13A}$ is substituted, it is substituted with at least one lower substituent group.

In embodiments, $R^{13A}$ is

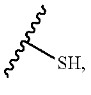 , 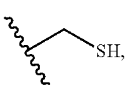 , 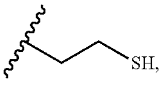 ,

-continued

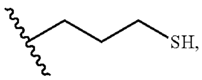 , 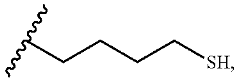 , or

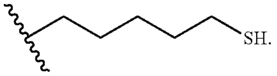 .

In embodiments, $R^{13B}$ is hydrogen. In embodiments, $R^{13B}$ is substituted or unsubstituted $C_1$-$C_{10}$ alkyl. In embodiments, $R^{13B}$ is substituted or unsubstituted 2 to 10 membered heteroalkyl. In embodiments, $R^{13B}$ is substituted or unsubstituted $C_1$-$C_{10}$ thiol-alkyl or substituted or unsubstituted 2 to 10 membered thiol-heteroalkyl. In embodiments, $R^{13B}$ is unsubstituted $C_1$-$C_{10}$ thiol-alkyl or unsubstituted 2 to 10 membered thiol-heteroalkyl. In embodiments, $R^{13B}$ is —C(O)-(substituted or unsubstituted $C_1$-$C_{10}$ alkyl). In embodiments, $R^{13B}$ is —C(O)-(substituted or unsubstituted $C_1$-$C_{10}$ thiol-alkyl). In embodiments, $R^{13B}$ is —C(O)-(substituted or unsubstituted 2 to 10 membered thiol-heteroalkyl).

In embodiments, a substituted $R^{13B}$ (e.g., substituted alkyl and/or substituted heteroalkyl) is substituted with at least one substituent group, size-limited substituent group, or lower substituent group; wherein if the substituted $R^{13B}$ is substituted with a plurality of groups selected from substituent groups, size-limited substituent groups, and lower substituent groups; each substituent group, size-limited substituent group, and/or lower substituent group may optionally be different. In embodiments, when $R^{13B}$ is substituted, itis substituted with at least one substituent group. In embodiments, when $R^{13B}$ is substituted, it is substituted with at least one size-limited substituent group. In embodiments, when $R^{13B}$ is substituted, it is substituted with at least one lower substituent group.

In embodiments, $R^{13C}$ is hydrogen. In embodiments, $R^{13C}$ is substituted or unsubstituted $C_1$-$C_{10}$ alkyl. In embodiments, $R^{13C}$ is substituted or unsubstituted 2 to 10 membered heteroalkyl. In embodiments, $R^{13C}$ is substituted or unsubstituted $C_1$-$C_{10}$ thiol-alkyl or substituted or unsubstituted 2 to 10 membered thiol-heteroalkyl. In embodiments, $R^{13C}$ is unsubstituted $C_1$-$C_{10}$ thiol-alkyl or unsubstituted 2 to 10 membered thiol-heteroalkyl.

In embodiments, a substituted $R^{13C}$ (e.g., substituted alkyl and/or substituted heteroalkyl) is substituted with at least one substituent group, size-limited substituent group, or lower substituent group; wherein if the substituted $R^{13C}$ is substituted with a plurality of groups selected from substituent groups, size-limited substituent groups, and lower substituent groups; each substituent group, size-limited substituent group, and/or lower substituent group may optionally be different. In embodiments, when $R^{13C}$ is substituted, it is substituted with at least one substituent group. In embodiments, when $R^{13C}$ is substituted, it is substituted with at least one size-limited substituent group. In embodiments, when $R^{13C}$ is substituted, it is substituted with at least one lower substituent group.

In embodiments, $R^{14}$ is —$SR^{14A}$. In embodiments, $R^{14}$ is —$OR^{14A}$. In embodiments, $R^{14}$ is —$NR^{14B}R^{14C}$. In embodiments, $R^{14}$ is —$NR^{14B}C(O)R^{14C}$. In embodiments, $R^{14}$ is —$NR^{14B}C(O)OR^{14C}$c. In embodiments, $R^{14}$ is —SH. In embodiments, $R^{14}$ is —OH. In embodiments, $R^{14}$ is —$NH_2$. In embodiments, $R^{14}$ is —NHC(O)H. In embodiments, $R^{14}$ is —NHC(O)$CH_3$. In embodiments, $R^{14}$ is —NHC(O)OH. In embodiments, $R^{14}$ is substituted or unsubstituted $C_1$-$C_{10}$ alkyl. In embodiments, $R^{14}$ is unsubstituted $C_1$-$C_5$ alkyl. In embodiments, $R^{14}$ is unsubstituted methyl. In embodiments, $R^{14}$ is unsubstituted ethyl. In embodiments, $R^{14}$ is unsubstituted propyl. In embodiments, $R^{14}$ is unsubstituted n-propyl. In embodiments, $R^{14}$ is unsubstituted isopropyl. In embodiments, $R^{14}$ is unsubstituted butyl. In embodiments, $R^{14}$ is unsubstituted n-butyl. In embodiments, $R^{14}$ is unsubstituted tert-butyl. In embodiments, $R^{14}$ is substituted or unsubstituted 2 to 10 membered heteroalkyl. In embodiments, $R^{14}$ is substituted or unsubstituted $C_1$-$C_{10}$ thiol-alkyl or substituted or unsubstituted 2 to 10 membered thiol-heteroalkyl. In embodiments, $R^{14}$ is unsubstituted $C_1$-$C_{10}$ thiol-alkyl or unsubstituted 2 to 10 membered thiol-heteroalkyl. In embodiments, $R^{14}$ is unsubstituted thiomethyl (e.g., $-CH_2SH$), unsubstituted thioethyl (e.g., $-(CH_2)_2SH$), unsubstituted thiopropyl (e.g., $-(CH_2)_3SH$), unsubstituted thiobutyl (e.g., $-(CH_2)_4SH$), unsubstituted thiopentyl (e.g., $-(CH_2)_5SH$), unsubstituted thiohexyl (e.g., $-(CH_2)_6SH$), unsubstituted thioheptyl (e.g., $-(CH_2)_7SH$), unsubstituted thiooctyl (e.g., $-(CH_2)_8SH$), unsubstituted thiononyl (e.g., $-(CH_2)_9SH$), or unsubstituted thiodecyl (e.g., $-(CH_2)_{10}SH$). In embodiments, $R^{14}$ is unsubstituted thioethyl. In embodiments, $R^{14}$ is unsubstituted thiopropyl. In embodiments, $R^{14}$ is unsubstituted thiobutyl. In embodiments, $R^{14}$ is unsubstituted thiopentyl. In embodiments, $R^{14}$ is unsubstituted alkoxy. In embodiments, $R^{14}$ is —O-(unsubstituted $C_1$-$C_4$ alkyl). In embodiments, $R^{14}$ is unsubstituted methoxy. In embodiments, $R^{14}$ is unsubstituted ethoxy. In embodiments, $R^{14}$ is unsubstituted propoxy. In embodiments, $R^{14}$ is unsubstituted n-propoxy. In embodiments, $R^{14}$ is unsubstituted isopropoxy. In embodiments, $R^{14}$ is unsubstituted butoxy. In embodiments, $R^{14}$ is unsubstituted n-butoxy. In embodiments, $R^{14}$ is unsubstituted tert-butoxy.

In embodiments, a substituted $R^{14}$ (e.g., substituted alkyl and/or substituted heteroalkyl) is substituted with at least one substituent group, size-limited substituent group, or lower substituent group; wherein if the substituted $R^{14}$ is substituted with a plurality of groups selected from substituent groups, size-limited substituent groups, and lower substituent groups; each substituent group, size-limited substituent group, and/or lower substituent group may optionally be different. In embodiments, when $R^{14}$ is substituted, it is substituted with at least one substituent group. In embodiments, when $R^{14}$ is substituted, it is substituted with at least one size-limited substituent group. In embodiments, when $R^{14}$ is substituted, it is substituted with at least one lower substituent group.

In embodiments, $R^{14A}$ is hydrogen. In embodiments, $R^{14A}$ is substituted or unsubstituted $C_1$-$C_{10}$ alkyl. In embodiments, $R^{14A}$ is substituted or unsubstituted 2 to 10 membered heteroalkyl. In embodiments, $R^{14A}$ is substituted or unsubstituted $C_1$-$C_{10}$ thiol-alkyl or substituted or unsubstituted 2 to 10 membered thiol-heteroalkyl. In embodiments, $R^{14A}$ is unsubstituted $C_1$-$C_{10}$ thiol-alkyl or unsubstituted 2 to 10 membered thiol-heteroalkyl.

In embodiments, a substituted $R^{14A}$ (e.g., substituted alkyl and/or substituted heteroalkyl) is substituted with at least one substituent group, size-limited substituent group, or lower substituent group; wherein if the substituted $R^{14A}$ is substituted with a plurality of groups selected from substituent groups, size-limited substituent groups, and lower substituent groups; each substituent group, size-limited substituent group, and/or lower substituent group may optionally be different. In embodiments, when $R^{14A}$ is substituted, it is substituted with at least one substituent group. In embodiments, when $R^{14A}$ is substituted, it is substituted with at least one size-limited substituent group. In embodiments, when $R^{14A}$ is substituted, it is substituted with at least one lower substituent group.

In embodiments, $R^{14A}$ is

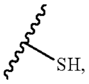,
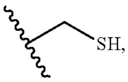,
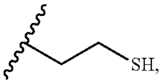,
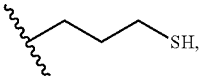,
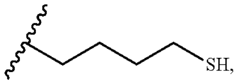, or
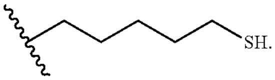.

In embodiments, $R^{14B}$ is hydrogen. In embodiments, $R^{14B}$ is substituted or unsubstituted $C_1$-$C_{10}$ alkyl. In embodiments, $R^{14B}$ is substituted or unsubstituted 2 to 10 membered heteroalkyl. In embodiments, $R^{14B}$ is substituted or unsubstituted $C_1$-$C_{10}$ thiol-alkyl or substituted or unsubstituted 2 to 10 membered thiol-heteroalkyl. In embodiments, $R^{14B}$ is unsubstituted $C_1$-$C_{10}$ thiol-alkyl or unsubstituted 2 to 10 membered thiol-heteroalkyl. In embodiments, $R^{14B}$ is —C(O)-(substituted or unsubstituted $C_1$-$C_{10}$ alkyl). In embodiments, $R^{14B}$ is —C(O)-(substituted or unsubstituted $C_1$-$C_{10}$ thiol-alkyl). In embodiments, $R^{14}$ is —C(O)-(substituted or unsubstituted 2 to 10 membered thiol-heteroalkyl).

In embodiments, a substituted $R^{14B}$ (e.g., substituted alkyl and/or substituted heteroalkyl) is substituted with at least one substituent group, size-limited substituent group, or lower substituent group; wherein if the substituted $R^{14B}$ is substituted with a plurality of groups selected from substituent groups, size-limited substituent groups, and lower substituent groups; each substituent group, size-limited substituent group, and/or lower substituent group may optionally be different. In embodiments, when $R^{14B}$ is substituted, it is substituted with at least one substituent group. In embodiments, when $R^{14B}$ is substituted, it is substituted with at least one size-limited substituent group. In embodiments, when $R^{14B}$ is substituted, it is substituted with at least one lower substituent group.

In embodiments, $R^{14C}$ is hydrogen. In embodiments, $R^{14C}$ is substituted or unsubstituted $C_1$-$C_{10}$ alkyl. In embodiments, $R^{14C}$ is substituted or unsubstituted 2 to 10 membered heteroalkyl. In embodiments, $R^{14C}$ is substituted or unsubstituted $C_1$-$C_{10}$ thiol-alkyl or substituted or unsubstituted 2 to 10 membered thiol-heteroalkyl. In embodiments, $R^{14C}$ is unsubstituted $C_1$-$C_{10}$ thiol-alkyl or unsubstituted 2 to 10 membered thiol-heteroalkyl.

In embodiments, a substituted $R^{14C}$ (e.g., substituted alkyl and/or substituted heteroalkyl) is substituted with at least one substituent group, size-limited substituent group, or lower substituent group; wherein if the substituted $R^{14C}$ is substituted with a plurality of groups selected from substituent groups, size-limited substituent groups, and lower substituent groups; each substituent group, size-limited substituent group, and/or lower substituent group may optionally be different. In embodiments, when $R^{14C}$ is substituted, it is substituted with at least one substituent group. In embodiments, when $R^{14C}$ is substituted, it is substituted with at least one size-limited substituent group. In embodiments, when $R^{14C}$ is substituted, it is substituted with at least one lower substituent group.

In embodiments, $R^{15}$ is —$SR^{15A}$. In embodiments, $R^{15}$ is —$OR^{15A}$. In embodiments, $R^{15}$ is —$NR^{15B}R^{15C}$. In embodiments, $R^{15}$ is —$NR^{15B}C(O)R^{15C}$. In embodiments, $R^{15}$ is —$NR^{15B}$—$C(O)OR^{15C}$. In embodiments, $R^{15}$ is —SH. In embodiments, $R^{15}$ is —OH. In embodiments, $R^{15}$ is —$NH_2$. In embodiments, $R^{15}$ is —NHC(O)H. In embodiments, $R^{15}$ is —$NHC(O)CH_3$. In embodiments, $R^{15}$ is —NHC(O)OH. In embodiments, $R^{15}$ is substituted or unsubstituted $C_1$-$C_{10}$ alkyl. In embodiments, $R^{15}$ is unsubstituted $C_1$-$C_5$ alkyl. In embodiments, $R^{15}$ is unsubstituted methyl. In embodiments, $R^{15}$ is unsubstituted ethyl. In embodiments, $R^{15}$ is unsubstituted propyl. In embodiments, $R^{15}$ is unsubstituted n-propyl. In embodiments, $R^{15}$ is unsubstituted isopropyl. In embodiments, $R^{15}$ is unsubstituted butyl. In embodiments, $R^{15}$ is unsubstituted n-butyl. In embodiments, $R^{15}$ is unsubstituted tert-butyl. In embodiments, $R^{15}$ is substituted or unsubstituted 2 to 10 membered heteroalkyl. In embodiments, $R^{15}$ is substituted or unsubstituted $C_1$-$C_{10}$ thiol-alkyl or substituted or unsubstituted 2 to 10 membered thiol-heteroalkyl. In embodiments, $R^{15}$ is unsubstituted $C_1$-$C_{10}$ thiol-alkyl or unsubstituted 2 to 10 membered thiol-heteroalkyl. In embodiments, $R^{15}$ is unsubstituted thiomethyl (e.g., —$CH_2SH$), unsubstituted thioethyl (e.g., —$(CH_2)_2SH$), unsubstituted thiopropyl (e.g., —$(CH_2)_3SH$), unsubstituted thiobutyl (e.g., —$(CH_2)_4SH$), unsubstituted thiopentyl (e.g., —$(CH_2)_5SH$), unsubstituted thiohexyl (e.g., —$(CH_2)_6SH$), unsubstituted thioheptyl (e.g., —$(CH_2)_7SH$), unsubstituted thiooctyl (e.g., —$(CH_2)_8SH$), unsubstituted thiononyl (e.g., —$(CH_2)_9SH$), or unsubstituted thiodecyl (e.g., —$(CH_2)_{10}SH$). In embodiments, $R^{15}$ is unsubstituted thioethyl. In embodiments, $R^{15}$ is unsubstituted thiopropyl. In embodiments, $R^{15}$ is unsubstituted thiobutyl. In embodiments, $R^{15}$ is unsubstituted thiopentyl. In embodiments, $R^{15}$ is unsubstituted alkoxy. In embodiments, $R^{15}$ is —O-(unsubstituted $C_1$-$C_4$ alkyl). In embodiments, $R^{15}$ is unsubstituted methoxy. In embodiments, $R^{15}$ is unsubstituted ethoxy. In embodiments, $R^{15}$ is unsubstituted propoxy. In embodiments, $R^{15}$ is unsubstituted n-propoxy. In embodiments, $R^{15}$ is unsubstituted isopropoxy. In embodiments, $R^{15}$ is unsubstituted butoxy. In embodiments, $R^{15}$ is unsubstituted n-butoxy. In embodiments, $R^{15}$ is unsubstituted tert-butoxy.

In embodiments, a substituted $R^{15}$ (e.g., substituted alkyl and/or substituted heteroalkyl) is substituted with at least one substituent group, size-limited substituent group, or lower substituent group; wherein if the substituted $R^{15}$ is substituted with a plurality of groups selected from substituent groups, size-limited substituent groups, and lower substituent groups; each substituent group, size-limited substituent group, and/or lower substituent group may optionally be different. In embodiments, when $R^{15}$ is substituted, it is substituted with at least one substituent group. In embodiments, when $R^{15}$ is substituted, it is substituted with at least one size-limited substituent group. In embodiments, when $R^{15}$ is substituted, it is substituted with at least one lower substituent group.

In embodiments, $R^{15A}$ is hydrogen. In embodiments, $R^{15A}$ is substituted or unsubstituted $C_1$-$C_{10}$ alkyl. In embodiments, $R^{15A}$ is substituted or unsubstituted 2 to 10 membered heteroalkyl. In embodiments, $R^{15A}$ is substituted or unsubstituted $C_1$-$C_{10}$ thiol-alkyl or substituted or unsubstituted 2 to 10 membered thiol-heteroalkyl. In embodiments, $R^{15A}$ is unsubstituted $C_1$-$C_{10}$ thiol-alkyl or unsubstituted 2 to 10 membered thiol-heteroalkyl.

In embodiments, a substituted $R^{15A}$ (e.g., substituted alkyl and/or substituted heteroalkyl) is substituted with at least one substituent group, size-limited substituent group, or lower substituent group; wherein if the substituted $R^{5A}$ is substituted with a plurality of groups selected from substituent groups, size-limited substituent groups, and lower substituent groups; each substituent group, size-limited substituent group, and/or lower substituent group may optionally be different. In embodiments, when $R^{15A}$ is substituted, it is substituted with at least one substituent group. In embodiments, when $R^{15A}$ is substituted, it is substituted with at least one size-limited substituent group. In embodiments, when $R^{15A}$ is substituted, it is substituted with at least one lower substituent group.

In embodiments, $R^{15A}$ is

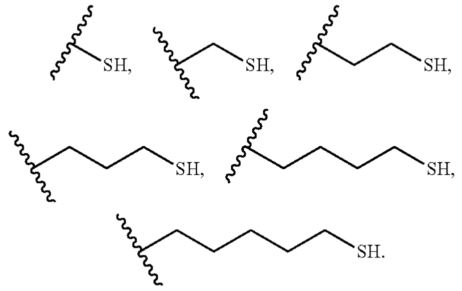

or

In embodiments, $R^{15B}$ is hydrogen. In embodiments, $R^{15B}$ is substituted or unsubstituted $C_1$-$C_{10}$ alkyl. In embodiments, $R^{15B}$ is substituted or unsubstituted 2 to 10 membered heteroalkyl. In embodiments, $R^{15B}$ is substituted or unsubstituted $C_1$-$C_{10}$ thiol-alkyl or substituted or unsubstituted 2 to 10 membered thiol-heteroalkyl. In embodiments, $R^{15B}$ is unsubstituted $C_1$-$C_{10}$ thiol-alkyl or unsubstituted 2 to 10 membered thiol-heteroalkyl. In embodiments, $R^{15B}$ is —C(O)-(substituted or unsubstituted $C_1$-$C_{10}$ alkyl). In embodiments, $R^{15B}$ is —C(O)-(substituted or unsubstituted $C_1$-$C_{10}$ thiol-alkyl). In embodiments, $R^{15}$ is —C(O)-(substituted or unsubstituted 2 to 10 membered thiol-heteroalkyl).

In embodiments, a substituted $R^{15B}$ (e.g., substituted alkyl and/or substituted heteroalkyl) is substituted with at least one substituent group, size-limited substituent group, or lower substituent group; wherein if the substituted $R^{15B}$ is substituted with a plurality of groups selected from substituent groups, size-limited substituent groups, and lower substituent groups; each substituent group, size-limited substituent group, and/or lower substituent group may optionally be different. In embodiments, when $R^{15B}$ is substituted, it is substituted with at least one substituent group. In embodiments, when $R^{15B}$ is substituted, it is substituted with at least one size-limited substituent group. In embodiments, when $R^{15B}$ is substituted, it is substituted with at least one lower substituent group.

In embodiments, $R^{15C}$ is hydrogen. In embodiments, $R^{15C}$ is substituted or unsubstituted $C_1$-$C_{10}$ alkyl. In embodiments, $R^{15C}$ is substituted or unsubstituted 2 to 10 membered heteroalkyl. In embodiments, $R^{15C}$ is substituted or unsubstituted $C_1$-$C_{10}$ thiol-alkyl or substituted or unsubstituted 2 to 10 membered thiol-heteroalkyl. In embodiments, $R^{15C}$ is unsubstituted $C_1$-$C_{10}$ thiol-alkyl or unsubstituted 2 to 10 membered thiol-heteroalkyl.

In embodiments, a substituted $R^{15C}$ (e.g., substituted alkyl and/or substituted heteroalkyl) is substituted with at least one substituent group, size-limited substituent group, or lower substituent group; wherein if the substituted $R^{15C}$ is substituted with a plurality of groups selected from substituent groups, size-limited substituent groups, and lower substituent groups; each substituent group, size-limited substituent group, size-limited substituent group, and/or lower substituent group may optionally be different. In embodiments, when $R^{15C}$ is substituted, it is substituted with at least one substituent group. In embodiments, when $R^{15C}$ is substituted, it is substituted with at least one size-limited substituent group. In embodiments, when $R^{15C}$ is substituted, it is substituted with at least one lower substituent group.

In embodiments, $R^{15}$ is hydrogen. In embodiments, $R^{16}$ is $-SR^{16A}$. In embodiments, $R^{16}$ is $-OR^{16A}$. In embodiments, $R^{16}$ is $-NR^{16B}R^{16C}$. In embodiments, $R^{16}$ is $-NR^{16B}C(O)R^{16C}$. In embodiments, $R^{16}$ is $-NR^{16B}C(O)OR^{16C}$. In embodiments, $R^{16}$ is —SH. In embodiments, $R^{16}$ is —OH. In embodiments, $R^{16}$ is $-NH_2$. In embodiments, $R^{16}$ is —NHC(O)H. In embodiments, $R^{16}$ is $-NHC(O)CH_3$. In embodiments, $R^{16}$ is —NHC(O)OH. In embodiments, $R^{16}$ is substituted or unsubstituted $C_1$-$C_{10}$ alkyl. In embodiments, $R^{16}$ is unsubstituted $C_1$-$C_5$ alkyl. In embodiments, $R^{16}$ is unsubstituted methyl. In embodiments, $R^{16}$ is unsubstituted ethyl. In embodiments, $R^{16}$ is unsubstituted propyl. In embodiments, $R^{16}$ is unsubstituted n-propyl. In embodiments, $R^{16}$ is unsubstituted isopropyl. In embodiments, $R^{16}$ is unsubstituted butyl. In embodiments, $R^{16}$ is unsubstituted n-butyl. In embodiments, $R^{16}$ is unsubstituted tert-butyl. In embodiments, $R^{16}$ is substituted or unsubstituted 2 to 10 membered heteroalkyl. In embodiments, $R^{16}$ is substituted or unsubstituted $C_1$-$C_{10}$ thiol-alkyl or substituted or unsubstituted 2 to 10 membered thiol-heteroalkyl. In embodiments, $R^{16}$ is unsubstituted $C_1$-$C_{10}$ thiol-alkyl or unsubstituted 2 to 10 membered thiol-heteroalkyl. In embodiments, $R^{16}$ is unsubstituted thiomethyl (e.g., $-CH_2SH$), unsubstituted thioethyl (e.g., $-(CH_2)_2SH$), unsubstituted thiopropyl (e.g., $-(CH_2)_3SH$), unsubstituted thiobutyl (e.g., $-(CH_2)_4SH$), unsubstituted thiopentyl (e.g., $-(CH_2)_5SH$), unsubstituted thiohexyl (e.g., $-(CH_2)_6SH$), unsubstituted thioheptyl (e.g., $-(CH_2)_7SH$), unsubstituted thiooctyl (e.g., $-(CH_2)_8SH$), unsubstituted thiononyl (e.g., $-(CH_2)_9SH$), or unsubstituted thiodecyl (e.g., $-(CH_2)_{10}SH$). In embodiments, $R^{16}$ is unsubstituted thioethyl. In embodiments, $R^{16}$ is unsubstituted thiopropyl. In embodiments, $R^{16}$ is unsubstituted thiobutyl. In embodiments, $R^{16}$ is unsubstituted thiopentyl. In embodiments, $R^{16}$ is unsubstituted alkoxy. In embodiments, $R^{16}$ is —O-(unsubstituted $C_1$-$C_4$ alkyl). In embodiments, $R^{16}$ is unsubstituted methoxy. In embodiments, $R^{16}$ is unsubstituted ethoxy. In embodiments, $R^{16}$ is unsubstituted propoxy. In embodiments, $R^{16}$ is unsubstituted n-propoxy. In embodiments, $R^{16}$ is unsubstituted isopropoxy. In embodiments, $R^{16}$ is unsubstituted butoxy. In embodiments, $R^{16}$ is unsubstituted n-butoxy. In embodiments, $R^{16}$ is unsubstituted tert-butoxy.

In embodiments, a substituted $R^{16}$ (e.g., substituted alkyl and/or substituted heteroalkyl) is substituted with at least one substituent group, size-limited substituent group, or lower substituent group; wherein if the substituted $R^{16}$ is substituted with a plurality of groups selected from substituent groups, size-limited substituent groups, and lower substituent groups; each substituent group, size-limited substituent group, and/or lower substituent group may optionally be different. In embodiments, when $R^{16}$ is substituted, it is substituted with at least one substituent group. In embodiments, when $R^{16}$ is substituted, it is substituted with at least one size-limited substituent group. In embodiments, when $R^{16}$ is substituted, it is substituted with at least one lower substituent group.

In embodiments, $R^{16A}$ is hydrogen. In embodiments, $R^{16A}$ is substituted or unsubstituted $C_1$-$C_{10}$ alkyl. In embodiments, $R^{16A}$ is substituted or unsubstituted 2 to 10 membered heteroalkyl. In embodiments, $R^{16A}$ is substituted or unsubstituted $C_1$-$C_{10}$ thiol-alkyl or substituted or unsubstituted 2 to 10 membered thiol-heteroalkyl. In embodiments, $R^{16A}$ is unsubstituted $C_1$-$C_{10}$ thiol-alkyl or unsubstituted 2 to 10 membered thiol-heteroalkyl.

In embodiments, a substituted $R^{16A}$ (e.g., substituted alkyl and/or substituted heteroalkyl) is substituted with at least one substituent group, size-limited substituent group, or lower substituent group; wherein if the substituted $R^{16A}$ is substituted with a plurality of groups selected from substituent groups, size-limited substituent groups, and lower substituent groups; each substituent group, size-limited substituent group, and/or lower substituent group may optionally be different. In embodiments, when $R^{16A}$ is substituted, it is substituted with at least one substituent group. In embodiments, when $R^{16A}$ is substituted, it is substituted with at least one size-limited substituent group. In embodiments, when $R^{16A}$ is substituted, it is substituted with at least one lower substituent group.

In embodiments, $R^{16A}$

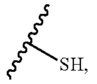,
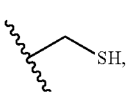,
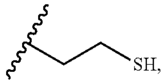,
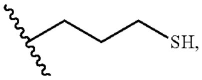,
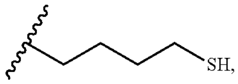, or
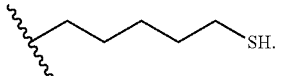.

In embodiments, $R^{16B}$ is hydrogen. In embodiments, $R^{16B}$ is substituted or unsubstituted $C_1$-$C_{10}$ alkyl. In embodiments, $R^{16B}$ is substituted or unsubstituted 2 to 10 membered heteroalkyl. In embodiments, $R^{16B}$ is substituted or unsubstituted $C_1$-$C_{10}$ thiol-alkyl or substituted or unsubstituted 2 to 10 membered thiol-heteroalkyl. In embodiments, $R^{16B}$ is unsubstituted $C_1$-$C_{10}$ thiol-alkyl or unsubstituted 2 to 10 membered thiol-heteroalkyl. In embodiments, $R^{16B}$ is —C(O)-(substituted or unsubstituted $C_1$-$C_{10}$ alkyl). In embodiments, $R^{16B}$ is —C(O)-(substituted or unsubstituted $C_1$-$C_{10}$ thiol-alkyl). In embodiments, $R^{16B}$ is —C(O)-(substituted or unsubstituted 2 to 10 membered thiol-heteroalkyl).

In embodiments, a substituted $R^{16B}$ (e.g., substituted alkyl and/or substituted heteroalkyl) is substituted with at least one substituent group, size-limited substituent group, or lower substituent group; wherein if the substituted $R^{16B}$ is substituted with a plurality of groups selected from substituent groups, size-limited substituent groups, and lower substituent groups; each substituent group, size-limited substituent group, and/or lower substituent group may optionally be different. In embodiments, when $R^{16B}$ is substituted, it is substituted with at least one substituent group. In embodiments, when $R^{16B}$ is substituted, it is substituted with at least one size-limited substituent group. In embodiments, when $R^{16B}$ is substituted, it is substituted with at least one lower substituent group.

In embodiments, $R^{16C}$ is hydrogen. In embodiments, $R^{16C}$ is substituted or unsubstituted $C_1$-$C_{10}$ alkyl. In embodiments, $R^{16C}$ is substituted or unsubstituted 2 to 10 membered heteroalkyl. In embodiments, $R^{16C}$ is substituted or unsubstituted $C_1$-$C_{10}$ thiol-alkyl or substituted or unsubstituted 2 to 10 membered thiol-heteroalkyl. In embodiments, $R^{16C}$ is unsubstituted $C_1$-$C_{10}$ thiol-alkyl or unsubstituted 2 to 10 membered thiol-heteroalkyl.

In embodiments, a substituted $R^{16C}$ (e.g., substituted alkyl and/or substituted heteroalkyl) is substituted with at least one substituent group, size-limited substituent group, or lower substituent group; wherein if the substituted $R^{16C}$ is substituted with a plurality of groups selected from substituent groups, size-limited substituent groups, and lower substituent groups; each substituent group, size-limited substituent group, and/or lower substituent group may optionally be different. In embodiments, when $R^{16C}$ is substituted, it is substituted with at least one substituent group. In embodiments, when $R^{16}$ is substituted, it is substituted with at least one size-limited substituent group. In embodiments, when $R^{16C}$ is substituted, it is substituted with at least one lower substituent group.

In embodiments, $R^{17}$ is hydrogen. In embodiments, $R^{17}$ is —$SR^{17A}$. In embodiments, $R^{17}$ is —$OR^{17A}$. In embodiments, $R^{17}$ is —$NR^{17B}R^{17C}$. In embodiments, $R^{17}$ is —$NR^{17B}C(O)R^{17C}$. In embodiments, $R^{17}$ is —$NR^{17B}C(O)OR^{17C}$. In embodiments, $R^{17}$ is —SH. In embodiments, $R^{17}$ is —OH. In embodiments, $R^{17}$ is —$NH_2$. In embodiments, $R^{17}$ is —NHC(O)H. In embodiments, $R^{17}$ is —$NHC(O)CH_3$. In embodiments, $R^{17}$ is —NHC(O)OH. In embodiments, $R^{17}$ is substituted or unsubstituted $C_1$-$C_{10}$ alkyl. In embodiments, $R^{17}$ is unsubstituted $C_1$-$C_5$ alkyl. In embodiments, $R^{17}$ is unsubstituted methyl. In embodiments, $R^{17}$ is unsubstituted ethyl. In embodiments, $R^{17}$ is unsubstituted propyl. In embodiments, $R^{17}$ is unsubstituted n-propyl. In embodiments, $R^{17}$ is unsubstituted isopropyl. In embodiments, $R^{17}$ is unsubstituted butyl. In embodiments, $R^{17}$ is unsubstituted n-butyl. In embodiments, $R^{17}$ is unsubstituted tert-butyl. In embodiments, $R^{17}$ is substituted or unsubstituted 2 to 10 membered heteroalkyl. In embodiments, $R^{17}$ is substituted or unsubstituted $C_1$-$C_{10}$ thiol-alkyl or substituted or unsubstituted 2 to 10 membered thiol-heteroalkyl. In embodiments, $R^{17}$ is unsubstituted $C_1$-$C_{10}$ thiol-alkyl or unsubstituted 2 to 10 membered thiol-heteroalkyl. In embodiments, $R^{17}$ is unsubstituted thiomethyl (e.g., —$CH_2SH$), unsubstituted thioethyl (e.g., —$(CH_2)_2SH$), unsubstituted thiopropyl (e.g., —$(CH_2)_3SH$), unsubstituted thiobutyl (e.g., —$(CH_2)_4SH$), unsubstituted thiopentyl (e.g., —$(CH_2)_5SH$), unsubstituted thiohexyl (e.g., —$(CH_2)_6SH$), unsubstituted thioheptyl (e.g., —$(CH_2)_7SH$), unsubstituted thiooctyl (e.g., —$(CH_2)_8SH$), unsubstituted thiononyl (e.g., —$(CH_2)_9SH$), or unsubstituted thiodecyl (e.g., —$(CH_2)_{10}SH$). In embodiments, $R^{17}$ is unsubstituted thioethyl. In embodiments, $R^{17}$ is unsubstituted thiopropyl. In embodiments, $R^{17}$ is unsubstituted thiobutyl. In embodiments, $R^{17}$ is unsubstituted thiopentyl. In embodiments, $R^{17}$ is unsubstituted alkoxy. In embodiments, $R^{17}$ is —O-(unsubstituted $C_1$-$C_4$ alkyl). In embodiments, $R^{17}$ is unsubstituted methoxy. In embodiments, $R^{17}$ is unsubstituted ethoxy. In embodiments, $R^{17}$ is unsubstituted propoxy. In embodiments, $R^{17}$ is unsubstituted n-propoxy. In embodiments, $R^{17}$ is unsubstituted isopropoxy. In embodiments, $R^{17}$ is unsubstituted butoxy. In embodiments, $R^{17}$ is unsubstituted n-butoxy. In embodiments, $R^{17}$ is unsubstituted tert-butoxy.

In embodiments, a substituted $R^{17}$ (e.g., substituted alkyl and/or substituted heteroalkyl) is substituted with at least one substituent group, size-limited substituent group, or lower substituent group; wherein if the substituted $R^{17}$ is substituted with a plurality of groups selected from substituent groups, size-limited substituent groups, and lower substituent groups; each substituent group, size-limited substituent group, and/or lower substituent group may optionally be different. In embodiments, when $R^{17}$ is substituted, it is substituted with at least one substituent group. In embodiments, when $R^{17}$ is substituted, it is substituted with at least one size-limited substituent group. In embodiments, when $R^{17}$ is substituted, it is substituted with at least one lower substituent group.

In embodiments, $R^{17A}$ is hydrogen. In embodiments, $R^{17A}$ is substituted or unsubstituted $C_1$-$C_{10}$ alkyl. In embodiments, $R^{17A}$ is substituted or unsubstituted 2 to 10 membered heteroalkyl. In embodiments, $R^{17A}$ is substituted or unsubstituted $C_1$-$C_{10}$ thiol-alkyl or substituted or unsubstituted 2 to 10 membered thiol-heteroalkyl. In embodiments, $R^{17A}$ is unsubstituted $C_1$-$C_{10}$ thiol-alkyl or unsubstituted 2 to 10 membered thiol-heteroalkyl.

In embodiments, a substituted $R^{17A}$ (e.g., substituted alkyl and/or substituted heteroalkyl) is substituted with at least one substituent group, size-limited substituent group, or lower substituent group; wherein if the substituted $R^{17A}$ is substituted with a plurality of groups selected from substituent groups, size-limited substituent groups, and lower substituent groups; each substituent group, size-limited substituent group, and/or lower substituent group may optionally be different. In embodiments, when $R^{17A}$ is substituted, it is substituted with at least one substituent group. In embodiments, when $R^{17A}$ is substituted, it is substituted with at least one size-limited substituent group. In embodiments, when $R^{17A}$ is substituted, it is substituted with at least one lower substituent group.

In embodiments, $R^{17A}$ is

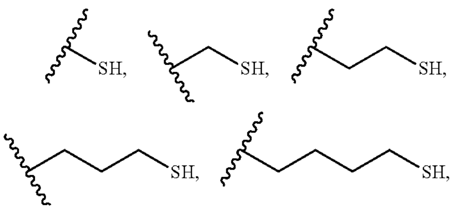

or

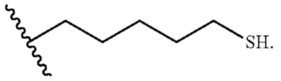

In embodiments, $R^{17B}$ is hydrogen. In embodiments, $R^{17B}$ is substituted or unsubstituted $C_1$-$C_{10}$ alkyl. In embodiments, $R^{17B}$ is substituted or unsubstituted 2 to 10 membered heteroalkyl. In embodiments, $R^{17B}$ is substituted or unsubstituted $C_1$-$C_{10}$ thiol-alkyl or substituted or unsubstituted 2 to 10 membered thiol-heteroalkyl. In embodiments, $R^{17B}$ is unsubstituted $C_1$-$C_{10}$ thiol-alkyl or unsubstituted 2 to 10 membered thiol-heteroalkyl. In embodiments, $R^{17B}$ is —C(O)-(substituted or unsubstituted $C_1$-$C_{10}$ alkyl). In embodiments, $R^{17B}$ is —C(O)-(substituted or unsubstituted $C_1$-$C_{10}$ thiol-alkyl). In embodiments, $R^{17B}$ is —C(O)-(substituted or unsubstituted 2 to 10 membered thiol-heteroalkyl).

In embodiments, a substituted $R^{17B}$ (e.g., substituted alkyl and/or substituted heteroalkyl) is substituted with at least one substituent group, size-limited substituent group, or lower substituent group; wherein if the substituted $R^{17B}$ is substituted with a plurality of groups selected from substituent groups, size-limited substituent groups, and lower substituent groups; each substituent group, size-limited substituent group, and/or lower substituent group may optionally be different. In embodiments, when $R^{17B}$ is substituted, it is substituted with at least one substituent group. In embodiments, when $R^{17B}$ is substituted, it is substituted with at least one size-limited substituent group. In embodiments, when $R^{17B}$ is substituted, it is substituted with at least one lower substituent group.

In embodiments, $R^{17C}$ is hydrogen. In embodiments, $R^{17C}$ is substituted or unsubstituted $C_1$-$C_{10}$ alkyl. In embodiments, $R^{17C}$ is substituted or unsubstituted 2 to 10 membered heteroalkyl. In embodiments, $R^{17C}$ is substituted or unsubstituted $C_1$-$C_{10}$ thiol-alkyl or substituted or unsubstituted 2 to 10 membered thiol-heteroalkyl. In embodiments, $R^{17C}$ is unsubstituted $C_1$-$C_{10}$ thiol-alkyl or unsubstituted 2 to 10 membered thiol-heteroalkyl.

In embodiments, a substituted $R^{17C}$ (e.g., substituted alkyl and/or substituted heteroalkyl) is substituted with at least one substituent group, size-limited substituent group, or lower substituent group; wherein if the substituted $R^{17C}$ is substituted with a plurality of groups selected from substituent groups, size-limited substituent groups, and lower substituent groups; each substituent group, size-limited substituent group, and/or lower substituent group may optionally be different. In embodiments, when $R^{17C}$ is substituted, it is substituted with at least one substituent group. In embodiments, when $R^{17C}$ is substituted, it is substituted with at least one size-limited substituent group. In embodiments, when $R^{17C}$ is substituted, it is substituted with at least one lower substituent group.

In embodiments, $R^{18}$ is —$SR^{18A}$. In embodiments, $R^{18}$ is —$OR^{18A}$. In embodiments, $R^{18}$ is —$NR^{18B}R^{18C}$. In embodiments, $R^{18}$ is —$NR^{18B}C(O)R^{18C}$. In embodiments, $R^{18}$ is —$NR^{18B}C(O)OR^{18C}$. In embodiments, $R^{18}$ is —SH. In embodiments, $R^{18}$ m is —OH. In embodiments, $R^{18}$ is —$NH_2$. In embodiments, $R^{18}$ is —NHC(O)H. In embodiments, $R^{18}$ is —$NHC(O)CH_3$. In embodiments, $R^{18}$ is —NHC(O)OH. In embodiments, $R^{18}$ is substituted or unsubstituted $C_1$-$C_{10}$ alkyl. In embodiments, $R^{18}$ is unsubstituted $C_1$-$C_5$ alkyl. In embodiments, $R^{18}$ is unsubstituted methyl. In embodiments, $R^{18}$ is unsubstituted ethyl. In embodiments, $R^{18}$ is unsubstituted propyl. In embodiments, $R^{18}$ is unsubstituted n-propyl. In embodiments, $R^{18}$ is unsubstituted isopropyl. In embodiments, $R^{18}$ is unsubstituted butyl. In embodiments, $R^{18}$ is unsubstituted n-butyl. In embodiments, $R^{18}$ is unsubstituted tert-butyl. In embodiments, $R^{18}$ is substituted or unsubstituted 2 to 10 membered heteroalkyl. In embodiments, $R^{18}$ is substituted or unsubstituted $C_1$-$C_{10}$ thiol-alkyl or substituted or unsubstituted 2 to 10 membered thiol-heteroalkyl. In embodiments, $R^{18}$ is unsubstituted $C_1$-$C_{10}$ thiol-alkyl or unsubstituted 2 to 10 membered thiol-heteroalkyl. In embodiments, $R^{18}$ is unsubstituted thiomethyl (e.g., —$CH_2SH$), unsubstituted thioethyl (e.g., —$(CH_2)_2SH$), unsubstituted thiopropyl (e.g., —$(CH_2)_3$ SH), unsubstituted thiobutyl (e.g., —$(CH_2)_4SH$), unsubstituted thiopentyl (e.g., —$(CH_2)_5SH$), unsubstituted thiohexyl (e.g., —$(CH_2)_6SH$), unsubstituted thioheptyl (e.g., —$(CH_2)_7SH$), unsubstituted thiooctyl (e.g., —$(CH_2)_8SH$), unsubstituted thiononyl (e.g., —$(CH_2)_9SH$), or unsubstituted thiodecyl (e.g., —$(CH_2)_{10}SH$). In embodiments, $R^{18}$ is unsubstituted thioethyl. In embodiments, $R^{18}$ is unsubstituted thiopropyl. In embodiments, $R^{18}$ is unsubstituted thiobutyl. In embodiments, $R^{18}$ is unsubstituted thiopentyl. In embodiments, $R^{18}$ is unsubstituted alkoxy. In embodiments, $R^{18}$ is —O-(unsubstituted $C_1$-$C_4$ alkyl). In embodiments, $R^{18}$ is unsubstituted methoxy. In embodiments, $R^{18}$ is unsubstituted ethoxy. In embodiments, $R^{18}$ is unsubstituted propoxy. In embodiments, $R^{18}$ is unsubstituted n-propoxy. In embodiments, $R^{18}$ is unsubstituted isopropoxy. In embodiments, $R^{18}$ is unsubstituted butoxy. In embodiments, $R^{18}$ is unsubstituted n-butoxy. In embodiments, $R^{18}$ is unsubstituted tert-butoxy.

In embodiments, a substituted $R^{18}$ (e.g., substituted alkyl and/or substituted heteroalkyl) is substituted with at least one substituent group, size-limited substituent group, or lower substituent group; wherein if the substituted $R^{18}$ is substituted with a plurality of groups selected from substituent groups, size-limited substituent groups, and lower substituent groups; each substituent group, size-limited substituent group, and/or lower substituent group may optionally be different. In embodiments, when $R^{18}$ is substituted, it is substituted with at least one substituent group. In embodiments, when $R^{18}$ is substituted, it is substituted with at least one size-limited substituent group. In embodiments, when $R^{18}$ is substituted, it is substituted with at least one lower substituent group.

In embodiments, $R^{18A}$ is hydrogen. In embodiments, $R^{18A}$ is substituted or unsubstituted $C_1$-$C_{10}$ alkyl. In embodiments, $R^{18A}$ is substituted or unsubstituted 2 to 10 membered heteroalkyl. In embodiments, $R^{18A}$ is substituted or unsubstituted $C_1$-$C_{10}$ thiol-alkyl or substituted or unsubstituted 2 to 10 membered thiol-heteroalkyl. In embodiments, $R^{18A}$ is unsubstituted $C_1$-$C_{10}$ thiol-alkyl or unsubstituted 2 to 10 membered thiol-heteroalkyl.

In embodiments, a substituted $R^{18A}$ (e.g., substituted alkyl and/or substituted heteroalkyl) is substituted with at least one substituent group, size-limited substituent group, or lower substituent group; wherein if the substituted $R^{18A}$ is substituted with a plurality of groups selected from substituent groups, size-limited substituent groups, and lower substituent groups; each substituent group, size-limited substituent group, and/or lower substituent group may optionally be different. In embodiments, when $R^{18A}$ is substituted, it is substituted with at least one substituent group. In embodiments, when $R^{18A}$ is substituted, it is substituted with at least one size-limited substituent group. In embodiments, when $R^{18A}$ is substituted, it is substituted with at least one lower substituent group.

In embodiments, $R^{18A}$ is

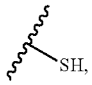,
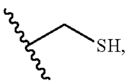,
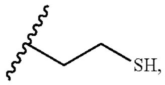,
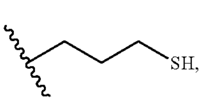,
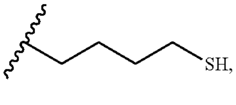, or
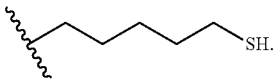.

In embodiments, $R^{18B}$ is hydrogen. In embodiments, $R^{18B}$ is substituted or unsubstituted $C_1$-$C_{10}$ alkyl. In embodiments, $R^{18B}$ is substituted or unsubstituted 2 to 10 membered heteroalkyl. In embodiments, $R^{18B}$ is substituted or unsubstituted $C_1$-$C_{10}$ thiol-alkyl or substituted or unsubstituted 2 to 10 membered thiol-heteroalkyl. In embodiments, $R^{18B}$ is unsubstituted $C_1$-$C_{10}$ thiol-alkyl or unsubstituted 2 to 10 membered thiol-heteroalkyl. In embodiments, $R^{18B}$ is —C(O)-(substituted or unsubstituted $C_1$-$C_{10}$ alkyl). In embodiments, $R^{18B}$ is —C(O)-(substituted or unsubstituted $C_1$-$C_{10}$ thiol-alkyl). In embodiments, $R^{18B}$ is —C(O)-(substituted or unsubstituted 2 to 10 membered thiol-heteroalkyl).

In embodiments, a substituted $R^{18B}$ (e.g., substituted alkyl and/or substituted heteroalkyl) is substituted with at least one substituent group, size-limited substituent group, or lower substituent group; wherein if the substituted $R^{18B}$ is substituted with a plurality of groups selected from substituent groups, size-limited substituent groups, and lower substituent groups; each substituent group, size-limited substituent group, and/or lower substituent group may optionally be different. In embodiments, when $R^{18B}$ is substituted, it is substituted with at least one substituent group. In embodiments, when $R^{18B}$ is substituted, it is substituted with at least one size-limited substituent group. In embodiments, when $R^{18B}$ is substituted, it is substituted with at least one lower substituent group.

In embodiments, $R^{18C}$ is hydrogen. In embodiments, $R^{18C}$ is substituted or unsubstituted $C_1$-$C_{10}$ alkyl. In embodiments, $R^{18C}$ is substituted or unsubstituted 2 to 10 membered heteroalkyl. In embodiments, $R^{18C}$ is substituted or unsubstituted $C_1$-$C_{10}$ thiol-alkyl or substituted or unsubstituted 2 to 10 membered thiol-heteroalkyl. In embodiments, $R^{18C}$ is unsubstituted $C_1$-$C_{10}$ thiol-alkyl or unsubstituted 2 to 10 membered thiol-heteroalkyl.

In embodiments, a substituted $R^{18C}$ (e.g., substituted alkyl and/or substituted heteroalkyl) is substituted with at least one substituent group, size-limited substituent group, or lower substituent group; wherein if the substituted $R^{18C}$ is substituted with a plurality of groups selected from substituent groups, size-limited substituent groups, and lower substituent groups; each substituent group, size-limited substituent group, and/or lower substituent group may optionally be different. In embodiments, when $R^{18C}$ is substituted, it is substituted with at least one substituent group. In embodiments, when $R^{18C}$ is substituted, it is substituted with at least one size-limited substituent group. In embodiments, when $R^{18C}$ is substituted, it is substituted with at least one lower substituent group.

In embodiments, $R^{19}$ is hydrogen. In embodiments, $R^{19}$ is —$SR^{19A}$. In embodiments, $R^{19}$ is —$OR^{19A}$. In embodiments, $R^{19}$ is —$NR^{19B}R^{19C}$. In embodiments, $R^{19}$ is —$NR^{19B}C(O)R^{19C}$. In embodiments, $R^{19}$ is —$NR^{19B}C(O)OR^{19C}$. In embodiments, $R^{19}$ is —SH. In embodiments, $R^{19}$ is —OH. In embodiments, $R^{19}$ is —$NH_2$. In embodiments, $R^{19}$ is —NHC(O)H. In embodiments, $R^{19}$ is —$NHC(O)CH_3$. In embodiments, $R^{19}$ is —NHC(O)OH. In embodiments, $R^{19}$ is substituted or unsubstituted $C_1$-$C_{10}$ alkyl. In embodiments, $R^{19}$ is unsubstituted $C_1$-$C_5$ alkyl. In embodiments, $R^{19}$ is unsubstituted methyl. In embodiments, $R^{19}$ is unsubstituted ethyl. In embodiments, $R^{19}$ is unsubstituted propyl. In embodiments, $R^{19}$ is unsubstituted n-propyl. In embodiments, $R^{19}$ is unsubstituted isopropyl. In embodiments, $R^{19}$ is unsubstituted butyl. In embodiments, $R^{19}$ is unsubstituted n-butyl. In embodiments, $R^{19}$ is unsubstituted tert-butyl. In embodiments, $R^{19}$ is substituted or unsubstituted 2 to 10 membered heteroalkyl. In embodiments, $R^{19}$ is substituted or unsubstituted $C_1$-$C_{10}$ thiol-alkyl or substituted or unsubstituted 2 to 10 membered thiol-heteroalkyl. In embodiments, $R^{19}$ is unsubstituted $C_1$-$C_{10}$ thiol-alkyl or unsubstituted 2 to 10 membered thiol-heteroalkyl. In embodiments, $R^{19}$ is unsubstituted thiomethyl (e.g., —$CH_2SH$), unsubstituted thioethyl (e.g., —$(CH_2)_2SH$), unsubstituted thiopropyl (e.g., —$(CH_2)_3SH$), unsubstituted thiobutyl (e.g., —$(CH_2)_4SH$), unsubstituted thiopentyl (e.g., —$(CH_2)_5SH$), unsubstituted thiohexyl (e.g., —$(CH_2)_6SH$), unsubstituted thioheptyl (e.g., —$(CH_2)_7SH$), unsubstituted thiooctyl (e.g., —$(CH_2)_8SH$), unsubstituted thiononyl (e.g., —$(CH_2)_9SH$), or unsubstituted thiodecyl (e.g., —$(CH_2)_{10}SH$). In embodiments, $R^{19}$ is unsubstituted thioethyl. In embodiments, $R^{19}$ is unsubstituted thiopropyl. In embodiments, $R^{19}$ is unsubstituted thiobutyl. In embodiments, $R^{19}$ is unsubstituted thiopentyl. In embodiments, $R^{19}$ is unsubstituted alkoxy. In embodiments, $R^{19}$ is —O-(unsubstituted $C_1$-$C_4$ alkyl). In embodiments, $R^{19}$ is unsubstituted methoxy. In embodiments, $R^{19}$ is unsubstituted ethoxy. In embodiments, $R^{19}$ is unsubstituted propoxy. In embodiments, $R^{19}$ is unsubstituted n-propoxy. In embodiments, $R^{19}$ is unsubstituted isopropoxy. In embodiments, $R^{19}$ is unsubstituted butoxy. In embodiments, $R^{19}$ is unsubstituted n-butoxy. In embodiments, $R^{19}$ is unsubstituted tert-butoxy.

In embodiments, a substituted $R^{19}$ (e.g., substituted alkyl and/or substituted heteroalkyl) is substituted with at least one substituent group, size-limited substituent group, or lower substituent group; wherein if the substituted $R^{19}$ is substituted with a plurality of groups selected from substituent groups, size-limited substituent groups, and lower substituent groups; each substituent group, size-limited substituent group, and/or lower substituent group may optionally be different. In embodiments, when $R^{19}$ is substituted, it is substituted with at least one substituent group. In embodiments, when $R^{19}$ is substituted, it is substituted with at least one size-limited substituent group. In embodiments, when $R^{19}$ is substituted, it is substituted with at least one lower substituent group.

In embodiments, $R^{19A}$ is hydrogen. In embodiments, $R^{19A}$ is substituted or unsubstituted $C_1$-$C_{10}$ alkyl. In embodiments, $R^{19A}$ is substituted or unsubstituted 2 to 10 membered heteroalkyl. In embodiments, $R^{19A}$ is substituted or unsubstituted $C_1$-$C_{10}$ thiol-alkyl or substituted or unsubstituted 2 to 10 membered thiol-heteroalkyl. In embodiments, $R^{19A}$ is unsubstituted $C_1$-$C_{10}$ thiol-alkyl or unsubstituted 2 to 10 membered thiol-heteroalkyl.

In embodiments, a substituted $R^{19A}$ (e.g., substituted alkyl and/or substituted heteroalkyl) is substituted with at least one substituent group, size-limited substituent group, or lower substituent group; wherein if the substituted $R^{19A}$ is substituted with a plurality of groups selected from substituent groups, size-limited substituent groups, and lower substituent groups; each substituent group, size-limited substituent group, and/or lower substituent group may optionally be different. In embodiments, when $R^{19A}$ is substituted, it is substituted with at least one substituent group. In embodiments, when $R^{19A}$ is substituted, it is substituted with at least one size-limited substituent group. In embodiments, when $R^{19A}$ is substituted, it is substituted with at least one lower substituent group.

In embodiments, $R^{19A}$ is

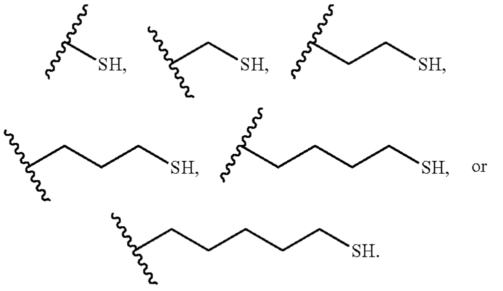

In embodiments, $R^{19B}$ is hydrogen. In embodiments, $R^{19B}$ is substituted or unsubstituted $C_1$-$C_{10}$ alkyl. In embodiments, $R^{19B}$ is substituted or unsubstituted 2 to 10 membered heteroalkyl. In embodiments, $R^{19B}$ is substituted or unsubstituted $C_1$-$C_{10}$ thiol-alkyl or substituted or unsubstituted 2 to 10 membered thiol-heteroalkyl. In embodiments, $R^{19B}$ is unsubstituted $C_1$-$C_{10}$ thiol-alkyl or unsubstituted 2 to 10 membered thiol-heteroalkyl. In embodiments, $R^{19B}$ is —C(O)-(substituted or unsubstituted $C_1$-$C_{10}$ alkyl). In embodiments, $R^{19B}$ is —C(O)-(substituted or unsubstituted $C_1$-$C_{10}$ thiol-alkyl). In embodiments, $R^{19B}$ is —C(O)-(substituted or unsubstituted 2 to 10 membered thiol-heteroalkyl).

In embodiments, a substituted $R^{19B}$ (e.g., substituted alkyl and/or substituted heteroalkyl) is substituted with at least one substituent group, size-limited substituent group, or lower substituent group; wherein if the substituted $R^{19B}$ is substituted with a plurality of groups selected from substituent groups, size-limited substituent groups, and lower substituent groups; each substituent group, size-limited substituent group, and/or lower substituent group may optionally be different. In embodiments, when $R^{19B}$ is substituted, it is substituted with at least one substituent group. In embodiments, when $R^{19B}$ is substituted, it is substituted with at least one size-limited substituent group. In embodiments, when $R^{19B}$ is substituted, it is substituted with at least one lower substituent group.

In embodiments, $R^{19C}$ is hydrogen. In embodiments, $R^{19C}$ is substituted or unsubstituted $C_1$-$C_{10}$ alkyl. In embodiments, $R^{19C}$ is substituted or unsubstituted 2 to 10 membered heteroalkyl. In embodiments, $R^{19C}$ is substituted or unsubstituted $C_1$-$C_{10}$ thiol-alkyl or substituted or unsubstituted 2 to 10 membered thiol-heteroalkyl. In embodiments, $R^{19C}$ is unsubstituted $C_1$-$C_{10}$ thiol-alkyl or unsubstituted 2 to 10 membered thiol-heteroalkyl.

In embodiments, a substituted $R^{19C}$ (e.g., substituted alkyl and/or substituted heteroalkyl) is substituted with at least one substituent group, size-limited substituent group, or lower substituent group; wherein if the substituted $R^{19C}$ is substituted with a plurality of groups selected from substituent groups, size-limited substituent groups, and lower substituent groups; each substituent group, size-limited substituent group, and/or lower substituent group may optionally be different. In embodiments, when $R^{19C}$ is substituted, it is substituted with at least one substituent group. In embodiments, when $R^{19C}$ is substituted, it is substituted with at least one size-limited substituent group. In embodiments, when $R^{19C}$ is substituted, it is substituted with at least one lower substituent group.

In embodiments, $R^{20}$ is —$SR^{20A}$. In embodiments, $R^{20}$ is —$OR^{20A}$. In embodiments, $R^{20}$ is —$NR^{20B}R^{20C}$. In embodiments, $R^{20}$ is —$NR^{20B}C(O)R^{20C}$. In embodiments, $R^{20}$ is —$NRC(O)OR^{20B}$. In embodiments, $R^{20}$ is —SH. In embodiments, $R^{20}$ is —OH. In embodiments, $R^{20}$ is —$NH_2$. In embodiments, $R^{20}$ is —NHC(O)H. In embodiments, $R^{20}$ is —$NHC(O)CH_3$. In embodiments, $R^{20}$ is —NHC(O)OH. In embodiments, $R^{20}$ is substituted or unsubstituted $C_1$-$C_{10}$ alkyl. In embodiments, $R^{20}$ is unsubstituted $C_1$-$C_5$ alkyl. In embodiments, $R^{20}$ is unsubstituted methyl. In embodiments, $R^{20}$ is unsubstituted ethyl. In embodiments, $R^{20}$ is unsubstituted propyl. In embodiments, $R^{20}$ is unsubstituted n-propyl. In embodiments, $R^{20}$ is unsubstituted isopropyl. In embodiments, $R^{20}$ is unsubstituted butyl. In embodiments, $R^{20}$ is unsubstituted n-butyl. In embodiments, $R^{20}$ is unsubstituted tert-butyl. In embodiments, $R^{20}$ is substituted or unsubstituted 2 to 10 membered heteroalkyl. In embodiments, $R^{20}$ is substituted or unsubstituted $C_1$-$C_{10}$ thiol-alkyl or substituted or unsubstituted 2 to 10 membered thiol-heteroalkyl. In embodiments, $R^{20}$ is unsubstituted $C_1$-$C_{10}$ thiol-alkyl or unsubstituted 2 to 10 membered thiol-heteroalkyl. In embodiments, $R^{20}$ is unsubstituted thiomethyl (e.g., —$CH_2SH$), unsubstituted thioethyl (e.g., —$(CH_2)_2SH$), unsubstituted thiopropyl (e.g., —$(CH_2)_3SH$), unsubstituted thiobutyl (e.g., —$(CH_2)_4SH$), unsubstituted thiopentyl (e.g., —$(CH_2)_5SH$), unsubstituted thiohexyl (e.g., —$(CH_2)_6SH$), unsubstituted thioheptyl (e.g., —$(CH_2)_7SH$), unsubstituted thiooctyl (e.g., —$(CH_2)_8SH$), unsubstituted thiononyl (e.g., —$(CH_2)_9SH$), or unsubstituted thiodecyl (e.g., —$(CH_2)_{10}SH$). In embodiments, $R^2$ is unsubstituted thioethyl. In embodiments, $R^2$ is unsubstituted thiopropyl. In embodiments, $R^0$ is unsubstituted thiobutyl. In embodiments, $R^2$ is unsubstituted thiopentyl. In embodiments, $R^0$ is unsubstituted alkoxy. In embodiments, $R^2$ is —O-(unsubstituted $C_1$-$C_4$ alkyl). In embodiments, $R^{20}$ is unsubstituted methoxy. In embodiments, $R^{20}$ is unsubstituted ethoxy. In embodiments, $R^{20}$ is unsubstituted propoxy. In embodiments, $R^{20}$ is unsubstituted n-propoxy. In embodiments, $R^{20}$ is unsubstituted isopropoxy. In embodiments, $R^{20}$ is unsubstituted butoxy. In embodiments, $R^{20}$ is unsubstituted n-butoxy. In embodiments, $R^{20}$ is unsubstituted tert-butoxy.

In embodiments, a substituted $R^{20}$ (e.g., substituted alkyl and/or substituted heteroalkyl) is substituted with at least one substituent group, size-limited substituent group, or lower substituent group; wherein if the substituted $R^{20}$ is substituted with a plurality of groups selected from substituent groups, size-limited substituent groups, and lower substituent groups; each substituent group, size-limited substituent group, and/or lower substituent group may optionally be different. In embodiments, when $R^{20}$ is substituted, it is substituted with at least one substituent group. In embodiments, when $R^{20}$ is substituted, it is substituted with at least one size-limited substituent group. In embodiments, when $R^{20}$ is substituted, it is substituted with at least one lower substituent group.

In embodiments, $R^{20A}$ is hydrogen. In embodiments, $R^{20A}$ is substituted or unsubstituted $C_1$-$C_{10}$ alkyl. In embodiments, $R^{20A}$ is substituted or unsubstituted 2 to 10 membered heteroalkyl. In embodiments, $R^{20A}$ is substituted or unsubstituted $C_1$-$C_{10}$ thiol-alkyl or substituted or unsubstituted 2 to 10 membered thiol-heteroalkyl. In embodiments, $R^{20A}$ is unsubstituted $C_1$-$C_{10}$ thiol-alkyl or unsubstituted 2 to 10 membered thiol-heteroalkyl.

In embodiments, a substituted $R^{20A}$ (e.g., substituted alkyl and/or substituted heteroalkyl) is substituted with at least one substituent group, size-limited substituent group, or lower substituent group; wherein if the substituted $R^{20A}$ is substituted with a plurality of groups selected from substituent groups, size-limited substituent groups, and lower substituent groups; each substituent group, size-limited substituent group, and/or lower substituent group may optionally be different. In embodiments, when $R^{20A}$ is substituted, it is substituted with at least one substituent group. In embodiments, when $R^{20A}$ is substituted, it is substituted with at least one size-limited substituent group. In embodiments, when $R^{20A}$ is substituted, it is substituted with at least one lower substituent group.

In embodiments, $R^{20A}$ is

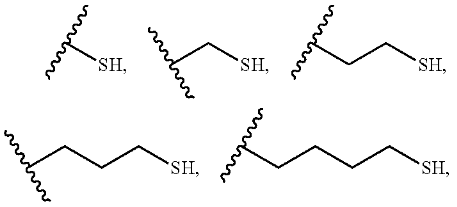

or

-continued

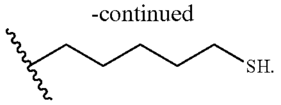

In embodiments, $R^{20B}$ is hydrogen. In embodiments, $R^{20B}$ is substituted or unsubstituted $C_1$-$C_{10}$ alkyl. In embodiments, $R^{20B}$ is substituted or unsubstituted 2 to 10 membered heteroalkyl. In embodiments, $R^{20B}$ is substituted or unsubstituted $C_1$-$C_{10}$ thiol-alkyl or substituted or unsubstituted 2 to 10 membered thiol-heteroalkyl. In embodiments, $R^{20B}$ is unsubstituted $C_1$-$C_{10}$ thiol-alkyl or unsubstituted 2 to 10 membered thiol-heteroalkyl. In embodiments, $R^{20B}$ is —C(O)-(substituted or unsubstituted $C_1$-$C_{10}$ alkyl). In embodiments, $R^{20B}$ is —C(O)-(substituted or unsubstituted $C_1$-$C_{10}$ thiol-alkyl). In embodiments, $R^B$ is —C(O)-(substituted or unsubstituted 2 to 10 membered thiol-heteroalkyl).

In embodiments, a substituted $R^{20B}$ (e.g., substituted alkyl and/or substituted heteroalkyl) is substituted with at least one substituent group, size-limited substituent group, or lower substituent group; wherein if the substituted $R^{20B}$ is substituted with a plurality of groups selected from substituent groups, size-limited substituent groups, and lower substituent groups; each substituent group, size-limited substituent group, and/or lower substituent group may optionally be different. In embodiments, when $R^{20B}$ is substituted, it is substituted with at least one substituent group. In embodiments, when $R^{20B}$ is substituted, it is substituted with at least one size-limited substituent group. In embodiments, when $R^{20B}$ is substituted, it is substituted with at least one lower substituent group.

In embodiments, $R^{20C}$ is hydrogen. In embodiments, $R^{20C}$ is substituted or unsubstituted $C_1$-$C_{10}$ alkyl. In embodiments, $R^{20C}$ is substituted or unsubstituted 2 to 10 membered heteroalkyl. In embodiments, $R^{20C}$ is substituted or unsubstituted $C_1$-$C_{10}$ thiol-alkyl or substituted or unsubstituted 2 to 10 membered thiol-heteroalkyl. In embodiments, $R^{20C}$ is unsubstituted $C_1$-$C_{10}$ thiol-alkyl or unsubstituted 2 to 10 membered thiol-heteroalkyl.

In embodiments, a substituted $R^{20C}$ (e.g., substituted alkyl and/or substituted heteroalkyl) is substituted with at least one substituent group, size-limited substituent group, or lower substituent group; wherein if the substituted $R^{20C}$ is substituted with a plurality of groups selected from substituent groups, size-limited substituent groups, and lower substituent groups; each substituent group, size-limited substituent group, and/or lower substituent group may optionally be different. In embodiments, when $R^{20C}$ is substituted, it is substituted with at least one substituent group. In embodiments, when $R^{20C}$ is substituted, it is substituted with at least one size-limited substituent group. In embodiments, when $R^{20C}$ is substituted, it is substituted with at least one lower substituent group.

In embodiments, the thiosaccharide compound has the formula:

(V-1)

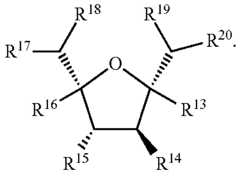

$R^{13}$, $R^{14}$, $R^{15}$, $R^{16}$, $R^{17}$, $R^{18}$, $R^{19}$, and $R^{20}$ are as described herein, including in embodiments.

In embodiments, the thiosaccharide compound has the formula:

(V-2)

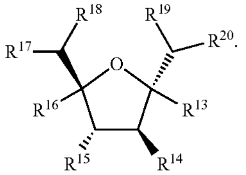

$R^{13}$, $R^{14}$, $R^{15}$, $R^{16}$, $R^{17}$, $R^{18}$, $R^{19}$, and $R^{20}$ are as described herein, including in embodiments.

In embodiments, $R^{13}$ is hydrogen, —$SR^{13A}$, —$OR^{13A}$, substituted or unsubstituted $C_1$-$C_{10}$ alkyl, or substituted or unsubstituted 2 to 10 membered heteroalkyl; $R^{14}$ is —$SR^{14A}$, —$OR^{14A}$, substituted or unsubstituted $C_1$-$C_{10}$ alkyl, or substituted or unsubstituted 2 to 10 membered heteroalkyl; $R^{15}$ is —$SR^{15A}$, —$OR^{15A}$, substituted or unsubstituted $C_1$-$C_{10}$ alkyl, or substituted or unsubstituted 2 to 10 membered heteroalkyl; $R^{16}$ is hydrogen, —$SR^{16A}$, —$OR^{16A}$, substituted or unsubstituted $C_1$-$C_{10}$ alkyl, or substituted or unsubstituted 2 to 10 membered heteroalkyl; $R^{17}$ is hydrogen, —$SR^{17A}$, —$OR^{17A}$, substituted or unsubstituted $C_1$-$C_{10}$ alkyl, or substituted or unsubstituted 2 to 10 membered heteroalkyl; $R^{18}$ is —$SR^{18A}$, —$OR^{18A}$, substituted or unsubstituted $C_1$-$C_{10}$ alkyl, or substituted or unsubstituted 2 to 10 membered heteroalkyl; $R^{19}$ is hydrogen, —$SR^{19A}$, —$OR^{19A}$, substituted or unsubstituted $C_1$-$C_{10}$ alkyl, or substituted or unsubstituted 2 to 10 membered heteroalkyl; and $R^{20}$ is —$SR^{20A}$, —$OR^{20A}$, substituted or unsubstituted $C_1$-$C_{10}$ alkyl, or substituted or unsubstituted 2 to 10 membered heteroalkyl.

In embodiments, $R^{13}$ is hydrogen, —$SR^{13A}$, —$OR^{13A}$, substituted or unsubstituted $C_1$-$C_{10}$ thiol-alkyl, or substituted or unsubstituted 2 to 10 membered thiol-heteroalkyl; $R^{14}$ is —$SR^{14A}$, —$OR^{14A}$, substituted or unsubstituted $C_1$-$C_{10}$ thiol-alkyl, or substituted or unsubstituted 2 to 10 membered thiol-heteroalkyl; $R^{15}$ is —$SR^{15A}$, —$OR^{15A}$, substituted or unsubstituted $C_1$-$C_{10}$ thiol-alkyl, or substituted or unsubstituted 2 to 10 membered thiol-heteroalkyl; $R^{16}$ is hydrogen, —$SR^{16A}$, —$OR^{16A}$, substituted or unsubstituted $C_1$-$C_{10}$ thiol-alkyl, or substituted or unsubstituted 2 to 10 membered thiol-heteroalkyl; $R^{17}$ is hydrogen, —$SR^{17A}$, —$OR^{17A}$, substituted or unsubstituted $C_1$-$C_{10}$ thiol-alkyl, or substituted or unsubstituted 2 to 10 membered thiol-heteroalkyl; $R^{18}$ is —$SR^{18A}$, —$OR^{18A}$, substituted or unsubstituted $C_1$-$C_{10}$ thiol-alkyl, or substituted or unsubstituted 2 to 10 membered thiol-heteroalkyl; $R^{19}$ is hydrogen, —$SR^{19A}$, —$OR^{19A}$, substituted or unsubstituted $C_1$-$C_{10}$ thiol-alkyl, or substituted or unsubstituted 2 to 10 membered thiol-heteroalkyl; and $R^{20}$ is —$SR^{20A}$, —$OR^{20A}$, substituted or unsubstituted $C_1$-$C_{10}$ thiol-alkyl, or substituted or unsubstituted 2 to 10 membered thiol-heteroalkyl.

In embodiments, $R^{13}$ is hydrogen, —$SR^{13A}$, or —$OR^{13A}$; $R^{14}$ is —$SR^{14A}$ or —$OR^{14A}$; $R^{15}$ is —$SR^{15A}$ or —$OR^{15A}$; $R^{16}$ is hydrogen, —$SR^{16A}$, or —$OR^{16A}$; $R^{18}$ is —$SR^{18A}$ or —$OR^{15A}$; and $R^{20}$ is —$SR^{20A}$ or —$OR^{20A}$. In embodiments, $R^{13}$ is hydrogen, —SH, or —OH; $R^{14}$ is —SH or —OH; $R^{15}$ is —SH or —OH; $R^{16}$ is hydrogen, —SH, or —OH; $R^{18}$ is —SH or —OH; and $R^{20}$ is —SH or —OH.

In embodiments, the thiosaccharide compound has the formula:

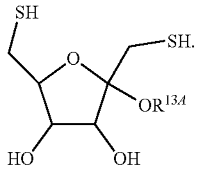

$R^{13A}$ is as described herein, including in embodiments.

In embodiments, the thiosaccharide compound has the formula:

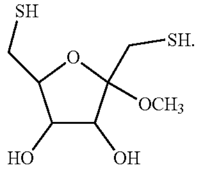 [SMILES: COC1(CS)OC(CS)C(O)C1O]

In embodiments, the thiosaccharide compound has the formula:

(VI)

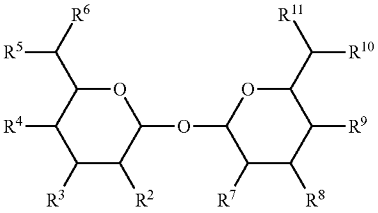

or (VII)

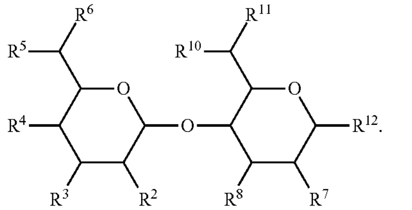

$R^2$, $R^3$, $R^4$, $R^5$, $R^6$ are as described herein, including in embodiments. $R^7$ is —$SR^{7A}$, —$OR^{7A}$, —$NR^{7B}R^{7C}$, —$NR^{7B}C(O)R^{7C}$, —$NR^{7B}C(O)OR^{7C}$, substituted or unsubstituted alkyl (e.g., $C_1$-$C_{10}$, $C_1$-$C_6$, $C_1$-$C_4$, or $C_1$-$C_2$), or substituted or unsubstituted heteroalkyl (e.g., 2 to 10 membered, 2 to 6 membered, 4 to 6 membered, or 2 to 3 membered). $R^8$ is —$SR^{8A}$, —$OR^{8A}$, —$NR^{8B}R^{8C}$, —$NR^{8B}C(O)R^{8C}$, —$NR^{8B}C(O)OR^{8C}$, substituted or unsubstituted alkyl (e.g., $C_1$-$C_{10}$, $C_1$-$C_6$, $C_1$-$C_4$, or $C_1$-$C_2$), or substituted or unsubstituted heteroalkyl (e.g., 2 to 10 membered, 2 to 6 membered, 4 to 6 membered, or 2 to 3 membered). $R^9$ is —$SR^{9A}$, —$SC(O)R^{9A}$, —$OR^{9A}$, —$NR^{9B}R^{9C}$, —$NR^{9B}C(O)R^{9C}$, —$NR^{9B}C(O)OR^{9C}$, substituted or unsubstituted alkyl (e.g., $C_1$-$C_{10}$, $C_1$-$C_6$, $C_1$-$C_4$, or $C_1$-$C_2$), or substituted or unsubstituted heteroalkyl (e.g., 2 to 10 membered, 2 to 6 membered, 4 to 6 membered, or 2 to 3 membered). $R^{10}$ is hydrogen, —$SR^{10A}$, —$SC(O)R^{10A}$, —$OR^{10A}$, —$NR^{10B}R^{10C}$, —$NR^{10B}C(O)R^{10C}$, —$NR^{10B}C(O)OR^{10C}$, substituted or unsubstituted alkyl (e.g., $C_1$-$C_{10}$, $C_1$-$C_6$, $C_1$-4, or $C_1$-$C_2$), or substituted or unsubstituted heteroalkyl (e.g., 2 to 10 membered, 2 to 6 membered, 4 to 6 membered, or 2 to 3 membered). $R^{11}$ is hydrogen, —$SR^{11A}$, —$OR^{11A}$, —$NR^{11B}R^{11C}$, —$NR^{11B}C(O)R^{11C}$, —$NR^{11B}C(O)OR^{11C}$, substituted or unsubstituted alkyl (e.g., $C_1$-$C_{10}$, $C_1$-$C_6$, $C_1$-$C_4$, or $C_1$-$C_2$), or substituted or unsubstituted heteroalkyl (e.g., 2 to 10 membered, 2 to 6 membered, 4 to 6 membered, or 2 to 3 membered). $R^{12}$ is —$SR^{12A}$, —$OR^{12A}$, —$NR^{12B}R^{12C}$, —$NR^{12B}C(O)R^{12C}$, —$NR^{12B}C(O)OR^{12C}$, substituted or unsubstituted alkyl (e.g., $C_1$-$C_{10}$, $C_1$-$C_6$, $C_1$-$C_4$, or $C_1$-$C_2$), or substituted or unsubstituted heteroalkyl (e.g., 2 to 10 membered, 2 to 6 membered, 4 to 6 membered, or 2 to 3 membered). $R^{7A}$, $R^{7B}$, $R^{7C}$, $R^{8A}$, $R^{8B}$, $R^{8C}$, $R^{9A}$, $R^{9B}$, $R^{9C}$, $R^{10A}$, $R^{10B}$, $R^{10C}$, $R^{11A}$, $R^{11B}$, $R^{11C}$, $R^{12A}$, $R^{12B}$, and $R^{12C}$ are each independently hydrogen, substituted or unsubstituted alkyl (e.g., $C_1$-$C_{10}$, $C_1$-$C_6$, $C_1$-4, or $C_1$-$C_2$), or substituted or unsubstituted heteroalkyl (e.g., 2 to 10 membered, 2 to 6 membered, 4 to 6 membered, or 2 to 3 membered).

In embodiments, the thiosaccharide compound has the formula:

(VI)

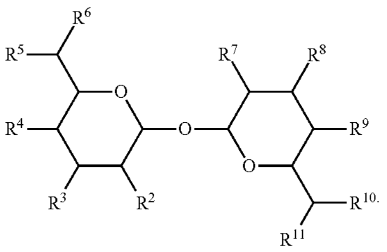

$R^2$, $R^3$, $R^4$, $R^5$, $R^6$, $R^7$, $R^8$, $R^9$, $R^{10}$, and $R^{11}$ are as described herein, including in embodiments.

In embodiments, the thiosaccharide compound has the formula:

(VII)

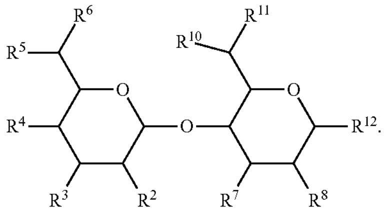

$R^2$, $R^3$, $R^4$, $R^5$, $R^6$, $R^7$, $R^8$, $R^{10}$, $R^{11}$, and $R^{12}$ are as described herein, including in embodiments.

In embodiments, $R^7$ is —$SR^{7A}$. In embodiments, $R^7$ is —$OR^{7A}$. In embodiments, $R^7$ is —$NR^{7B}R^{7C}$. In embodiments, $R^7$ is —$NR^{7B}C(O)R^{7C}$. In embodiments, $R^7$ is —$NR^{7B}C(O)OR^{7C}$. In embodiments, $R^7$ is —SH. In embodiments, $R^7$ is —OH. In embodiments, $R^7$ is —$NH_2$. In embodiments, $R^7$ is —NHC(O)H. In embodiments, $R^7$ is —$NHC(O)CH_3$. In embodiments, $R^7$ is —NHC(O)OH. In embodiments, $R^7$ is substituted or unsubstituted $C_1$-$C_{10}$ alkyl. In embodiments, $R^7$ is unsubstituted $C_1$-$C_5$ alkyl. In embodiments, $R^7$ is unsubstituted methyl. In embodiments, $R^7$ is unsubstituted ethyl. In embodiments, $R^7$ is unsubstituted propyl. In embodiments, $R^7$ is unsubstituted n-propyl. In embodiments, $R^7$ is unsubstituted isopropyl. In embodiments, $R^7$ is unsubstituted butyl. In embodiments, $R^7$ is unsubstituted n-butyl. In embodiments, $R^7$ is unsubstituted tert-butyl. In embodiments, $R^7$ is substituted or unsubstituted 2 to 10 membered heteroalkyl. In embodiments, $R^7$ is substituted or unsubstituted $C_1$-$C_{10}$ thiol-alkyl or substituted or unsubstituted 2 to 10 membered thiol-heteroalkyl. In embodiments, $R^7$ is unsubstituted $C_1$-$C_{10}$ thiol-alkyl or unsubstituted 2 to 10 membered thiol-heteroalkyl. In embodiments, $R^7$ is unsubstituted thiomethyl (e.g., —$CH_2SH$), unsubstituted thioethyl (e.g., —$(CH_2)_2SH$), unsubstituted thiopropyl (e.g., —$(CH_2)_3SH$), unsubstituted thiobutyl (e.g., —$(CH_2)_4SH$), unsubstituted thiopentyl (e.g., —$(CH_2)_5SH$), unsubstituted thiohexyl (e.g., —$(CH_2)_6SH$), unsubstituted thioheptyl (e.g., —$(CH_2)_7SH$), unsubstituted thiooctyl (e.g., —$(CH_2)_8SH$), unsubstituted thiononyl (e.g., —$(CH_2)_9SH$), or unsubstituted thiodecyl (e.g., —$(CH_2)_{10}SH$). In embodiments, $R^7$ is unsubstituted thioethyl. In embodiments, $R^7$ is unsubstituted thiopropyl. In embodiments, $R^7$ is unsubstituted thiobutyl. In embodiments, $R^7$ is unsubstituted thiopentyl. In embodiments, $R^7$ is unsubstituted alkoxy. In embodiments, $R^7$ is —O-(unsubstituted $C_1$-$C_4$ alkyl). In embodiments, $R^7$ is unsubstituted methoxy. In embodiments, $R^7$ is unsubstituted ethoxy. In embodiments, $R^7$ is unsubstituted propoxy. In embodiments, $R^7$ is unsubstituted n-propoxy. In embodiments, $R^7$ is unsubstituted isopropoxy. In embodiments, $R^7$ is unsubstituted butoxy. In embodiments, $R^7$ is unsubstituted n-butoxy. In embodiments, $R^7$ is unsubstituted tert-butoxy.

In embodiments, a substituted $R^7$ (e.g., substituted alkyl and/or substituted heteroalkyl) is substituted with at least one substituent group, size-limited substituent group, or lower substituent group; wherein if the substituted $R^7$ is substituted with a plurality of groups selected from substituent groups, size-limited substituent groups, and lower substituent groups; each substituent group, size-limited substituent group, and/or lower substituent group may optionally be different. In embodiments, when $R^7$ is substituted, it is substituted with at least one substituent group. In embodiments, when $R^7$ is substituted, it is substituted with at least one size-limited substituent group. In embodiments, when $R^7$ is substituted, it is substituted with at least one lower substituent group.

In embodiments, $R^{7A}$ is hydrogen. In embodiments, $R^{7A}$ is substituted or unsubstituted $C_1$-$C_{10}$ alkyl. In embodiments, $R^{7A}$ is substituted or unsubstituted 2 to 10 membered heteroalkyl. In embodiments, $R^{7A}$ is substituted or unsubstituted $C_1$-$C_{10}$ thiol-alkyl or substituted or unsubstituted 2 to 10 membered thiol-heteroalkyl. In embodiments, $R^{7A}$ is unsubstituted $C_1$-$C_{10}$ thiol-alkyl or unsubstituted 2 to 10 membered thiol-heteroalkyl.

In embodiments, a substituted $R^{7A}$ (e.g., substituted alkyl and/or substituted heteroalkyl) is substituted with at least one substituent group, size-limited substituent group, or lower substituent group; wherein if the substituted $R^{7A}$ is substituted with a plurality of groups selected from substituent groups, size-limited substituent groups, and lower substituent groups; each substituent group, size-limited substituent group, and/or lower substituent group may optionally be different. In embodiments, when $R^{7A}$ is substituted, it is substituted with at least one substituent group. In embodiments, when $R^{7A}$ is substituted, it is substituted with at least one size-limited substituent group. In embodiments, when $R^{7A}$ is substituted, it is substituted with at least one lower substituent group.

In embodiments, $R^{7A}$ is

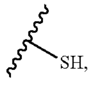,

-continued

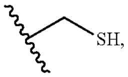,

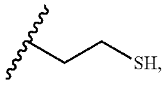,

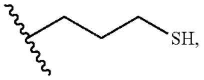,

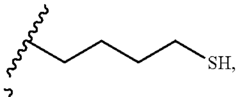, or

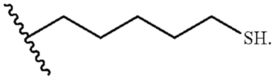.

In embodiments, $R^{7B}$ is hydrogen. In embodiments, $R^{7B}$ is substituted or unsubstituted $C_1$-$C_{10}$ alkyl. In embodiments, $R^{7B}$ is substituted or unsubstituted 2 to 10 membered heteroalkyl. In embodiments, $R^{7B}$ is substituted or unsubstituted $C_1$-$C_{10}$ thiol-alkyl or substituted or unsubstituted 2 to 10 membered thiol-heteroalkyl. In embodiments, $R^{7B}$ is unsubstituted $C_1$-$C_{10}$ thiol-alkyl or unsubstituted 2 to 10 membered thiol-heteroalkyl. In embodiments, $R^7$ is —C(O)-(substituted or unsubstituted $C_1$-$C_{10}$ alkyl). In embodiments, $R^{7B}$ is —C(O)-(substituted or unsubstituted $C_1$-$C_{10}$ thiol-alkyl). In embodiments, $R^{7B}$ is —C(O)-(substituted or unsubstituted 2 to 10 membered thiol-heteroalkyl).

In embodiments, a substituted $R^{7B}$ (e.g., substituted alkyl and/or substituted heteroalkyl) is substituted with at least one substituent group, size-limited substituent group, or lower substituent group; wherein if the substituted $R^{7B}$ is substituted with a plurality of groups selected from substituent groups, size-limited substituent groups, and lower substituent groups; each substituent group, size-limited substituent group, and/or lower substituent group may optionally be different. In embodiments, when $R^{7B}$ is substituted, it is substituted with at least one substituent group. In embodiments, when $R^{7B}$ is substituted, it is substituted with at least one size-limited substituent group. In embodiments, when $R^{7B}$ is substituted, it is substituted with at least one lower substituent group.

In embodiments, $R^{7C}$ is hydrogen. In embodiments, $R^{7C}$ is substituted or unsubstituted $C_1$-$C_{10}$ alkyl. In embodiments, $R^{7C}$ is substituted or unsubstituted 2 to 10 membered heteroalkyl. In embodiments, $R^{7C}$ is substituted or unsubstituted $C_1$-$C_{10}$ thiol-alkyl or substituted or unsubstituted 2 to 10 membered thiol-heteroalkyl. In embodiments, $R^{7C}$ is unsubstituted $C_1$-$C_{10}$ thiol-alkyl or unsubstituted 2 to 10 membered thiol-heteroalkyl.

In embodiments, a substituted $R^{7C}$ (e.g., substituted alkyl and/or substituted heteroalkyl) is substituted with at least one substituent group, size-limited substituent group, or lower substituent group; wherein if the substituted $R^{7C}$ is substituted with a plurality of groups selected from substituent groups, size-limited substituent groups, and lower substituent groups; each substituent group, size-limited substituent group, and/or lower substituent group may optionally be different. In embodiments, when $R^{7C}$ is substituted, it is substituted with at least one substituent group. In embodiments, when $R^{7C}$ is substituted, it is substituted with at least one size-limited substituent group. In embodiments, when $R^{7C}$ is substituted, it is substituted with at least one lower substituent group.

In embodiments, $R^8$ is —$SR^{8A}$. In embodiments, $R^8$ is —$OR^{8A}$. In embodiments, $R^8$ is —$NR^{8B}R^{8C}$. In embodiments, $R^8$ is —$NR^{8B}C(O)R^{8C}$. In embodiments, $R^8$ is —$NR^{8B}C(O)OR^{8C}$. In embodiments, $R^8$ is —SH. In embodiments, $R^8$ is —OH. In embodiments, $R^8$ is —$NH_2$. In embodiments, $R^8$ is —NHC(O)H. In embodiments, $R^8$ is —NHC(O)OH. In embodiments, $R^8$ is substituted or unsubstituted $C_1$-$C_{10}$ alkyl. In embodiments, $R^8$ is unsubstituted $C_1$-$C_5$ alkyl. In embodiments, $R^8$ is unsubstituted methyl. In embodiments, $R^8$ is unsubstituted ethyl. In embodiments, $R^8$ is unsubstituted propyl. In embodiments, $R^8$ is unsubstituted n-propyl. In embodiments, $R^8$ is unsubstituted isopropyl. In embodiments, $R^8$ is unsubstituted butyl. In embodiments, $R^8$ is unsubstituted n-butyl. In embodiments, $R^8$ is unsubstituted tert-butyl. In embodiments, $R^8$ is substituted or unsubstituted 2 to 10 membered heteroalkyl. In embodiments, $R^8$ is substituted or unsubstituted $C_1$-$C_{10}$ thiol-alkyl or substituted or unsubstituted 2 to 10 membered thiol-heteroalkyl. In embodiments, $R^8$ is unsubstituted $C_1$-$C_{10}$ thiol-alkyl or unsubstituted 2 to 10 membered thiol-heteroalkyl. In embodiments, $R^8$ is unsubstituted thiomethyl (e.g., —$CH_2SH$), unsubstituted thioethyl (e.g., —$(CH_2)_2SH$), unsubstituted thiopropyl (e.g., —$(CH_2)_3SH$), unsubstituted thiobutyl (e.g., —$(CH_2)_4SH$), unsubstituted thiopentyl (e.g., —$(CH_2)_5SH$), unsubstituted thiohexyl (e.g., —$(CH_2)_6SH$), unsubstituted thioheptyl (e.g., —$(CH_2)_7SH$), unsubstituted thiooctyl (e.g., —$(CH_2)_8SH$), unsubstituted thiononyl (e.g., —$(CH_2)_9SH$), or unsubstituted thiodecyl (e.g., —$(CH_2)_{10}$SH). In embodiments, $R^8$ is unsubstituted thioethyl. In embodiments, $R^8$ is unsubstituted thiopropyl. In embodiments, $R^8$ is unsubstituted thiobutyl. In embodiments, $R^8$ is unsubstituted thiopentyl. In embodiments, $R^8$ is unsubstituted alkoxy. In embodiments, $R^8$ is —O-(unsubstituted $C_1$-$C_4$ alkyl). In embodiments, $R^8$ is unsubstituted methoxy. In embodiments, $R^8$ is unsubstituted ethoxy. In embodiments, $R^8$ is unsubstituted propoxy. In embodiments, $R^8$ is unsubstituted n-propoxy. In embodiments, $R^8$ is unsubstituted isopropoxy. In embodiments, $R^8$ is unsubstituted butoxy. In embodiments, $R^8$ is unsubstituted n-butoxy. In embodiments, $R^8$ is unsubstituted tert-butoxy.

In embodiments, a substituted $R^8$ (e.g., substituted alkyl and/or substituted heteroalkyl) is substituted with at least one substituent group, size-limited substituent group, or lower substituent group; wherein if the substituted $R^8$ is substituted with a plurality of groups selected from substituent groups, size-limited substituent groups, and lower substituent groups; each substituent group, size-limited substituent group, and/or lower substituent group may optionally be different. In embodiments, when $R^8$ is substituted, it is substituted with at least one substituent group. In embodiments, when $R^8$ is substituted, it is substituted with at least one size-limited substituent group. In embodiments, when $R^8$ is substituted, it is substituted with at least one lower substituent group.

In embodiments, $R^{8A}$ is hydrogen. In embodiments, $R^{8A}$ is substituted or unsubstituted $C_1$-$C_{10}$ alkyl. In embodiments, $R^{8A}$ is substituted or unsubstituted 2 to 10 membered heteroalkyl. In embodiments, $R^{8A}$ is substituted or unsubstituted $C_1$-$C_{10}$ thiol-alkyl or substituted or unsubstituted 2 to 10 membered thiol-heteroalkyl. In embodiments, $R^{8A}$ is unsubstituted $C_1$-$C_{10}$ thiol-alkyl or unsubstituted 2 to 10 membered thiol-heteroalkyl.

In embodiments, a substituted $R^{8A}$ (e.g., substituted alkyl and/or substituted heteroalkyl) is substituted with at least one substituent group, size-limited substituent group, or lower substituent group; wherein if the substituted $R^{8A}$ is substituted with a plurality of groups selected from substituent groups, size-limited substituent groups, and lower substituent groups; each substituent group, size-limited substituent group, and/or lower substituent group may optionally be different. In embodiments, when $R^{8A}$ is substituted, it is substituted with at least one substituent group. In embodiments, when $R^{8A}$ is substituted, it is substituted with at least one size-limited substituent group. In embodiments, when $R^{8A}$ is substituted, it is substituted with at least one lower substituent group.

In embodiments, $R^{8A}$ is

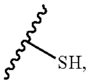
,
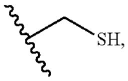
,
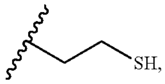
,
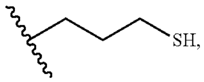
,
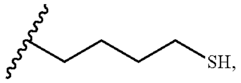
, or
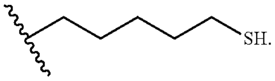
.

In embodiments, $R^{8B}$ is hydrogen. In embodiments, $R^{8B}$ is substituted or unsubstituted $C_1$-$C_{10}$ alkyl. In embodiments, $R^{8B}$ is substituted or unsubstituted 2 to 10 membered heteroalkyl. In embodiments, $R^{8B}$ is substituted or unsubstituted $C_1$-$C_{10}$ thiol-alkyl or substituted or unsubstituted 2 to 10 membered thiol-heteroalkyl. In embodiments, $R^{8B}$ is unsubstituted $C_1$-$C_{10}$ thiol-alkyl or unsubstituted 2 to 10 membered thiol-heteroalkyl. In embodiments, $R^{8B}$ is —C(O)-(substituted or unsubstituted $C_1$-$C_{10}$ alkyl). In embodiments, $R^{8B}$ is —C(O)-(substituted or unsubstituted $C_1$-$C_{10}$ thiol-alkyl). In embodiments, $R^{8B}$ is —C(O)-(substituted or unsubstituted 2 to 10 membered thiol-heteroalkyl).

In embodiments, a substituted $R^{8B}$ (e.g., substituted alkyl and/or substituted heteroalkyl) is substituted with at least one substituent group, size-limited substituent group, or lower substituent group; wherein if the substituted $R^{8B}$ is substituted with a plurality of groups selected from substituent groups, size-limited substituent groups, and lower substituent groups; each substituent group, size-limited substituent group, and/or lower substituent group may optionally be different. In embodiments, when $R^{8B}$ is substituted, it is substituted with at least one substituent group. In embodiments, when $R^{8B}$ is substituted, it is substituted with at least one size-limited substituent group. In embodiments, when $R^{8B}$ is substituted, it is substituted with at least one lower substituent group.

In embodiments, $R^{8C}$ is hydrogen. In embodiments, $R^{8C}$ is substituted or unsubstituted $C_1$-$C_{10}$ alkyl. In embodiments, $R^{8C}$ is substituted or unsubstituted 2 to 10 membered heteroalkyl. In embodiments, $R^{8C}$ is substituted or unsubstituted $C_1$-$C_{10}$ thiol-alkyl or substituted or unsubstituted 2 to 10 membered thiol-heteroalkyl. In embodiments, $R^{8C}$ is unsubstituted $C_1$-$C_{10}$ thiol-alkyl or unsubstituted 2 to 10 membered thiol-heteroalkyl.

In embodiments, a substituted $R^{8C}$ (e.g., substituted alkyl and/or substituted heteroalkyl) is substituted with at least one substituent group, size-limited substituent group, or lower substituent group; wherein if the substituted $R^{8C}$ is substituted with a plurality of groups selected from substituent groups, size-limited substituent groups, and lower substituent groups; each substituent group, size-limited substituent group, and/or lower substituent group may optionally be different. In embodiments, when $R^{8C}$ is substituted, it is substituted with at least one substituent group. In embodiments, when $R^{8C}$ is substituted, it is substituted with at least one size-limited substituent group. In embodiments, when $R^{8C}$ is substituted, it is substituted with at least one lower substituent group.

In embodiments, $R^9$ is —$SR^{9A}$. In embodiments, $R^9$ is —$SC(O)R^{9A}$. In embodiments, $R^9$ is —$OR^{9A}$. In embodiments, $R^9$ is —$NR^{9B}R^{9C}$. In embodiments, $R^9$ is —$NR^{9B}C(O)R^{9C}$. In embodiments, $R^9$ is —$NR^{9B}C(O)OR^{9C}$. In embodiments, $R^9$ is —SH. In embodiments, $R^9$ is —$SC(O)CH_3$. In embodiments, $R^9$ is —OH. In embodiments, $R^9$ is —$NH_2$. In embodiments, $R^9$ is —NHC(O)H. In embodiments, $R^9$ is —NHC(O)OH. In embodiments, $R^9$ is substituted or unsubstituted $C_1$-$C_{10}$ alkyl. In embodiments, $R^9$ is unsubstituted $C_1$-$C_5$ alkyl. In embodiments, $R^9$ is unsubstituted methyl. In embodiments, $R^9$ is unsubstituted ethyl. In embodiments, $R^9$ is unsubstituted propyl. In embodiments, $R^9$ is unsubstituted n-propyl. In embodiments, $R^9$ is unsubstituted isopropyl. In embodiments, $R^9$ is unsubstituted butyl. In embodiments, $R^9$ is unsubstituted n-butyl. In embodiments, $R^9$ is unsubstituted tert-butyl. In embodiments, $R^9$ is substituted or unsubstituted 2 to 10 membered heteroalkyl. In embodiments, $R^9$ is substituted or unsubstituted $C_1$-$C_{10}$ thiol-alkyl or substituted or unsubstituted 2 to 10 membered thiol-heteroalkyl. In embodiments, $R^9$ is unsubstituted $C_1$-$C_{10}$ thiol-alkyl or unsubstituted 2 to 10 membered thiol-heteroalkyl. In embodiments, $R^9$ is unsubstituted thiomethyl (e.g., —$CH_2SH$), unsubstituted thioethyl (e.g., —$(CH_2)_2SH$), unsubstituted thiopropyl (e.g., —$(CH_2)_3$ SH), unsubstituted thiobutyl (e.g., —$(CH_2)_4SH$), unsubstituted thiopentyl (e.g., —$(CH_2)_5SH$), unsubstituted thiohexyl (e.g., —$(CH_2)_6SH$), unsubstituted thioheptyl (e.g., —$(CH_2)_7SH$), unsubstituted thiooctyl (e.g., —$(CH_2)_8SH$), unsubstituted thiononyl (e.g., —$(CH_2)_9SH$), or unsubstituted thiodecyl (e.g., —$(CH_2)_{10}SH$). In embodiments, $R^9$ is unsubstituted thioethyl. In embodiments, $R^9$ is unsubstituted thiopropyl.

In embodiments, $R^9$ is unsubstituted thiobutyl. In embodiments, $R^9$ is unsubstituted thiopentyl. In embodiments, $R^9$ is unsubstituted alkoxy. In embodiments, $R^9$ is —O-(unsubstituted $C_1$-$C_4$ alkyl). In embodiments, $R^9$ is unsubstituted methoxy. In embodiments, $R^9$ is unsubstituted ethoxy. In embodiments, $R^9$ is unsubstituted propoxy. In embodiments, $R^9$ is unsubstituted n-propoxy. In embodiments, $R^9$ is unsubstituted isopropoxy. In embodiments, $R^9$ is unsubstituted butoxy. In embodiments, $R^9$ is unsubstituted n-butoxy. In embodiments, $R^9$ is unsubstituted tert-butoxy.

In embodiments, a substituted $R^9$ (e.g., substituted alkyl and/or substituted heteroalkyl) is substituted with at least one substituent group, size-limited substituent group, or lower substituent group; wherein if the substituted $R^9$ is substituted with a plurality of groups selected from substituent groups, size-limited substituent groups, and lower substituent groups; each substituent group, size-limited substituent group, and/or lower substituent group may optionally be different. In embodiments, when $R^9$ is substituted, it is substituted with at least one substituent group. In embodiments, when $R^9$ is substituted, it is substituted with at least one size-limited substituent group. In embodiments, when $R^9$ is substituted, it is substituted with at least one lower substituent group.

In embodiments, $R^{9A}$ is hydrogen. In embodiments, $R^{9A}$ is substituted or unsubstituted $C_1$-$C_{10}$ alkyl. In embodiments, $R^{9A}$ is substituted or unsubstituted 2 to 10 membered heteroalkyl. In embodiments, $R^{9A}$ is substituted or unsubstituted $C_1$-$C_{10}$ thiol-alkyl or substituted or unsubstituted 2 to 10 membered thiol-heteroalkyl. In embodiments, $R^{9A}$ is unsubstituted $C_1$-$C_{10}$ thiol-alkyl or unsubstituted 2 to 10 membered thiol-heteroalkyl.

In embodiments, a substituted $R^{9A}$ (e.g., substituted alkyl and/or substituted heteroalkyl) is substituted with at least one substituent group, size-limited substituent group, or lower substituent group; wherein if the substituted $R^{9A}$ is substituted with a plurality of groups selected from substituent groups, size-limited substituent groups, and lower substituent groups; each substituent group, size-limited substituent group, and/or lower substituent group may optionally be different. In embodiments, when $R^{9A}$ is substituted, it is substituted with at least one substituent group. In embodiments, when $R^{9A}$ is substituted, it is substituted with at least one size-limited substituent group. In embodiments, when $R^{9A}$ is substituted, it is substituted with at least one lower substituent group.

In embodiments, $R^{9A}$ is

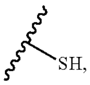,

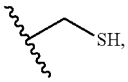,

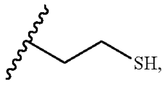,

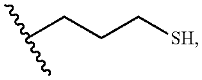,

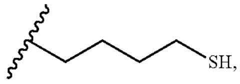, or

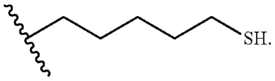.

In embodiments, $R^{9B}$ is hydrogen. In embodiments, $R^{9B}$ is substituted or unsubstituted $C_1$-$C_{10}$ alkyl. In embodiments, $R^{9B}$ is substituted or unsubstituted 2 to 10 membered heteroalkyl. In embodiments, $R^{9B}$ is substituted or unsubstituted $C_1$-$C_{10}$ thiol-alkyl or substituted or unsubstituted 2 to 10 membered thiol-heteroalkyl. In embodiments, $R^{9B}$ is unsubstituted $C_1$-$C_{10}$ thiol-alkyl or unsubstituted 2 to 10 membered thiol-heteroalkyl. In embodiments, $R^{9B}$ is —C(O)-(substituted or unsubstituted $C_1$-$C_{10}$ alkyl). In embodiments, $R^{9B}$ is —C(O)-(substituted or unsubstituted $C_1$-$C_{10}$ thiol-alkyl). In embodiments, $R^{9B}$ is —C(O)-(substituted or unsubstituted 2 to 10 membered thiol-heteroalkyl).

In embodiments, a substituted $R^{9B}$ (e.g., substituted alkyl and/or substituted heteroalkyl) is substituted with at least one substituent group, size-limited substituent group, or lower substituent group; wherein if the substituted $R^{9B}$ is substituted with a plurality of groups selected from substituent groups, size-limited substituent groups, and lower substituent groups; each substituent group, size-limited substituent group, and/or lower substituent group may optionally be different. In embodiments, when $R^{9B}$ is substituted, it is substituted with at least one substituent group. In embodiments, when $R^{9B}$ is substituted, it is substituted with at least one size-limited substituent group. In embodiments, when $R^{9B}$ is substituted, it is substituted with at least one lower substituent group.

In embodiments, $R^{9C}$ is hydrogen. In embodiments, $R^{9C}$ is substituted or unsubstituted $C_1$-$C_{10}$ alkyl. In embodiments, $R^{9C}$ is substituted or unsubstituted 2 to 10 membered heteroalkyl. In embodiments, $R^{9C}$ is substituted or unsubstituted $C_1$-$C_{10}$ thiol-alkyl or substituted or unsubstituted 2 to 10 membered thiol-heteroalkyl. In embodiments, $R^{C}$ is unsubstituted $C_1$-$C_{10}$ thiol-alkyl or unsubstituted 2 to 10 membered thiol-heteroalkyl.

In embodiments, a substituted $R^{9C}$ (e.g., substituted alkyl and/or substituted heteroalkyl) is substituted with at least one substituent group, size-limited substituent group, or lower substituent group; wherein if the substituted $R^{9C}$ is substituted with a plurality of groups selected from substituent groups, size-limited substituent groups, and lower substituent groups; each substituent group, size-limited substituent group, and/or lower substituent group may optionally be different. In embodiments, when $R^{9C}$ is substituted, it is substituted with at least one substituent group. In embodiments, when $R^{9C}$ is substituted, it is substituted with at least one size-limited substituent group. In embodiments, when $R^{9C}$ is substituted, it is substituted with at least one lower substituent group.

In embodiments, $R^{10}$ is —$SR^{10A}$. In embodiments, $R^{10}$ is —$SC(O)R^{10A}$. In embodiments, $R^{10}$ is —$OR^{10A}$. In embodiments, $R^{10}$ is —$NR^{10B}R^{10C}$. In embodiments, $R^{10}$ is —$NR^{10B}C(O)R^{10C}$. In embodiments, $R^{10}$ is —$NR^{10B}C(O)OR^{10C}$. In embodiments, $R^{10}$ is —SH. In embodiments, $R^{10}$ is —$SC(O)CH_3$. In embodiments, $R^{10}$ is —OH. In embodiments, $R^{10}$ is —$NH_2$. In embodiments, $R^{10}$ is —NHC(O)H. In embodiments, $R^{10}$ is —NHC(O)OH. In embodiments, $R^{10}$ is substituted or unsubstituted $C_1$-$C_{10}$ alkyl. In embodiments, $R^{10}$ is unsubstituted $C_1$-$C_5$ alkyl. In embodiments, $R^{10}$ is unsubstituted methyl. In embodiments, $R^{10}$ is unsubstituted ethyl. In embodiments, $R^{10}$ is unsubstituted propyl. In embodiments, $R^{10}$ is unsubstituted n-propyl. In embodiments, $R^{10}$ is unsubstituted isopropyl. In embodiments, $R^{10}$ is unsubstituted butyl. In embodiments, $R^{10}$ is unsubstituted n-butyl. In embodiments, $R^{10}$ is unsubstituted tert-butyl. In embodiments, $R^{10}$ is substituted or unsubstituted 2 to 10 membered heteroalkyl. In embodiments, $R^{10}$ is substituted or unsubstituted $C_1$-$C_{10}$ thiol-alkyl or substituted or unsubstituted 2 to 10 membered thiol-heteroalkyl. In embodiments, $R^{10}$ is unsubstituted $C_1$-$C_{10}$ thiol-alkyl or unsubstituted 2 to 10 membered thiol-heteroalkyl. In embodiments, $R^{10}$ is unsubstituted thiomethyl (e.g., —$CH_2SH$), unsubstituted thioethyl (e.g., —$(CH_2)_2SH$), unsubstituted thiopropyl (e.g., —$(CH_2)_3SH$), unsubstituted thiobutyl (e.g., —$(CH_2)_4SH$), unsubstituted thiopentyl (e.g., —$(CH_2)_5SH$), unsubstituted thiohexyl (e.g., —$(CH_2)_6SH$), unsubstituted thioheptyl (e.g., —$(CH_2)_7SH$), unsubstituted thiooctyl (e.g., —$(CH_2)_8SH$), unsubstituted thiononyl (e.g., —$(CH_2)_9SH$), or unsubstituted thiodecyl (e.g., —$(CH_2)_{10}SH$). In embodiments, $R^{10}$ is unsubstituted thioethyl. In embodiments, $R^{10}$ is unsubstituted thiopropyl. In embodiments, $R^{10}$ is unsubstituted thiobutyl. In embodiments, $R^{10}$ is unsubstituted thiopentyl. In embodiments, $R^{10}$ is unsubstituted alkoxy. In embodiments, $R^{10}$ is —O-(unsubstituted $C_1$-$C_4$ alkyl). In embodiments, $R^{10}$ is unsubstituted methoxy. In embodiments, $R^{10}$ is unsubstituted ethoxy. In embodiments, $R^{10}$ is unsubstituted propoxy. In embodiments, $R^{10}$ is unsubstituted n-propoxy. In embodiments, $R^{10}$ is unsubstituted isopropoxy. In embodiments, $R^{10}$ is unsubstituted butoxy. In embodiments, $R^{10}$ is unsubstituted n-butoxy. In embodiments, $R^{10}$ is unsubstituted tert-butoxy.

In embodiments, a substituted $R^{10}$ (e.g., substituted alkyl and/or substituted heteroalkyl) is substituted with at least one substituent group, size-limited substituent group, or lower substituent group; wherein if the substituted $R^{10}$ is substituted with a plurality of groups selected from substituent groups, size-limited substituent groups, and lower substituent groups; each substituent group, size-limited substituent group, and/or lower substituent group may optionally be different. In embodiments, when $R^{10}$ is substituted, it is substituted with at least one substituent group. In embodiments, when $R^{10}$ is substituted, it is substituted with at least one size-limited substituent group. In embodiments, when $R^{10}$ is substituted, it is substituted with at least one lower substituent group.

In embodiments, $R^{10A}$ is hydrogen. In embodiments, $R^{10A}$ is substituted or unsubstituted $C_1$-$C_{10}$ alkyl. In embodiments, $R^{10A}$ is unsubstituted $C_1$-$C_{10}$ alkyl. IIn embodiments, $R^{10A}$ is unsubstituted methyl. In embodiments, $R^{10A}$ is unsubstituted ethyl. In embodiments, $R^{10A}$ is unsubstituted propyl. In embodiments, $R^{10A}$ is unsubstituted n-propyl. In embodiments, $R^{10A}$ is unsubstituted isopropyl. In embodiments, $R^{10A}$ is unsubstituted butyl. In embodiments, $R^{10A}$ is unsubstituted n-butyl. In embodiments, $R^{10A}$ is unsubstituted tert-butyl. In embodiments, $R^{10A}$ is substituted or unsubstituted 2 to 10 membered heteroalkyl. In embodiments, $R^{10A}$ is substituted or unsubstituted $C_1$-$C_{10}$ thiol-alkyl or substituted or unsubstituted 2 to 10 membered thiol-heteroalkyl. In embodiments, $R^{10A}$ is unsubstituted $C_1$-$C_{10}$ thiol-alkyl or unsubstituted 2 to 10 membered thiol-heteroalkyl. In embodiments, $R^{10A}$ is unsubstituted thiomethyl (e.g., —$CH_2SH$), unsubstituted thioethyl (e.g., —$(CH_2)_2SH$), unsubstituted thiopropyl (e.g., —$(CH_2)_3SH$), unsubstituted thiobutyl (e.g., —$(CH_2)_4SH$), unsubstituted thiopentyl (e.g., —$(CH_2)_5SH$), unsubstituted thiohexyl (e.g., —$(CH_2)_6SH$), unsubstituted thioheptyl (e.g., —$(CH_2)_7SH$), unsubstituted thiooctyl (e.g., —$(CH_2)_8SH$), unsubstituted thiononyl (e.g., —$(CH_2)_9SH$), or unsubstituted thiodecyl (e.g., —$(CH_2)_{10}SH$). In embodiments, $R^{10A}$ is unsubstituted thioethyl. In embodiments, $R^{10A}$ is unsubstituted thiopropyl. In embodiments, $R^{10A}$ is unsubstituted thiobutyl. In embodiments, $R^{10A}$ is unsubstituted thiopentyl.

In embodiments, a substituted $R^{10A}$ (e.g., substituted alkyl and/or substituted heteroalkyl) is substituted with at least one substituent group, size-limited substituent group, or lower substituent group; wherein if the substituted $R^{10A}$ is substituted with a plurality of groups selected from substituent groups, size-limited substituent groups, and lower substituent groups; each substituent group, size-limited substituent group, and/or lower substituent group may optionally be different. In embodiments, when $R^{10A}$ is substituted, it is substituted with at least one substituent group. In embodiments, when $R^{10A}$ is substituted, it is substituted with at least one size-limited substituent group. In embodiments, when $R^{10A}$ is substituted, it is substituted with at least one lower substituent group.

In embodiments, $R^{10A}$ is

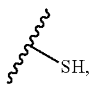

-continued

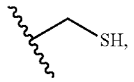

,

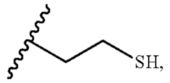

,

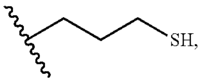

,

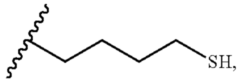

, or

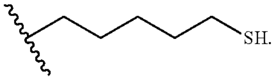

.

In embodiments, $R^{10B}$ is hydrogen. In embodiments, $R^{10B}$ is substituted or unsubstituted $C_1$-$C_{10}$ alkyl. In embodiments, $R^{10B}$ is substituted or unsubstituted 2 to 10 membered heteroalkyl. In embodiments, $R^{10B}$ is substituted or unsubstituted $C_1$-$C_{10}$ thiol-alkyl or substituted or unsubstituted 2 to 10 membered thiol-heteroalkyl. In embodiments, $R^{10B}$ is unsubstituted $C_1$-$C_{10}$ thiol-alkyl or unsubstituted 2 to 10 membered thiol-heteroalkyl. In embodiments, $R^{10B}$ is —C(O)-(substituted or unsubstituted $C_1$-$C_{10}$ alkyl). In embodiments, $R^{10B}$ is —C(O)-(substituted or unsubstituted $C_1$-$C_{10}$ thiol-alkyl). In embodiments, $R^{10B}$ is —C(O)-(substituted or unsubstituted 2 to 10 membered thiol-heteroalkyl).

In embodiments, a substituted $R^{10B}$(e.g., substituted alkyl and/or substituted heteroalkyl) is substituted with at least one substituent group, size-limited substituent group, or lower substituent group; wherein if the substituted $R^{10B}$ is substituted with a plurality of groups selected from substituent groups, size-limited substituent groups, and lower substituent groups; each substituent group, size-limited substituent group, and/or lower substituent group may optionally be different. In embodiments, when $R^{10B}$ is substituted, it is substituted with at least one substituent group. In embodiments, when $R^{10B}$ is substituted, it is substituted with at least one size-limited substituent group. In embodiments, when $R^{10B}$ is substituted, it is substituted with at least one lower substituent group.

In embodiments, $R^{10C}$ is hydrogen. In embodiments, $R^{10C}$ is substituted or unsubstituted $C_1$-$C_{10}$ alkyl. In embodiments, $R^{10C}$ is substituted or unsubstituted 2 to 10 membered heteroalkyl. In embodiments, $R^{10C}$ is substituted or unsubstituted $C_1$-$C_{10}$ thiol-alkyl or substituted or unsubstituted 2 to 10 membered thiol-heteroalkyl. In embodiments, $R^{10C}$ is unsubstituted $C_1$-$C_{10}$ thiol-alkyl or unsubstituted 2 to 10 membered thiol-heteroalkyl.

In embodiments, a substituted $R^{10C}$ (e.g., substituted alkyl and/or substituted heteroalkyl) is substituted with at least one substituent group, size-limited substituent group, or lower substituent group; wherein if the substituted $R^{10C}$ is substituted with a plurality of groups selected from substituent groups, size-limited substituent groups, and lower substituent groups; each substituent group, size-limited substituent group, and/or lower substituent group may optionally be different. In embodiments, when $R^{10C}$ is substituted, it is substituted with at least one substituent group. In embodiments, when $R^{10C}$ is substituted, it is substituted with at least one size-limited substituent group. In embodiments, when $R^{10C}$ is substituted, it is substituted with at least one lower substituent group.

In embodiments, $R^{11}$ is —$SR^{11A}$. In embodiments, $R^{11}$ is —$OR^{11A}$. In embodiments, $R^{11}$ is —$NR^{11B}R^{11C}$. In embodiments, $R^{11}$ is —$NR^{11B}C(O)R^{11C}$. In embodiments, $R^{11}$ is —$NR^{11B}C(O)OR^{11C}$. In embodiments, $R^{11}$ is —SH. In embodiments, $R^{11}$ is —OH. In embodiments, $R^{11}$ is —$NH_2$. In embodiments, $R^{11}$ is —NHC(O)H. In embodiments, $R^{11}$ is —NHC(O)OH. In embodiments, $R^{11}$ is substituted or unsubstituted $C_1$-$C_{10}$ alkyl. In embodiments, $R^{11}$ is unsubstituted $C_1$-$C_5$ alkyl. In embodiments, $R^{11}$ is unsubstituted methyl. In embodiments, $R^{11}$ is unsubstituted ethyl. In embodiments, $R^{11}$ is unsubstituted propyl. In embodiments, $R^{11}$ is unsubstituted n-propyl. In embodiments, $R^{11}$ is unsubstituted isopropyl. In embodiments, $R^{11}$ is unsubstituted butyl. In embodiments, $R^{11}$ is unsubstituted n-butyl. In embodiments, $R^{11}$ is unsubstituted tert-butyl. In embodiments, $R^{11}$ is substituted or unsubstituted 2 to 10 membered heteroalkyl. In embodiments, $R^{11}$ is substituted or unsubstituted $C_1$-$C_{10}$ thiol-alkyl or substituted or unsubstituted 2 to 10 membered thiol-heteroalkyl. In embodiments, $R^{11}$ is unsubstituted $C_1$-$C_{10}$ thiol-alkyl or unsubstituted 2 to 10 membered thiol-heteroalkyl. In embodiments, $R^{11}$ is unsubstituted thiomethyl (e.g., —$CH_2SH$), unsubstituted thioethyl (e.g., —$(CH_2)_2SH$), unsubstituted thiopropyl (e.g., —$(CH_2)_3$ SH), unsubstituted thiobutyl (e.g., —$(CH_2)_4SH$), unsubstituted thiopentyl (e.g., —$(CH_2)_5SH$), unsubstituted thiohexyl (e.g., —$(CH_2)_6SH$), unsubstituted thioheptyl (e.g., —$(CH_2)_7SH$), unsubstituted thiooctyl (e.g., —$(CH_2)_8SH$), unsubstituted thiononyl (e.g., —$(CH_2)_9SH$), or unsubstituted thiodecyl (e.g., —$(CH_2)_{10}SH$). In embodiments, $R^{11}$ is unsubstituted thioethyl. In embodiments, $R^{11}$ is unsubstituted thiopropyl. In embodiments, $R^{11}$ is unsubstituted thiobutyl. In embodiments, $R^{11}$ is unsubstituted thiopentyl. In embodiments, $R^{11}$ is unsubstituted alkoxy. In embodiments, $R^{11}$ is —O-(unsubstituted $C_1$-$C_4$ alkyl). In embodiments, $R^{11}$ is unsubstituted methoxy. In embodiments, $R^{11}$ is unsubstituted ethoxy. In embodiments, $R^{11}$ is unsubstituted propoxy. In embodiments, $R^{11}$ is unsubstituted n-propoxy. In embodiments, $R^{11}$ is unsubstituted isopropoxy. In embodiments, $R^{11}$ is unsubstituted butoxy. In embodiments, $R^{11}$ is unsubstituted n-butoxy. In embodiments, $R^{11}$ is unsubstituted tert-butoxy.

In embodiments, a substituted $R^{11}$ (e.g., substituted alkyl and/or substituted heteroalkyl) is substituted with at least one substituent group, size-limited substituent group, or lower substituent group; wherein if the substituted $R^{11}$ is substituted with a plurality of groups selected from substituent groups, size-limited substituent groups, and lower substituent groups; each substituent group, size-limited substituent group, and/or lower substituent group may optionally be different. In embodiments, when $R^{11}$ is substituted, it is substituted with at least one substituent group. In embodiments, when $R^{11}$ is substituted, it is substituted with at least one size-limited substituent group. In embodiments, when $R^{11}$ is substituted, it is substituted with at least one lower substituent group.

In embodiments, $R^{11A}$ is hydrogen. In embodiments, $R^{11A}$ is substituted or unsubstituted $C_1$-$C_{10}$ alkyl. In embodiments, $R^{11A}$ is unsubstituted $C_1$-$C_{10}$ alkyl. IIn embodiments, $R^{11A}$ is unsubstituted methyl. In embodiments, $R^{11A}$ is unsubstituted ethyl. In embodiments, $R^{11A}$ is unsubstituted propyl. In embodiments, $R^{11A}$ is unsubstituted n-propyl. In embodiments, $R^{11A}$ is unsubstituted isopropyl. In embodiments, $R^{11A}$ is unsubstituted butyl. In embodiments, $R^{11A}$ is unsubstituted n-butyl. In embodiments, $R^{11A}$ is unsubstituted tert-butyl. In embodiments, $R^{11A}$ is substituted or unsubstituted 2 to 10 membered heteroalkyl. In embodiments, $R^{11A}$ is substituted or unsubstituted $C_1$-$C_{10}$ thiol-alkyl or substituted or unsubstituted 2 to 10 membered thiol-heteroalkyl. In embodiments, $R^{11A}$ is unsubstituted $C_1$-$C_{10}$ thiol-alkyl or unsubstituted 2 to 10 membered thiol-heteroalkyl. In embodiments, $R^{11A}$ is unsubstituted thiomethyl (e.g., $—CH_2SH$), unsubstituted thioethyl (e.g., $—(CH_2)_2SH$), unsubstituted thiopropyl (e.g., $—(CH_2)_3SH$), unsubstituted thiobutyl (e.g., $—(CH_2)_4SH$), unsubstituted thiopentyl (e.g., $—(CH_2)_5SH$), unsubstituted thiohexyl (e.g., $—(CH_2)_6SH$), unsubstituted thioheptyl (e.g., $—(CH_2)_7SH$), unsubstituted thiooctyl (e.g., $—(CH_2)_8SH$), unsubstituted thiononyl (e.g., $—(CH_2)_9SH$), or unsubstituted thiodecyl (e.g., $—(CH_2)_{10}SH$). In embodiments, $R^{11A}$ is unsubstituted thioethyl. In embodiments, $R^{11A}$ is unsubstituted thiopropyl. In embodiments, $R^{11A}$ is unsubstituted thiobutyl. In embodiments, $R^{11A}$ is unsubstituted thiopentyl.

In embodiments, a substituted $R^{11A}$ (e.g., substituted alkyl and/or substituted heteroalkyl) is substituted with at least one substituent group, size-limited substituent group, or lower substituent group; wherein if the substituted $R^{11A}$ is substituted with a plurality of groups selected from substituent groups, size-limited substituent groups, and lower substituent groups; each substituent group, size-limited substituent group, and/or lower substituent group may optionally be different. In embodiments, when $R^{11A}$ is substituted, it is substituted with at least one substituent group. In embodiments, when $R^{11A}$ is substituted, it is substituted with at least one size-limited substituent group. In embodiments, when $R^{11A}$ is substituted, it is substituted with at least one lower substituent group.

In embodiments, $R^{11A}$ is

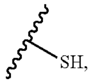
,
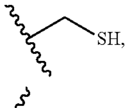
,
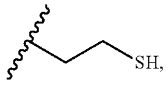
,
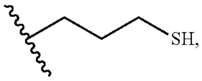
,
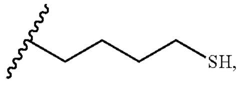
, or
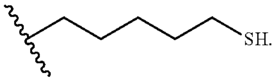
.

In embodiments, $R^{11B}$ is hydrogen. In embodiments, $R^{11B}$ is substituted or unsubstituted $C_1$-$C_{10}$ alkyl. In embodiments, $R^{11B}$ is substituted or unsubstituted 2 to 10 membered heteroalkyl. In embodiments, $R^{11B}$ is substituted or unsubstituted $C_1$-$C_{10}$ thiol-alkyl or substituted or unsubstituted 2 to 10 membered thiol-heteroalkyl. In embodiments, $R^{11B}$ is unsubstituted $C_1$-$C_{10}$ thiol-alkyl or unsubstituted 2 to 10 membered thiol-heteroalkyl. In embodiments, $R^{11B}$ is —C(O)-(substituted or unsubstituted $C_1$-$C_{10}$ alkyl). In embodiments, $R^{11B}$ is —C(O)-(substituted or unsubstituted $C_1$-$C_{10}$ thiol-alkyl). In embodiments, $R^{11B}$ is —C(O)-(substituted or unsubstituted 2 to 10 membered thiol-heteroalkyl).

In embodiments, a substituted $R^{11B}$ (e.g., substituted alkyl and/or substituted heteroalkyl) is substituted with at least one substituent group, size-limited substituent group, or lower substituent group; wherein if the substituted $R^{11B}$ is substituted with a plurality of groups selected from substituent groups, size-limited substituent groups, and lower substituent groups; each substituent group, size-limited substituent group, and/or lower substituent group may optionally be different. In embodiments, when $R^{1B}$ is substituted, itis substituted with at least one substituent group. In embodiments, when $R^{11B}$ is substituted, it is substituted with at least one size-limited substituent group. In embodiments, when $R^{11B}$ is substituted, it is substituted with at least one lower substituent group.

In embodiments, $R^{11C}$ is hydrogen. In embodiments, $R^{11C}$ is substituted or unsubstituted $C_1$-$C_{10}$ alkyl. In embodiments, $R^{11C}$ is substituted or unsubstituted 2 to 10 membered heteroalkyl. In embodiments, $R^{11C}$ is substituted or unsubstituted $C_1$-$C_{10}$ thiol-alkyl or substituted or unsubstituted 2 to 10 membered thiol-heteroalkyl. In embodiments, $R^{11C}$ is unsubstituted $C_1$-$C_{10}$ thiol-alkyl or unsubstituted 2 to 10 membered thiol-heteroalkyl.

In embodiments, a substituted $R^{11C}$ (e.g., substituted alkyl and/or substituted heteroalkyl) is substituted with at least one substituent group, size-limited substituent group, or lower substituent group; wherein if the substituted $R^{11C}$ is substituted with a plurality of groups selected from substituent groups, size-limited substituent groups, and lower substituent groups; each substituent group, size-limited substituent group, and/or lower substituent group may optionally be different. In embodiments, when $R^{11C}$ is substituted, it is substituted with at least one substituent group. In embodiments, when $R^{11C}$ is substituted, it is substituted with at least one size-limited substituent group. In embodiments, when $R^{11C}$ is substituted, it is substituted with at least one lower substituent group.

In embodiments, $R^{12}$ is $—SR^{12A}$. In embodiments, $R^{12}$ is $—OR^{12A}$. In embodiments, $R^{12}$ is $—NR^{12B}R^{12C}$. In embodiments, $R^{12}$ is $—NR^{12B}C(O)R^{12C}$. In embodiments, $R^{12}$ is $—NR^{12B}C(O)OR^{12C}$. In embodiments, $R^{12}$ is —SH. In embodiments, $R^{12}$ is —OH. In embodiments, $R^{12}$ is $—NH_2$. In embodiments, $R^{12}$ is —NHC(O)H. In embodiments, $R^{12}$ is —NHC(O)OH. In embodiments, $R^{12}$ is substituted or unsubstituted $C_1$-$C_{10}$ alkyl. In embodiments, $R^{12}$ is unsubstituted $C_1$-$C_5$ alkyl. In embodiments, $R^{12}$ is unsubstituted methyl. In embodiments, $R^{12}$ is unsubstituted ethyl. In embodiments, $R^{12}$ is unsubstituted propyl. In embodiments, $R^{12}$ is unsubstituted n-propyl. In embodiments, $R^{12}$ is unsubstituted isopropyl. In embodiments, $R^{12}$ is unsubstituted butyl. In embodiments, $R^{12}$ is unsubstituted n-butyl. In embodiments, $R^{12}$ is unsubstituted tert-butyl. In embodiments, $R^{12}$ is substituted or unsubstituted 2 to 10 membered heteroalkyl. In embodiments, $R^{12}$ is substituted or unsubstituted $C_1$-$C_{10}$ thiol-alkyl or substituted or unsubstituted 2 to 10 membered thiol-heteroalkyl. In embodiments, $R^{12}$ is unsubstituted $C_1$-$C_{10}$ thiol-alkyl or unsubstituted 2 to 10 membered thiol-heteroalkyl. In embodiments, $R^{12}$ is unsubstituted thiomethyl (e.g., $—CH_2SH$), unsubstituted thioethyl (e.g., $—(CH_2)_2SH$), unsubstituted thiopropyl (e.g., $—(CH_2)_3 SH$), unsubstituted thiobutyl (e.g., $—(CH_2)_4SH$), unsubstituted thiopentyl (e.g., $—(CH_2)_5SH$), unsubstituted thiohexyl (e.g., $—(CH_2)_6SH$), unsubstituted thioheptyl (e.g., $—(CH_2)_7SH$), unsubstituted thiooctyl (e.g., $—(CH_2)_8SH$), unsubstituted thiononyl (e.g., $—(CH_2)_9SH$), or unsubstituted thiodecyl (e.g., $—(CH_2)_{10}SH$). In embodiments, $R^{12}$ is unsubstituted thioethyl. In embodiments, $R^{12}$ is unsubstituted thiopropyl. In embodiments, $R^{12}$ is unsubstituted thiobutyl. In embodiments, $R^{12}$ is unsubstituted thiopentyl. In embodiments, $R^{12}$ is unsubstituted thioethyloxyethyl. In embodiments, $R^{12}$ is unsubstituted alkoxy. In embodiments, $R^{12}$ is —O-(unsubstituted $C_1$-$C_4$ alkyl). In embodiments, $R^{12}$ is unsubstituted methoxy. In embodiments, $R^{12}$ is unsubstituted ethoxy. In embodiments, $R^{12}$ is unsubstituted propoxy. In embodiments, $R^{12}$ is unsubstituted n-propoxy. In embodiments, $R^{12}$ is unsubstituted isopropoxy. In embodiments, $R^{12}$ is unsubstituted butoxy. In embodiments, $R^{12}$ is unsubstituted n-butoxy. In embodiments, $R^{12}$ is unsubstituted tert-butoxy.

In embodiments, a substituted $R^{12}$ (e.g., substituted alkyl and/or substituted heteroalkyl) is substituted with at least one substituent group, size-limited substituent group, or lower substituent group; wherein if the substituted $R^{12}$ is substituted with a plurality of groups selected from substituent groups, size-limited substituent groups, and lower substituent groups; each substituent group, size-limited substituent group, and/or lower substituent group may optionally be different. In embodiments, when $R^{12}$ is substituted, it is substituted with at least one substituent group. In embodiments, when $R^{12}$ is substituted, it is substituted with at least one size-limited substituent group. In embodiments, when $R^{12}$ is substituted, it is substituted with at least one lower substituent group.

In embodiments, $R^{12A}$ is hydrogen. In embodiments, $R^{12A}$ is substituted or unsubstituted $C_1$-$C_{10}$ alkyl. In embodiments, $R^{12A}$ is unsubstituted $C_1$-$C_{10}$ alkyl. In embodiments, $R^{12A}$ is unsubstituted $C_1$-$C_5$ alkyl. In embodiments, $R^{12A}$ is unsubstituted methyl. In embodiments, $R^{12A}$ is unsubstituted ethyl. In embodiments, $R^{12A}$ is unsubstituted propyl. In embodiments, $R^{12A}$ is unsubstituted n-propyl. In embodiments, $R^{12A}$ is unsubstituted isopropyl. In embodiments, $R^{12A}$ is unsubstituted butyl. In embodiments, $R^{12A}$ is unsubstituted n-butyl. In embodiments, $R^{12A}$ is unsubstituted tert-butyl. In embodiments, $R^{12A}$ is substituted or unsubstituted 2 to 10 membered heteroalkyl. In embodiments, $R^{12A}$ is unsubstituted 2 to 6 membered heteroalkyl. In embodiments, $R^{12A}$ is substituted or unsubstituted $C_1$-$C_{10}$ thiol-alkyl or substituted or unsubstituted 2 to 10 membered thiol-heteroalkyl. In embodiments, $R^{12A}$ is unsubstituted $C_1$-$C_{10}$ thiol-alkyl or unsubstituted 2 to 10 membered thiol-heteroalkyl. In embodiments, $R^{12A}$ is unsubstituted thiomethyl (e.g., $—CH_2SH$), unsubstituted thioethyl (e.g., $—(CH_2)_2SH$), unsubstituted thiopropyl (e.g., $—(CH_2)_3SH$), unsubstituted thiobutyl (e.g., $—(CH_2)_4SH$), unsubstituted thiopentyl (e.g., $—(CH_2)_5SH$), unsubstituted thiohexyl (e.g., $—(CH_2)_6SH$), unsubstituted thioheptyl (e.g., $—(CH_2)_7SH$), unsubstituted thiooctyl (e.g., $—(CH_2)_8SH$), unsubstituted thiononyl (e.g., $—(CH_2)_9SH$), or unsubstituted thiodecyl (e.g., $—(CH_2)_{10}SH$). In embodiments, $R^{12A}$ is unsubstituted thioethyl. In embodiments, $R^{12A}$ is unsubstituted thiopropyl. In embodiments, $R^{12A}$ is unsubstituted thiobutyl. In embodiments, $R^{12A}$ is unsubstituted thiopentyl. In embodiments, $R^{12A}$ is unsubstituted thioethyloxyethyl.

In embodiments, a substituted $R^{12A}$ (e.g., substituted alkyl and/or substituted heteroalkyl) is substituted with at least one substituent group, size-limited substituent group, or lower substituent group; wherein if the substituted $R^{12A}$ is substituted with a plurality of groups selected from substituent groups, size-limited substituent groups, and lower substituent groups; each substituent group, size-limited substituent group, and/or lower substituent group may optionally be different. In embodiments, when $R^{12A}$ is substituted, it is substituted with at least one substituent group. In embodiments, when $R^{12A}$ is substituted, it is substituted with at least one size-limited substituent group. In embodiments, when $R^{12A}$ is substituted, it is substituted with at least one lower substituent group.

In embodiments, $R^{12A}$ is

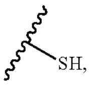
,
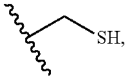
,
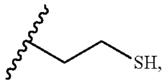
,
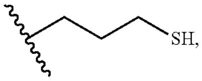
,
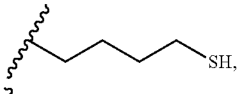
, or
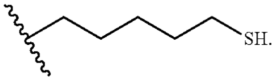
.

In embodiments, $R^{12B}$ is hydrogen. In embodiments, $R^{12B}$ is substituted or unsubstituted $C_1$-$C_{10}$ alkyl. In embodiments, $R^{12B}$ is substituted or unsubstituted 2 to 10 membered heteroalkyl. In embodiments, $R^{12B}$ is substituted or unsubstituted $C_1$-$C_{10}$ thiol-alkyl or substituted or unsubstituted 2 to 10 membered thiol-heteroalkyl. In embodiments, $R^{12B}$ is unsubstituted $C_1$-$C_{10}$ thiol-alkyl or unsubstituted 2 to 10 membered thiol-heteroalkyl. In embodiments, $R^{12B}$ is —C(O)-(substituted or unsubstituted $C_1$-$C_{10}$ alkyl). In embodiments, $R^{12B}$ is —C(O)-(substituted or unsubstituted $C_1$-$C_{10}$ thiol-alkyl). In embodiments, $R^{12}$ is —C(O)-(substituted or unsubstituted 2 to 10 membered thiol-heteroalkyl).

In embodiments, a substituted $R^{12B}$ (e.g., substituted alkyl and/or substituted heteroalkyl) is substituted with at least one substituent group, size-limited substituent group, or lower substituent group; wherein if the substituted $R^{12B}$ is substituted with a plurality of groups selected from substituent groups, size-limited substituent groups, and lower substituent groups; each substituent group, size-limited substituent group, and/or lower substituent group may optionally be different. In embodiments, when $R^{12B}$ is substituted, it is substituted with at least one substituent group. In embodiments, when $R^{12B}$ is substituted, it is substituted with at least one size-limited substituent group. In embodiments, when $R^{12B}$ is substituted, it is substituted with at least one lower substituent group.

In embodiments, $R^{12C}$ is hydrogen. In embodiments, $R^{12C}$ is substituted or unsubstituted $C_1$-$C_{10}$ alkyl. In embodiments, $R^{12C}$ is substituted or unsubstituted 2 to 10 membered heteroalkyl. In embodiments, $R^{12C}$ is substituted or unsubstituted $C_1$-$C_{10}$ thiol-alkyl or substituted or unsubstituted 2 to 10 membered thiol-heteroalkyl. In embodiments, $R^{12C}$ is unsubstituted $C_1$-$C_{10}$ thiol-alkyl or unsubstituted 2 to 10 membered thiol-heteroalkyl.

In embodiments, a substituted $R^{12C}$ (e.g., substituted alkyl and/or substituted heteroalkyl) is substituted with at least one substituent group, size-limited substituent group, or lower substituent group; wherein if the substituted $R^{12C}$ is substituted with a plurality of groups selected from substituent groups, size-limited substituent groups, and lower substituent groups; each substituent group, size-limited substituent group, and/or lower substituent group may optionally be different. In embodiments, when $R^{12C}$ is substituted, it is substituted with at least one substituent group. In embodiments, when $R^{12C}$ is substituted, it is substituted with at least one size-limited substituent group. In embodiments, when $R^{12C}$ is substituted, it is substituted with at least one lower substituent group.

In embodiments, the thiosaccharide compound has the formula:

(VI-1)

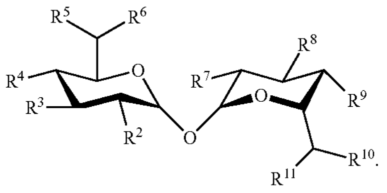

$R^2$, $R^3$, $R^4$, $R^5$, $R^6$, $R^7$, $R^8$, $R^9$, $R^{10}$, and $R^{11}$ are as described herein, including in embodiments.

In embodiments, the thiosaccharide compound has the formula:

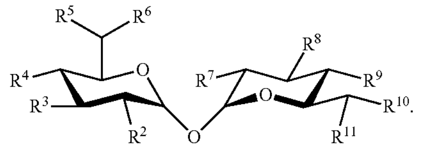

$R^2$, $R^3$, $R^4$, $R^5$, $R^6$, $R^7$, $R^8$, $R^9$, $R^{10}$, and $R^{11}$ as described herein, including in embodiments.

In embodiments, the thiosaccharide compound has the formula:

(VII-1)

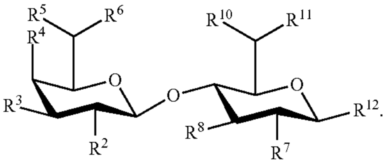

$R^2$, $R^3$, $R^4$, $R^5$, $R^6$, $R^7$, $R^8$, $R^{10}$, $R^{11}$, and $R^{12}$ are as described herein, including in embodiments.

In embodiments, the thiosaccharide compound has the formula:

(VII-2)

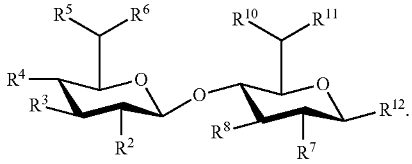

$R^2$, $R^3$, $R^4$, $R^5$, $R^6$, $R^7$, $R^8$, $R^{10}$, $R^{11}$, and $R^{12}$ are as described herein, including in embodiments.

In embodiments, the thiosaccharide compound has the formula:

(VII-3)

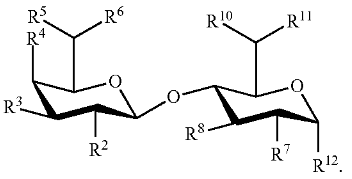

$R^2$, $R^3$, $R^4$, $R^5$, $R^6$, $R^7$, $R^8$, $R^{10}$, $R^{11}$, and $R^{12}$ are as described herein, including in embodiments.

In embodiments, the thiosaccharide compound has the formula:

(VII-4)

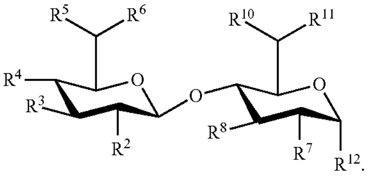

$R^2$, $R^3$, $R^4$, $R^5$, $R^6$, $R^7$, $R^8$, $R^{10}$, $R^{11}$, and $R^{12}$ are as described herein, including in embodiments.

In embodiments, $R^2$ is —$SR^{2A}$, —$OR^{2A}$, substituted or unsubstituted $C_1$-$C_{10}$ alkyl, or substituted or unsubstituted 2 to 10 membered heteroalkyl; $R^3$ is —$SR^{3A}$, —$OR^{3A}$, substituted or unsubstituted $C_1$-$C_{10}$ alkyl, or substituted or unsubstituted 2 to 10 membered heteroalkyl; $R^4$ is —$SR^{4A}$, —$OR^{4A}$, substituted or unsubstituted $C_1$-$C_{10}$ alkyl, or substituted or unsubstituted 2 to 10 membered heteroalkyl; $R^5$ is hydrogen, —$SR^{5A}$, —$OR^{5A}$, substituted or unsubstituted $C_1$-$C_{10}$ alkyl, or substituted or unsubstituted 2 to 10 membered heteroalkyl; $R^6$ is —$SR^{6A}$, —$OR^{6A}$, substituted or unsubstituted $C_1$-$C_{10}$ alkyl, or substituted or unsubstituted 2 to 10 membered heteroalkyl; $R^7$ is —$SR^{7A}$, —$OR^{7A}$, substituted or unsubstituted $C_1$-$C_{10}$ alkyl, or substituted or unsubstituted 2 to 10 membered heteroalkyl; $R^8$ is —$SR^{8A}$, —$OR^{8A}$, substituted or unsubstituted $C_1$-$C_{10}$ alkyl, or substituted or unsubstituted 2 to 10 membered heteroalkyl; $R^9$ is —$SR^{9A}$, —$OR^{9A}$, substituted or unsubstituted $C_1$-$C_{10}$ alkyl, or substituted or unsubstituted 2 to 10 membered heteroalkyl; $R^{10}$ is hydrogen, —$SR^{10A}$, —$OR^{10A}$, substituted or unsubstituted $C_1$-$C_{10}$ alkyl, or substituted or unsubstituted 2 to 10 membered heteroalkyl; $R^{11}$ is —$SR^{11A}$, —$OR^{11A}$, substituted or unsubstituted $C_1$-$C_{10}$ alkyl, or substituted or unsubstituted 2 to 10 membered heteroalkyl; and $R^{12}$ is —$SR^{12A}$, —$OR^{12A}$, substituted or unsubstituted $C_1$-$C_{10}$ alkyl, or substituted or unsubstituted 2 to 10 membered heteroalkyl.

In embodiments, $R^2$ is —$SR^{2A}$, —$OR^{2A}$, substituted or unsubstituted $C_1$-$C_{10}$ thiol-alkyl, or substituted or unsubstituted 2 to 10 membered thiol-heteroalkyl; $R^3$ is —$SR^{3A}$, —$OR^{3A}$, substituted or unsubstituted $C_1$-$C_{10}$ thiol-alkyl, or substituted or unsubstituted 2 to 10 membered thiol-heteroalkyl; $R^4$ is —$SR^{4A}$, —$OR^{4A}$, substituted or unsubstituted $C_1$-$C_{10}$ thiol-alkyl, or substituted or unsubstituted 2 to 10 membered thiol-heteroalkyl; $R^{11}$ is hydrogen, —$SR^{5A}$, —$OR^{5A}$, substituted or unsubstituted $C_1$-$C_{10}$ thiol-alkyl, or substituted or unsubstituted 2 to 10 membered thiol-heteroalkyl; $R^6$ is —$SR^{6A}$, —$OR^{6A}$, substituted or unsubstituted $C_1$-$C_{10}$ thiol-alkyl, or substituted or unsubstituted 2 to 10 membered thiol-heteroalkyl; $R^7$ is —$SR^{7A}$, —$OR^{7A}$, substituted or unsubstituted $C_1$-$C_{10}$ thiol-alkyl, or substituted or unsubstituted 2 to 10 membered thiol-heteroalkyl; $R^8$ is $-SR^{8A}$, $-OR^{8A}$, substituted or unsubstituted $C_1$-$C_{10}$ thiol-alkyl, or substituted or unsubstituted 2 to 10 membered thiol-heteroalkyl; $R^9$ is $-SR^{9A}$, $-OR^{9A}$, substituted or unsubstituted $C_1$-$C_{10}$ thiol-alkyl, or substituted or unsubstituted 2 to 10 membered thiol-heteroalkyl; $R^{10}$ is hydrogen, $-SR^{10A}$, $-OR^{10A}$, substituted or unsubstituted $C_1$-$C_{10}$ thiol-alkyl, or substituted or unsubstituted 2 to 10 membered thiol-heteroalkyl; $R^{11}$ is $-SR^{11A}$, $-OR^{11A}$, substituted or unsubstituted $C_1$-$C_{10}$ thiol-alkyl, or substituted or unsubstituted 2 to 10 membered thiol-heteroalkyl; and $R^{12}$ is $-SR^{12A}$, $-OR^{12A}$, substituted or unsubstituted $C_1$-$C_{10}$ thiol-alkyl, or substituted or unsubstituted 2 to 10 membered thiol-heteroalkyl.

In embodiments, $R^2$ is $-SR^{2A}$ or $-OR^{2A}$; $R^3$ is $-SR^{3A}$ or $-OR^{3A}$; $R^4$ is $-SR^{4A}$ or $-OR^{4A}$; $R^6$ is $-SR^{6A}$ or $-OR^{6A}$; $R^7$ is $-SR^{7A}$ or $-OR^{7A}$; $R^8$ is $-SR^{8A}$ or $-OR^{8A}$; $R^9$ is $-SR^{9A}$ or $-OR^{9A}$; and $R^{11}$ is $-SR^{11A}$ or $-OR^{11A}$. In embodiments, $R^2$ is —SH or —OH; $R^3$ is —SH or —OH; $R^4$ is —SH or —OH; $R^6$ is —SH or —OH; $R^7$ is —SH or —OH; $R^8$ is —SH or —OH; $R^9$ is —SH or —OH; and $R^{11}$ is —SH or —OH.

In embodiments, the thiosaccharide compound has the formula:

(VIIa)

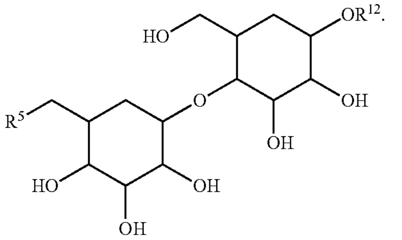

$R^5$ and $R^{12}$ are as described herein, including in embodiments.

In embodiments, the thiosaccharide compound has the formula:

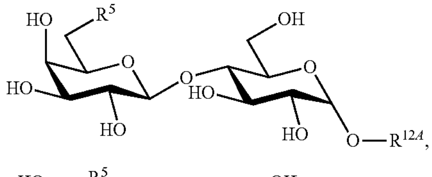

,

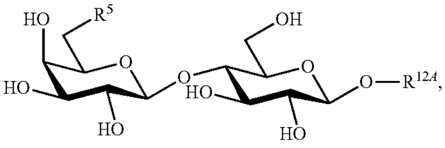

,

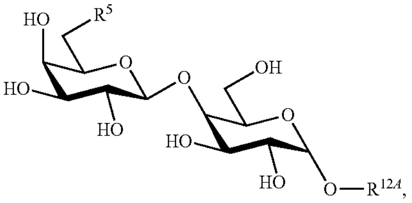

, or

-continued

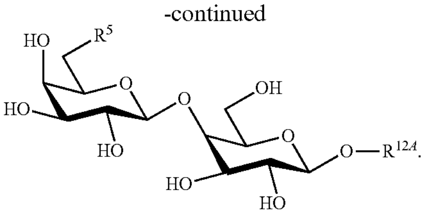

.

$R^5$ and $R^{12A}$ are as described herein, including in embodiments.

In embodiments, the thiosaccharide compound has the formula:

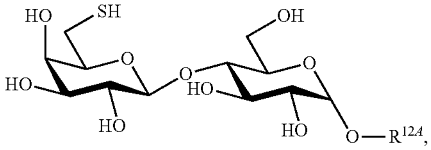

,

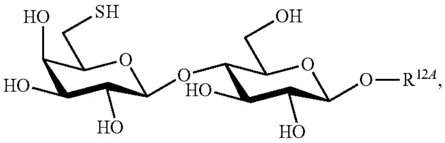

,

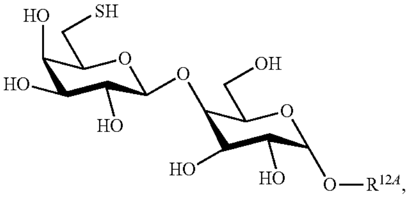

, or

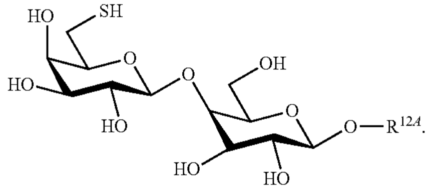

.

$R^{12A}$ is as described herein, including in embodiments.

In embodiments, the thiosaccharide compound has the formula:

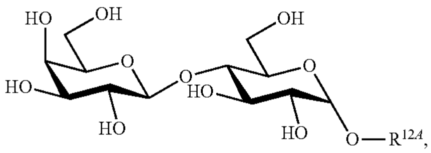

,

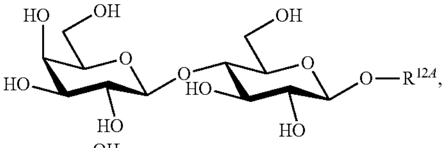

,

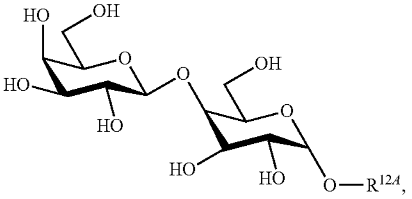

, or

-continued

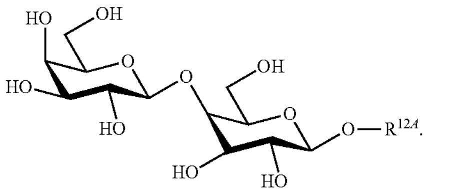

$R^2$ is as described herein, including in embodiments.

In embodiments, the thiosaccharide compound has the formula:

(VIIb)

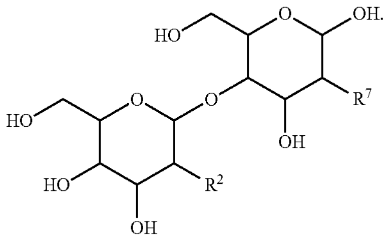

$R^2$ and $R^7$ are as described herein, including in embodiments.

In embodiments, the thiosaccharide compound has the formula:

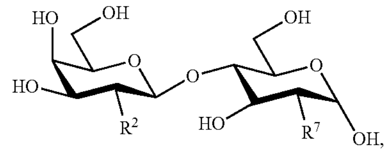

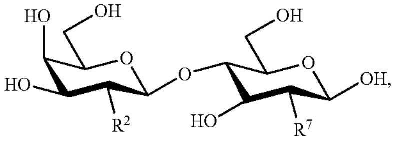

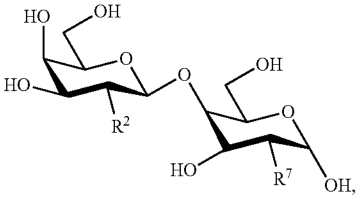

or

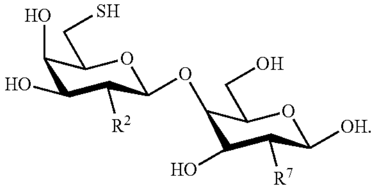

$R^2$ and $R^7$ are as described herein, including in embodiments.

In embodiments, the thiosaccharide compound has the formula:

(VIIc)

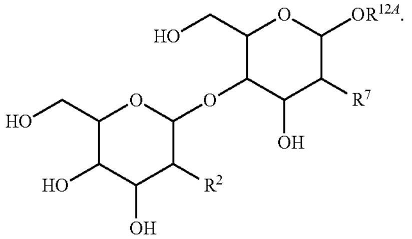

$R^2$, $R^7$, and $R^{12A}$ are as described herein, including in embodiments.

In embodiments, the thiosaccharide compound has the formula:

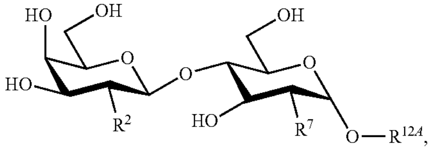

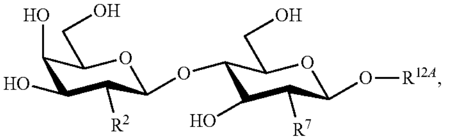

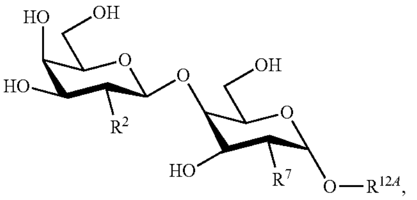

or

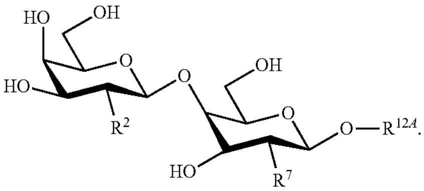

$R^2$, $R^7$, and $R^{12A}$ are as described herein, including in embodiments.

In embodiments, the thiosaccharide compound has the formula:

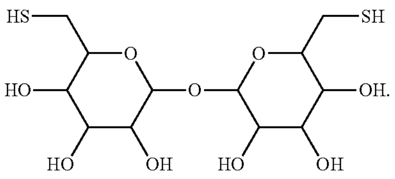 [SMILES: OC1C(CS)OC(OC2OC(CS)C(O)C(O)C2O)C(O)C1O]

In embodiments, the thiosaccharide compound has the formula:

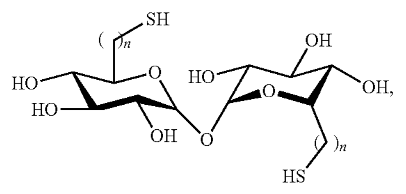

wherein n is independently an integer from 1 to 5. In embodiments, n is independently an integer from 1 to 3.

In embodiments, the thiosaccharide compound has the formula:

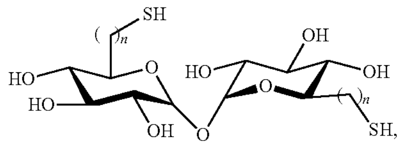

wherein n is independently an integer from 1 to 5. In embodiments, n is independently an integer from 1 to 3.

In embodiments, n is 1. In embodiments, n is 2. In embodiments, n is 3. In embodiments, n is 4. In embodiments, n is 5.

In embodiments, the thiosaccharide compound has the formula:

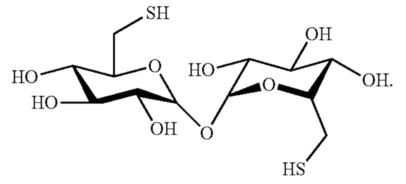

In embodiments, the thiosaccharide compound has the formula

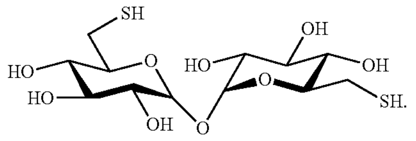

In embodiments, the thiosaccharide compound is 6,6'-dithiotrehalose. In embodiments, 6,6'-dithiotrehalose is referred to herein as MUC, MUC-31, MUC-031, or TS21.

In embodiments, the thiosaccharide compound has the formula:

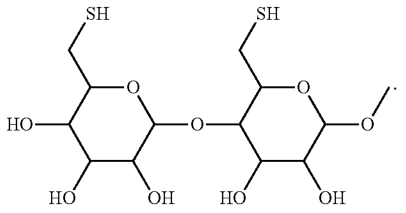 [SMILES: COC1OC(CS)C(OC2OC(CS)C(O)C(O)C2O)C(O)C1O]

In embodiments, the thiosaccharide compound has the formula:

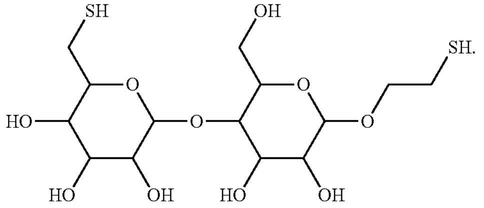 [SMILES: OCC1OC(OCCS)C(O)C(O)C1OC1OC(CS)C(O)C(O)C1O]

In embodiments, the thiosaccharide compound has the formula:

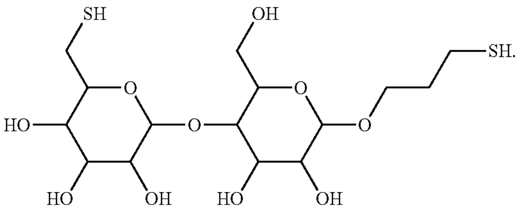 [SMILES: OCC1OC(OCCCS)C(O)C(O)C1OC1OC(CS)C(O)C(O)C1O]

In embodiments, the thiosaccharide compound has the formula:

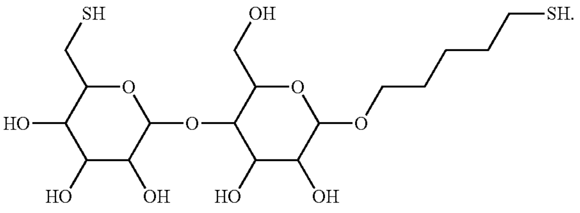 [SMILES: OCC1OC(OCCCCCS)C(O)C(O)C1OC1OC(CS)C(O)C(O)C1O]

In embodiments, the thiosaccharide compound has the formula:

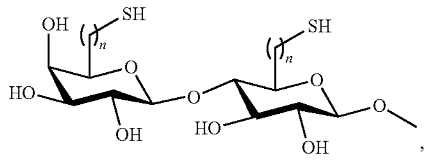

-continued

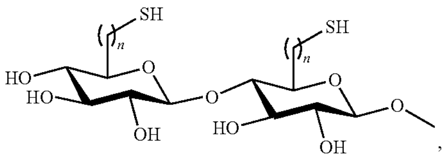

, or

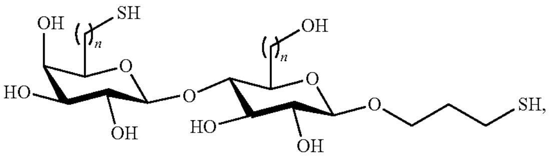

wherein n is as described herein, including in embodiments.

In embodiments, the thiosaccharide compound has the formula:

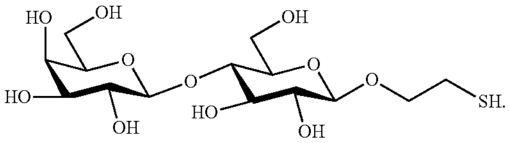

In embodiments, the thiosaccharide compound has the formula:

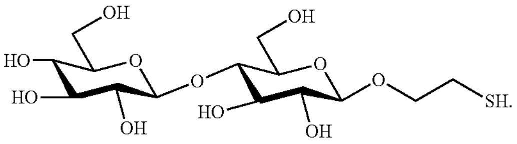

In embodiments, the thiosaccharide compound has the formula:

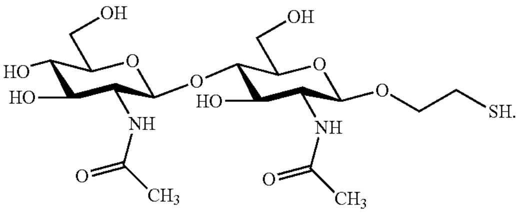

In embodiments, the thiosaccharide compound has the formula:

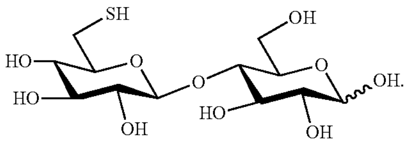

In embodiments, the thiosaccharide compound has the formula:

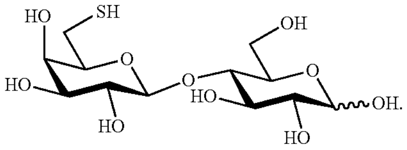

In embodiments, the thiosaccharide compound has the formula:

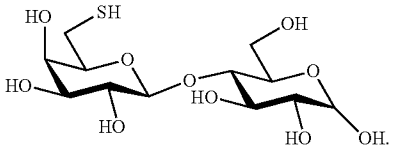

In embodiments, the thiosaccharide compound has the formula:

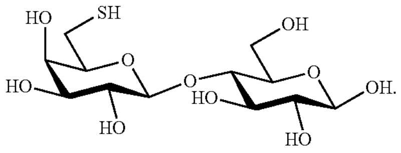

In embodiments, the thiosaccharide compound has the formula:

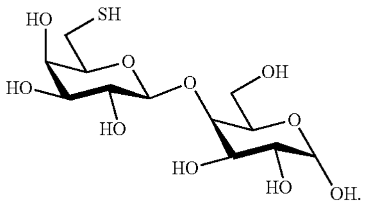

In embodiments, the thiosaccharide compound has the formula:

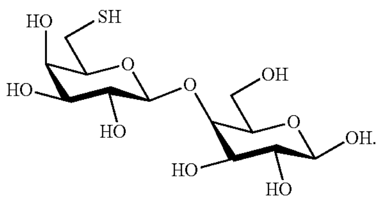

In embodiments, the thiosaccharide compound has the formula:

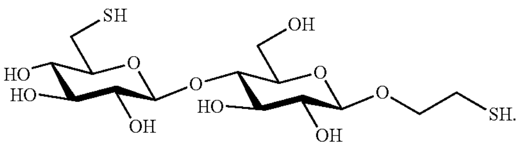

In embodiments, the thiosaccharide compound has the formula:

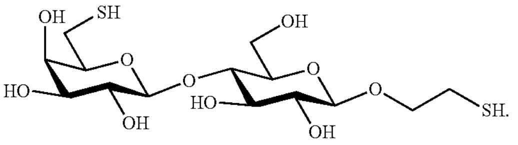

In embodiments, the thiosaccharide compound has the formula:

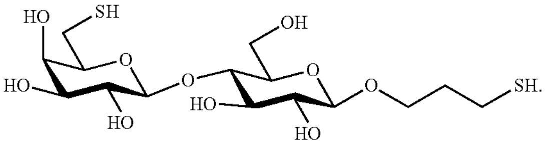

In embodiments, the thiosaccharide compound has the formula:

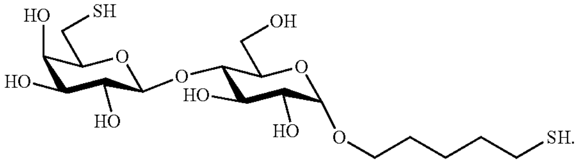

In embodiments, the thiosaccharide compound has the formula:

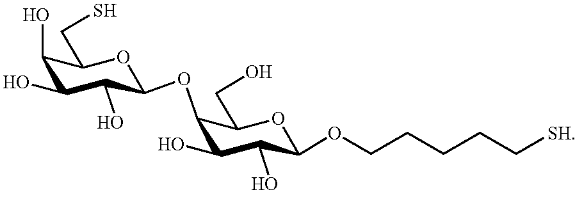

In embodiments, the thiosaccharide compound has the formula:

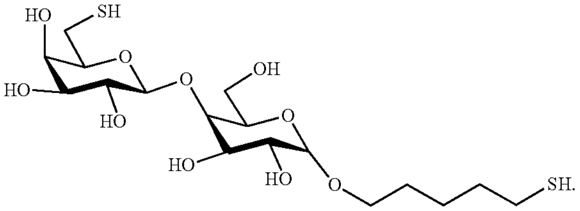

In embodiments, the thiosaccharide compound has the formula:

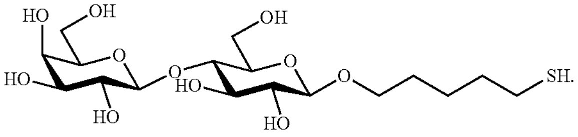

In embodiments, the thiosaccharide compound has the formula:

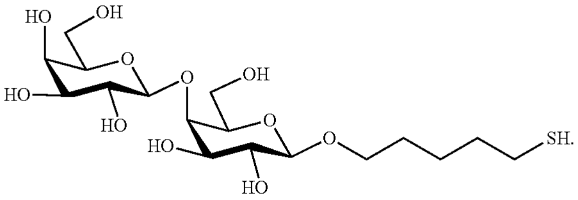

In embodiments, the thiosaccharide compound has the formula:

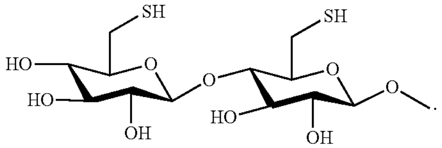

In embodiments, the thiosaccharide compound has the formula:

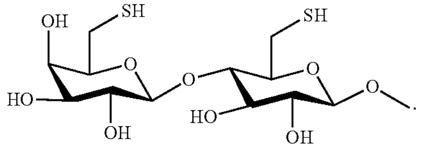

In embodiments, the thiosaccharide compound has the formula:

(VIII)

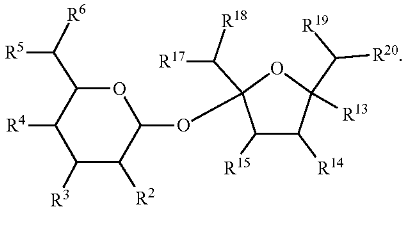

$R^2$, $R^3$, $R^4$, $R^5$, $R^6$, $R^{13}$, $R^{14}$, $R^{15}$, $R^{17}$, $R^{18}$, $R^{19}$, and are as described herein, including in embodiments.

In embodiments, $R^2$ is —$SR^{2A}$, —$OR^{2A}$, substituted or unsubstituted $C_1$-$C_{10}$ alkyl, or substituted or unsubstituted 2 to 10 membered heteroalkyl; $R^3$ is —$SR^{3A}$, —$OR^{3A}$, substituted or unsubstituted $C_1$-$C_{10}$ alkyl, or substituted or unsubstituted 2 to 10 membered heteroalkyl; $R^4$ is —$SR^{4A}$, —$OR^{4A}$, substituted or unsubstituted $C_1$-$C_{10}$ alkyl, or substituted or unsubstituted 2 to 10 membered heteroalkyl; $R^5$ is hydrogen, —$SR^{5A}$, —$OR^{5A}$, substituted or unsubstituted $C_1$-$C_{10}$ alkyl, or substituted or unsubstituted 2 to 10 membered heteroalkyl; $R^6$ is —$SR^{6A}$, —$OR^{6A}$, substituted or unsubstituted $C_1$-$C_{10}$ alkyl, or substituted or unsubstituted 2 to 10 membered heteroalkyl; $R^{13}$ is hydrogen, —$SR^{13A}$, —$OR^{13A}$, substituted or unsubstituted $C_1$-$C_{10}$ alkyl, or substituted or unsubstituted 2 to 10 membered heteroalkyl; $R^{14}$ is —$SR^{14A}$, —$OR^{14A}$, substituted or unsubstituted $C_1$-$C_{10}$ alkyl, or substituted or unsubstituted 2 to 10 membered heteroalkyl; $R^{15}$ is —$SR^{15A}$, —$OR^{15A}$, substituted or unsubstituted $C_1$-$C_{10}$ alkyl, or substituted or unsubstituted 2 to 10 membered heteroalkyl; $R^{17}$ is hydrogen, —$SR^{17A}$, —$OR^{17A}$, substituted or unsubstituted $C_1$-$C_{10}$ alkyl, or substituted or unsubstituted 2 to 10 membered heteroalkyl; $R^{18}$ is —$SR^{18A}$, —$OR^{18A}$, substituted or unsubstituted $C_1$-$C_{10}$ alkyl, or substituted or unsubstituted 2 to 10 membered heteroalkyl; $R^{19}$ is hydrogen, —$SR^{19A}$, —$OR^{19A}$, substituted or unsubstituted $C_1$-$C_{10}$ alkyl, or substituted or unsubstituted 2 to 10 membered heteroalkyl; and $R^{20}$ is —$SR^{20A}$, —$OR^{20A}$, substituted or unsubstituted $C_1$-$C_{10}$ alkyl, or substituted or unsubstituted 2 to 10 membered heteroalkyl.

In embodiments, $R^2$ is —$SR^{2A}$, —$OR^{2A}$, substituted or unsubstituted $C_1$-$C_{10}$ thiol-alkyl, or substituted or unsubstituted 2 to 10 membered thiol-heteroalkyl; $R^3$ is —$SR^{3A}$, —$OR^{3A}$, substituted or unsubstituted $C_1$-$C_{10}$ thiol-alkyl, or substituted or unsubstituted 2 to 10 membered thiol-heteroalkyl; $R^4$ is —$SR^{4A}$, —$OR^{4A}$, substituted or unsubstituted $C_1$-$C_{10}$ thiol-alkyl, or substituted or unsubstituted 2 to 10 membered thiol-heteroalkyl; $R^5$ is hydrogen, —$SR^{5A}$, —$OR^{5A}$, substituted or unsubstituted $C_1$-$C_{10}$ thiol-alkyl, or substituted or unsubstituted 2 to 10 membered thiol-heteroalkyl; $R^6$ is —$SR^{6A}$, —$OR^{6A}$, substituted or unsubstituted $C_1$-$C_{10}$ thiol-alkyl, or substituted or unsubstituted 2 to 10 membered thiol-heteroalkyl; $R^{13}$ is hydrogen, —$SR^{13A}$, —$OR^{13A}$, substituted or unsubstituted $C_1$-$C_{10}$ thiol-alkyl, or substituted or unsubstituted 2 to 10 membered thiol-heteroalkyl; $R^{14}$ is —$SR^{14A}$, —$OR^{14A}$, substituted or unsubstituted $C_1$-$C_{10}$ thiol-alkyl, or substituted or unsubstituted 2 to 10 membered thiol-heteroalkyl; $R^{15}$ is —$SR^{15A}$, —$OR^{15A}$, substituted or unsubstituted $C_1$-$C_{10}$ thiol-alkyl, or substituted or unsubstituted 2 to 10 membered thiol-heteroalkyl; $R^{17}$ is hydrogen, —$SR^{17A}$, —$OR^{17A}$, substituted or unsubstituted $C_1$-$C_{10}$ thiol-alkyl, or substituted or unsubstituted 2 to 10 membered thiol-heteroalkyl; $R^{18}$ is —$SR^{18A}$, —$OR^{18A}$, substituted or unsubstituted $C_1$-$C_{10}$ thiol-alkyl, or substituted or unsubstituted 2 to 10 membered thiol-heteroalkyl; $R^{19}$ is hydrogen, —$SR^{19A}$, —$OR^{19A}$, substituted or unsubstituted $C_1$-$C_{10}$ thiol-alkyl, or substituted or unsubstituted 2 to 10 membered thiol-heteroalkyl; and $R^{20}$ is —$SR^{20A}$, —$OR^{20A}$, substituted or unsubstituted $C_1$-$C_{10}$ thiol-alkyl, or substituted or unsubstituted 2 to 10 membered thiol-heteroalkyl.

In embodiments, $R^2$ is —$SR^{2A}$ or —$OR^{2A}$; $R^3$ is —$SR^{3A}$ or —$OR^{3A}$; $R^4$ is —$SR^{4A}$ or —$OR^{4A}$; $R^6$ is —$SR^{6A}$ or —$OR^{6A}$; $R^{13}$ is hydrogen, —$SR^{13A}$, or —$OR^{3A}$; $R^{14}$ is —$SR^{14A}$ or —$OR^{14}$; $R^{15}$ is —$SR^{15A}$ or —$OR^{15A}$; $R^{18}$ is —$SR^{18A}$ or —$OR^{18A}$; and $R^{20}$ is —$SR^{20A}$ or —$OR^{20A}$. In embodiments, $R^2$ is —SH or —OH; $R^3$ is —SH or —OH; $R^4$ is —SH or —OH; $R^6$ is —SH or —OH; $R^{13}$ is hydrogen, —SH, or —OH; $R^{14}$ is —SH or —OH; $R^{15}$ is —SH or —OH; $R^{18}$ is —SH or —OH; and $R^{20}$ is —SH or —OH.

In embodiments, the thiosaccharide compound has the formula:

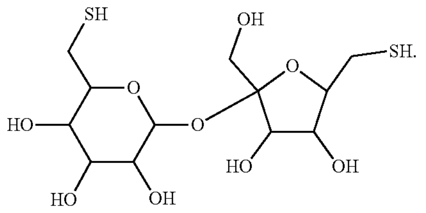 [SMILES: OCC1(OC2OC(CS)C(O)C(O)C2O)OC(CS)C(O)C1O]

In embodiments, the thiosaccharide compound has the formula:

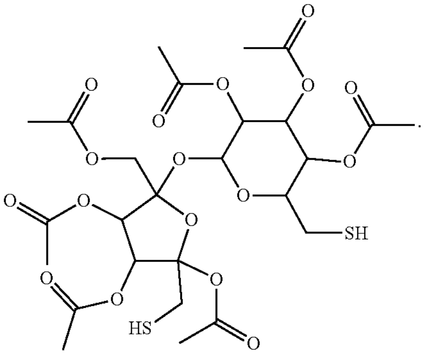 [SMILES: CC(=O)OCC1(OC2OC(CS)C(OC(C)=O)C(OC(C)=O)C2OC(C)=O)OC(CS)(OC(C)=O)C(OC(C)=O)C1OC(C)=O]

In embodiments, the thiosaccharide compound has the formula:

(IX)

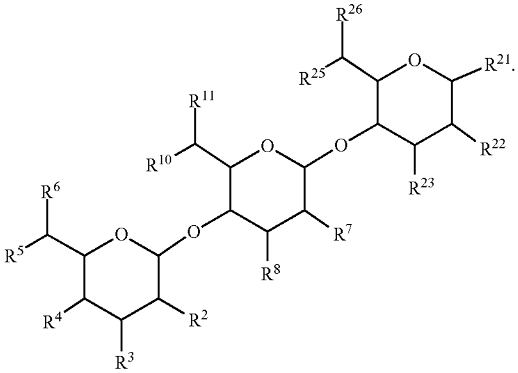

$R^2$, $R^3$, $R^4$, $R^5$, $R^6$, $R^7$, $R^8$, $R^{10}$, and $R^{11}$ are as described herein, including in embodiments. $R^{21}$ is —$SR^{21A}$, —$OR^{21A}$, —$NR^{21B}R^{21C}$, —$NR^{21B}C(O)R^{21C}$, —$NR^{21B}C(O)OR^{21C}$, substituted or unsubstituted alkyl (e.g., $C_1$-$C_{10}$, $C_1$-$C_6$, $C_1$-$C_4$, or $C_1$-$C_2$), or substituted or unsubstituted heteroalkyl (e.g., 2 to 10 membered, 2 to 6 membered, 4 to 6 membered, or 2 to 3 membered). $R^{22}$ is —$SR^{22A}$, —$OR^{22A}$, —$NR^{22B}R^{22C}$, —$NR^{22B}C(O)R^{22C}$, —$NR^{22B}C(O)OR^{22C}$, substituted or unsubstituted alkyl (e.g., $C_1$-$C_{10}$, $C_1$-$C_6$, $C_1$-$C_4$, or $C_1$-$C_2$), or substituted or unsubstituted heteroalkyl (e.g., 2 to 10 membered, 2 to 6 membered, 4 to 6 membered, or 2 to 3 membered). $R^{23}$ is —$SR^{23A}$, —$OR^{23A}$, —$NR^{23B}R^{23C}$, —$NR^{23B}C(O)R^{23C}$, —$NR^{23B}C(O)OR^{23C}$, substituted or unsubstituted alkyl (e.g., $C_1$-$C_{10}$, $C_1$-$C_6$, $C_1$-$C_4$, or $C_1$-$C_2$), or substituted or unsubstituted heteroalkyl (e.g., 2 to 10 membered, 2 to 6 membered, 4 to 6 membered, or 2 to 3 membered). $R^{25}$ is hydrogen, $—SR^{25A}$, $—SC(O)R^{25A}$, $—OR^{25A}$, $—NR^{25B}R^{25C}$, $—NR^{25B}C(O)R^{25C}$, $—NR^{25B}C(O)OR^{25C}$, or substituted or unsubstituted alkyl (e.g., $C_1$-$C_{10}$, $C_1$-$C_6$, $C_1$-$C_4$, or $C_1$-$C_2$), or substituted or unsubstituted heteroalkyl (e.g., 2 to 10 membered, 2 to 6 membered, 4 to 6 membered, or 2 to 3 membered). $R^{26}$ is hydrogen, $—SR^{26A}$, $—OR^{26A}$, $—NR^{26B}R^{25C}$, $—NR^{26B}C(O)R^{26C}$, $—NR^{26B}C(O)OR^{26C}$, or substituted or unsubstituted alkyl (e.g., $C_1$-$C_{10}$, $C_1$-$C_6$, $C_1$-$C_4$, or $C_1$-$C_2$), or substituted or unsubstituted heteroalkyl (e.g., 2 to 10 membered, 2 to 6 membered, 4 to 6 membered, or 2 to 3 membered). $R^{21A}$, $R^{21B}$, $R^{21C}$, $R^{22A}$, $R^{22B}$, $R^{22C}$, $R^{23A}$, $R^{23B}$, $R^{23C}$, $R^{25A}$, $R^{25B}$, $R^{25C}$, $R^{26A}$, $R^{26B}$, and $R^{26C}$ are each independently hydrogen, substituted or unsubstituted alkyl (e.g., $C_1$-$C_{10}$, $C_1$-$C_6$, $C_1$-$C_4$, or $C_1$-$C_2$), or substituted or unsubstituted heteroalkyl (e.g., 2 to 10 membered, 2 to 6 membered, 4 to 6 membered, or 2 to 3 membered).

In embodiments, $R^{21}$ is $—SR^{21A}$. In embodiments, $R^{21}$ is $—OR^{21A}$. In embodiments, $R^{21}$ is $—NR^{21B}R^{21C}$. In embodiments, $R^{21}$ is $—NR^{21B}C(O)R^{21C}$. In embodiments, $R^{21}$ is $—NR^{21B}C(O)OR^{21C}$. In embodiments, $R^{21}$ is —SH. In embodiments, $R^{21}$ is —OH. In embodiments, $R^{21}$ is $—NH_2$. In embodiments, $R^{21}$ is —NHC(O)H. In embodiments, $R^{21}$ is —NHC(O)OH. In embodiments, $R^{21}$ is substituted or unsubstituted $C_1$-$C_{10}$ alkyl. In embodiments, $R^{21}$ is unsubstituted $C_1$-$C_5$ alkyl. In embodiments, $R^{21}$ is unsubstituted methyl. In embodiments, $R^{21}$ is unsubstituted ethyl. In embodiments, $R^{21}$ is unsubstituted propyl. In embodiments, $R^{21}$ is unsubstituted n-propyl. In embodiments, $R^{21}$ is unsubstituted isopropyl. In embodiments, $R^{21}$ is unsubstituted butyl. In embodiments, $R^{21}$ is unsubstituted n-butyl. In embodiments, $R^{21}$ is unsubstituted tert-butyl. In embodiments, $R^{21}$ is substituted or unsubstituted 2 to 10 membered heteroalkyl. In embodiments, $R^{21}$ is substituted or unsubstituted $C_1$-$C_{10}$ thiol-alkyl or substituted or unsubstituted 2 to 10 membered thiol-heteroalkyl. In embodiments, $R^{21}$ is unsubstituted $C_1$-$C_{10}$ thiol-alkyl or unsubstituted 2 to 10 membered thiol-heteroalkyl. In embodiments, $R^{21}$ is unsubstituted thiomethyl (e.g., $—CH_2SH$), unsubstituted thioethyl (e.g., $—(CH_2)_2SH$), unsubstituted thiopropyl (e.g., $—(CH_2)_3$ SH), unsubstituted thiobutyl (e.g., $—(CH_2)_4SH$), unsubstituted thiopentyl (e.g., $—(CH_2)_5SH$), unsubstituted thiohexyl (e.g., $—(CH_2)_6SH$), unsubstituted thioheptyl (e.g., $—(CH_2)_7SH$), unsubstituted thiooctyl (e.g., $—(CH_2)_8SH$), unsubstituted thiononyl (e.g., $—(CH_2)_9SH$), or unsubstituted thiodecyl (e.g., $—(CH_2)_{10}SH$). In embodiments, $R^{21}$ is unsubstituted thioethyl. In embodiments, $R^{21}$ is unsubstituted thiopropyl. In embodiments, $R^{21}$ is unsubstituted thiobutyl. In embodiments, $R^{21}$ is unsubstituted thiopentyl. In embodiments, $R^{21}$ is unsubstituted thioethyloxyethyl. In embodiments, $R^{21}$ is unsubstituted alkoxy. In embodiments, $R^{21}$ is —O-(unsubstituted $C_1$-$C_4$ alkyl). In embodiments, $R^{21}$ is unsubstituted methoxy. In embodiments, $R^{21}$ is unsubstituted ethoxy. In embodiments, $R^{21}$ is unsubstituted propoxy. In embodiments, $R^{21}$ is unsubstituted n-propoxy. In embodiments, $R^{21}$ is unsubstituted isopropoxy. In embodiments, $R^{21}$ is unsubstituted butoxy. In embodiments, $R^{21}$ is unsubstituted n-butoxy. In embodiments, $R^{21}$ is unsubstituted tert-butoxy.

In embodiments, a substituted $R^{21}$ (e.g., substituted alkyl and/or substituted heteroalkyl) is substituted with at least one substituent group, size-limited substituent group, or lower substituent group; wherein if the substituted $R^{21}$ is substituted with a plurality of groups selected from substituent groups, size-limited substituent groups, and lower substituent groups; each substituent group, size-limited substituent group, and/or lower substituent group may optionally be different. In embodiments, when $R^{21}$ is substituted, it is substituted with at least one substituent group. In embodiments, when $R^{21}$ is substituted, it is substituted with at least one size-limited substituent group. In embodiments, when $R^{21}$ is substituted, it is substituted with at least one lower substituent group.

In embodiments, $R^{21A}$ is hydrogen. In embodiments, $R^{21A}$ is substituted or unsubstituted $C_1$-$C_{10}$ alkyl. In embodiments, $R^{21A}$ is unsubstituted $C_1$-$C_{10}$ alkyl. In embodiments, $R^{21A}$ is unsubstituted $C_1$-$C_5$ alkyl. In embodiments, $R^{21A}$ is unsubstituted methyl. In embodiments, $R^{21A}$ is unsubstituted ethyl. In embodiments, $R^{21A}$ is unsubstituted propyl. In embodiments, $R^{21A}$ is unsubstituted n-propyl. In embodiments, $R^{21A}$ is unsubstituted isopropyl. In embodiments, $R^{21A}$ is unsubstituted butyl. In embodiments, $R^{21A}$ is unsubstituted n-butyl. In embodiments, $R^{21A}$ is unsubstituted tert-butyl. In embodiments, $R^{21A}$ is substituted or unsubstituted 2 to 10 membered heteroalkyl. In embodiments, $R^{21A}$ is unsubstituted 2 to 6 membered heteroalkyl. In embodiments, $R^{21A}$ is substituted or unsubstituted $C_1$-$C_{10}$ thiol-alkyl or substituted or unsubstituted 2 to 10 membered thiol-heteroalkyl. In embodiments, $R^{21A}$ is unsubstituted $C_1$-$C_{10}$ thiol-alkyl or unsubstituted 2 to 10 membered thiol-heteroalkyl. In embodiments, $R^{21A}$ is unsubstituted thiomethyl (e.g., $—CH_2SH$), unsubstituted thioethyl (e.g., $—(CH_2)_2SH$), unsubstituted thiopropyl (e.g., $—(CH_2)_3SH$), unsubstituted thiobutyl (e.g., $—(CH_2)_4SH$), unsubstituted thiopentyl (e.g., $—(CH_2)_5SH$), unsubstituted thiohexyl (e.g., $—(CH_2)_6SH$), unsubstituted thioheptyl (e.g., $—(CH_2)_7SH$), unsubstituted thiooctyl (e.g., $—(CH_2)_8SH$), unsubstituted thiononyl (e.g., $—(CH_2)_9SH$), or unsubstituted thiodecyl (e.g., $—(CH_2)_{10}$ SH). In embodiments, $R^{21A}$ is unsubstituted thioethyl. In embodiments, $R^{21A}$ is unsubstituted thiopropyl. In embodiments, $R^{21A}$ is unsubstituted thiobutyl. In embodiments, $R^{21A}$ is unsubstituted thiopentyl. In embodiments, $R^{21A}$ is unsubstituted thioethyloxyethyl.

In embodiments, a substituted $R^{21A}$ (e.g., substituted alkyl and/or substituted heteroalkyl) is substituted with at least one substituent group, size-limited substituent group, or lower substituent group; wherein if the substituted $R^{21A}$ is substituted with a plurality of groups selected from substituent groups, size-limited substituent groups, and lower substituent groups; each substituent group, size-limited substituent group, and/or lower substituent group may optionally be different. In embodiments, when $R^{21A}$ is substituted, it is substituted with at least one substituent group. In embodiments, when $R^{21A}$ is substituted, it is substituted with at least one size-limited substituent group. In embodiments, when $R^{21A}$ is substituted, it is substituted with at least one lower substituent group.

In embodiments, $R^{21A}$ is

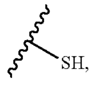, 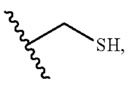,

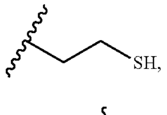, 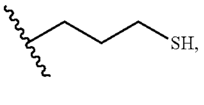,

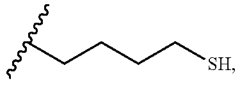, or

-continued

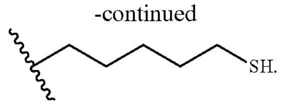

In embodiments, $R^{21B}$ is hydrogen. In embodiments, $R^{21B}$ is substituted or unsubstituted $C_1$-$C_{10}$ alkyl. In embodiments, $R^{21B}$ is substituted or unsubstituted 2 to 10 membered heteroalkyl. In embodiments, $R^{21B}$ is substituted or unsubstituted $C_1$-$C_{10}$ thiol-alkyl or substituted or unsubstituted 2 to 10 membered thiol-heteroalkyl. In embodiments, $R^{21B}$ is unsubstituted $C_1$-$C_{10}$ thiol-alkyl or unsubstituted 2 to 10 membered thiol-heteroalkyl. In embodiments, $R^{21B}$ is —C(O)-(substituted or unsubstituted $C_1$-$C_{10}$ alkyl). In embodiments, $R^{21B}$ is —C(O)-(substituted or unsubstituted $C_1$-$C_{10}$ thiol-alkyl). In embodiments, $R^{21B}$ is —C(O)-(substituted or unsubstituted 2 to 10 membered thiol-heteroalkyl).

In embodiments, a substituted $R^{21B}$ (e.g., substituted alkyl and/or substituted heteroalkyl) is substituted with at least one substituent group, size-limited substituent group, or lower substituent group; wherein if the substituted $R^{21B}$ is substituted with a plurality of groups selected from substituent groups, size-limited substituent groups, and lower substituent groups; each substituent group, size-limited substituent group, and/or lower substituent group may optionally be different. In embodiments, when $R^{21B}$ is substituted, it is substituted with at least one substituent group. In embodiments, when $R^{21B}$ is substituted, it is substituted with at least one size-limited substituent group. In embodiments, when $R^{21B}$ is substituted, it is substituted with at least one lower substituent group.

In embodiments, $R^{21C}$ is hydrogen. In embodiments, $R^{21C}$ is substituted or unsubstituted $C_1$-$C_{10}$ alkyl. In embodiments, $R^{21C}$ is substituted or unsubstituted 2 to 10 membered heteroalkyl. In embodiments, $R^{21C}$ is substituted or unsubstituted $C_1$-$C_{10}$ thiol-alkyl or substituted or unsubstituted 2 to 10 membered thiol-heteroalkyl. In embodiments, $R^{21C}$ is unsubstituted $C_1$-$C_{10}$ thiol-alkyl or unsubstituted 2 to 10 membered thiol-heteroalkyl.

In embodiments, a substituted $R^{21C}$ (e.g., substituted alkyl and/or substituted heteroalkyl) is substituted with at least one substituent group, size-limited substituent group, or lower substituent group; wherein if the substituted $R^{21C}$ is substituted with a plurality of groups selected from substituent groups, size-limited substituent groups, and lower substituent groups; each substituent group, size-limited substituent group, and/or lower substituent group may optionally be different. In embodiments, when $R^{21C}$ is substituted, it is substituted with at least one substituent group. In embodiments, when $R^{21C}$ is substituted, it is substituted with at least one size-limited substituent group. In embodiments, when $R^{21C}$ is substituted, it is substituted with at least one lower substituent group.

In embodiments, $R^{22}$ is —$SR^{22A}$. In embodiments, $R^{22}$ is —$OR^{22A}$. In embodiments, $R^{22}$ is —$NR^{22B}R^{22C}$. In embodiments, $R^{22}$ is —$NR^{22B}C(O)R^{22C}$. In embodiments, $R^{22}$ is —$NR^{22B}C(O)OR^{22C}$. In embodiments, $R^{22}$ is —SH. In embodiments, $R^{22}$ is —OH. In embodiments, $R^{22}$ is —$NH_2$. In embodiments, $R^{22}$ is —NHC(O)H. In embodiments, $R^{22}$ is —$NHC(O)CH_3$. In embodiments, $R^{22}$ is —NHC(O)OH. In embodiments, $R^{22}$ is substituted or unsubstituted $C_1$-$C_{10}$ alkyl. In embodiments, RP is unsubstituted $C_1$-$C_5$ alkyl. In embodiments, $R^{22}$ is unsubstituted methyl. In embodiments, $R^{22}$ is unsubstituted ethyl. In embodiments, $R^{22}$ is unsubstituted propyl. In embodiments, $R^{22}$ is unsubstituted n-propyl. In embodiments, $R^{22}$ is unsubstituted isopropyl. In embodiments, $R^{22}$ is unsubstituted butyl. In embodiments, $R^{22}$ is unsubstituted n-butyl. In embodiments, $R^{22}$ is unsubstituted tert-butyl. In embodiments, $R^{22}$ is substituted or unsubstituted 2 to 10 membered heteroalkyl. In embodiments, $R^{22}$ is substituted or unsubstituted $C_1$-$C_{10}$ thiol-alkyl or substituted or unsubstituted 2 to 10 membered thiol-heteroalkyl. In embodiments, $R^2$ is unsubstituted $C_1$-$C_{10}$ thiol-alkyl or unsubstituted 2 to 10 membered thiol-heteroalkyl. In embodiments, $R^2$ is unsubstituted thiomethyl (e.g., —$CH_2SH$), unsubstituted thioethyl (e.g., —$(CH_2)_2SH$), unsubstituted thiopropyl (e.g., —$(CH_2)_3SH$), unsubstituted thiobutyl (e.g., —$(CH_2)_4SH$), unsubstituted thiopentyl (e.g., —$(CH_2)_5SH$), unsubstituted thiohexyl (e.g., —$(CH_2)_6SH$), unsubstituted thioheptyl (e.g., —$(CH_2)_7SH$), unsubstituted thiooctyl (e.g., —$(CH_2)_8SH$), unsubstituted thiononyl (e.g., —$(CH_2)_9SH$), or unsubstituted thiodecyl (e.g., —$(CH_2)_{10}SH$). In embodiments, $R^{22}$ is unsubstituted thioethyl. In embodiments, $R^{22}$ is unsubstituted thiopropyl. In embodiments, $R^2$ is unsubstituted thiobutyl. In embodiments, $R^{22}$ is unsubstituted thiopentyl. In embodiments, $R^{22}$ is unsubstituted alkoxy. In embodiments, $R^{22}$ is —O-(unsubstituted $C_1$-$C_4$ alkyl). In embodiments, $R^{22}$ is unsubstituted methoxy. In embodiments, $R^{22}$ is unsubstituted ethoxy. In embodiments, $R^{22}$ is unsubstituted propoxy. In embodiments, $R^{22}$ is unsubstituted n-propoxy. In embodiments, $R^{22}$ is unsubstituted isopropoxy. In embodiments, $R^{22}$ is unsubstituted butoxy. In embodiments, $R^{22}$ is unsubstituted n-butoxy. In embodiments, $R^{22}$ is unsubstituted tert-butoxy.

In embodiments, a substituted $R^{22}$ (e.g., substituted alkyl and/or substituted heteroalkyl) is substituted with at least one substituent group, size-limited substituent group, or lower substituent group; wherein if the substituted $R^{22}$ is substituted with a plurality of groups selected from substituent groups, size-limited substituent groups, and lower substituent groups; each substituent group, size-limited substituent group, and/or lower substituent group may optionally be different. In embodiments, when $R^{22}$ is substituted, it is substituted with at least one substituent group. In embodiments, when $R^{22}$ is substituted, it is substituted with at least one size-limited substituent group. In embodiments, when $R^{22}$ is substituted, it is substituted with at least one lower substituent group.

In embodiments, $R^{22A}$ is hydrogen. In embodiments, $R^{22A}$ is substituted or unsubstituted $C_1$-$C_{10}$ alkyl. In embodiments, $R^{22A}$ is substituted or unsubstituted 2 to 10 membered heteroalkyl. In embodiments, $R^{22A}$ is substituted or unsubstituted $C_1$-$C_{10}$ thiol-alkyl or substituted or unsubstituted 2 to 10 membered thiol-heteroalkyl. In embodiments, $R^{22A}$ is unsubstituted $C_1$-$C_{10}$ thiol-alkyl or unsubstituted 2 to 10 membered thiol-heteroalkyl.

In embodiments, a substituted $R^{22A}$ (e.g., substituted alkyl and/or substituted heteroalkyl) is substituted with at least one substituent group, size-limited substituent group, or lower substituent group; wherein if the substituted $R^{22A}$ is substituted with a plurality of groups selected from substituent groups, size-limited substituent groups, and lower substituent groups; each substituent group, size-limited substituent group, and/or lower substituent group may optionally be different. In embodiments, when $R^{22A}$ is substituted, it is substituted with at least one substituent group. In embodiments, when $R^{22A}$ is substituted, it is substituted with at least one size-limited substituent group. In embodiments, when $R^{22A}$ is substituted, it is substituted with at least one lower substituent group.

In embodiments, $R^{22A}$ is

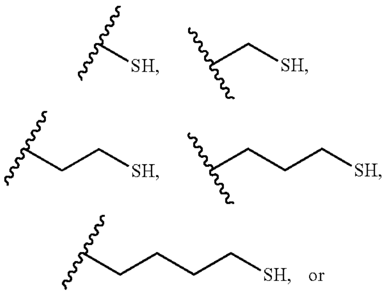

or

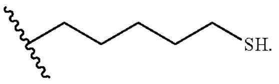

In embodiments, $R^{22B}$ is hydrogen. In embodiments, $R^{22B}$ is substituted or unsubstituted $C_1$-$C_{10}$ alkyl. In embodiments, $R^{22B}$ is substituted or unsubstituted 2 to 10 membered heteroalkyl. In embodiments, $R^{22B}$ is substituted or unsubstituted $C_1$-$C_{10}$ thiol-alkyl or substituted or unsubstituted 2 to 10 membered thiol-heteroalkyl. In embodiments, $R^{22B}$ is unsubstituted $C_1$-$C_{10}$ thiol-alkyl or unsubstituted 2 to 10 membered thiol-heteroalkyl. In embodiments, $R^{22B}$ is —C(O)-(substituted or unsubstituted $C_1$-$C_{10}$ alkyl). In embodiments, $R^{22B}$ is —C(O)-(substituted or unsubstituted $C_1$-$C_{10}$ thiol-alkyl). In embodiments, $R^{22B}$ is —C(O)-(substituted or unsubstituted 2 to 10 membered thiol-heteroalkyl).

In embodiments, a substituted $R^{22B}$ (e.g., substituted alkyl and/or substituted heteroalkyl) is substituted with at least one substituent group, size-limited substituent group, or lower substituent group; wherein if the substituted $R^{22B}$ is substituted with a plurality of groups selected from substituent groups, size-limited substituent groups, and lower substituent groups; each substituent group, size-limited substituent group, and/or lower substituent group may optionally be different. In embodiments, when $R^{22B}$ is substituted, it is substituted with at least one substituent group. In embodiments, when $R^{22B}$ is substituted, it is substituted with at least one size-limited substituent group. In embodiments, when $R^{22B}$ is substituted, it is substituted with at least one lower substituent group.

In embodiments, $R^{22C}$ is hydrogen. In embodiments, $R^{22C}$ is substituted or unsubstituted $C_1$-$C_{10}$ alkyl. In embodiments, $R^{22C}$ is substituted or unsubstituted 2 to 10 membered heteroalkyl. In embodiments, $R^{22C}$ is substituted or unsubstituted $C_1$-$C_{10}$ thiol-alkyl or substituted or unsubstituted 2 to 10 membered thiol-heteroalkyl. In embodiments, $R^7$ is unsubstituted $C_1$-$C_{10}$ thiol-alkyl or unsubstituted 2 to 10 membered thiol-heteroalkyl.

In embodiments, a substituted $R^{22C}$ (e.g., substituted alkyl and/or substituted heteroalkyl) is substituted with at least one substituent group, size-limited substituent group, or lower substituent group; wherein if the substituted $R^{22C}$ is substituted with a plurality of groups selected from substituent groups, size-limited substituent groups, and lower substituent groups; each substituent group, size-limited substituent group, and/or lower substituent group may optionally be different. In embodiments, when $R^{22C}$ is substituted, it is substituted with at least one substituent group. In embodiments, when $R^{22C}$ is substituted, it is substituted with at least one size-limited substituent group. In embodiments, when $R^{22C}$ is substituted, it is substituted with at least one lower substituent group.

In embodiments, $R^{23}$ is —$SR^{23A}$. In embodiments, $R^{23}$ is —$OR^{23A}$. In embodiments, $R^{23}$ is —$NR^{23B}R^{23C}$. In embodiments, $R^{23}$ is —$NR^{23B}C(O)R^{23C}$. In embodiments, $R^{23}$ is —$NR^{23B}C(O)OR^{23C}$. In embodiments, $R^{23}$ is —SH. In embodiments, $R^{23}$ is —OH. In embodiments, $R^{23}$ is —$NH_2$. In embodiments, $R^{23}$ is —NHC(O)H. In embodiments, $R^{23}$ is —NHC(O)OH. In embodiments, $R^{23}$ is substituted or unsubstituted $C_1$-$C_{10}$ alkyl. In embodiments, $R^{23}$ is unsubstituted $C_1$-$C_5$ alkyl. In embodiments, $R^{23}$ is unsubstituted methyl. In embodiments, $R^{23}$ is unsubstituted ethyl. In embodiments, $R^{23}$ is unsubstituted propyl. In embodiments, $R^{23}$ is unsubstituted n-propyl. In embodiments, $R^{23}$ is unsubstituted isopropyl. In embodiments, $R^{23}$ is unsubstituted butyl. In embodiments, $R^{23}$ is unsubstituted n-butyl. In embodiments, $R^{23}$ is unsubstituted tert-butyl. In embodiments, $R^{23}$ is substituted or unsubstituted 2 to 10 membered heteroalkyl. In embodiments, $R^{23}$ is substituted or unsubstituted $C_1$-$C_{10}$ thiol-alkyl or substituted or unsubstituted 2 to 10 membered thiol-heteroalkyl. In embodiments, $R^{23}$ is unsubstituted $C_1$-$C_{10}$ thiol-alkyl or unsubstituted 2 to 10 membered thiol-heteroalkyl. In embodiments, $R^2$ is unsubstituted thiomethyl (e.g., —$CH_2SH$), unsubstituted thioethyl (e.g., —$(CH_2)_2SH$), unsubstituted thiopropyl (e.g., —$(CH_2)_2$ SH), unsubstituted thiobutyl (e.g., —$(CH_2)_4SH$), unsubstituted thiopentyl (e.g., —$(CH_2)_5SH$), unsubstituted thiohexyl (e.g., —$(CH_2)_6SH$), unsubstituted thioheptyl (e.g., —$(CH_2)_7SH$), unsubstituted thiooctyl (e.g., —$(CH_2)_8SH$), unsubstituted thiononyl (e.g., —$(CH_2)_9SH$), or unsubstituted thiodecyl (e.g., —$(CH_2)_{10}SH$). In embodiments, $R^{23}$ is unsubstituted thioethyl. In embodiments, $R^{23}$ is unsubstituted thiopropyl. In embodiments, $R^{23}$ is unsubstituted thiobutyl. In embodiments, $R^{23}$ is unsubstituted thiopentyl. In embodiments, $R^{23}$ is unsubstituted alkoxy. In embodiments, $R^{23}$ is —O-(unsubstituted $C_1$-$C_4$ alkyl). In embodiments, $R^{23}$ is unsubstituted methoxy. In embodiments, $R^{23}$ is unsubstituted ethoxy. In embodiments, $R^{23}$ is unsubstituted propoxy. In embodiments, $R^{23}$ is unsubstituted n-propoxy. In embodiments, $R^{23}$ is unsubstituted isopropoxy. In embodiments, $R^{23}$ is unsubstituted butoxy. In embodiments, $R^{23}$ is unsubstituted n-butoxy. In embodiments, $R^{23}$ is unsubstituted tert-butoxy.

In embodiments, a substituted $R^{23}$ (e.g., substituted alkyl and/or substituted heteroalkyl) is substituted with at least one substituent group, size-limited substituent group, or lower substituent group; wherein if the substituted $R^{23}$ is substituted with a plurality of groups selected from substituent groups, size-limited substituent groups, and lower substituent groups; each substituent group, size-limited substituent group, and/or lower substituent group may optionally be different. In embodiments, when $R^{23}$ is substituted, it is substituted with at least one substituent group. In embodiments, when $R^{23}$ is substituted, it is substituted with at least one size-limited substituent group. In embodiments, when $R^{23}$ is substituted, it is substituted with at least one lower substituent group.

In embodiments, $R^{23A}$ is hydrogen. In embodiments, $R^{23A}$ is substituted or unsubstituted $C_1$-$C_{10}$ alkyl. In embodiments, $R^{23A}$ is substituted or unsubstituted 2 to 10 membered heteroalkyl. In embodiments, $R^{23A}$ is substituted or unsubstituted $C_1$-$C_{10}$ thiol-alkyl or substituted or unsubstituted 2 to 10 membered thiol-heteroalkyl. In embodiments, $R^{23A}$ is unsubstituted $C_1$-$C_{10}$ thiol-alkyl or unsubstituted 2 to 10 membered thiol-heteroalkyl.

In embodiments, a substituted $R^{23A}$ (e.g., substituted alkyl and/or substituted heteroalkyl) is substituted with at least one substituent group, size-limited substituent group, or lower substituent group; wherein if the substituted $R^{23A}$ is substituted with a plurality of groups selected from substituent groups, size-limited substituent groups, and lower substituent groups; each substituent group, size-limited substituent group, and/or lower substituent group may optionally be different. In embodiments, when $R^{23A}$ is substituted, it is substituted with at least one substituent group. In embodiments, when $R^{23A}$ is substituted, it is substituted with at least one size-limited substituent group. In embodiments, when $R^{23A}$ is substituted, it is substituted with at least one lower substituent group.

In embodiments, $R^{23A}$ is

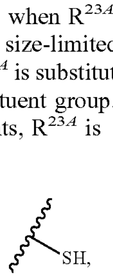,
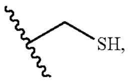,
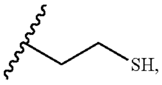,
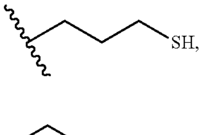,
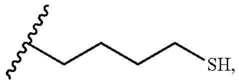, or
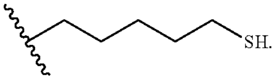.

In embodiments, $R^{23B}$ is hydrogen. In embodiments, $R^{23B}$ is substituted or unsubstituted $C_1$-$C_{10}$ alkyl. In embodiments, $R^{23B}$ is substituted or unsubstituted 2 to 10 membered heteroalkyl. In embodiments, $R^{23B}$ is substituted or unsubstituted $C_1$-$C_{10}$ thiol-alkyl or substituted or unsubstituted 2 to 10 membered thiol-heteroalkyl. In embodiments, $R^{23B}$ is unsubstituted $C_1$-$C_{10}$ thiol-alkyl or unsubstituted 2 to 10 membered thiol-heteroalkyl. In embodiments, $R^{23B}$ is —C(O)-(substituted or unsubstituted $C_1$-$C_{10}$ alkyl). In embodiments, $R^{23B}$ is —C(O)-(substituted or unsubstituted $C_1$-$C_{10}$ thiol-alkyl). In embodiments, $R^{23B}$ is —C(O)-(substituted or unsubstituted 2 to 10 membered thiol-heteroalkyl).

In embodiments, a substituted $R^{23B}$ (e.g., substituted alkyl and/or substituted heteroalkyl) is substituted with at least one substituent group, size-limited substituent group, or lower substituent group; wherein if the substituted $R^{23B}$ is substituted with a plurality of groups selected from substituent groups, size-limited substituent groups, and lower substituent groups; each substituent group, size-limited substituent group, and/or lower substituent group may optionally be different. In embodiments, when $R^{23B}$ is substituted, itis substituted with at least one substituent group. In embodiments, when $R^{23B}$ is substituted, it is substituted with at least one size-limited substituent group. In embodiments, when $R^{23B}$ is substituted, it is substituted with at least one lower substituent group.

In embodiments, $R^{23C}$ is hydrogen. In embodiments, $R^{23C}$ is substituted or unsubstituted $C_1$-$C_{10}$ alkyl. In embodiments, $R^{23C}$ is substituted or unsubstituted 2 to 10 membered heteroalkyl. In embodiments, $R^{23C}$ is substituted or unsubstituted $C_1$-$C_{10}$ thiol-alkyl or substituted or unsubstituted 2 to 10 membered thiol-heteroalkyl. In embodiments, $R^{23C}$ is unsubstituted $C_1$-$C_{10}$ thiol-alkyl or unsubstituted 2 to 10 membered thiol-heteroalkyl.

In embodiments, a substituted $R^{23C}$ (e.g., substituted alkyl and/or substituted heteroalkyl) is substituted with at least one substituent group, size-limited substituent group, or lower substituent group; wherein if the substituted $R^{23C}$ is substituted with a plurality of groups selected from substituent groups, size-limited substituent groups, and lower substituent groups; each substituent group, size-limited substituent group, and/or lower substituent group may optionally be different. In embodiments, when $R^{23C}$ is substituted, it is substituted with at least one substituent group. In embodiments, when $R^{23C}$ is substituted, it is substituted with at least one size-limited substituent group. In embodiments, when $R^{23C}$ is substituted, it is substituted with at least one lower substituent group.

In embodiments, $R^{25}$ is hydrogen. In embodiments, $R^{25}$ is —$SR^{25A}$. In embodiments, $R^{25}$ is —$SC(O)R^{25A}$. In embodiments, $R^{25}$ is —$OR^{25A}$. In embodiments, $R^{25}$ is —$NR^{25B}R^{25C}$. In embodiments, $R^{25}$ is —$NR^{25B}C(O)R^{25C}$. In embodiments, $R^{25}$ is —$NR^{25B}C(O)OR^{25C}$. In embodiments, $R^{25}$ is —SH. In embodiments, $R^{25}$ is —$SC(O)CH_3$. In embodiments, $R^{25}$ is —OH. In embodiments, $R^{25}$ is —$NH_2$. In embodiments, $R^{25}$ is —NHC(O)H. In embodiments, Ru is —NHC(O)OH. In embodiments, $R^{25}$ is substituted or unsubstituted $C_1$-$C_{10}$ alkyl. In embodiments, $R^{25}$ is unsubstituted $C_1$-$C_5$ alkyl. In embodiments, $R^{25}$ is unsubstituted methyl. In embodiments, $R^{25}$ is unsubstituted ethyl. In embodiments, $R^{25}$ is unsubstituted propyl. In embodiments, $R^{25}$ is unsubstituted n-propyl. In embodiments, $R^{25}$ is unsubstituted isopropyl. In embodiments, $R^{25}$ is unsubstituted butyl. In embodiments, $R^{25}$ is unsubstituted n-butyl. In embodiments, $R^{25}$ is unsubstituted tert-butyl. In embodiments, $R^{25}$ is substituted or unsubstituted 2 to 10 membered heteroalkyl. In embodiments, $R^{25}$ is substituted or unsubstituted $C_1$-$C_{10}$ thiol-alkyl or substituted or unsubstituted 2 to 10 membered thiol-heteroalkyl. In embodiments, $R^{25}$ is unsubstituted $C_1$-$C_{10}$ thiol-alkyl or unsubstituted 2 to 10 membered thiol-heteroalkyl. In embodiments, $R^{25}$ is unsubstituted thiomethyl (e.g., —$CH_2SH$), unsubstituted thioethyl (e.g., —$(CH_2)_2SH$), unsubstituted thiopropyl (e.g., —$(CH_2)_3$ SH), unsubstituted thiobutyl (e.g., —$(CH_2)_4SH$), unsubstituted thiopentyl (e.g., —$(CH_2)_5SH$), unsubstituted thiohexyl (e.g., —$(CH_2)_6SH$), unsubstituted thioheptyl (e.g., —$(CH_2)_7SH$), unsubstituted thiooctyl (e.g., —$(CH_2)_8SH$), unsubstituted thiononyl (e.g., —$(CH_2)_9SH$), or unsubstituted thiodecyl (e.g., —$(CH_2)_{10}SH$). In embodiments, $R^2$ is unsubstituted thioethyl. In embodiments, $R^{25}$ is unsubstituted thiopropyl. In embodiments, Ru is unsubstituted thiobutyl. In embodiments, $R^{25}$ is unsubstituted thiopentyl. In embodiments, $R^{25}$ is unsubstituted alkoxy. In embodiments, $R^{25}$ is —O-(unsubstituted $C_1$-$C_4$ alkyl). In embodiments, $R^{25}$ is unsubstituted methoxy. In embodiments, $R^{25}$ is unsubstituted ethoxy. In embodiments, $R^{25}$ is unsubstituted propoxy. In embodiments, $R^{25}$ is unsubstituted n-propoxy. In embodiments, $R^{25}$ is unsubstituted isopropoxy. In embodiments, $R^{25}$ is unsubstituted butoxy. In embodiments, $R^{25}$ is unsubstituted n-butoxy. In embodiments, Ru is unsubstituted tert-butoxy.

In embodiments, a substituted $R^{25}$ (e.g., substituted alkyl and/or substituted heteroalkyl) is substituted with at least one substituent group, size-limited substituent group, or lower substituent group; wherein if the substituted $R^{25}$ is substituted with a plurality of groups selected from substituent groups, size-limited substituent groups, and lower substituent groups; each substituent group, size-limited substituent group, and/or lower substituent group may optionally be different. In embodiments, when $R^{25}$ is substituted, it is substituted with at least one substituent group. In embodiments, when $R^{25}$ is substituted, it is substituted with at least one size-limited substituent group. In embodiments, when $R^{25}$ is substituted, it is substituted with at least one lower substituent group.

In embodiments, $R^{25A}$ is hydrogen. In embodiments, $R^{25A}$ is substituted or unsubstituted $C_1$-$C_{10}$ alkyl. In embodiments, $R^{25A}$ is unsubstituted $C_1$-$C_{10}$ alkyl. In embodiments, $R^{25A}$ is unsubstituted methyl. In embodiments, $R^{25A}$ is unsubstituted ethyl. In embodiments, $R^{25A}$ is unsubstituted propyl. In embodiments, $R^{25A}$ is unsubstituted n-propyl. In embodiments, $R^{25A}$ is unsubstituted isopropyl. In embodiments, $R^{25A}$ is unsubstituted butyl. In embodiments, $R^{25A}$ is unsubstituted n-butyl. In embodiments, $R^{25A}$ is unsubstituted tert-butyl. In embodiments, $R^{25A}$ is substituted or unsubstituted 2 to 10 membered heteroalkyl. In embodiments, $R^{25A}$ is substituted or unsubstituted $C_1$-$C_{10}$ thiol-alkyl or substituted or unsubstituted 2 to 10 membered thiol-heteroalkyl. In embodiments, $R^{25A}$ is unsubstituted $C_1$-$C_{10}$ thiol-alkyl or unsubstituted 2 to 10 membered thiol-heteroalkyl. In embodiments, $R^{25A}$ is unsubstituted thiomethyl (e.g., $-CH_2SH$), unsubstituted thioethyl (e.g., $-(CH_2)_2SH$), unsubstituted thiopropyl (e.g., $-(CH_2)_3SH$), unsubstituted thiobutyl (e.g., $-(CH_2)_4SH$), unsubstituted thiopentyl (e.g., $-(CH_2)_5SH$), unsubstituted thiohexyl (e.g., $-(CH_2)_6SH$), unsubstituted thioheptyl (e.g., $-(CH_2)_7SH$), unsubstituted thiooctyl (e.g., $-(CH_2)_8SH$), unsubstituted thiononyl (e.g., $-(CH_2)_9SH$), or unsubstituted thiodecyl (e.g., $-(CH_2)_{10}SH$). In embodiments, $R^{25A}$ is unsubstituted thioethyl. In embodiments, $R^{25A}$ is unsubstituted thiopropyl. In embodiments, $R^{25A}$ is unsubstituted thiobutyl. In embodiments, $R^{25A}$ is unsubstituted thiopentyl.

In embodiments, a substituted $R^{25A}$ (e.g., substituted alkyl and/or substituted heteroalkyl) is substituted with at least one substituent group, size-limited substituent group, or lower substituent group; wherein if the substituted $R^{25A}$ is substituted with a plurality of groups selected from substituent groups, size-limited substituent groups, and lower substituent groups; each substituent group, size-limited substituent group, and/or lower substituent group may optionally be different. In embodiments, when $R^{25A}$ is substituted, it is substituted with at least one substituent group. In embodiments, when $R^{25A}$ is substituted, it is substituted with at least one size-limited substituent group. In embodiments, when $R^{25A}$ is substituted, it is substituted with at least one lower substituent group.

In embodiments, $R^{25A}$ is

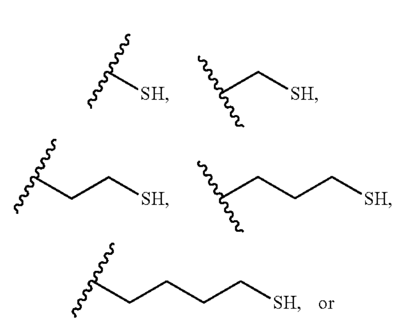

or

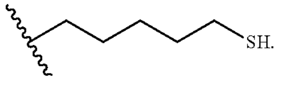

In embodiments, $R^{25B}$ is hydrogen. In embodiments, $R^{25B}$ is substituted or unsubstituted $C_1$-$C_{10}$ alkyl. In embodiments, $R^{25B}$ is substituted or unsubstituted 2 to 10 membered heteroalkyl. In embodiments, $R^{25B}$ is substituted or unsubstituted $C_1$-$C_{10}$ thiol-alkyl or substituted or unsubstituted 2 to 10 membered thiol-heteroalkyl. In embodiments, $R^{25B}$ is unsubstituted $C_1$-$C_{10}$ thiol-alkyl or unsubstituted 2 to 10 membered thiol-heteroalkyl. In embodiments, $R^{25B}$ is —C(O)-(substituted or unsubstituted $C_1$-$C_{10}$ alkyl). In embodiments, $R^{25B}$ is —C(O)-(substituted or unsubstituted $C_1$-$C_{10}$ thiol-alkyl). In embodiments, $R^{25B}$ is —C(O)-(substituted or unsubstituted 2 to 10 membered thiol-heteroalkyl).

In embodiments, a substituted $R^{25B}$ (e.g., substituted alkyl and/or substituted heteroalkyl) is substituted with at least one substituent group, size-limited substituent group, or lower substituent group; wherein if the substituted $R^{25B}$ is substituted with a plurality of groups selected from substituent groups, size-limited substituent groups, and lower substituent groups; each substituent group, size-limited substituent group, and/or lower substituent group may optionally be different. In embodiments, when $R^{25B}$ is substituted, it is substituted with at least one substituent group. In embodiments, when $R^{25B}$ is substituted, it is substituted with at least one size-limited substituent group. In embodiments, when $R^{25B}$ is substituted, it is substituted with at least one lower substituent group.

In embodiments, $R^{25C}$ is hydrogen. In embodiments, $R^{25C}$ is substituted or unsubstituted $C_1$-$C_{10}$ alkyl. In embodiments, $R^{25C}$ is substituted or unsubstituted 2 to 10 membered heteroalkyl. In embodiments, $R^{25C}$ is substituted or unsubstituted $C_1$-$C_{10}$ thiol-alkyl or substituted or unsubstituted 2 to 10 membered thiol-heteroalkyl. In embodiments, $R^{25C}$ is unsubstituted $C_1$-$C_{10}$ thiol-alkyl or unsubstituted 2 to 10 membered thiol-heteroalkyl.

In embodiments, a substituted $R^{25C}$ (e.g., substituted alkyl and/or substituted heteroalkyl) is substituted with at least one substituent group, size-limited substituent group, or lower substituent group; wherein if the substituted $R^{25C}$ is substituted with a plurality of groups selected from substituent groups, size-limited substituent groups, and lower substituent groups; each substituent group, size-limited substituent group, and/or lower substituent group may optionally be different. In embodiments, when $R^{25C}$ is substituted, it is substituted with at least one substituent group. In embodiments, when $R^{25C}$ is substituted, it is substituted with at least one size-limited substituent group. In embodiments, when $R^{25C}$ is substituted, it is substituted with at least one lower substituent group.

In embodiments, $R^{26}$ is hydrogen. In embodiments, $R^{26}$ is $-SR^{26A}$. In embodiments, $R^{26}$ is $-OR^{26A}$. In embodiments, $R^{26}$ is $-NR^{16B}R^{26C}$. In embodiments, $R^{26}$ is $-NR^{26B}C(O)R^{26C}$. In embodiments, $R^{26}$ is $-NR^{26B}C(O)OR^{26C}$. In embodiments, $R^{26}$ is —SH. In embodiments, $R^{26}$ is —OH. In embodiments, $R^{26}$ is $-NH_2$. In embodiments, $R^{26}$ is —NHC(O)H. In embodiments, $R^{26}$ is —NHC(O)OH. In embodiments, $R^{26}$ is substituted or unsubstituted $C_1$-$C_{10}$ alkyl. In embodiments, $R^{26}$ is unsubstituted $C_1$-$C_5$ alkyl. In embodiments, $R^{26}$ is unsubstituted methyl. In embodiments, $R^{26}$ is unsubstituted ethyl. In embodiments, $R^{26}$ is unsubstituted propyl. In embodiments, $R^{26}$ is unsubstituted n-propyl. In embodiments, $R^{26}$ is unsubstituted isopropyl. In embodiments, $R^{26}$ is unsubstituted butyl. In embodiments, $R^{26}$ is unsubstituted n-butyl. In embodiments, $R^{26}$ is unsubstituted tert-butyl. In embodiments, $R^{26}$ is substituted or unsubstituted 2 to 10 membered heteroalkyl. In embodiments, $R^{26}$ is substituted or unsubstituted $C_1$-$C_{10}$ thiol-alkyl or substituted or unsubstituted 2 to 10 membered thiol-heteroalkyl. In embodiments, $R^{26}$ is unsubstituted $C_1$-$C_{10}$ thiol-alkyl or unsubstituted 2 to 10 membered thiol-heteroalkyl. In embodiments, $R^{26}$ is unsubstituted thiomethyl (e.g., —$CH_2SH$), unsubstituted thioethyl (e.g., —$(CH_2)_2SH$), unsubstituted thiopropyl (e.g., —$(CH_2)_3SH$), unsubstituted thiobutyl (e.g., —$(CH_2)_4SH$), unsubstituted thiopentyl (e.g., —$(CH_2)_5SH$), unsubstituted thiohexyl (e.g., —$(CH_2)_6SH$), unsubstituted thioheptyl (e.g., —$(CH_2)_7SH$), unsubstituted thiooctyl (e.g., —$(CH_2)_8SH$), unsubstituted thiononyl (e.g., —$(CH_2)_9SH$), or unsubstituted thiodecyl (e.g., —$(CH_2)_{10}SH$). In embodiments, $R^{26}$ is unsubstituted thioethyl. In embodiments, $R^{26}$ is unsubstituted thiopropyl. In embodiments, $R^{26}$ is unsubstituted thiobutyl. In embodiments, $R^{26}$ is unsubstituted thiopentyl. In embodiments, $R^{26}$ is unsubstituted alkoxy. In embodiments, $R^{26}$ is —O-(unsubstituted $C_1$-$C_4$ alkyl). In embodiments, $R^{26}$ is unsubstituted methoxy. In embodiments, $R^{26}$ is unsubstituted ethoxy. In embodiments, $R^{26}$ is unsubstituted propoxy. In embodiments, $R^{26}$ is unsubstituted n-propoxy. In embodiments, $R^{26}$ is unsubstituted isopropoxy. In embodiments, $R^{26}$ is unsubstituted butoxy. In embodiments, $R^{26}$ is unsubstituted n-butoxy. In embodiments, $R^{26}$ is unsubstituted tert-butoxy.

In embodiments, a substituted $R^{26}$ (e.g., substituted alkyl and/or substituted heteroalkyl) is substituted with at least one substituent group, size-limited substituent group, or lower substituent group; wherein if the substituted $R^{26}$ is substituted with a plurality of groups selected from substituent groups, size-limited substituent groups, and lower substituent groups; each substituent group, size-limited substituent group, and/or lower substituent group may optionally be different. In embodiments, when $R^{26}$ is substituted, it is substituted with at least one substituent group. In embodiments, when $R^{26}$ is substituted, it is substituted with at least one size-limited substituent group. In embodiments, when $R^{26}$ is substituted, it is substituted with at least one lower substituent group.

In embodiments, $R^{26A}$ is hydrogen. In embodiments, $R^{26A}$ is substituted or unsubstituted $C_1$-$C_{10}$ alkyl. In embodiments, $R^{26A}$ is unsubstituted $C_1$-$C_{10}$ alkyl. In embodiments, $R^{26A}$ is unsubstituted methyl. In embodiments, $R^{26A}$ is unsubstituted ethyl. In embodiments, $R^{26A}$ is unsubstituted propyl. In embodiments, $R^{26A}$ is unsubstituted n-propyl. In embodiments, $R^{26A}$ is unsubstituted isopropyl. In embodiments, $R^{26A}$ is unsubstituted butyl. In embodiments, $R^{26A}$ is unsubstituted n-butyl. In embodiments, $R^{26A}$ is unsubstituted tert-butyl. In embodiments, $R^{26A}$ is substituted or unsubstituted 2 to 10 membered heteroalkyl. In embodiments, $R^{26A}$ is substituted or unsubstituted $C_1$-$C_{10}$ thiol-alkyl or substituted or unsubstituted 2 to 10 membered thiol-heteroalkyl. In embodiments, $R^{26A}$ is unsubstituted $C_1$-$C_{10}$ thiol-alkyl or unsubstituted 2 to 10 membered thiol-heteroalkyl. In embodiments, $R^{26A}$ is unsubstituted thiomethyl (e.g., —$CH_2SH$), unsubstituted thioethyl (e.g., —$(CH_2)_2SH$), unsubstituted thiopropyl (e.g., —$(CH_2)_3SH$), unsubstituted thiobutyl (e.g., —$(CH_2)_4SH$), unsubstituted thiopentyl (e.g., —$(CH_2)_5SH$), unsubstituted thiohexyl (e.g., —$(CH_2)_6SH$), unsubstituted thioheptyl (e.g., —$(CH_2)_7SH$), unsubstituted thiooctyl (e.g., —$(CH_2)_8SH$), unsubstituted thiononyl (e.g., —$(CH_2)_9SH$), or unsubstituted thiodecyl (e.g., —$(CH_2)_{10}SH$). In embodiments, $R^{26A}$ is unsubstituted thioethyl. In embodiments, $R^{26A}$ is unsubstituted thiopropyl. In embodiments, $R^{26A}$ is unsubstituted thiobutyl. In embodiments, $R^{26A}$ is unsubstituted thiopentyl.

In embodiments, a substituted $R^{26A}$ (e.g., substituted alkyl and/or substituted heteroalkyl) is substituted with at least one substituent group, size-limited substituent group, or lower substituent group; wherein if the substituted $R^{26A}$ is substituted with a plurality of groups selected from substituent groups, size-limited substituent groups, and lower substituent groups; each substituent group, size-limited substituent group, and/or lower substituent group may optionally be different. In embodiments, when $R^{26A}$ is substituted, it is substituted with at least one substituent group. In embodiments, when $R^{26A}$ is substituted, it is substituted with at least one size-limited substituent group. In embodiments, when $R^{26A}$ is substituted, it is substituted with at least one lower substituent group.

In embodiments, $R^{26A}$ is

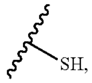,
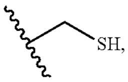,
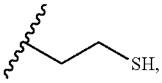,
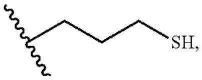,
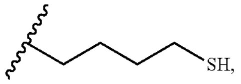, or
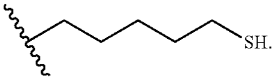.

In embodiments, $R^{26B}$ is hydrogen. In embodiments, $R^{26B}$ is substituted or unsubstituted $C_1$-$C_{10}$ alkyl. In embodiments, $R^{26B}$ is substituted or unsubstituted 2 to 10 membered heteroalkyl. In embodiments, $R^{26B}$ is substituted or unsubstituted $C_1$-$C_{10}$ thiol-alkyl or substituted or unsubstituted 2 to 10 membered thiol-heteroalkyl. In embodiments, $R^{26B}$ is unsubstituted $C_1$-$C_{10}$ thiol-alkyl or unsubstituted 2 to 10 membered thiol-heteroalkyl. In embodiments, $R^{26B}$ is —C(O)-(substituted or unsubstituted $C_1$-$C_{10}$ alkyl). In embodiments, $R^{26B}$ is —C(O)-(substituted or unsubstituted $C_1$-$C_{10}$ thiol-alkyl). In embodiments, $R^{26B}$ is —C(O)-(substituted or unsubstituted 2 to 10 membered thiol-heteroalkyl).

In embodiments, a substituted $R^{26B}$ (e.g., substituted alkyl and/or substituted heteroalkyl) is substituted with at least one substituent group, size-limited substituent group, or lower substituent group; wherein if the substituted $R^{26B}$ is substituted with a plurality of groups selected from substituent groups, size-limited substituent groups, and lower substituent groups; each substituent group, size-limited substituent group, and/or lower substituent group may optionally be different. In embodiments, when $R^{26B}$ is substituted, it is substituted with at least one substituent group. In embodiments, when $R^{26B}$ is substituted, it is substituted with at least one size-limited substituent group. In embodiments, when $R^{26B}$ is substituted, it is substituted with at least one lower substituent group.

In embodiments, $R^{26C}$ is hydrogen. In embodiments, $R^{26C}$ is substituted or unsubstituted $C_1$-$C_{10}$ alkyl. In embodiments, $R^{26C}$ is substituted or unsubstituted 2 to 10 membered heteroalkyl. In embodiments, $R^{26C}$ is substituted or unsubstituted $C_1$-$C_{10}$ thiol-alkyl or substituted or unsubstituted 2 to 10 membered thiol-heteroalkyl. In embodiments, $R^{26C}$ is unsubstituted $C_1$-$C_{10}$ thiol-alkyl or unsubstituted 2 to 10 membered thiol-heteroalkyl.

In embodiments, a substituted $R^{26C}$ (e.g., substituted alkyl and/or substituted heteroalkyl) is substituted with at least one substituent group, size-limited substituent group, or lower substituent group; wherein if the substituted $R^{26C}$ is substituted with a plurality of groups selected from substituent groups, size-limited substituent groups, and lower substituent groups; each substituent group, size-limited substituent group, and/or lower substituent group may optionally be different. In embodiments, when $R^{26C}$ is substituted, it is substituted with at least one substituent group. In embodiments, when $R^{26C}$ is substituted, it is substituted with at least one size-limited substituent group. In embodiments, when $R^{26C}$ is substituted, it is substituted with at least one lower substituent group.

In embodiments, $R^2$ is —$SR^{2A}$, —$OR^{2A}$, substituted or unsubstituted $C_1$-$C_{10}$ alkyl, or substituted or unsubstituted 2 to 10 membered heteroalkyl; $R^3$ is —$SR^{3A}$, —$OR^{3A}$, substituted or unsubstituted $C_1$-$C_{10}$ alkyl, or substituted or unsubstituted 2 to 10 membered heteroalkyl; $R^4$ is —$SR^{4A}$, —$OR^{4A}$, substituted or unsubstituted $C_1$-$C_{10}$ alkyl, or substituted or unsubstituted 2 to 10 membered heteroalkyl; $R^5$ is hydrogen, —$SR^{5A}$, —$OR^{5A}$, substituted or unsubstituted $C_1$-$C_{10}$ alkyl, or substituted or unsubstituted 2 to 10 membered heteroalkyl; $R^6$ is —$SR^{6A}$, —$OR^{6A}$, substituted or unsubstituted $C_1$-$C_{10}$ alkyl, or substituted or unsubstituted 2 to 10 membered heteroalkyl; $R^7$ is —$SR^{7A}$, —$OR^{7A}$, substituted or unsubstituted $C_1$-$C_{10}$ alkyl, or substituted or unsubstituted 2 to 10 membered heteroalkyl; $R^8$ is —$SR^{8A}$, —$OR^{8A}$, substituted or unsubstituted $C_1$-$C_{10}$ alkyl, or substituted or unsubstituted 2 to 10 membered heteroalkyl; $R^{10}$ is hydrogen, —$SR^{10A}$, —$OR^{10A}$, substituted or unsubstituted $C_1$-$C_{10}$ alkyl, or substituted or unsubstituted 2 to 10 membered heteroalkyl; $R^{11}$ is —$SR^{11A}$, —$OR^{11A}$, substituted or unsubstituted $C_1$-$C_{10}$ alkyl, or substituted or unsubstituted 2 to 10 membered heteroalkyl; $R^{21}$ is —$SR^{21A}$, —$OR^{21A}$, substituted or unsubstituted $C_1$-$C_{10}$ alkyl, or substituted or unsubstituted 2 to 10 membered heteroalkyl; $R^{22}$ is —$SR^{22A}$, —$OR^{22A}$, substituted or unsubstituted $C_1$-$C_{10}$ alkyl, or substituted or unsubstituted 2 to 10 membered heteroalkyl; $R^{23}$ is —$SR^{23A}$, —$OR^{23A}$, substituted or unsubstituted $C_1$-$C_{10}$ alkyl, or substituted or unsubstituted 2 to 10 membered heteroalkyl; $R^5$ is hydrogen, —$SR^{25A}$, —$OR^{25A}$, substituted or unsubstituted $C_1$-$C_{10}$ alkyl, or substituted or unsubstituted 2 to 10 membered heteroalkyl; and $R^{26}$ is —$SR^{26A}$, —$OR^{26A}$, substituted or unsubstituted $C_1$-$C_{10}$ alkyl, or substituted or unsubstituted 2 to 10 membered heteroalkyl.

In embodiments, $R^2$ is —$SR^{2A}$, —$OR^{2A}$, substituted or unsubstituted $C_1$-$C_{10}$ thiol-alkyl, or substituted or unsubstituted 2 to 10 membered thiol-heteroalkyl; $R^3$ is —$SR^{3A}$, —$OR^{3A}$, substituted or unsubstituted $C_1$-$C_{10}$ thiol-alkyl, or substituted or unsubstituted 2 to 10 membered thiol-heteroalkyl; $R^4$ is —$SR^{4A}$, —$OR^{4A}$, substituted or unsubstituted $C_1$-$C_{10}$ thiol-alkyl, or substituted or unsubstituted 2 to 10 membered thiol-heteroalkyl; $R^5$ is hydrogen, —$SR^{5A}$, —$OR^{5A}$, substituted or unsubstituted $C_1$-$C_{10}$ thiol-alkyl, or substituted or unsubstituted 2 to 10 membered thiol-heteroalkyl; $R^6$ is —$SR^{6A}$, —$OR^{6A}$, substituted or unsubstituted $C_1$-$C_{10}$ thiol-alkyl, or substituted or unsubstituted 2 to 10 membered thiol-heteroalkyl; $R^7$ is —$SR^{7A}$, —$OR^{7A}$, substituted or unsubstituted $C_1$-$C_{10}$ thiol-alkyl, or substituted or unsubstituted 2 to 10 membered thiol-heteroalkyl; $R^8$ is —$SR^{8A}$, —$OR^{8A}$, substituted or unsubstituted $C_1$-$C_{10}$ thiol-alkyl, or substituted or unsubstituted 2 to 10 membered thiol-heteroalkyl; $R^{10}$ is hydrogen, —$SR^{10A}$, —$OR^{10A}$, substituted or unsubstituted $C_1$-$C_{10}$ thiol-alkyl, or substituted or unsubstituted 2 to 10 membered thiol-heteroalkyl; $R^{11}$ is —$SR^{11A}$, —$OR^{11A}$, substituted or unsubstituted $C_1$-$C_{10}$ thiol-alkyl, or substituted or unsubstituted 2 to 10 membered thiol-heteroalkyl; $R^{21}$ is —$SR^{21A}$, —$OR^{21A}$, substituted or unsubstituted $C_1$-$C_{10}$ thiol-alkyl, or substituted or unsubstituted 2 to 10 membered thiol-heteroalkyl; $R^{22}$ is —$SR^{22A}$, —$OR^{22A}$, substituted or unsubstituted $C_1$-$C_{10}$ thiol-alkyl, or substituted or unsubstituted 2 to 10 membered thiol-heteroalkyl; $R^{23}$ is —$SR^{23A}$, —$OR^{23A}$, substituted or unsubstituted $C_1$-$C_{10}$ thiol-alkyl, or substituted or unsubstituted 2 to 10 membered thiol-heteroalkyl; $R^{26}$ is hydrogen, —$SR^{25A}$, —$OR^{25A}$, substituted or unsubstituted $C_1$-$C_{10}$ thiol-alkyl, or substituted or unsubstituted 2 to 10 membered thiol-heteroalkyl; and $R^{26}$ is —$SR^{26A}$, —$OR^{26A}$, substituted or unsubstituted $C_1$-$C_{10}$ thiol-alkyl, or substituted or unsubstituted 2 to 10 membered thiol-heteroalkyl.

In embodiments, $R^2$ is —$SR^{2A}$ or —$OR^{2A}$; $R^3$ is —$SR^{3A}$ or —$OR^{3A}$; $R^4$ is —$SR^{4A}$ or —$OR^{4A}$; $R^6$ is —$SR^{6A}$, or —$OR^{6A}$; $R^7$ is —$SR^{7A}$ or —$OR^{7A}$; $R^8$ is —$SR^{8A}$ or —$OR^{8A}$; $R^{11}$ is —$SR^{11A}$ or —$OR^{11A}$; $R^{21}$ is —$SR^{21A}$ or —$OR^{21A}$; $R^{22}$ is —$SR^{22A}$ or —$OR^{22A}$; $R^{23}$ is —$SR^{23A}$ or —$OR^{23A}$; and $R^{26}$ is —$SR^{26A}$ or —$OR^{26A}$. In embodiments, $R^2$ is —SH or —OH; $R^3$ is —SH or —OH; $R^4$ is —SH or —OH; $R^6$ is —SH or —OH; $R^7$ is hydrogen, —SH, or —OH; $R^8$ is —SH or —OH; $R^{11}$ is —SH or —OH; $R^{21}$ is —SH or —OH; $R^{21}$ is —SH or —OH; $R^{23}$ is —SH or —OH; and $R^{26}$ is —SH or —OH.

In embodiments, the thiosaccharide compound has the formula:

(IXa)

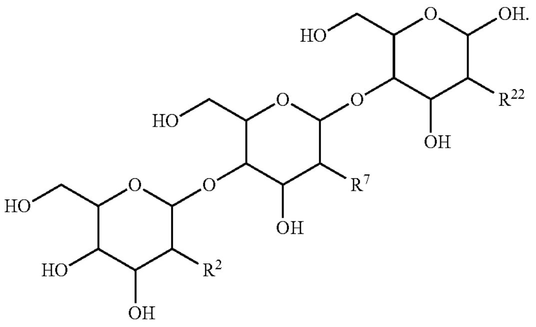

$R^2$, $R^7$, and $R^{22}$ are as described herein, including in embodiments.

In embodiments, the thiosaccharide compound has the formula:

(IXb)

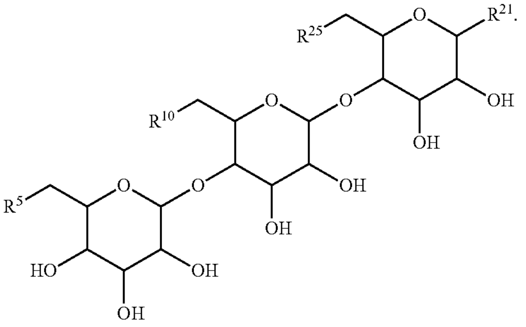

$R^5$, $R^{10}$, $R^{21}$, and $R^{25}$ are as described herein, including in embodiments.

In embodiments, the thiosaccharide compound has the formula:

(X)

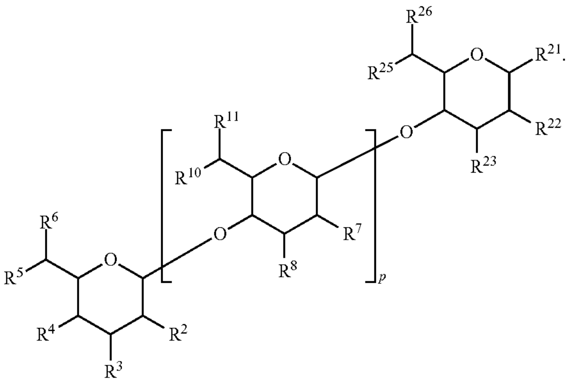

$R^2$, $R^3$, $R^4$, $R^5$, $R^6$, $R^7$, $R^8$, $R^{10}$, $R^{11}$, $R^{21}$, $R^{22}$, $R^{23}$, $R^{25}$, and $R^{26}$, are as described herein, including in embodiments. The variable p is an integer from 2 to 10.

In embodiments, p is 2. In embodiments, p is 3. In embodiments, p is 4. In embodiments, p is 5. In embodiments, p is 6. In embodiments, p is 7. In embodiments, p is 8. In embodiments, p is 9. In embodiments, p is 10.

In embodiments, when $R^1$ is substituted, $R^1$ is substituted with one or more first substituent groups denoted by $R^{1.1}$ as explained in the definitions section above in the description of "first substituent group(s)". In embodiments, when an $R^{1.1}$ substituent group is substituted, the $R^{1.1}$ substituent group is substituted with one or more second substituent groups denoted by $R^{1.2}$ as explained in the definitions section above in the description of "first substituent group(s)". In embodiments, when an $R^{1.2}$ substituent group is substituted, the $R^{1.2}$ substituent group is substituted with one or more third substituent groups denoted by $R^{1.3}$ as explained in the definitions section above in the description of "first substituent group(s)". In the above embodiments, $R^1$, $R^{1.1}$, $R^{1.2}$, and $R^{1.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^1$, $R^{1.1}$, $R^{1.2}$, and $R^{1.3}$, respectively.

In embodiments, when $R^{1A}$ is substituted, $R^{1A}$ is substituted with one or more first substituent groups denoted by $R^{1A.1}$ as explained in the definitions section above in the description of "first substituent group(s)". In embodiments, when an $R^{1A.1}$ substituent group is substituted, the $R^{1A.1}$ substituent group is substituted with one or more second substituent groups denoted by $R^{1A.2}$ as explained in the definitions section above in the description of "first substituent group(s)". In embodiments, when an $R^{1A.2}$ substituent group is substituted, the $R^{1A.2}$ substituent group is substituted with one or more third substituent groups denoted by $R^{1A.3}$ as explained in the definitions section above in the description of "first substituent group(s)". In the above embodiments, $R^{1A}$, $R^{1A.1}$, $R^{1A.2}$, and $R^{1A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{1A}$, $R^{1A.1}$, $R^{1A.2}$, AND $R^{1A.3}$, respectively.

In embodiments, when $R^{1B}$ is substituted, $R^{1B}$ is substituted with one or more first substituent groups denoted by $R^{1B.1}$ as explained in the definitions section above in the description of "first substituent group(s)". In embodiments, when an $R^{1B.1}$ substituent group is substituted, the $R^{1B.1}$ substituent group is substituted with one or more second substituent groups denoted by $R^{1B.2}$ as explained in the definitions section above in the description of "first substituent group(s)". In embodiments, when an $R^{1B.2}$ substituent group is substituted, the $R^{1B.2}$ substituent group is substituted with one or more third substituent groups denoted by $R^{1B.3}$ as explained in the definitions section above in the description of "first substituent group(s)". In the above embodiments, $R^{1B}$, $R^{1B.1}$, $R^{1B.2}$, and $R^{1B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{1B}$, $R^{1B.1}$, $R^{1B.2}$, and $R^{1B.3}$, respectively.

In embodiments, when $R^{1C}$ is substituted, $R^{1C}$ is substituted with one or more first substituent groups denoted by $R^{1C.1}$ as explained in the definitions section above in the description of "first substituent group(s)". In embodiments, when an $R^{1C.1}$ substituent group is substituted, the $R^{1C.1}$ substituent group is substituted with one or more second substituent groups denoted by $R^{1C.2}$ as explained in the definitions section above in the description of "first substituent group(s)". In embodiments, when an $R^{1C.2}$ substituent group is substituted, the $R^{1C.2}$ substituent group is substituted with one or more third substituent groups denoted by $R^{1C.3}$ as explained in the definitions section above in the description of "first substituent group(s)". In the above embodiments, $R^{1C}$, $R^{1C.1}$, $R^{1C.2}$, and $R^{1C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{1C}$, $R^{1C.1}$, $R^{1C.2}$, and $R^{1C.3}$, respectively.

In embodiments, when $R^2$ is substituted, $R^2$ is substituted with one or more first substituent groups denoted by $R^{2.1}$ as explained in the definitions section above in the description of "first substituent group(s)". In embodiments, when an $R^{2.1}$ substituent group is substituted, the $R^{2.1}$ substituent group is substituted with one or more second substituent groups denoted by $R^{2.2}$ as explained in the definitions section above in the description of "first substituent group(s)". In embodiments, when an $R^{2.2}$ substituent group is substituted, the $R^{2.2}$ substituent group is substituted with one or more third substituent groups denoted by $R^{2.3}$ as explained in the definitions section above in the description of "first substituent group(s)". In the above embodiments, $R^2$, $R^{2.1}$, $R^{2.2}$, and $R^{2.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^2$, $R^{2.1}$, $R^{2.2}$, and $R^{2.3}$, respectively.

In embodiments, when $R^{2A}$ is substituted, $R^{2A}$ is substituted with one or more first substituent groups denoted by $R^{2A.1}$ as explained in the definitions section above in the description of "first substituent group(s)". In embodiments, when an $R^{2A.1}$ substituent group is substituted, the $R^{2A.1}$ substituent group is substituted with one or more second substituent groups denoted by $R^{2A.2}$ as explained in the definitions section above in the description of "first substituent group(s)". In embodiments, when an $R^{2A.2}$ substituent group is substituted, the $R^{2A.2}$ substituent group is substituted with one or more third substituent groups denoted by $R^{2A.3}$ as explained in the definitions section above in the description of "first substituent group(s)". In the above embodiments, $R^{2A}$, $R^{2A.1}$, $R^{2A.2}$, and $R^{2A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{2A}$, $R^{2A.1}$, $R^{2A.2}$, and $R^{2A.3}$, respectively.

In embodiments, when $R^{2B}$ is substituted, $R^{2B}$ is substituted with one or more first substituent groups denoted by $R^{2B.1}$ as explained in the definitions section above in the description of "first substituent group(s)". In embodiments, when an $R^{2B.1}$ substituent group is substituted, the $R^{2B.1}$ substituent group is substituted with one or more second substituent groups denoted by $R^{2B.2}$ as explained in the definitions section above in the description of "first substituent group(s)". In embodiments, when an $R^{2B.2}$ substituent group is substituted, the $R^{2B.2}$ substituent group is substituted with one or more third substituent groups denoted by $R^{2B.3}$ as explained in the definitions section above in the description of "first substituent group(s)". In the above embodiments, $R^{2B}$, $R^{2B.1}$, $R^{2B.2}$, and $R^{2B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{2B}$, $R^{2B.1}$, $R^{2B.2}$, and $R^{2B.3}$, respectively.

In embodiments, when $R^{2C}$ is substituted, $R^{2C}$ is substituted with one or more first substituent groups denoted by $R^{2C.1}$ as explained in the definitions section above in the description of "first substituent group(s)". In embodiments, when an $R^{2C.1}$ substituent group is substituted, the $R^{2C.1}$ substituent group is substituted with one or more second substituent groups denoted by $R^{2C.2}$ as explained in the definitions section above in the description of "first substituent group(s)". In embodiments, when an $R^{2C.2}$ substituent group is substituted, the $R^{2C.2}$ substituent group is substituted with one or more third substituent groups denoted by $R^{2C.3}$ as explained in the definitions section above in the description of "first substituent group(s)". In the above embodiments, $R^{2C}$, $R^{2C.1}$, $R^{2C.2}$, and $R^{2C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{2}$, $R^{2C.1}$, $R^{2C.2}$, and $R^{2C.3}$, respectively.

In embodiments, when $R^3$ is substituted, $R^3$ is substituted with one or more first substituent groups denoted by $R^{3.1}$ as explained in the definitions section above in the description of "first substituent group(s)". In embodiments, when an $R^{3.1}$ substituent group is substituted, the $R^{3.1}$ substituent group is substituted with one or more second substituent groups denoted by $R^{3.2}$ as explained in the definitions section above in the description of "first substituent group(s)". In embodiments, when an $R^{3.2}$ substituent group is substituted, the $R^{3.2}$ substituent group is substituted with one or more third substituent groups denoted by $R^{3.3}$ as explained in the definitions section above in the description of "first substituent group(s)". In the above embodiments, $R^3$, $R^{3.1}$, $R^{3.2}$, and $R^{3.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^3$, $R^{3.1}$, $R^{3.2}$, and $R^{3.3}$, respectively.

In embodiments, when $R^{3A}$ is substituted, $R^{3A}$ is substituted with one or more first substituent groups denoted by $R^{3A.1}$ as explained in the definitions section above in the description of "first substituent group(s)". In embodiments, when an $R^{3A.1}$ substituent group is substituted, the $R^{3A.1}$ substituent group is substituted with one or more second substituent groups denoted by $R^{3A.2}$ as explained in the definitions section above in the description of "first substituent group(s)". In embodiments, when an $R^{3A.2}$ substituent group is substituted, the $R^{3A.2}$ substituent group is substituted with one or more third substituent groups denoted by $R^{3A.3}$ as explained in the definitions section above in the description of "first substituent group(s)". In the above embodiments, $R^{3A}$, $R^{3A.1}$, $R^{3A.2}$, and $R^{3A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{3A}$, $R^{3A.1}$, $R^{3A.2}$, and $R^{3A.3}$, respectively.

In embodiments, when $R^{3B}$ is substituted, $R^{3B}$ is substituted with one or more first substituent groups denoted by $R^{3B.1}$ as explained in the definitions section above in the description of "first substituent group(s)". In embodiments, when an $R^{3B.1}$ substituent group is substituted, the $R^{3B.1}$ substituent group is substituted with one or more second substituent groups denoted by $R^{3B.2}$ as explained in the definitions section above in the description of "first substituent group(s)". In embodiments, when an $R^{3B.2}$ substituent group is substituted, the $R^{3B.2}$ substituent group is substituted with one or more third substituent groups denoted by $R^{3B.3}$ as explained in the definitions section above in the description of "first substituent group(s)". In the above embodiments, $R^{3B}$, $R^{3B.1}$, $R^{3B.2}$, and $R^{3B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{3B}$, $R^{3B.1}$, $R^{3B.2}$, and $R^{3B.3}$, respectively.

In embodiments, when $R^{3C}$ is substituted, $R^{3C}$ is substituted with one or more first substituent groups denoted by $R^{3C.1}$ as explained in the definitions section above in the description of "first substituent group(s)". In embodiments, when an $R^{3C.1}$ substituent group is substituted, the $R^{3C.1}$ substituent group is substituted with one or more second substituent groups denoted by $R^{3C.2}$ as explained in the definitions section above in the description of "first substituent group(s)". In embodiments, when an $R^{3C.2}$ substituent group is substituted, the $R^{3C.2}$ substituent group is substituted with one or more third substituent groups denoted by $R^{3C.3}$ as explained in the definitions section above in the description of "first substituent group(s)". In the above embodiments, $R^{3C}$, $R^{3C.1}$, $R^{3C.2}$, and $R^{3C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{3C}$, $R^{3C.1}$, $R^{3C.2}$, and $R^{3C.3}$, respectively.

In embodiments, when $R^4$ is substituted, $R^4$ is substituted with one or more first substituent groups denoted by $R^{4.1}$ as explained in the definitions section above in the description of "first substituent group(s)". In embodiments, when an $R^{4.1}$ substituent group is substituted, the $R^{4.1}$ substituent group is substituted with one or more second substituent groups denoted by $R^{4.2}$ as explained in the definitions section above in the description of "first substituent group(s)". In embodiments, when an $R^{4.2}$ substituent group is substituted, the $R^{4.2}$ substituent group is substituted with one or more third substituent groups denoted by $R^{4.3}$ as explained in the definitions section above in the description of "first substituent group(s)". In the above embodiments, $R^4$, $R^{4.1}$, $R^{4.2}$, and $R^{4.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^4$, $R^{4.1}$, $R^{4.2}$, and $R^{4.3}$, respectively.

In embodiments, when $R^{4A}$ is substituted, $R^{4A}$ is substituted with one or more first substituent groups denoted by $R^{4A.1}$ as explained in the definitions section above in the description of "first substituent group(s)". In embodiments, when an $R^{4A.1}$ substituent group is substituted, the $R^{4A.1}$ substituent group is substituted with one or more second substituent groups denoted by $R^{4A.2}$ as explained in the definitions section above in the description of "first substituent group(s)". In embodiments, when an $R^{4A.2}$ substituent group is substituted, the $R^{4A.2}$ substituent group is substituted with one or more third substituent groups denoted by $R^{4A.3}$ as explained in the definitions section above in the description of "first substituent group(s)". In the above embodiments, $R^{4A}$, $R^{4A.1}$, $R^{4A.2}$, and $R^{4A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{4A}$, $R^{4A.1}$, $R^{4A.2}$, and $R^{4A.3}$, respectively.

In embodiments, when $R^{4B}$ is substituted, $R^{4B}$ is substituted with one or more first substituent groups denoted by $R^{4B.1}$ as explained in the definitions section above in the description of "first substituent group(s)". In embodiments, when an $R^{4B.1}$ substituent group is substituted, the $R^{4B.1}$ substituent group is substituted with one or more second substituent groups denoted by $R^{4B.2}$ as explained in the definitions section above in the description of "first substituent group(s)". In embodiments, when an $R^{4B.2}$ substituent group is substituted, the $R^{4B.2}$ substituent group is substituted with one or more third substituent groups denoted by $R^{4B.3}$ as explained in the definitions section above in the description of "first substituent group(s)". In the above embodiments, $R^{4B}$, $R^{4B.1}$, $R^{4B.2}$, and $R^{4B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{4B}$, $R^{4B.1}$, $R^{4B.2}$, and $R^{4B.3}$, respectively.

In embodiments, when $R^{4C}$ is substituted, $R^{4C}$ is substituted with one or more first substituent groups denoted by $R^{4C.1}$ as explained in the definitions section above in the description of "first substituent group(s)". In embodiments, when an $R^{4C.1}$ substituent group is substituted, the $R^{4C.1}$ substituent group is substituted with one or more second substituent groups denoted by $R^{4C.2}$ as explained in the definitions section above in the description of "first substituent group(s)". In embodiments, when an $R^{4C.2}$ substituent group is substituted, the $R^{4C.2}$ substituent group is substituted with one or more third substituent groups denoted by $R^{4C.3}$ as explained in the definitions section above in the description of "first substituent group(s)". In the above embodiments, $R^{4C}$, $R^{4C.1}$, $R^{4C.2}$, and $R^{4C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{4C}$, $R^{4C.1}$, $R^{4C.2}$, and $R^{4C.3}$, respectively.

In embodiments, when $R^5$ is substituted, $R^5$ is substituted with one or more first substituent groups denoted by $R^{5.1}$ as explained in the definitions section above in the description of "first substituent group(s)". In embodiments, when an $R^{5.1}$ substituent group is substituted, the $R^{5.1}$ substituent group is substituted with one or more second substituent groups denoted by $R^{5.2}$ as explained in the definitions section above in the description of "first substituent group(s)". In embodiments, when an $R^{5.2}$ substituent group is substituted, the $R^{5.2}$ substituent group is substituted with one or more third substituent groups denoted by $R^{5.3}$ as explained in the definitions section above in the description of "first substituent group(s)". In the above embodiments, $R^5$, $R^{5.1}$, $R^{5.2}$, and $R^{5.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^5$, $R^{5.1}$, $R^{5.2}$, and $R^{5.3}$, respectively.

In embodiments, when $R^{5A}$ is substituted, $R^{5A}$ is substituted with one or more first substituent groups denoted by $R^{5A.1}$ as explained in the definitions section above in the description of "first substituent group(s)". In embodiments, when an $R^{5A.1}$ substituent group is substituted, the $R^{5A.1}$ substituent group is substituted with one or more second substituent groups denoted by $R^{5A.2}$ as explained in the definitions section above in the description of "first substituent group(s)". In embodiments, when an $R^{5A.2}$ substituent group is substituted, the $R^{5A.2}$ substituent group is substituted with one or more third substituent groups denoted by $R^{5A.3}$ as explained in the definitions section above in the description of "first substituent group(s)". In the above embodiments, $R^{5A}$, $R^{5A.1}$, $R^{5A.2}$, and $R^{5A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{5A}$, $R^{5A.1}$, $R^{5A.2}$, and $R^{5A.3}$, respectively.

In embodiments, when $R^{5B}$ is substituted, $R^{5B}$ is substituted with one or more first substituent groups denoted by $R^{5B.1}$ as explained in the definitions section above in the description of "first substituent group(s)". In embodiments, when an $R^{5B.1}$ substituent group is substituted, the $R^{5B.1}$ substituent group is substituted with one or more second substituent groups denoted by $R^{5B.2}$ as explained in the definitions section above in the description of "first substituent group(s)". In embodiments, when an $R^{5B.2}$ substituent group is substituted, the $R^{5B.2}$ substituent group is substituted with one or more third substituent groups denoted by $R^{5B.3}$ as explained in the definitions section above in the description of "first substituent group(s)". In the above embodiments, $R^{5B}$, $R^{5B.1}$, $R^{5B.2}$, and $R^{5B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{5B}$, $R^{5B.1}$, $R^{5B.2}$, and $R^{5B.3}$, respectively.

In embodiments, when $R^{5C}$ is substituted, Rx is substituted with one or more first substituent groups denoted by $R^{5C.1}$ as explained in the definitions section above in the description of "first substituent group(s)". In embodiments, when an $R^{5C.1}$ substituent group is substituted, the $R^{5C.1}$ substituent group is substituted with one or more second substituent groups denoted by $R^{5C.2}$ as explained in the definitions section above in the description of "first substituent group(s)". In embodiments, when an $R^{5C.2}$ substituent group is substituted, the $R^{5C.2}$ substituent group is substituted with one or more third substituent groups denoted by $R^{5C.3}$ as explained in the definitions section above in the description of “first substituent group(s)”. In the above embodiments, $R^{5C}$, $R^{5C.1}$, $R^{5C.2}$, and $R^{5C.3}$ have values corresponding to the values of $R^{WW}$, $R^{WW.1}$, $R^{WW.2}$, and $R^{WW.3}$, respectively, as explained in the definitions section above in the description of “first substituent group(s)”, wherein $R^{WW}$, $R^{WW.1}$, $R^{WW.2}$, and $R^{WW.3}$ correspond to $R^{5C}$, $R^{5C.1}$, $R^{5C.2}$, and $R^{5C.3}$, respectively.

In embodiments, when $R^6$ is substituted, $R^6$ is substituted with one or more first substituent groups denoted by $R^{6.1}$ as explained in the definitions section above in the description of “first substituent group(s)”. In embodiments, when an $R^{6.1}$ substituent group is substituted, the $R^{6.1}$ substituent group is substituted with one or more second substituent groups denoted by $R^{6.2}$ as explained in the definitions section above in the description of “first substituent group(s)”. In embodiments, when an $R^{6.2}$ substituent group is substituted, the $R^{6.2}$ substituent group is substituted with one or more third substituent groups denoted by $R^{6.3}$ as explained in the definitions section above in the description of “first substituent group(s)”. In the above embodiments, $R^6$, $R^{6.1}$, $R^{6.2}$, and $R^{6.3}$ have values corresponding to the values of $R^{WW}$, $R^{WW.1}$, $R^{WW.2}$, and $R^{WW.3}$, respectively, as explained in the definitions section above in the description of “first substituent group(s)”, wherein $R^{WW}$, $R^{WW.1}$, $R^{WW.2}$, and $R^{WW.3}$ correspond to $R^6$, $R^{6.1}$, $R^{6.2}$, and $R^{6.3}$, respectively.

In embodiments, when $R^{6A}$ is substituted, $R^{6A}$ is substituted with one or more first substituent groups denoted by $R^{6A.1}$ as explained in the definitions section above in the description of “first substituent group(s)”. In embodiments, when an $R^{6A.1}$ substituent group is substituted, the $R^{6A.1}$ substituent group is substituted with one or more second substituent groups denoted by $R^{6A.2}$ as explained in the definitions section above in the description of “first substituent group(s)”. In embodiments, when an $R^{12}$ substituent group is substituted, the $R^{6A.2}$ substituent group is substituted with one or more third substituent groups denoted by $R^{6A.3}$ as explained in the definitions section above in the description of “first substituent group(s)”. In the above embodiments, $R^{6A}$, $R^{6A.1}$, $R^{6A.2}$, and $R^{6A.3}$ have values corresponding to the values of $R^{WW}$, $R^{WW.1}$, $R^{WW.2}$, and $R^{WW.3}$, respectively, as explained in the definitions section above in the description of “first substituent group(s)”, wherein $R^{WW}$, $R^{WW.1}$, $R^{WW.2}$, and $R^{WW.3}$ correspond to $R^{6A}$, $R^{6A.1}$, $R^{6A.2}$, and $R^{6A.3}$, respectively.

In embodiments, when $R^{6B}$ is substituted, $R^{6B}$ is substituted with one or more first substituent groups denoted by $R^{6B.1}$ as explained in the definitions section above in the description of “first substituent group(s)”. In embodiments, when an $R^{6B.1}$ substituent group is substituted, the $R^{6B.1}$ substituent group is substituted with one or more second substituent groups denoted by $R^{6B.2}$ as explained in the definitions section above in the description of “first substituent group(s)”. In embodiments, when an $R^{6B.2}$ substituent group is substituted, the $R^{6B.2}$ substituent group is substituted with one or more third substituent groups denoted by $R^{6B.3}$ as explained in the definitions section above in the description of “first substituent group(s)”. In the above embodiments, $R^{6B}$, $R^{6B.1}$, $R^{6B.2}$, and $R^{6B.3}$ have values corresponding to the values of $R^{WW}$, $R^{WW.1}$, $R^{WW.2}$, and $R^{WW.3}$, respectively, as explained in the definitions section above in the description of “first substituent group(s)”, wherein $R^{WW}$, $R^{WW.1}$, $R^{WW.2}$, and $R^{WW.3}$ correspond to $R^{6B}$, $R^{6B.1}$, $R^{6B.2}$, and $R^{6B.3}$, respectively.

In embodiments, when $R^{6C}$ is substituted, $R^{6C}$ is substituted with one or more first substituent groups denoted by $R^{6C.1}$ as explained in the definitions section above in the description of “first substituent group(s)”. In embodiments, when an $R^{6C.1}$ substituent group is substituted, the $R^{6C.1}$ substituent group is substituted with one or more second substituent groups denoted by $R^{6C.2}$ as explained in the definitions section above in the description of “first substituent group(s)”. In embodiments, when an $R^{6C.2}$ substituent group is substituted, the $R^{6C.2}$ substituent group is substituted with one or more third substituent groups denoted by $R^{6C.3}$ as explained in the definitions section above in the description of “first substituent group(s)”. In the above embodiments, $R^6$, $R^{6C.1}$, $R^{6C.2}$, and $R^{6C.3}$ have values corresponding to the values of $R^{WW}$, $R^{WW.1}$, $R^{WW.2}$, and $R^{WW.3}$, respectively, as explained in the definitions section above in the description of “first substituent group(s)”, wherein $R^{WW}$, $R^{WW.1}$, $R^{WW.2}$, and $R^{WW.3}$ correspond to $R^6$, $R^{6C.1}$, $R^{6C.2}$, and $R^{6C.3}$, respectively.

In embodiments, when $R^7$ is substituted, $R^7$ is substituted with one or more first substituent groups denoted by $R^{7.1}$ as explained in the definitions section above in the description of “first substituent group(s)”. In embodiments, when an $R^{7.1}$ substituent group is substituted, the $R^{7.1}$ substituent group is substituted with one or more second substituent groups denoted by $R^{7.2}$ as explained in the definitions section above in the description of “first substituent group(s)”. In embodiments, when an $R^{7.2}$ substituent group is substituted, the $R^{7.2}$ substituent group is substituted with one or more third substituent groups denoted by $R^{7.3}$ as explained in the definitions section above in the description of “first substituent group(s)”. In the above embodiments, $R^7$, $R^{7.1}$, $R^{7.2}$, and $R^{7.3}$ have values corresponding to the values of $R^{WW}$, $R^{WW.1}$, $R^{WW.2}$, and $R^{WW.3}$, respectively, as explained in the definitions section above in the description of “first substituent group(s)”, wherein $R^{WW}$, $R^{WW.1}$, $R^{WW.2}$, and $R^{WW.3}$ correspond to $R^7$, $R^{7.1}$, $R^{7.2}$, and $R^{7.3}$, respectively.

In embodiments, when $R^{7A}$ is substituted, $R^{7A}$ is substituted with one or more first substituent groups denoted by $R^{7A.1}$ as explained in the definitions section above in the description of “first substituent group(s)”. In embodiments, when an $R^{7A.1}$ substituent group is substituted, the $R^{7A.1}$ substituent group is substituted with one or more second substituent groups denoted by $R^{7A.2}$ as explained in the definitions section above in the description of “first substituent group(s)”. In embodiments, when an $R^{7A.2}$ substituent group is substituted, the $R^{7A.2}$ substituent group is substituted with one or more third substituent groups denoted by $R^{7A.3}$ as explained in the definitions section above in the description of “first substituent group(s)”. In the above embodiments, $R^{7A}$, $R^{7A.1}$, $R^{7A.2}$, and $R^{7A.3}$ have values corresponding to the values of $R^{WW}$, $R^{WW.1}$, $R^{WW.2}$, and $R^{WW.3}$, respectively, as explained in the definitions section above in the description of “first substituent group(s)”, wherein $R^{WW}$, $R^{WW.1}$, $R^{WW.2}$, and $R^{WW.3}$ correspond to $R^{7A}$, $R^{7A.1}$, $R^{7A.2}$, and $R^{7A.3}$, respectively.

In embodiments, when $R^{7B}$ is substituted, $R^{7B}$ is substituted with one or more first substituent groups denoted by $R^{7B.1}$ as explained in the definitions section above in the description of “first substituent group(s)”. In embodiments, when an $R^{7B.1}$ substituent group is substituted, the $R^{7B.1}$ substituent group is substituted with one or more second substituent groups denoted by $R^{7B.2}$ as explained in the definitions section above in the description of “first substituent group(s)”. In embodiments, when an $R^{7B.2}$ substituent group is substituted, the $R^{7B.2}$ substituent group is substituted with one or more third substituent groups denoted by $R^{7B.3}$ as explained in the definitions section above in the description of "first substituent group(s)". In the above embodiments, $R^{7B}$, $R^{7B.1}$, $R^{7B.2}$, and $R^{7B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{7B}$, $R^{7B.1}$, $R^{7B.2}$, and $R^{7B.3}$, respectively.

In embodiments, when $R^{7C}$ is substituted, $R^{7C}$ is substituted with one or more first substituent groups denoted by $R^{7C.1}$ as explained in the definitions section above in the description of "first substituent group(s)". In embodiments, when an $R^{7C.1}$ substituent group is substituted, the $R^{7C.1}$ substituent group is substituted with one or more second substituent groups denoted by $R^{7C.2}$ as explained in the definitions section above in the description of "first substituent group(s)". In embodiments, when an $R^{7C.2}$ substituent group is substituted, the $R^{7C.2}$ substituent group is substituted with one or more third substituent groups denoted by $R^{7C.3}$ as explained in the definitions section above in the description of "first substituent group(s)". In the above embodiments, $R^{7C}$, $R^{7C.1}$, $R^{7C.2}$, and $R^{7C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{7C}$, $R^{7C.1}$, $R^{7C.2}$, and $R^{7C.3}$, respectively.

In embodiments, when $R^{8}$ is substituted, $R^{8}$ is substituted with one or more first substituent groups denoted by $R^{8.1}$ as explained in the definitions section above in the description of "first substituent group(s)". In embodiments, when an $R^{8.1}$ substituent group is substituted, the $R^{8.1}$ substituent group is substituted with one or more second substituent groups denoted by $R^{8.2}$ as explained in the definitions section above in the description of "first substituent group(s)". In embodiments, when an $R^{8.2}$ substituent group is substituted, the $R^{8.2}$ substituent group is substituted with one or more third substituent groups denoted by $R^{8.3}$ as explained in the definitions section above in the description of "first substituent group(s)". In the above embodiments, $R^{8}$, $R^{8.1}$, $R^{8.2}$, and $R^{8.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{8}$, $R^{8.1}$, $R^{8.2}$, and $R^{8.3}$, respectively.

In embodiments, when $R^{8A}$ is substituted, $R^{8A}$ is substituted with one or more first substituent groups denoted by $R^{8A.1}$ as explained in the definitions section above in the description of "first substituent group(s)". In embodiments, when an $R^{8A.1}$ substituent group is substituted, the $R^{8A.1}$ substituent group is substituted with one or more second substituent groups denoted by $R^{8A.2}$ as explained in the definitions section above in the description of "first substituent group(s)". In embodiments, when an $R^{8A.2}$ substituent group is substituted, the $R^{8A.2}$ substituent group is substituted with one or more third substituent groups denoted by $R^{8A.3}$ as explained in the definitions section above in the description of "first substituent group(s)". In the above embodiments, $R^{8A}$, $R^{8A.1}$, $R^{8A.2}$, and $R^{8A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{8A}$, $R^{8A.1}$, $R^{8A.2}$, and $R^{8A.3}$, respectively.

In embodiments, when $R^{8B}$ is substituted, $R^{8B}$ is substituted with one or more first substituent groups denoted by $R^{8B.1}$ as explained in the definitions section above in the description of "first substituent group(s)". In embodiments, when an $R^{8B.1}$ substituent group is substituted, the $R^{8B.1}$ substituent group is substituted with one or more second substituent groups denoted by $R^{8B.2}$ as explained in the definitions section above in the description of "first substituent group(s)". In embodiments, when an $R^{8B.2}$ substituent group is substituted, the $R^{8B.2}$ substituent group is substituted with one or more third substituent groups denoted by $R^{8B.3}$ as explained in the definitions section above in the description of "first substituent group(s)". In the above embodiments, $R^{8B}$, $R^{8B.1}$, $R^{8B.2}$, and $R^{8B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{8B}$, $R^{8B.1}$, $R^{8B.2}$, and $R^{8B.3}$, respectively.

In embodiments, when $R^{8C}$ is substituted, $R^{8C}$ is substituted with one or more first substituent groups denoted by $R^{8C.1}$ as explained in the definitions section above in the description of "first substituent group(s)". In embodiments, when an $R^{8C.1}$ substituent group is substituted, the $R^{8C.1}$ substituent group is substituted with one or more second substituent groups denoted by $R^{8C.2}$ as explained in the definitions section above in the description of "first substituent group(s)". In embodiments, when an $R^{8C.2}$ substituent group is substituted, the $R^{8C.2}$ substituent group is substituted with one or more third substituent groups denoted by $R^{8C.3}$ as explained in the definitions section above in the description of "first substituent group(s)". In the above embodiments, $R^{8C}$, $R^{8C.1}$, $R^{8C.2}$, and $R^{8C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{8C}$, $R^{8C.1}$, $R^{8C.2}$, and $R^{8C.3}$, respectively.

In embodiments, when $R^{9}$ is substituted, $R^{9}$ is substituted with one or more first substituent groups denoted by $R^{9.1}$ as explained in the definitions section above in the description of "first substituent group(s)". In embodiments, when an $R^{9.1}$ substituent group is substituted, the $R^{9.1}$ substituent group is substituted with one or more second substituent groups denoted by $R^{9.2}$ as explained in the definitions section above in the description of "first substituent group(s)". In embodiments, when an $R^{9.2}$ substituent group is substituted, the $R^{9.2}$ substituent group is substituted with one or more third substituent groups denoted by $R^{9.3}$ as explained in the definitions section above in the description of "first substituent group(s)". In the above embodiments, $R^{9}$, $R^{9.1}$, $R^{9.2}$, and $R^{9.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{9}$, $R^{9.1}$, $R^{9.2}$, and $R^{9.3}$, respectively.

In embodiments, when $R^{9A}$ is substituted, $R^{9A}$ is substituted with one or more first substituent groups denoted by $R^{9A.1}$ as explained in the definitions section above in the description of "first substituent group(s)". In embodiments, when an $R^{9A.1}$ substituent group is substituted, the $R^{9A.1}$ substituent group is substituted with one or more second substituent groups denoted by $R^{9A.2}$ as explained in the definitions section above in the description of "first substituent group(s)". In embodiments, when an $R^{9A.2}$ substituent group is substituted, the $R^{9A.2}$ substituent group is substituted with one or more third substituent groups denoted by $R^{9A.3}$ as explained in the definitions section above in the description of "first substituent group(s)". In the above embodiments, $R^{9A}$, $R^{9A.1}$, $R^{9A.2}$, and $R^{9A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{9A}$, $R^{9A.1}$, $R^{9A.2}$, and $R^{9A.3}$, respectively.

In embodiments, when $R^{9B}$ is substituted, $R^{9B}$ is substituted with one or more first substituent groups denoted by $R^{9B.1}$ as explained in the definitions section above in the description of "first substituent group(s)". In embodiments, when an $R^{9B.1}$ substituent group is substituted, the $R^{9B.1}$ substituent group is substituted with one or more second substituent groups denoted by $R^{9B.2}$ as explained in the definitions section above in the description of "first substituent group(s)". In embodiments, when an $R^{9B.2}$ substituent group is substituted, the $R^{9B.2}$ substituent group is substituted with one or more third substituent groups denoted by $R^{9B.3}$ as explained in the definitions section above in the description of "first substituent group(s)". In the above embodiments, $R^{9B}$, $R^{9B.1}$, $R^{9B.2}$, and $R^{9B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{9B}$, $R^{9B.1}$, $R^{9B.2}$, and $R^{9B.3}$, respectively.

In embodiments, when $R^{9C}$ is substituted, $R^{9C}$ is substituted with one or more first substituent groups denoted by $R^{9C.1}$ as explained in the definitions section above in the description of "first substituent group(s)". In embodiments, when an $R^{9C.1}$ substituent group is substituted, the $R^{9C.1}$ substituent group is substituted with one or more second substituent groups denoted by $R^{9C.2}$ as explained in the definitions section above in the description of "first substituent group(s)". In embodiments, when an $R^{9C.2}$ substituent group is substituted, the $R^{9C.2}$ substituent group is substituted with one or more third substituent groups denoted by $R^{9C.3}$ as explained in the definitions section above in the description of "first substituent group(s)". In the above embodiments, $R^{9C}$, $R^{9C.1}$, $R^{9C.2}$, and $R^{9C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{9C}$, $R^{9C.1}$, $R^{9C.2}$, and $R^{9C.3}$, respectively.

In embodiments, when $R^{10}$ is substituted, $R^{10}$ is substituted with one or more first substituent groups denoted by $R^{10.1}$ as explained in the definitions section above in the description of "first substituent group(s)". In embodiments, when an $R^{10.1}$ substituent group is substituted, the $R^{10.1}$ substituent group is substituted with one or more second substituent groups denoted by $R^{10.2}$ as explained in the definitions section above in the description of "first substituent group(s)". In embodiments, when an $R^{10.2}$ substituent group is substituted, the $R^{10.2}$ substituent group is substituted with one or more third substituent groups denoted by $R^{10.3}$ as explained in the definitions section above in the description of "first substituent group(s)". In the above embodiments, $R^{10}$, $R^{10.1}$, $R^{10.2}$, and $R^{10.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10}$, $R^{10.1}$, $R^{10.2}$, and $R^{10.3}$, respectively.

In embodiments, when $R^{10A}$ is substituted, $R^{10A}$ is substituted with one or more first substituent groups denoted by $R^{10A.1}$ as explained in the definitions section above in the description of "first substituent group(s)". In embodiments, when an $R^{10A.1}$ substituent group is substituted, the $R^{10A.1}$ substituent group is substituted with one or more second substituent groups denoted by $R^{10A.2}$ as explained in the definitions section above in the description of "first substituent group(s)". In embodiments, when an $R^{10A.2}$ substituent group is substituted, the $R^{10A.2}$ substituent group is substituted with one or more third substituent groups denoted by $R^{10A.3}$ as explained in the definitions section above in the description of "first substituent group(s)". In the above embodiments, $R^{10A}$, $R^{10A.1}$, $R^{10A.2}$, and $R^{10A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10A}$, $R^{10A.1}$, $R^{10A.2}$, and $R^{10A.3}$, respectively.

In embodiments, when $R^{10B}$ is substituted, $R^{10B}$ is substituted with one or more first substituent groups denoted by $R^{10B.1}$ as explained in the definitions section above in the description of "first substituent group(s)". In embodiments, when an $R^{10B.1}$ substituent group is substituted, the $R^{10B.1}$ substituent group is substituted with one or more second substituent groups denoted by $R^{10B.2}$ as explained in the definitions section above in the description of "first substituent group(s)". In embodiments, when an $R^{10B.2}$ substituent group is substituted, the $R^{10B.2}$ substituent group is substituted with one or more third substituent groups denoted by $R^{10B.3}$ as explained in the definitions section above in the description of "first substituent group(s)". In the above embodiments, $R^{10B}$, $R^{10B.1}$, $R^{10B.2}$, and $R^{10B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10B}$, $R^{10B.1}$, $R^{10B.2}$, and $R^{10B.3}$, respectively.

In embodiments, when $R^{10C}$ is substituted, $R^{10C}$ is substituted with one or more first substituent groups denoted by $R^{10C.1}$ as explained in the definitions section above in the description of "first substituent group(s)". In embodiments, when an $R^{10C.1}$ substituent group is substituted, the $R^{10C.1}$ substituent group is substituted with one or more second substituent groups denoted by $R^{10C.2}$ as explained in the definitions section above in the description of "first substituent group(s)". In embodiments, when an $R^{10C.2}$ substituent group is substituted, the $R^{10C.2}$ substituent group is substituted with one or more third substituent groups denoted by $R^{10C.3}$ as explained in the definitions section above in the description of "first substituent group(s)". In the above embodiments, $R^{10C}$, $R^{10C.1}$, $R^{10C.2}$, and $R^{10C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{10C}$, $R^{10C.1}$, $R^{10C.2}$, and $R^{10C.3}$, respectively.

In embodiments, when $R^{11}$ is substituted, $R^{11}$ is substituted with one or more first substituent groups denoted by $R^{11.1}$ as explained in the definitions section above in the description of "first substituent group(s)". In embodiments, when an $R^{11.1}$ substituent group is substituted, the $R^{11.1}$ substituent group is substituted with one or more second substituent groups denoted by $R^{11.2}$ as explained in the definitions section above in the description of "first substituent group(s)". In embodiments, when an $R^{11.2}$ substituent group is substituted, the $R^{11.2}$ substituent group is substituted with one or more third substituent groups denoted by $R^{11.3}$ as explained in the definitions section above in the description of "first substituent group(s)". In the above embodiments, $R^{11}$, $R^{11.1}$, $R^{11.2}$, and $R^{11.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{11}$, $R^{11.1}$, $R^{11.2}$, and $R^{11.3}$, respectively.

In embodiments, when $R^{11A}$ is substituted, $R^{11A}$ is substituted with one or more first substituent groups denoted by $R^{11A.1}$ as explained in the definitions section above in the description of "first substituent group(s)". In embodiments, when an $R^{11A.1}$ substituent group is substituted, the $R^{11A.1}$ substituent group is substituted with one or more second substituent groups denoted by $R^{11A.2}$ as explained in the definitions section above in the description of "first substituent group(s)". In embodiments, when an $R^{11A.2}$ substituent group is substituted, the $R^{11A.2}$ substituent group is substituted with one or more third substituent groups denoted by $R^{11A.3}$ as explained in the definitions section above in the description of "first substituent group(s)". In the above embodiments, $R^{11A}$, $R^{11A.1}$, $R^{11A.2}$, and $R^{11A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{11A}$, $R^{11A.1}$, $R^{11A.2}$, and $R^{11A.3}$, respectively.

In embodiments, when $R^{11B}$ is substituted, $R^{11B}$ is substituted with one or more first substituent groups denoted by $R^{11B.1}$ as explained in the definitions section above in the description of "first substituent group(s)". In embodiments, when an $R^{11B.1}$ substituent group is substituted, the $R^{11B.1}$ substituent group is Substituted with one or more second substituent groups denoted by $R^{11B.2}$ as explained in the definitions section above in the description of "first substituent group(s)". In embodiments, when an $R^{11B.2}$ substituent group is substituted, the $R^{11B.2}$ substituent group is substituted with one or mom third substituent groups denoted by $R^{11B.3}$ as explained in the definitions section above in the description of "first substituent group(s)". In the above embodiments, $R^{11B}$, $R^{11B.1}$, $R^{11B.2}$, and $R^{11B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{11B}$, $R^{11B.1}$, $R^{11B.2}$, and $R^{11B.3}$, respectively.

In embodiments, when $R^{11C}$ is substituted, $R^{11C}$ is substituted with one or more first substituent groups denoted by $R^{11C.1}$ as explained in the definitions section above in the description of "first substituent group(s)". In embodiments, when an $R^{11C.1}$ substituent group is substituted, the $R^{11C.1}$ substituent group is substituted with one or more second substituent groups denoted by $R^{11C.2}$ as explained in the definitions section above in the description of "first substituent group(s)". In embodiments, when an $R^{11C.2}$ substituent group is substituted, the $R^{11C.2}$ substituent group is substituted with one or more third substituent groups denoted by $R^{11C.3}$ as explained in the definitions section above in the description of "first substituent group(s)". In the above embodiments, $R^{11C}$, $R^{11C.1}$, $R^{11C.2}$, and $R^{11C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{11C}$, $R^{11C.1}$, $R^{11C.2}$, and $R^{11C.3}$, respectively.

In embodiments, when $R^{12}$ is substituted, $R^{12}$ is substituted with one or more first substituent groups denoted by $R^{12.1}$ as explained in the definitions section above in the description of "first substituent group(s)". In embodiments, when an $R^{12.1}$ substituent group is substituted, the $R^{12.1}$ substituent group is substituted with one or more second substituent groups denoted by $R^{12.2}$ as explained in the definitions section above in the description of "first substituent group(s)". In embodiments, when an $R^{12.2}$ substituent group is substituted, the $R^{12.2}$ substituent group is substituted with one or more third substituent groups denoted by $R^{12.3}$ as explained in the definitions section above in the description of "first substituent group(s)". In the above embodiments, $R^{12}$, $R^{12.1}$, $R^{12.2}$, and $R^{12.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{12}$, $R^{12.1}$, $R^{12.2}$, and $R^{12.3}$, respectively.

In embodiments, when $R^{12A}$ is substituted, $R^{12A}$ is substituted with one or more first substituent groups denoted by $R^{12A.1}$ as explained in the definitions section above in the description of "first substituent group(s)". In embodiments, when an $R^{12A.1}$ substituent group is substituted, the $R^{12A.1}$ substituent group is substituted with one or more second substituent groups denoted by $R^{12A.2}$ as explained in the definitions section above in the description of "first substituent group(s)". In embodiments, when an $R^{12A.2}$ substituent group is substituted, the $R^{12A.2}$ substituent group is substituted with one or more third substituent groups denoted by $R^{12A.3}$ as explained in the definitions section above in the description of "first substituent group(s)". In the above embodiments, $R^{12A}$, $R^{12A.1}$, $R^{12A.2}$, and $R^{12A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{12A}$, $R^{12A.1}$, $R^{12A.2}$, and $R^{12A.3}$, respectively.

In embodiments, when $R^{12B}$ is substituted, $R^{12B}$ is substituted with one or more first substituent groups denoted by $R^{12B.1}$ as explained in the definitions section above in the description of "first substituent group(s)". In embodiments, when an $R^{12B.1}$ substituent group is substituted, the $R^{12B.1}$ substituent group is substituted with one or more second substituent groups denoted by $R^{12B.2}$ as explained in the definitions section above in the description of "first substituent group(s)". In embodiments, when an $R^{12B.2}$ substituent group is substituted, the $R^{12B.2}$ substituent group is substituted with one or more third substituent groups denoted by $R^{12B.3}$ as explained in the definitions section above in the description of "first substituent group(s)". In the above embodiments, $R^{12B}$, $R^{12B.1}$, $R^{12B.2}$, and $R^{12B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{12B}$, $R^{12B.1}$, $R^{12B.2}$, and $R^{12B.3}$, respectively.

In embodiments, when $R^{12C}$ is substituted, $R^{12C}$ is substituted with one or more first substituent groups denoted by $R^{12C.1}$ as explained in the definitions section above in the description of "first substituent group(s)". In embodiments, when an $R^{12C.1}$ substituent group is substituted, the $R^{12C.1}$ substituent group is substituted with one or more second substituent groups denoted by $R^{12C.2}$ as explained in the definitions section above in the description of "first substituent group(s)". In embodiments, when an $R^{12C.2}$ substituent group is substituted, the $R^{12C.2}$ substituent group is substituted with one or more third substituent groups denoted by $R^{12C.3}$ as explained in the definitions section above in the description of "first substituent group(s)". In the above embodiments, $R^{12C}$, $R^{12C.1}$, $R^{12C.2}$, and $R^{12C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{12C}$, $R^{12C.1}$, $R^{12C.2}$, and $R^{12C.3}$, respectively.

In embodiments, when $R^{13}$ is substituted, $R^{13}$ is substituted with one or more first substituent groups denoted by $R^{13.1}$ as explained in the definitions section above in the description of "first substituent group(s)". In embodiments, when an $R^{13.1}$ substituent group is substituted, the $R^{13.1}$ substituent group is substituted with one or more second substituent groups denoted by $R^{13.2}$ as explained in the definitions section above in the description of "first substituent group(s)". In embodiments, when an $R^{13.2}$ substituent group is substituted, the $R^{13.2}$ substituent group is substituted with one or more third substituent groups denoted by $R^{13.3}$ as explained in the definitions section above in the description of "first substituent group(s)". In the above embodiments, $R^{13}$, $R^{13.1}$, $R^{13.2}$, and $R^{13.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{13}$, $R^{13.1}$, $R^{13.2}$, and $R^{13.3}$, respectively.

In embodiments, when $R^{13A}$ is substituted, $R^{13A}$ is substituted with one or more first substituent groups denoted by $R^{13A.1}$ as explained in the definitions section above in the description of "first substituent group(s)". In embodiments, when an $R^{13A.1}$ substituent group is substituted, the $R^{13A.1}$ substituent group is substituted with one or more second substituent groups denoted by $R^{13A.2}$ as explained in the definitions section above in the description of "first substituent group(s)". In embodiments, when an $R^{13A.2}$ substituent group is substituted, the $R^{13A.2}$ substituent group is substituted with one or more third substituent groups denoted by $R^{13A.3}$ as explained in the definitions section above in the description of "first substituent group(s)". In the above embodiments, $R^{13A}$, $R^{13A.1}$, $R^{13A.2}$, and $R^{13A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{13A}$, $R^{13A.1}$, $R^{13A.2}$, and $R^{13A.3}$, respectively.

In embodiments, when $R^{13B}$ is substituted, $R^{13B}$ is substituted with one or more first substituent groups denoted by $R^{13B.1}$ as explained in the definitions section above in the description of "first substituent group(s)". In embodiments, when an $R^{13B.1}$ substituent group is substituted, the $R^{13B.1}$ substituent group is Substituted with one or more second substituent groups denoted by $R^{13B.2}$ as explained in the definitions section above in the description of "first substituent group(s)". In embodiments, when an $R^{13B.2}$ substituent group is substituted, the $R^{13B.2}$ substituent group is substituted with one or more third substituent groups denoted by $R^{13B.3}$ as explained in the definitions section above in the description of "first substituent group(s)". In the above embodiments, $R^{13B}$, $R^{13B.1}$, $R^{13B.2}$, and $R^{13B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{13B}$, $R^{13B.1}$, $R^{13B.2}$, and $R^{13B.3}$, respectively.

In embodiments, when $R^{13C}$ is substituted, $R^{13C}$ is substituted with one or more first substituent groups denoted by $R^{13C.1}$ as explained in the definitions section above in the description of "first substituent group(s)". In embodiments, when an $R^{13C.1}$ substituent group is substituted, the $R^{13C.1}$ substituent group is substituted with one or more second substituent groups denoted by $R^{13C.2}$ as explained in the definitions section above in the description of "first substituent group(s)". In embodiments, when an $R^{13C.2}$ substituent group is substituted, the $R^{13C.2}$ substituent group is substituted with one or more third substituent groups denoted by $R^{13C.3}$ as explained in the definitions section above in the description of "first substituent group(s)". In the above embodiments, $R^{13C}$, $R^{13C.1}$, $R^{13C.2}$, and $R^{13C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{13C}$, $R^{13C.1}$, $R^{13C.2}$, and $R^{13C.3}$, respectively.

In embodiments, when $R^{14}$ is substituted, $R^{14}$ is substituted with one or more first substituent groups denoted by $R^{14.1}$ as explained in the definitions section above in the description of "first substituent group(s)". In embodiments, when an $R^{14.1}$ substituent group is substituted, the $R^{14.1}$ substituent group is substituted with one or more second substituent groups denoted by $R^{14.2}$ as explained in the definitions section above in the description of "first substituent group(s)". In embodiments, when an $R^{14.2}$ substituent group is substituted, the $R^{14.2}$ substituent group is substituted with one or more third substituent groups denoted by $R^{14.3}$ as explained in the definitions section above in the description of "first substituent group(s)". In the above embodiments, $R^{14}$, $R^{14.1}$, $R^{14.2}$, and $R^{14.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{14}$, $R^{14.1}$, $R^{14.2}$, and $R^{14.3}$, respectively.

In embodiments, when $R^{14A}$ is substituted, $R^{14A}$ is substituted with one or more first substituent groups denoted by $R^{14A.1}$ as explained in the definitions section above in the description of "first substituent group(s)". In embodiments, when an $R^{14A.1}$ substituent group is substituted, the $R^{14A.1}$ substituent group is substituted with one or more second substituent groups denoted by $R^{14A.2}$ as explained in the definitions section above in the description of "first substituent group(s)". In embodiments, when an $R^{14A.2}$ substituent group is substituted, the $R^{14A.2}$ substituent group is substituted with one or more third substituent groups denoted by $R^{14A.3}$ as explained in the definitions section above in the description of "first substituent group(s)". In the above embodiments, $R^{14A}$, $R^{14A.1}$, $R^{14A.2}$, and $R^{14A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{14A}$, $R^{14A.1}$, $R^{14A.2}$, and $R^{14A.3}$, respectively.

In embodiments, when $R^{14B}$ is substituted, $R^{14B}$ is substituted with one or more first substituent groups denoted by $R^{14B.1}$ as explained in the definitions section above in the description of "first substituent group(s)". In embodiments, when an $R^{14B.1}$ substituent group is substituted, the $R^{14B.1}$ substituent group is substituted with one or more second substituent groups denoted by $R^{14B.2}$ as explained in the definitions section above in the description of "first substituent group(s)". In embodiments, when an $R^{14B.2}$ substituent group is substituted, the $R^{14B.2}$ substituent group is substituted with one or more third substituent groups denoted by $R^{14B.3}$ as explained in the definitions section above in the description of "first substituent group(s)". In the above embodiments, $R^{14B}$, $R^{14B.1}$, $R^{14B.2}$, and $R^{14B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{14B}$, $R^{14B.1}$, $R^{14B.2}$, and $R^{14B.3}$, respectively.

In embodiments, when $R^{14C}$ is substituted, $R^{14C}$ is substituted with one or more first substituent groups denoted by $R^{14C.1}$ as explained in the definitions section above in the description of "first substituent group(s)". In embodiments, when an $R^{14C.1}$ substituent group is substituted, the $R^{14C.1}$ substituent group is substituted with one or more second substituent groups denoted by $R^{14C.2}$ as explained in the definitions section above in the description of "first substituent group(s)". In embodiments, when an $R^{14C.2}$ substituent group is substituted, the $R^{14C.2}$ substituent group is substituted with one or more third substituent groups denoted by $R^{14C.3}$ as explained in the definitions section above in the description of "first substituent group(s)". In the above embodiments, $R^{14C}$, $R^{14C.1}$, $R^{14C.2}$, and $R^{14C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{14C}$, $R^{14C.1}$, $R^{14C.2}$, and $R^{14C.3}$, respectively.

In embodiments, when $R^{15}$ is substituted, $R^{15}$ is substituted with one or more first substituent groups denoted by $R^{15}$ as explained in the definitions section above in the description of "first substituent group(s)". In embodiments, when an $R^{15.1}$ substituent group is substituted, the $R^{15.1}$ substituent group is substituted with one or more second substituent groups denoted by $R^{15.2}$ as explained in the definitions section above in the description of "first substituent group(s)". In embodiments, when an $R^{15.2}$ substituent group is substituted, the $R^{15.2}$ substituent group is substituted with one or more third substituent groups denoted by $R^{15.3}$ as explained in the definitions section above in the description of "first substituent group(s)". In the above embodiments, $R^{15}$, $R^{15.1}$, $R^{15.2}$, and $R^{15.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{15}$, $R^{15.1}$, $R^{15.2}$, and $R^{15.3}$, respectively.

In embodiments, when $R^{15A}$ is substituted, $R^{15A}$ is substituted with one or more first substituent groups denoted by $R^{15A.1}$ as explained in the definitions section above in the description of "first substituent group(s)". In embodiments, when an $R^{15A.1}$ substituent group is substituted, the $R^{15A.1}$ substituent group is substituted with one or more second substituent groups denoted by $R^{15A.2}$ as explained in the definitions section above in the description of "first substituent group(s)". In embodiments, when an $R^{15A.2}$ substituent group is substituted, the $R^{15A.2}$ substituent group is substituted with one or more third substituent groups denoted by $R^{15A.3}$ as explained in the definitions section above in the description of "first substituent group(s)". In the above embodiments, $R^{15A}$, $R^{15A.1}$, $R^{15A.2}$, and $R^{15A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{15A}$, $R^{15A.1}$, $R^{15A.2}$, and $R^{15A.3}$, respectively.

In embodiments, when $R^{15B}$ is substituted, $R^{15B}$ is substituted with one or more first substituent groups denoted by $R^{15B.1}$ as explained in the definitions section above in the description of "first substituent group(s)". In embodiments, when an $R^{15B.1}$ substituent group is substituted, the $R^{15B.1}$ substituent group is substituted with one or more second substituent groups denoted by $R^{15B.2}$ as explained in the definitions section above in the description of "first substituent group(s)". In embodiments, when an $R^{15B.2}$ substituent group is substituted, the $R^{15B.2}$ substituent group is substituted with one or more third substituent groups denoted by $R^{15B.3}$ as explained in the definitions section above in the description of "first substituent group(s)". In the above embodiments, $R^{15B}$, $R^{15B.1}$, $R^{15B.2}$, and $R^{15B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{15B}$, $R^{15B.1}$, $R^{15B.2}$, and $R^{15B.3}$, respectively.

In embodiments, when $R^{15C}$ is substituted, $R^{15C}$ is substituted with one or more first substituent groups denoted by $R^{15C.1}$ as explained in the definitions section above in the description of "first substituent group(s)". In embodiments, when an $R^{15C.1}$ substituent group is substituted, the $R^{15C.1}$ substituent group is substituted with one or more second substituent groups denoted by $R^{15C.2}$ as explained in the definitions section above in the description of "first substituent group(s)". In embodiments, when an $R^{15C.2}$ substituent group is substituted, the $R^{15C.2}$ substituent group is substituted with one or more third substituent groups denoted by $R^{15C.3}$ as explained in the definitions section above in the description of "first substituent group(s)". In the above embodiments, $R^{15C}$, $R^{15C.1}$, $R^{15C.2}$, and $R^{15C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{15C}$, $R^{15C.1}$, $R^{15C.2}$, and $R^{15C.3}$, respectively.

In embodiments, when $R^{16}$ is substituted, $R^{16}$ is substituted with one or more first substituent groups denoted by $R^{16.1}$ as explained in the definitions section above in the description of "first substituent group(s)". In embodiments, when an $R^{16.1}$ substituent group is substituted, the $R^{16.1}$ substituent group is substituted with one or more second substituent groups denoted by $R^{16.2}$ as explained in the definitions section above in the description of "first substituent group(s)". In embodiments, when an $R^{16.2}$ substituent group is substituted, the $R^{16.2}$ substituent group is substituted with one or more third substituent groups denoted by $R^{16.3}$ as explained in the definitions section above in the description of "first substituent group(s)". In the above embodiments, $R^{16}$, $R^{16.1}$, $R^{16.2}$, and $R^{16.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{16}$, $R^{16.1}$, $R^{16.2}$, and $R^{16.3}$, respectively.

In embodiments, when $R^{16A}$ is substituted, $R^{16A}$ is substituted with one or more first substituent groups denoted by $R^{16A.1}$ as explained in the definitions section above in the description of "first substituent group(s)". In embodiments, when an $R^{16A.1}$ substituent group is substituted, the $R^{16A.1}$ substituent group is substituted with one or more second substituent groups denoted by $R^{16A.2}$ as explained in the definitions section above in the description of "first substituent group(s)". In embodiments, when an $R^{16A.2}$ substituent group is substituted, the $R^{16A.2}$ substituent group is substituted with one or more third substituent groups denoted by $R^{16A.3}$ as explained in the definitions section above in the description of "first substituent group(s)". In the above embodiments, $R^{16A}$, $R^{16A.1}$, $R^{16A.2}$, and $R^{16A.4}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{16A}$, $R^{16A.1}$, $R^{16A.2}$, and $R^{16A.3}$, respectively.

In embodiments, when $R^{16B}$ is substituted, $R^{16B}$ is substituted with one or more first substituent groups denoted by $R^{16B.1}$ as explained in the definitions section above in the description of "first substituent group(s)". In embodiments, when an $R^{16B.1}$ substituent group is substituted, the $R^{16B.1}$ substituent group is substituted with one or more second substituent groups denoted by $R^{16B.2}$ as explained in the definitions section above in the description of "first substituent group(s)". In embodiments, when an $R^{16B.2}$ substituent group is substituted, the $R^{16B.2}$ substituent group is substituted with one or more third substituent groups denoted by $R^{16B.3}$ as explained in the definitions section above in the description of "first substituent group(s)". In the above embodiments, $R^{16B}$, $R^{16B.1}$, $R^{16B.2}$, and $R^{16B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{16B}$, $R^{16B.1}$, $R^{16B.2}$, and $R^{16B.3}$, respectively.

In embodiments, when $R^{16C}$ is substituted, $R^{16C}$ is substituted with one or more first substituent groups denoted by $R^{16C.1}$ as explained in the definitions section above in the description of "first substituent group(s)". In embodiments, when an $R^{16C.1}$ substituent group is substituted, the $R^{16C.1}$ substituent group is substituted with one or more second substituent groups denoted by $R^{16C.2}$ as explained in the definitions section above in the description of "first substituent group(s)". In embodiments, when an $R^{16C.2}$ substituent group is substituted, the $R^{16C.2}$ substituent group is substituted with one or more third substituent groups denoted by $R^{16C.3}$ as explained in the definitions section above in the description of "first substituent group(s)". In the above embodiments, $R^{16C}$, $R^{16C.1}$, $R^{16C.2}$, and $R^{16C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{16C}$, $R^{16C.1}$, $R^{16C.2}$, and $R^{16C.3}$, respectively.

In embodiments, when $R^{17}$ is substituted, $R^{17}$ is substituted with one or more first substituent groups denoted by $R^{17.1}$ as explained in the definitions section above in the description of "first substituent group(s)". In embodiments, when an $R^{17.1}$ substituent group is substituted, the $R^{17.1}$ substituent group is substituted with one or more second substituent groups denoted by $R^{17.2}$ as explained in the definitions section above in the description of "first substituent group(s)". In embodiments, when an $R^{17.2}$ substituent group is substituted, the $R^{17.2}$ substituent group is substituted with one or more third substituent groups denoted by $R^{17.3}$ as explained in the definitions section above in the description of "first substituent group(s)". In the above embodiments, $R^{17}$, $R^{17.1}$, $R^{17.2}$, and $R^{17.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{17}$, $R^{17.1}$, $R^{17.2}$, and $R^{17.3}$, respectively.

In embodiments, when $R^{17A}$ is substituted, $R^{17A}$ is substituted with one or more first substituent groups denoted by $R^{17A.1}$ as explained in the definitions section above in the description of "first substituent group(s)". In embodiments, when an $R^{17A.1}$ substituent group is substituted, the $R^{17A.1}$ substituent group is substituted with one or more second substituent groups denoted by $R^{17A.2}$ as explained in the definitions section above in the description of "first substituent group(s)". In embodiments, when an $R^{17A.2}$ substituent group is substituted, the $R^{17A.2}$ substituent group is substituted with one or more third substituent groups denoted by $R^{17A.3}$ as explained in the definitions section above in the description of "first substituent group(s)". In the above embodiments, $R^{17A}$, $R^{17A.1}$, $R^{17A.2}$, and $R^{17A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{17A}$, $R^{17A.1}$, $R^{17A.2}$, and $R^{17A.3}$, respectively.

In embodiments, when $R^{17B}$ is substituted, $R^{17B}$ is substituted with one or more first substituent groups denoted by $R^{17B.1}$ as explained in the definitions section above in the description of "first substituent group(s)". In embodiments, when an $R^{17B.1}$ substituent group is substituted, the $R^{17B.1}$ substituent group is substituted with one or more second substituent groups denoted by $R^{17B.2}$ as explained in the definitions section above in the description of "first substituent group(s)". In embodiments, when an $R^{17B.2}$ substituent group is substituted, the $R^{17B.2}$ substituent group is substituted with one or more third substituent groups denoted by $R^{17B.3}$ as explained in the definitions section above in the description of "first substituent group(s)". In the above embodiments, $R^{17B}$, $R^{17B.1}$, $R^{17B.2}$, and $R^{17B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{17B}$, $R^{17B.1}$, $R^{17B.2}$, and $R^{17B.3}$, respectively.

In embodiments, when $R^{17C}$ is substituted, $R^{17C}$ is substituted with one or more first substituent groups denoted by $R^{17C.1}$ as explained in the definitions section above in the description of "first substituent group(s)". In embodiments, when an $R^{17C.1}$ substituent group is substituted, the $R^{17C.1}$ substituent group is substituted with one or more second substituent groups denoted by $R^{17C.2}$ as explained in the definitions section above in the description of "first substituent group(s)". In embodiments, when an $R^{17C.2}$ substituent group is substituted, the $R^{17C.2}$ substituent group is substituted with one or more third substituent groups denoted by $R^{17C.3}$ as explained in the definitions section above in the description of "first substituent group(s)". In the above embodiments, $R^{17C}$, $R^{17C.1}$, $R^{17C.2}$, and $R^{17C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{17C}$, $R^{17C.1}$, $R^{17C.2}$, and $R^{17C.3}$, respectively.

In embodiments, when $R^{18}$ is substituted, $R^{18}$ is substituted with one or more first substituent groups denoted by $R^{18.1}$ as explained in the definitions section above in the description of "first substituent group(s)". In embodiments, when an $R^{18.1}$ substituent group is substituted, the $R^{18.1}$ substituent group is substituted with one or more second substituent groups denoted by $R^{18.2}$ as explained in the definitions section above in the description of "first substituent group(s)". In embodiments, when an $R^{18.2}$ substituent group is substituted, the $R^{18.2}$ substituent group is substituted with one or more third substituent groups denoted by $R^{18.3}$ as explained in the definitions section above in the description of “first substituent group(s)”. In the above embodiments, $R^{18}$, $R^{18.1}$, $R^{18.2}$, and $R^{18.3}$ have values corresponding to the values of $R^{WW}$, $R^{WW.1}$, $R^{WW.2}$, and $R^{WW.3}$, respectively, as explained in the definitions section above in the description of “first substituent group(s)”, wherein $R^{WW}$, $R^{WW.1}$, $R^{WW.2}$, and $R^{WW.3}$ correspond to $R^{18}$, $R^{18.1}$, $R^{18.2}$, and $R^{18.3}$, respectively.

In embodiments, when $R^{18A}$ is substituted, $R^{18A}$ is substituted with one or more first substituent groups denoted by $R^{18A.1}$ as explained in the definitions section above in the description of “first substituent group(s)”. In embodiments, when an $R^{18A.1}$ substituent group is substituted, the $R^{18A.1}$ substituent group is substituted with one or more second substituent groups denoted by $R^{18A.2}$ as explained in the definitions section above in the description of “first substituent group(s)”. In embodiments, when an $R^{18A.2}$ substituent group is substituted, the $R^{18A.2}$ substituent group is substituted with one or more third substituent groups denoted by $R^{18A.3}$ as explained in the definitions section above in the description of “first substituent group(s)”. In the above embodiments, $R^{18A}$, $R^{18A.1}$, $R^{18A.2}$, and $R^{18A.3}$ have values corresponding to the values of $R^{WW}$, $R^{WW.1}$, $R^{WW.2}$, and $R^{WW.3}$, respectively, as explained in the definitions section above in the description of “first substituent group(s)”, wherein $R^{WW}$, $R^{WW.1}$, $R^{WW.2}$, and $R^{WW.3}$ correspond to $R^{18A}$, $R^{18A.1}$, $R^{18A.2}$, and $R^{18A.3}$, respectively.

In embodiments, when $R^{18B}$ is substituted, $R^{18B}$ is substituted with one or more first substituent groups denoted by $R^{18B.1}$ as explained in the definitions section above in the description of “first substituent group(s)”. In embodiments, when an $R^{18B.1}$ substituent group is substituted, the $R^{18B.1}$ substituent group is substituted with one or more second substituent groups denoted by $R^{18B.2}$ as explained in the definitions section above in the description of “first substituent group(s)”. In embodiments, when an $R^{18B.2}$ substituent group is substituted, the $R^{18B.2}$ substituent group is substituted with one or more third substituent groups denoted by $R^{18B.3}$ as explained in the definitions section above in the description of “first substituent group(s)”. In the above embodiments, $R^{18B}$, $R^{18B.1}$, $R^{18B.2}$, and $R^{18B.3}$ have values corresponding to the values of $R^{WW}$, $R^{WW.1}$, $R^{WW.2}$, and $R^{WW.3}$, respectively, as explained in the definitions section above in the description of “first substituent group(s)”, wherein $R^{WW}$, $R^{WW.1}$, $R^{WW.2}$, and $R^{WW.3}$ correspond to $R^{18B}$, $R^{18B.1}$, $R^{18B.2}$, and $R^{18B.3}$, respectively.

In embodiments, when $R^{18C}$ is substituted, $R^{18C}$ is substituted with one or more first substituent groups denoted by $R^{18C.1}$ as explained in the definitions section above in the description of “first substituent group(s)”. In embodiments, when an $R^{18C.1}$ substituent group is substituted, the $R^{18C.1}$ substituent group is substituted with one or more second substituent groups denoted by $R^{18C.2}$ as explained in the definitions section above in the description of “first substituent group(s)”. In embodiments, when an $R^{18C.2}$ substituent group is substituted, the $R^{18C.2}$ substituent group is substituted with one or more third substituent groups denoted by $R^{18C.3}$ as explained in the definitions section above in the description of “first substituent group(s)”. In the above embodiments, $R^{18C}$, $R^{18C.1}$, $R^{18C.2}$, and $R^{18C.3}$ have values corresponding to the values of $R^{WW}$, $R^{WW.1}$, $R^{WW.2}$, and $R^{WW.3}$, respectively, as explained in the definitions section above in the description of “first substituent group(s)”, wherein $R^{WW}$, $R^{WW.1}$, $R^{WW.2}$, and $R^{WW.3}$ correspond to $R^{18C}$, $R^{18C.1}$, $R^{18C.2}$, and $R^{18C.3}$, respectively.

In embodiments, when $R^{19}$ is substituted, $R^{19}$ is substituted with one or more first substituent groups denoted by $R^{19.1}$ as explained in the definitions section above in the description of “first substituent group(s)”. In embodiments, when an $R^{19.1}$ substituent group is substituted, the $R^{19.1}$ substituent group is substituted with one or more second substituent groups denoted by $R^{19.2}$ as explained in the definitions section above in the description of “first substituent group(s)”. In embodiments, when an $R^{19.2}$ substituent group is substituted, the $R^{19.2}$ substituent group is substituted with one or more third substituent groups denoted by $R^{19.3}$ as explained in the definitions section above in the description of “first substituent group(s)”. In the above embodiments, $R^{19}$, $R^{19.1}$, $R^{19.2}$, and $R^{19.3}$ have values corresponding to the values of $R^{WW}$, $R^{WW.1}$, $R^{WW.2}$, and $R^{WW.3}$, respectively, as explained in the definitions section above in the description of “first substituent group(s)”, wherein $R^{WW}$, $R^{WW.1}$, $R^{WW.2}$, and $R^{WW.3}$ correspond to $R^{19}$, $R^{19.1}$, $R^{19.2}$, and $R^{19.3}$, respectively.

In embodiments, when $R^{19A}$ is substituted, $R^{19A}$ is substituted with one or more first substituent groups denoted by $R^{19A.1}$ as explained in the definitions section above in the description of “first substituent group(s)”. In embodiments, when an $R^{19A.1}$ substituent group is substituted, the $R^{19A.1}$ substituent group is substituted with one or more second substituent groups denoted by $R^{19A.2}$ as explained in the definitions section above in the description of “first substituent group(s)”. In embodiments, when an $R^{19A.2}$ substituent group is substituted, the $R^{19A.2}$ substituent group is substituted with one or more third substituent groups denoted by $R^{19A.3}$ as explained in the definitions section above in the description of “first substituent group(s)”. In the above embodiments, $R^{19A}$, $R^{19A.1}$, $R^{19A.2}$, and $R^{19A.3}$ have values corresponding to the values of $R^{WW}$, $R^{WW.1}$, $R^{WW.2}$, and $R^{WW.3}$, respectively, as explained in the definitions section above in the description of “first substituent group(s)”, wherein $R^{WW}$, $R^{WW.1}$, $R^{WW.2}$, and $R^{WW.3}$ correspond to $R^{19A}$, $R^{19A.1}$, $R^{19A.2}$, and $R^{19A.3}$, respectively.

In embodiments, when $R^{19B}$ is substituted, $R^{19B}$ is substituted with one or more first substituent groups denoted by $R^{19B.1}$ as explained in the definitions section above in the description of “first substituent group(s)”. In embodiments, when an $R^{19B.1}$ substituent group is substituted, the $R^{19B.1}$ substituent group is substituted with one or more second substituent groups denoted by $R^{19B.2}$ as explained in the definitions section above in the description of “first substituent group(s)”. In embodiments, when an $R^{19B.2}$ substituent group is substituted, the $R^{19B.2}$ substituent group is substituted with one or more third substituent groups denoted by $R^{19B.3}$ as explained in the definitions section above in the description of “first substituent group(s)”. In the above embodiments, $R^{19B}$, $R^{19B.1}$, $R^{19B.2}$, and $R^{19B.3}$ have values corresponding to the values of $R^{WW}$, $R^{WW.1}$, $R^{WW.2}$, and $R^{WW.3}$, respectively, as explained in the definitions section above in the description of “first substituent group(s)”, wherein $R^{WW}$, $R^{WW.1}$, $R^{WW.2}$, and $R^{WW.3}$ correspond to $R^{19B}$, $R^{19B.1}$, $R^{19B.2}$, and $R^{19B.3}$, respectively.

In embodiments, when $R^{19C}$ is substituted, $R^{19C}$ is substituted with one or more first substituent groups denoted by $R^{19C.1}$ as explained in the definitions section above in the description of “first substituent group(s)”. In embodiments, when an $R^{19C.1}$ substituent group is substituted, the $R^{19C.1}$ substituent group is substituted with one or more second substituent groups denoted by $R^{19C.2}$ as explained in the definitions section above in the description of “first substituent group(s)”. In embodiments, when an $R^{19C.2}$ substituent group is substituted, the $R^{19C.2}$ substituent group is substituted with one or more third substituent groups denoted by $R^{19C.3}$ as explained in the definitions section above in the description of "first substituent group(s)". In the above embodiments, $R^{19C}$, $R^{19C.1}$, $R^{19C.2}$, and $R^{19C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{19C}$, $R^{19C.1}$, $R^{19C.2}$, and $R^{19C.3}$, respectively.

In embodiments, when $R^{20}$ is substituted, $R^{20}$ is substituted with one or more first substituent groups denoted by $R^{20.1}$ as explained in the definitions section above in the description of "first substituent group(s)". In embodiments, when an $R^{20.1}$ substituent group is substituted, the $R^{20.1}$ substituent group is substituted with one or more second substituent groups denoted by $R^{20.2}$ as explained in the definitions section above in the description of "first substituent group(s)". In embodiments, when an $R^{20.2}$ substituent group is substituted, the $R^{20.2}$ substituent group is substituted with one or more third substituent groups denoted by $R^{20.3}$ as explained in the definitions section above in the description of "first substituent group(s)". In the above embodiments, $R^{20}$, $R^{20.1}$, $R^{20.2}$, and $R^{20.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{20}$, $R^{20.1}$, $R^{20.2}$, and $R^{20.3}$, respectively.

In embodiments, when $R^{20A}$ is substituted, $R^{20A}$ is substituted with one or more first substituent groups denoted by $R^{20A.1}$ as explained in the definitions section above in the description of "first substituent group(s)". In embodiments, when an $R^{20A.1}$ substituent group is substituted, the $R^{20A.1}$ substituent group is substituted with one or more second substituent groups denoted by $R^{20A.2}$ as explained in the definitions section above in the description of "first substituent group(s)". In embodiments, when an $R^{20A.2}$ substituent group is substituted, the $R^{20A.2}$ substituent group is substituted with one or more third substituent groups denoted by $R^{20A.3}$ as explained in the definitions section above in the description of "first substituent group(s)". In the above embodiments, $R^{20A}$, $R^{20A.1}$, $R^{20A.2}$, and $R^{20A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{20A}$, $R^{20A.1}$, $R^{20A.2}$, and $R^{20A.3}$, respectively.

In embodiments, when $R^{20B}$ is substituted, $R^{20B}$ is substituted with one or more first substituent groups denoted by $R^{20B.1}$ as explained in the definitions section above in the description of "first substituent group(s)". In embodiments, when an $R^{20B.1}$ substituent group is substituted, the $R^{20B.1}$ substituent group is substituted with one or more second substituent groups denoted by $R^{20B.2}$ as explained in the definitions section above in the description of "first substituent group(s)". In embodiments, when an $R^{20B.2}$ substituent group is substituted, the $R^{20B.2}$ substituent group is substituted with one or more third substituent groups denoted by $R^{20B.3}$ as explained in the definitions section above in the description of "first substituent group(s)". In the above embodiments, $R^{20B}$, $R^{20B.1}$, $R^{20B.2}$, and $R^{20B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{20B}$, $R^{20B.1}$, $R^{20B.2}$, and $R^{20B.3}$, respectively.

In embodiments, when $R^{20C}$ is substituted, $R^{20C}$ is substituted with one or more first substituent groups denoted by $R^{20C.1}$ as explained in the definitions section above in the description of "first substituent group(s)". In embodiments, when an $R^{20C.1}$ substituent group is substituted, the $R^{20C.1}$ substituent group is substituted with one or more second substituent groups denoted by $R^{20C.2}$ as explained in the definitions section above in the description of "first substituent group(s)". In embodiments, when an $R^{20C.2}$ substituent group is substituted, the $R^{20C.2}$ substituent group is substituted with one or more third substituent groups denoted by $R^{20C.3}$ as explained in the definitions section above in the description of "first substituent group(s)". In the above embodiments, $R^{20C}$, $R^{20C.1}$, $R^{20C.2}$, and $R^{20C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{20C}$, $R^{20C.1}$, $R^{20C.2}$, and $R^{20C.3}$, respectively.

In embodiments, when $R^{21}$ is substituted, $R^{21}$ is substituted with one or more first substituent groups denoted by $R^{21.1}$ as explained in the definitions section above in the description of "first substituent group(s)". In embodiments, when an $R^{21.1}$ substituent group is substituted, the $R^{21.1}$ substituent group is substituted with one or more second substituent groups denoted by $R^{21.2}$ as explained in the definitions section above in the description of "first substituent group(s)". In embodiments, when an $R^{21.2}$ substituent group is substituted, the $R^{21.2}$ substituent group is substituted with one or more third substituent groups denoted by $R^{21.3}$ as explained in the definitions section above in the description of "first substituent group(s)". In the above embodiments, $R^{21}$, $R^{21.1}$, $R^{21.2}$, and $R^{21.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{21}$, $R^{21.1}$, $R^{21.2}$, and $R^{21.3}$, respectively.

In embodiments, when $R^{21A}$ is substituted, $R^{21A}$ is substituted with one or more first substituent groups denoted by $R^{21A.1}$ as explained in the definitions section above in the description of "first substituent group(s)". In embodiments, when an $R^{21A.1}$ substituent group is substituted, the $R^{21A.1}$ substituent group is substituted with one or more second substituent groups denoted by $R^{21A.2}$ as explained in the definitions section above in the description of "first substituent group(s)". In embodiments, when an $R^{21A.2}$ substituent group is substituted, the $R^{21A.2}$ substituent group is substituted with one or more third substituent groups denoted by $R^{20A.3}$ as explained in the definitions section above in the description of "first substituent group(s)". In the above embodiments, $R^{21A}$, $R^{21A.1}$, $R^{21A.2}$, and $R^{21A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{21A}$, $R^{21A.1}$, $R^{21A.2}$, and $R^{21A.3}$, respectively.

In embodiments, when $R^{21B}$ is substituted, $R^{21B}$ is substituted with one or more first substituent groups denoted by $R^{21B.1}$ as explained in the definitions section above in the description of "first substituent group(s)". In embodiments, when an $R^{21B.1}$ substituent group is substituted, the $R^{21B.1}$ substituent group is substituted with one or more second substituent groups denoted by $R^{21B.2}$ as explained in the definitions section above in the description of "first substituent group(s)". In embodiments, when an $R^{21B.2}$ substituent group is substituted, the $R^{21B.2}$ substituent group is substituted with one or more third substituent groups denoted by $R^{21B}3$ as explained in the definitions section above in the description of "first substituent group(s)". In the above embodiments, $R^{21B}$, $R^{21B.1}$, $R^{21B.2}$, and $R^{21B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{21B}$, $R^{21B.1}$, $R^{21B.2}$, and $R^{21B.3}$, respectively.

In embodiments, when $R^{21C}$ is substituted, $R^{21C}$ is substituted with one or more first substituent groups denoted by $R^{21C.1}$ as explained in the definitions section above in the description of "first substituent group(s)". In embodiments, when an $R^{21C.1}$ substituent group is substituted, the $R^{21C.1}$ substituent group is substituted with one or more second substituent groups denoted by $R^{21C.2}$ as explained in the definitions section above in the description of "first substituent group(s)". In embodiments, when an $R^{21C.2}$ substituent group is substituted, the $R^{21C.2}$ substituent group is substituted with one or more third substituent groups denoted by $R^{21C.3}$ as explained in the definitions section above in the description of "first substituent group(s)". In the above embodiments, $R^{21C}$, $R^{21C.1}$, $R^{21C.2}$, and $R^{21C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{21C}$, $R^{21C.1}$, $R^{21C.2}$, and $R^{21C.3}$, respectively.

In embodiments, when $R^{22}$ is substituted, $R^{22}$ is substituted with one or more first substituent groups denoted by $R^{22.1}$ as explained in the definitions section above in the description of "first substituent group(s)". In embodiments, when an $R^{22.1}$ substituent group is substituted, the $R^{22.1}$ substituent group is substituted with one or more second substituent groups denoted by $R^{22.2}$ as explained in the definitions section above in the description of "first substituent group(s)". In embodiments, when an $R^{22.2}$ substituent group is substituted, the $R^{22.2}$ substituent group is substituted with one or more third substituent groups denoted by $R^{22.3}$ as explained in the definitions section above in the description of "first substituent group(s)". In the above embodiments, $R^{22}$, $R^{22.1}$, $R^{22.2}$, and $R^{22.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{22}$, $R^{22.1}$, $R^{22.2}$, and $R^{22.3}$, respectively.

In embodiments, when $R^{22A}$ is substituted, $R^{22A}$ is substituted with one or more first substituent groups denoted by $R^{22A.1}$ as explained in the definitions section above in the description of "first substituent group(s)". In embodiments, when an $R^{22A.1}$ substituent group is substituted, the $R^{22A.1}$ substituent group is substituted with one or more second substituent groups denoted by $R^{22A.2}$ as explained in the definitions section above in the description of "first substituent group(s)". In embodiments, when an $R^{22A.2}$ substituent group is substituted, the $R^{22A.2}$ substituent group is substituted with one or more third substituent groups denoted by $R^{22A.3}$ as explained in the definitions section above in the description of "first substituent group(s)". In the above embodiments, $R^{22A}$, $R^{22A.1}$, $R^{22A.2}$, and $R^{22A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{22A}$, $R^{22A.1}$, $R^{22.2}$, and $R^{22A.3}$, respectively.

In embodiments, when $R^{22B}$ is substituted, $R^{22B}$ is substituted with one or more first substituent groups denoted by $R^{22B.1}$ as explained in the definitions section above in the description of "first substituent group(s)". In embodiments, when an $R^{22B.1}$ substituent group is substituted, the $R^{22B.1}$ substituent group is substituted with one or more second substituent groups denoted by $R^{22B.2}$ as explained in the definitions section above in the description of "first substituent group(s)". In embodiments, when an $R^{22B.2}$ substituent group is substituted, the $R^{22B.2}$ substituent group is substituted with one or more third substituent groups denoted by $R^{22B.3}$ as explained in the definitions section above in the description of "first substituent group(s)". In the above embodiments, $R^{22}$, $R^{22B.1}$, $R^{22B.2}$, and $R^{22B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{22B}$, $R^{22B.1}$, $R^{22B.2}$, and $R^{22B.3}$, respectively.

In embodiments, when $R^{22C}$ is substituted, $R^{22C}$ is substituted with one or more first substituent groups denoted by $R^{22C.1}$ as explained in the definitions section above in the description of "first substituent group(s)". In embodiments, when an $R^{22C.1}$ substituent group is substituted, the $R^{22C.1}$ substituent group is substituted with one or more second substituent groups denoted by $R^{22C.2}$ as explained in the definitions section above in the description of "first substituent group(s)". In embodiments, when an $R^{22C.2}$ substituent group is substituted, the $R^{22C.2}$ substituent group is substituted with one or more third substituent groups denoted by $R^{22C.3}$ as explained in the definitions section above in the description of "first substituent group(s)". In the above embodiments, $R^{22C}$, $R^{22C.1}$, $R^{22C.}$, and $R^{22C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{22C}$, $R^{22C.1}$, $R^{22C.2}$, and $R^{22C.3}$, respectively.

In embodiments, when $R^{23}$ is substituted, $R^{23}$ is substituted with one or more first substituent groups denoted by $R^{23.1}$ as explained in the definitions section above in the description of "first substituent group(s)". In embodiments, when an $R^{23.1}$ substituent group is substituted, the $R^{23.1}$ substituent group is substituted with one or more second substituent groups denoted by $R^{23.2}$ as explained in the definitions section above in the description of "first substituent group(s)". In embodiments, when an $R^{23.2}$ substituent group is substituted, the $R^{23.2}$ substituent group is substituted with one or more third substituent groups denoted by $R^{23.3}$ as explained in the definitions section above in the description of "first substituent group(s)". In the above embodiments, $R^{23}$, $R^{23.1}$, $R^{23.2}$, and $R^{23.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{23}$, $R^{23.1}$, $R^{23.2}$, and $R^{23.3}$, respectively.

In embodiments, when $R^{23A}$ is substituted, $R^{23A}$ is substituted with one or more first substituent groups denoted by $R^{23A.1}$ as explained in the definitions section above in the description of "first substituent group(s)". In embodiments, when an $R^{23A.1}$ substituent group is substituted, the $R^{23A.1}$ substituent group is substituted with one or more second substituent groups denoted by $R^{23A.2}$ as explained in the definitions section above in the description of "first substituent group(s)". In embodiments, when an $R^{23A.2}$ substituent group is substituted, the $R^{23A.2}$ substituent group is substituted with one or more third substituent groups denoted by $R^{23A.3}$ as explained in the definitions section above in the description of "first substituent group(s)". In the above embodiments, $R^{23A}$, $R^{23A.1}$, $R^{23A.2}$, and $R^{23A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{23A}$, $R^{23A.1}$, $R^{23A.2}$, and $R^{23A.3}$, respectively.

In embodiments, when $R^{23B}$ is substituted, $R^{23B}$ is substituted with one or more first substituent groups denoted by $R^{23B.1}$ as explained in the definitions section above in the description of "first substituent group(s)". In embodiments, when an $R^{23B.1}$ substituent group is substituted, the $R^{23B.1}$ substituent group is substituted with one or more second substituent groups denoted by $R^{23B.2}$ as explained in the definitions section above in the description of "first substituent group(s)". In embodiments, when an $R^{23B.2}$ substituent group is substituted, the $R^{23B.2}$ substituent group is substituted with one or more third substituent groups denoted by $R^{23B.3}$ as explained in the definitions section above in the description of "first substituent group(s)". In the above embodiments, $R^{23B}$, $R^{23B.1}$, $R^{23B.2}$, and $R^{23B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{23B}$, $R^{23B.1}$, $R^{23B.2}$, and $R^{23B.3}$, respectively.

In embodiments, when $R^{23C}$ is substituted, $R^{23C}$ is substituted with one or more first substituent groups denoted by $R^{23C.1}$ as explained in the definitions section above in the description of "first substituent group(s)". In embodiments, when an $R^{23C.1}$ substituent group is substituted, the $R^{23C.1}$ substituent group is substituted with one or more second substituent groups denoted by $R^{23C.2}$ as explained in the definitions section above in the description of "first substituent group(s)". In embodiments, when an $R^{23C.2}$ substituent group is substituted, the $R^{23C.2}$ substituent group is substituted with one or more third substituent groups denoted by $R^{23C.3}$ as explained in the definitions section above in the description of "first substituent group(s)". In the above embodiments, $R^{23C}$, $R^{23C.1}$, $R^{23C.2}$, and $R^{23C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{23C}$, $R^{23C.1}$, $R^{23C.2}$, and $R^{23C.3}$, respectively.

In embodiments, when $R^{25}$ is substituted, $R^{25}$ is substituted with one or more first substituent groups denoted by $R^{25.1}$ as explained in the definitions section above in the description of "first substituent group(s)". In embodiments, when an $R^{25A.1}$ substituent group is substituted, the $R^{25.1}$ substituent group is substituted with one or more second substituent groups denoted by $R^{25.2}$ as explained in the definitions section above in the description of "first substituent group(s)". In embodiments, when an $R^{25.2}$ substituent group is substituted, the $R^{25.2}$ substituent group is substituted with one or more third substituent groups denoted by $R^{25.3}$ as explained in the definitions section above in the description of "first substituent group(s)". In the above embodiments, $R^{25}$, $R^{25.1}$, $R^{25.2}$, and $R^{26.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{25}$, $R^{25.1}$, $R^{25.2}$, and $R^{25.3}$, respectively.

In embodiments, when $R^{25A}$ is substituted, $R^{25A}$ is substituted with one or more first substituent groups denoted by $R^{25A.1}$ as explained in the definitions section above in the description of "first substituent group(s)". In embodiments, when an $R^{25A.1}$ substituent group is substituted, the $R^{25A.1}$ substituent group is substituted with one or more second substituent groups denoted by $R^{25A.2}$ as explained in the definitions section above in the description of "first substituent group(s)". In embodiments, when an $R^{25A.2}$ substituent group is substituted, the $R^{25A.2}$ substituent group is substituted with one or more third substituent groups denoted by $R^{25A.3}$ as explained in the definitions section above in the description of "first substituent group(s)". In the above embodiments, $R^{25A}$, $R^{25A.1}$, $R^{25A.2}$, and $R^{25A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{25A}$, $R^{25A.1}$, $R^{25A.2}$, and $R^{25A.3}$, respectively.

In embodiments, when $R^{25B}$ is substituted, $R^{25B}$ is substituted with one or more first substituent groups denoted by $R^{25B.1}$ as explained in the definitions section above in the description of "first substituent group(s)". In embodiments, when an $R^{25B.1}$ substituent group is substituted, the $R^{25B.1}$ substituent group is substituted with one or more second substituent groups denoted by $R^{25B.2}$ as explained in the definitions section above in the description of "first substituent group(s)". In embodiments, when an $R^{25B.2}$ substituent group is substituted, the $R^{25B.2}$ substituent group is substituted with one or more third substituent groups denoted by $R^{25B.3}$ as explained in the definitions section above in the description of "first substituent group(s)". In the above embodiments, $R^{25B}$, $R^{25B.1}$, $R^{25B.2}$, and $R^{25B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{25B}$, $R^{25B.1}$, $R^{25B.2}$, and $R^{25B.3}$, respectively.

In embodiments, when $R^{25C}$ is substituted, $R^{25C}$ is substituted with one or more first substituent groups denoted by $R^{25C.1}$ as explained in the definitions section above in the description of "first substituent group(s)". In embodiments, when an $R^{25C.1}$ substituent group is substituted, the $R^{25C.1}$ substituent group is substituted with one or more second substituent groups denoted by $R^{25C.2}$ as explained in the definitions section above in the description of "first substituent group(s)". In embodiments, when an $R^{25C.2}$ substituent group is substituted, the $R^{25C.2}$ substituent group is substituted with one or more third substituent groups denoted by $R^{25C.3}$ as explained in the definitions section above in the description of "first substituent group(s)". In the above embodiments, $R^{25C}$, $R^{25C.1}$, $R^{25C.2}$, and $R^{25C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{25C}$, $R^{25C.1}$, $R^{25C.2}$, and $R^{25C.3}$, respectively.

In embodiments, when $R^{26}$ is substituted, $R^{26}$ is substituted with one or more first substituent groups denoted by $R^{26.1}$ as explained in the definitions section above in the description of "first substituent group(s)". In embodiments, when an $R^{26.1}$ substituent group is substituted, the $R^{26.1}$ substituent group is substituted with one or more second substituent groups denoted by $R^{26.2}$ as explained in the definitions section above in the description of "first substituent group(s)". In embodiments, when an $R^{26.2}$ substituent group is substituted, the $R^{26.2}$ substituent group is substituted with one or more third substituent groups denoted by $R^{26.3}$ as explained in the definitions section above in the description of "first substituent group(s)". In the above embodiments, $R^{26}$, $R^{26.1}$, $R^{26.2}$, and $R^{26.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{26}$, $R^{26.1}$, $R^{26.2}$, and $R^{26.3}$, respectively.

In embodiments, when $R^{26A}$ is substituted, $R^{26A}$ is substituted with one or more first substituent groups denoted by $R^{26A.1}$ as explained in the definitions section above in the description of "first substituent group(s)". In embodiments, when an $R^{26A.1}$ substituent group is substituted, the $R^{26A.1}$ substituent group is substituted with one or more second substituent groups denoted by $R^{26A.2}$ as explained in the definitions section above in the description of "first substituent group(s)". In embodiments, when an $R^{26A.2}$ substituent group is substituted, the $R^{26A.2}$ substituent group is substituted with one or more third substituent groups denoted by $R^{26A.3}$ as explained in the definitions section above in the description of "first substituent group(s)". In the above embodiments, $R^{26A}$, $R^{26A.1}$, $R^{26A.2}$, and $R^{26A.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{26A}$, $R^{26A.1}$, $R^{26A.2}$, and $R^{26A.3}$, respectively.

In embodiments, when $R^{26B}$ is substituted, $R^{26B}$ is substituted with one or more first substituent groups denoted by $R^{26B.1}$ as explained in the definitions section above in the description of "first substituent group(s)". In embodiments, when an $R^{26B.1}$ substituent group is substituted, the $R^{26B.1}$ substituent group is substituted with one or more second substituent groups denoted by $R^{26B.2}$ as explained in the definitions section above in the description of "first substituent group(s)". In embodiments, when an $R^{26B.2}$ substituent group is substituted, the $R^{26B.2}$ substituent group is substituted with one or more third substituent groups denoted by $R^{26B.3}$ as explained in the definitions section above in the description of "first substituent group(s)". In the above embodiments, $R^{26B}$, $R^{26B.1}$, $R^{26B.2}$, and $R^{26B.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{26B}$, $R^{26B.1}$, $R^{26B.2}$, and $R^{26B.3}$, respectively.

In embodiments, when $R^{26C}$ is substituted, $R^{26C}$ is substituted with one or more first substituent groups denoted by $R^{26C.1}$ as explained in the definitions section above in the description of "first substituent group(s)". In embodiments, when an $R^{26C.1}$ substituent group is substituted, the $R^{26C.1}$ substituent group is substituted with one or more second substituent groups denoted by $R^{26C.2}$ as explained in the definitions section above in the description of "first substituent group(s)". In embodiments, when an $R^{26C.2}$ substituent group is substituted, the $R^{26C.2}$ substituent group is substituted with one or more third substituent groups denoted by $R^{26C.3}$ as explained in the definitions section above in the description of "first substituent group(s)". In the above embodiments, $R^{26C}$, $R^{26C.1}$, $R^{26C.2}$, and $R^{26C.3}$ have values corresponding to the values of $R^{WW}$, $R^{WW.1}$, $R^{WW.2}$, and $R^{WW.3}$, respectively, as explained in the definitions section above in the description of "first substituent group(s)", wherein $R^{WW}$, $R^{WW.1}$, $R^{WW.2}$, and $R^{WW.3}$ correspond to $R^{26C}$, $R^{26C.1}$, $R^{26C.2}$, and $R^{26C.3}$, respectively.

In embodiments, the thiosaccharide compound is useful as a comparator compound. In embodiments, the comparator compound can be used to assess the activity of a test compound as set forth in an assay described herein (e.g., in the examples section, figures, or tables).

In embodiments, the thiosaccharide compound is a compound described herein (e.g., in an aspect, embodiment, example, table, figure, or claim).

In an aspect is provided a thiosaccharide compound for use in a method as described herein.

III. Pharmaceutical Compositions

In an aspect is provided a pharmaceutical composition including a pharmaceutically acceptable excipient and a thiosaccharide compound, or a pharmaceutically acceptable salt thereof. In embodiments, the thiosaccharide compound is a thiosaccharide compound as described herein, including in embodiments. In embodiments, the pharmaceutical composition is for use in a method as described herein.

In embodiments, the pharmaceutically acceptable excipient is sodium citrate. In embodiments, the pharmaceutically acceptable excipient is sodium chloride. In embodiments, the pharmaceutically acceptable excipient is sodium hydroxide.

The terms "pharmaceutical composition" and the like refer, in the usual and customary sense, to a composition which is generally recognized as safe and effective for administration to a subject. The terms "pharmaceutically acceptable excipient," "pharmaceutically acceptable carrier" and the like refer, the usual and customary sense, to pharmaceutical excipients, for example, pharmaceutically, physiologically, acceptable organic or inorganic carrier substances suitable for enteral or parenteral application that do not deleteriously react with the active agent. Suitable pharmaceutically acceptable carriers include water, salt solutions (e.g., Ringer's solution and the like), alcohols, oils, gelatins, and carbohydrates such as lactose, amylose or starch, fatty acid esters, hydroxymethycellulose, polyvinyl pyrrolidine, mannitol, and the parent sugar of a thiosaccharide agent as disclosed herein, wherein the thiosaccharide agent lacks a thiol functionality, e.g., D-glucopyranose, D-galactopyranose, D-mannopyranose, D-glucopyranoside, D-galactopyranoside, D-mannopyranoside, sucrose, lactose, lactulose, maltose, trehalose, cellobiose, chitobiose, or maltose. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. The thiosaccharide compounds described herein can be administered alone or can be co-administered to a subject. Co-administration is meant to include simultaneous or sequential administration of the compounds individually or in combination (more than one compound). The preparations can also be combined, when desired, with other active substances (e.g., to reduce metabolic degradation).

In embodiments, the thiosaccharide compound is co-administered with one or more additional anti-viral compounds, and/or one or more anti-inflammatory compounds. In general, an anti-viral compound is a compound known in the art for use in inhibiting a virus, such as inhibiting viral entry or replication. Several antiviral compounds are known in the art. In general, an anti-inflammatory compound is a compound known in the art for use in treating inflammation.

In embodiments, the thiosaccharide compound is co-administered with heparin, an antibiotic, or methylene blue.

In embodiments, the thiosaccharide compound is co-administered with heparin. In embodiments, the thiosaccharide compound is co-administered with an antibiotic. In embodiments, the thiosaccharide compound is co-administered with methylene blue. In embodiments, the thiosaccharide compound is co-administered with any one of heparin, an antibiotic, or methylene blue.

In embodiments, the thiosaccharide compound is not co-administered with heparin, an antibiotic, or methylene blue. In embodiments, the thiosaccharide compound is not co-administered with heparin. In embodiments, the thiosaccharide compound is not co-administered with an antibiotic. In embodiments, the thiosaccharide compound is not co-administered with methylene blue. In embodiments, the thiosaccharide compound is not co-administered with any one of heparin, an antibiotic, or methylene blue.

A. Formulations

The thiosaccharide compounds disclosed herein can be prepared and administered in a wide variety of inhalation, oral, parenteral, and topical dosage forms. In embodiments, the thiosaccharide compound (e.g., as described herein) is administered by injection (e.g., intravenously, intramuscularly, intracutaneously, subcutaneously, intraduodenally, or intraperitoneally). In embodiments, the thiosaccharide compound (e.g., as described herein) is administered intravenously. In embodiments, the thiosaccharide compound (e.g., as described herein) is administered intramuscularly. In embodiments, the thiosaccharide compound (e.g., as described herein) is administered intracutaneously. In embodiments, the thiosaccharide compound (e.g., as described herein) is administered subcutaneously. In embodiments, the thiosaccharide compound (e.g., as described herein) is administered intraduodenally. In embodiments, the thiosaccharide compound (e.g., as described herein) is administered intraperitoneally. In embodiments, the thiosaccharide compound (e.g., as described herein) is administered by pulmonary delivery. In embodiments, the thiosaccharide compound (e.g., as described herein) is administered as a liquid aerosol or a dry powder. In embodiments, the thiosaccharide compound (e.g., as described herein) is administered by inhalation. In embodiments, the thiosaccharide compound (e.g., as described herein) is administered orally. In embodiments, the thiosaccharide compound (e.g., as described herein) is administered by tablet, pill, or capsule. In embodiments, the thiosaccharide compound (e.g., as described herein) is administered as a lozenge. In embodiments, the thiosaccharide compound (e.g., as described herein) is administered by the intranasal route. In embodiments, the thiosaccharide compound (e.g., as described herein) is administered as a nasal spray. In embodiments, the thiosaccharide compound (e.g., as described herein) is administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable carrier or excipient and one or more compounds of the invention. In embodiments, the thiosaccharide compound (e.g., as described herein) is administered topically to an eye. In embodiments, the thiosaccharide compound (e.g., as described herein) is administered in an eye drop formulation.

For preparing pharmaceutical compositions from the thiosaccharide compounds described herein, pharmaceutically acceptable carriers can be either solid or liquid. Solid form preparations include powders, tablets, pills, capsules, lozenges, wafers, cachets, suppositories, and dispersible granules. A solid carrier can be one or more substance that may also act as diluents, flavoring agents, binders, preservatives, tablet disintegrating agents, or an encapsulating material.

In embodiments, a powder is provided in which the carrier is a finely divided solid in a mixture with the finely divided active component. In embodiments, a tablet is provided in which the active component is mixed with the carrier having the necessary binding properties in suitable proportions and compacted in the shape and size desired.

The powders and tablets preferably contain from 5% to 100% of the active compound. Suitable carriers include, but are not limited to, magnesium carbonate, magnesium stearate, talc, sugar, lactose, pectin, dextrin, starch, gelatin, tragacanth, methylcellulose, sodium carboxymethylcellulose, a low melting wax, cocoa butter, and the like.

Liquid form preparations include solutions (e.g., for oral ingestion), including, suspensions, elixirs, syrups, solutions, emulsions, for example, water or water/propylene glycol solutions, and effervescent solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. In embodiments, the thiosaccharide compound (e.g., as described herein) is incorporated into liposomes or administered via transdermal pumps or patches. Pharmaceutical admixtures suitable for use in the present invention include those described, for example, in PHARMACEUTICAL SCIENCES (17th Ed., Mack Pub. Co., Easton, PA) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral or inhaled administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10,000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions of the present invention may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

In an aspect is provided a pulmonary pharmaceutical composition comprising a pulmonary pharmaceutical carrier and a thiosaccharide compound. The terms "pulmonary pharmaceutical composition" and the like refer to pharmaceutical compositions intended for pulmonary administration. The terms "pulmonary administration" and the like refer, in the usual and customary sense, to administration to achieve inhalation therapy. The term "inhalation therapy" and the like refer to direct delivery of medications to the lungs by inhalation. In embodiments, the thiosaccharide compounds disclosed herein are effective when delivered directly to the lung by an inhaled drug delivery system. The term "pulmonary pharmaceutical liquid" refers to a pulmonary pharmaceutical composition which is a liquid. The terms "pulmonary pharmaceutical solid," "pulmonary pharmaceutical solid" and the like refer to a pulmonary pharmaceutical composition which is a solid (e.g., a powder).

There are three categories of inhaled drug delivery systems: (i) nebulizers; (ii) pressurized metered-dose inhalers (pMDIs); (iii) dry powder inhalers (DPIs). Nebulizers are distinctly different from both pMDIs and DPIs, in that the active agent is dissolved or suspended in a polar liquid, e.g., water. In contrast, pMDIs and DPIs are bolus drug delivery devices that contain active agent (e.g., solid thiosaccharide agent), suspended or dissolved in a nonpolar volatile propellant or in a dry powder mix that is fluidized when the patient inhales. pMDIs and DPIs have considerably reduced treatment time compared with nebulizers. The term "pulmonary pharmaceutical delivery device" and the like refer to an inhaled drug delivery system suitable for delivery (e.g., pulmonary delivery) of a pharmaceutical composition.

Without wishing to be bound by any theory, it is believed that the lung deposition characteristics and efficacy of an aerosol depend largely on the particle or droplet size. For example, particles of more than 10 μm in diameter are most likely to deposit in the mouth and throat, for those of 5-10 μm diameter a transition from mouth to airway deposition occurs, and particles smaller than 5 μm in diameter deposit more frequently in the lower airways and are appropriate for pharmaceutical aerosols (e.g., pulmonary pharmaceutical compositions). Aerodynamic particle size distribution is measured by methods known in the art, e.g., cascade impaction method. Micronization is a conventional approach for size reduction. Additional drug particle engineering technologies includes spray drying, sonocrystalization, or super critical fluids, and the like as known in the art. In embodiments, the particle is a nanoparticle, as known in the art. In all of these technologies, the particles can be delivered alone or co-formulated with carriers.

In embodiments, ideal inhaled particles are characterized as having uniform particle size with mono-dispersion, uniform density, non-cohesiveness, no agglomeration, no compaction, excellent flowability, and ready dispersal when delivered as an aerosol.

In embodiments, the attributes of an optimized inhaled delivery system include stability (i.e., consistent delivered dose through inhaler life), consistent aerodynamic particle size distribution (i.e., fine particle dose/fraction), and chemical and performance stability, as known in the art.

In embodiments, formulation considerations for the pulmonary pharmaceutical composition disclosed herein include consistent product performance on stability and through the labeled number of doses, uniform formulation upon shaking to ensure metering and delivery of accurate and consistent doses, drug suspension stabilized by forming loose agglomerates and readily re-dispersed upon shaking after storage, no particle growth due to aggregation or crystal growth to ensure aerosolization performance, no drug loss due to deposition on dispenser to ensure consistent doses through inhaler life, and protection from moisture ingression to ensure long term stability.

Regarding nebulizers, as known in the art, nebulizers ("atomizers") may, for example, employ compressor to force a gas air (or a blended mixture of air and oxygen through a solution) or electrical means (e.g., piezoelectric power to break up pharmaceutical compositions (e.g., solutions and suspensions)) into small aerosol droplets that can be directly inhaled from the nebulizer. The term "aerosol" and the like refer, in the usual and customary sense to a mixture of gas and liquid particles. The term "jet nebulizer" and the like refer, in the usual and customary sense, to any of a variety of devices connected by tubing to a compressor that causes compressed air or oxygen to flow at high velocity through a liquid medicine to turn it into an aerosol, which is then inhaled by the patient. Jet nebulizers are commonly used for patients in hospitals who have difficulty using inhalers or who require higher doses of drug than can be delivered with hand held devices such pressurized metered dose inhalers (pMDIs) or dry powder inhalers (DPIs). Jet nebulizers are also common in pediatric practice. The term "vibrating mesh nebulizer" refers to a nebulizer that generates aerosols as liquid passes through a mesh that is oscilated (e.g., by a piezo-element) to generate ultrasonic frequencies, and are becoming preferred devices for home use.

In embodiments, a thiosaccharide compound disclosed herein is administered in an aerosol as described herein. In embodiments, a thiosaccharide compound disclosed herein is formulated in a vehicle solution. In embodiments, a thiosaccharide compound disclosed herein is formulated at 5 mg/mL to 75 mg/mL (e.g., 5 mg/mL, 10 mg/mL, 15 mg/mL, 20 mg/mL, 25 mg/mL, 30 mg/mL, 35 mg/mL, 40 mg/mL, 45 mg/mL, 50 mg/mL, 55 mg/mL, 60 mg/mL, 65 mg/mL, 70 mg/mL, or 75 mg/mL) in a vehicle solution. In embodiments, a thiosaccharide compound disclosed herein is formulated at 5 mg/mL to 15 mg/mL in a vehicle solution. In embodiments, a thiosaccharide compound disclosed herein is formulated at 5 mg/mL in a vehicle solution. In embodiments, a thiosaccharide compound disclosed herein is formulated at 6 mg/mL in a vehicle solution. In embodiments, a thiosaccharide compound disclosed herein is formulated at 7 mg/mL in a vehicle solution. In embodiments, a thiosaccharide compound disclosed herein is formulated at 8 mg/mL in a vehicle solution. In embodiments, a thiosaccharide compound disclosed herein is formulated at 9 mg/mL in a vehicle solution. In embodiments, a thiosaccharide compound disclosed herein is formulated at 10 mg/mL in a vehicle solution. In embodiments, a thiosaccharide compound disclosed herein is formulated at 11 mg/mL in a vehicle solution. In embodiments, a thiosaccharide compound disclosed herein is formulated at 12 mg/mL in a vehicle solution. In embodiments, a thiosaccharide compound disclosed herein is formulated at 13 mg/mL in a vehicle solution. In embodiments, a thiosaccharide compound disclosed herein is formulated at 14 mg/mL in a vehicle solution. In embodiments, a thiosaccharide compound disclosed herein is formulated at 15 mg/mL in a vehicle solution. In embodiments, a thiosaccharide compound disclosed herein is formulated at 25 mg/mL in a vehicle solution. In embodiments, a thiosaccharide compound disclosed herein is formulated at 50 mg/mL in a vehicle solution. In embodiments, a thiosaccharide compound disclosed herein is formulated at 75 mg/mL in a vehicle solution. In embodiments, a thiosaccharide compound disclosed herein is formulated at about 5 mg/mL to about 75 mg/mL (e.g., about 5 mg/mL, about 10 mg/mL, about 15 mg/mL, about 20 mg/mL, about 25 mg/mL, about 30 mg/mL, about 35 mg/mL, about 40 mg/mL, about 45 mg/mL, about 50 mg/mL, about 55 mg/mL, about 60 mg/mL, about 65 mg/mL, about 70 mg/mL, or about 75 mg/mL) in a vehicle solution. In embodiments, a thiosaccharide compound disclosed herein is formulated at about 5 mg/mL to about 15 mg/mL in a vehicle solution. In embodiments, a thiosaccharide compound disclosed herein is formulated at about 5 mg/mL in a vehicle solution. In embodiments, a thiosaccharide compound disclosed herein is formulated at about 6 mg/mL in a vehicle solution. In embodiments, a thiosaccharide compound disclosed herein is formulated at about 7 mg/mL in a vehicle solution. In embodiments, a thiosaccharide compound disclosed herein is formulated at about 8 mg/mL in a vehicle solution. In embodiments, a thiosaccharide compound disclosed herein is formulated at about 9 mg/mL in a vehicle solution. In embodiments, a thiosaccharide compound disclosed herein is formulated at about 10 mg/mL in a vehicle solution. In embodiments, a thiosaccharide compound disclosed herein is formulated at about 11 mg/mL in a vehicle solution. In embodiments, a thiosaccharide compound disclosed herein is formulated at about 12 mg/mL in a vehicle solution. In embodiments, a thiosaccharide compound disclosed herein is formulated at about 13 mg/mL in a vehicle solution. In embodiments, a thiosaccharide compound disclosed herein is formulated at about 14 mg/mL in a vehicle solution. In embodiments, a thiosaccharide compound disclosed herein is formulated at about 15 mg/mL in a vehicle solution. In embodiments, a thiosaccharide compound disclosed herein is formulated at about 25 mg/mL in a vehicle solution. In embodiments, a thiosaccharide compound disclosed herein is formulated at about 50 mg/mL in a vehicle solution. In embodiments, a thiosaccharide compound disclosed herein is formulated at about 75 mg/mL in a vehicle solution. In embodiments, a thiosaccharide compound disclosed herein is formulated at greater than 15 mg/mL in a vehicle solution (e.g., 20 mg/mL, 25 mg/mL, 30 mg/mL, or higher). In embodiments, the vehicle solution includes sodium citrate. In embodiments, the vehicle solution includes sodium chloride. In embodiments, the vehicle solution includes sodium citrate and sodium chloride. In embodiments, the vehicle solution is 20 mM sodium citrate, pH 5.6 with 38.5 mM NaCl. In embodiments, the vehicle solution is about 20 mM sodium citrate, pH 5.6 with about 38.5 mM NaCl.

A dry powder inhaler (DPI) is a device that delivers medication to the lungs in the form of a dry powder. When a DPI is actuated, the formulation is fluidized and enters the patient's airways.

In embodiments, a thiosaccharide compound disclosed herein is administered in an amorphous powder. Non-limiting descriptions relating to amorphous powders are provided in Chen et al. 2016 Amorphous powders for inhalation drug delivery *Advanced Drug Delivery Reviews* 100:102-115, the entire content of which is incorporated by reference.

In embodiments, a thiosaccharide compound disclosed herein is administered as a micronized powder.

In embodiments, a powder composition for use in a DPI is packaged in single dose quantities in blisters or gel capsules containing the powdered medication to be drawn into the lungs by the user's own breath.

In embodiments, a DPI formulation must undergo flow, fluidization, and de-aggregation. In embodiments, an excipient is added to enhance the physical or chemical stability of the active pharmaceutical ingredient mechanical properties, and/or its pharmaceutical properties, such as dissolution and permeation.

In embodiments, a DPI formulation includes loose agglomerates. In embodiments, the agglomerates consist of particles of disparate sizes, as is the case when agent is prepared with large carrier particles, or particles of similar sizes prepared by unique methods of formation that result in ease of dispersion. In embodiments, a DPI formulation of particles of similar sizes is prepared by spray-drying.

In embodiments, after the formulation has been produced, it is filled into capsules, multi-dose blisters, or reservoirs for use with the inhaler device.

Regarding pressurized metered-dose inhalers (pMDIs), a formulation can be made up of the agent (e.g., a thiosaccharide compound as described herein), a liquefied gas propellant and, in many cases, stabilizing excipients. The actuator contains the mating discharge nozzle and generally includes a dust cap to prevent contamination. Actuation of the device releases a single metered dose of the formulation which contains the medication either dissolved or suspended in the propellant. Breakup of the volatile propellant into droplets, followed by rapid evaporation of these droplets, results in the generation of an aerosol consisting of micrometer-sized medication particles that are then inhaled. One of the most crucial components of a MDI is its propellant. The propellant provides the force to generate the aerosol cloud and is also the medium in which the active component must be suspended or dissolved. Propellants in MDIs typically make up more than 99% of the delivered dose, so it is the properties of the propellant that dominate more than any other individual factor. Suitable propellants must pass a stringent set of criteria, they must: have a boiling point in the range −100 to +30° C. have a density of approximately 1.2 to 1.5 g $cm^{-3}$ (approximately that of the drug to be suspended or dissolved) have a vapor pressure of 40 to 80 psig have no toxicity to the patient, be non-flammable and be able to dissolve common additives. Active ingredients can be either fully soluble or fully insoluble. In the early days of MDIs the most commonly used propellants were the chlorofluorocarbons, but hydrofluoroalkane propellants are now preferred because they have fewer environmental toxicities. General considerations for metered dose inhalers include consideration of the following: agent is dissolved in the liquefied propellant, compliance with applicable rules (e.g., formulation agent (e.g., HFA propellant, surfactant, sosolvent and/or excipient)), container closure system (e.g., can, metering valve), actuator, and dose compliance device, as known in the art. Suspension formulation issues can include micronized drug particles suspended in the liquefied propellant (e.g., air, $CO_2$, HFA134a, 227, and the like). The suspension formulation may contain surfactant and cosolvent to aid suspension, particularly with respect irregular particles, polydispersed (e.g., 0.5-10 μm) particles, or amorphous/crystalline particles.

In embodiments of the pulmonary pharmaceutical composition, the pulmonary pharmaceutical carrier is a pulmonary pharmaceutical liquid or pulmonary pharmaceutical powder. In embodiments, the pulmonary pharmaceutical carrier is a pulmonary pharmaceutical liquid. In embodiments, the pulmonary pharmaceutical carrier is a pulmonary pharmaceutical powder.

In embodiments of the pulmonary pharmaceutical composition, the pulmonary pharmaceutical liquid includes a polar liquid and the thiosaccharide compound is dissolved or suspended in the polar liquid. In embodiments, the polar liquid is water.

In embodiments of the pulmonary pharmaceutical composition, the pulmonary pharmaceutical carrier is lactose, mannitol, a phospholipid or cholesterol. In embodiments, the phospholipid is phosphatidyl choline. In embodiments, the pulmonary pharmaceutical carrier is the parent sugar of the thiosaccharide agent, wherein the parent sugar lacks a thiol moiety, e.g., D-glucopyranose, D-galactopyranose, D-mannopyranose, D-glucopyranoside, D-galactopyranoside, D-mannopyranoside, sucrose, lactose, lactulose, maltose, trehalose, cellobiose, chitobiose, or maltose.

In embodiments of the pulmonary pharmaceutical composition, the pulmonary pharmaceutical composition is within a pulmonary pharmaceutical delivery device. In embodiments, the pulmonary pharmaceutical delivery device is a pulmonary pharmaceutical nebulizer, a pulmonary pharmaceutical dry powder inhaler, or a pulmonary pharmaceutical pressurized metered dose inhaler.

In embodiments, the pharmaceutical composition further includes one or more additional therapeutic agents. In embodiments, the pharmaceutical composition further includes one additional therapeutic agent. In embodiments, the pharmaceutical composition further includes a plurality of additional therapeutic agents. In embodiments, the pharmaceutical composition further includes two additional therapeutic agents. In embodiments, the pharmaceutical composition further includes three additional therapeutic agents. In embodiments, the pharmaceutical composition further includes four additional therapeutic agents.

In embodiments, the additional therapeutic agent is a beta agonist, as known in the art. In embodiments, the additional therapeutic agent is a short-acting beta agonist, as known in the art. In embodiments, the additional therapeutic agent is a long-acting beta agonist, as known in the art. The term "short-acting" in the context of therapeutic agents refers, in the usual and customary sense, a therapeutic agent that elicits a transient effect, e.g., 1-60 seconds, 1-60 minutes, 1, 2, 3, 4, 5, 6, 7, 8, 9, 10, 11 or even 12 hours, as known in the art. The term "long-acting" in the context of therapeutic agents refers, in the usual and customary sense, a therapeutic agent that elicits a sustained effect, e.g., 1, 2, 3, 4, 5, 6, 7, 8, 9, 10, 11, 12, 13, 14, 15, 16, 17, 18, 19, 20, 21, 22, 23 or even 24 hours, 1, 2, 3, 4, 5, 6, or even 7 days, 1, 2, 3, 4 weeks or longer, as known in the art.

In embodiments, the additional therapeutic agent is a anticholinergic, as known in the art. In embodiments, the additional therapeutic agent is a short-acting anticholinergic, as known in the art. In embodiments, the additional therapeutic agent is a long-acting anticholinergic, as known in the art.

In embodiments, the additional therapeutic agent is a steroid as disclosed herein or as known in the art, e.g., fluticasone, budesonide, beclomethasone, momethasone, dexamethasone. In embodiments, the additional therapeutic agent is a corticosteroid as disclosed herein or as known in the art.

In embodiments, the additional therapeutic agent is an antibiotic, as known in the art.

In embodiments, the additional therapeutic agent is an anti-viral agent (e.g., remdesivir).

In embodiments, the additional therapeutic agent is rhDNAse, as known in the art.

B. Effective Dosages

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated.

The dosage and frequency (single or multiple doses) of compound administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds of the invention.

Therapeutically effective amounts for use in humans may be determined from animal models. For example, a dose for humans can be formulated to achieve a concentration that has been found to be effective in animals. In embodiments, a dose for humans can be formulated to achieve a concentration that has been found to be effective in binding assays or cell culture studies of relevance to viral infection of host cells. In embodiments, a dose for humans can be formulated to achieve a concentration that has been found to be effective in cell-based viral infection studies or binding inhibition studies.

Dosages may be varied depending upon the requirements of the patient and the thiosaccharide compound being employed. The dose administered to a patient, in the context of the present invention, should be sufficient to effect a beneficial therapeutic response in the patient over time. The size of the dose also will be determined by the existence, nature, and extent of any adverse side effects. Generally, treatment is initiated with smaller dosages, which are less than the optimum dose of the thiosaccharide compound. Thereafter, the dosage is increased by small increments until the optimum effect under circumstances is reached. In one embodiment of the invention, the dosage range is 0.001% to 10% w/v. In another embodiment, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

C. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See e.g., Fingl et al., In: THE PHARMACOLOGICAL BASIS OF THERAPEUTICS, Ch.1, p.1, 1975. The exact formulation, route of administration, and dosage can be chosen by the individual physician in view of the patient's condition and the particular method in which the thiosaccharide compound is used.

IV. Embodiments

Embodiment P1. A method of treating a coronavirus infection in a subject in need thereof, the method comprising administering to the subject in need thereof an effective amount of a thiol saccharide compound, or a pharmaceutically acceptable salt thereof.

Embodiment P2. The method of embodiment P1, wherein the coronavirus infection is a SARS-CoV-2 infection.

Embodiment P3. The method of one of embodiments P1 to P2, wherein the subject in need thereof has or is suspected of having COVID-19.

Embodiment P4. The method of one of embodiments P1 to P3, wherein the effective amount of the thiol saccharide compound is administered within 48 to 96 hours of the onset of one or more symptoms of the coronavirus infection.

Embodiment P5. The method of embodiment P4, wherein the effective amount of the thiol saccharide compound is administered within 72 hours of the onset of the one or more symptoms.

Embodiment P6. The method of embodiment P4, wherein the effective amount of the thiol saccharide compound is administered within 48 hours of the onset of the one or more symptoms.

Embodiment P7. The method of one of embodiments P1 to P6, wherein the effective amount of the thiol saccharide compound is effective to reduce viral load in the subject in need thereof.

Embodiment P8. The method of one of embodiments P1 to P7, wherein the thiol saccharide compound is administered by pulmonary delivery.

Embodiment P9. The method of embodiment P8, wherein the thiol saccharide compound is administered as a liquid aerosol or a dry powder.

Embodiment P10. The method of one of embodiments P1 to P7, wherein the thiol saccharide compound is administered orally.

Embodiment P11. The method of embodiment P10, wherein the thiol saccharide compound is administered as a lozenge.

Embodiment P12. The method of one of embodiments P1 to P7, wherein the thiol saccharide compound is administered as a nasal spray.

Embodiment P13. The method of one of embodiments P1 to P7, wherein the thiol saccharide compound is administered intravenously.

Embodiment P14. The method of one of embodiments P1 to P13, wherein the subject in need thereof is not hospitalized.

Embodiment P15. The method of one of embodiments P1 to P13, wherein the subject in need thereof is hospitalized.

Embodiment P16. The method of one of embodiments P1 to P13, wherein the subject in need thereof is in an intensive care unit.

Embodiment P17. The method of one of embodiments P1 to P16, wherein the thiol saccharide compound is a thiol monosaccharide compound, a thiol disaccharide compound, or a thiol trisaccharide compound.

Embodiment P18. The method of one of embodiments P1 to P16, wherein the thiol saccharide compound comprises D-glucopyranose, D-galactopyranose, D-mannopyranose, D-glucopyranoside, D-galactopyranoside, or D-mannopyranoside moieties.

Embodiment P19. The method of one of embodiments P1 to P16, wherein the thiol saccharide compound has the formula:

(I)

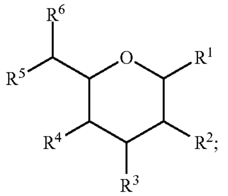

wherein $R^1$ is $-SR^{1A}$, $-OR^{1A}$, $-NR^{1B}R^{1C}$, $-NR^{1B}C(O)R^{1C}$, $-NR^{1B}C(O)OR^{1C}$, substituted or unsubstituted alkyl, or substituted or unsubstituted heteroalkyl;

$R^2$ is $-SR^{2A}$, $-OR^{2A}$, $-NR^{2B}R^{2C}$, $-NR^{2B}C(O)R^{2C}$, $-NR^{2B}C(O)OR^{2C}$, substituted or unsubstituted alkyl, or substituted or unsubstituted heteroalkyl;

$R^3$ is $-SR^{3A}$, $-OR^{3A}$, $-NR^{3B}R^{3C}$, $-NR^{3B}C(O)R^{3C}$, $-NR^{3B}C(O)OR^{3C}$, substituted or unsubstituted alkyl, or substituted or unsubstituted heteroalkyl;

$R^4$ is $-SR^{4A}$, $-SC(O)R^{4A}$, $-OR^{4A}$, $-NR^{4B}R^{4C}$, $-NR^{4B}C(O)R^{4C}$, $-NR^{4B}C(O)OR^{4C}$, substituted or unsubstituted alkyl, or substituted or unsubstituted heteroalkyl;

$R^5$ is hydrogen, $-SR^{5A}$, $-SC(O)R^{5A}$, $-OR^{5A}$, $-NR^{5B}R^{5C}$, $-NR^{5B}C(O)R^{5C}$, $-NR^{5B}C(O)OR^{5C}$, or substituted or unsubstituted alkyl, or substituted or unsubstituted heteroalkyl;

$R^6$ is hydrogen, $-SR^{6A}$, $-OR^{6A}$, $-NR^{6B}R^{6C}$, $-NR^{6B}C(O)R^{6C}$, $-NR^{6B}C(O)OR^{6C}$, substituted or unsubstituted alkyl, or substituted or unsubstituted heteroalkyl; and $R^{1A}$, $R^{1B}$, $R^{1C}$, $R^{2A}$, $R^{2B}$, $R^{2C}$, $R^{3A}$, $R^{3B}$, $R^{3C}$, $R^{4A}$, $R^{4B}$, $R^{4C}$, $R^{5A}$, $R^{5B}$, $R^{5C}$, $R^{6A}$, $R^{6B}$, and $R^{6C}$ are each independently hydrogen, substituted or unsubstituted alkyl, or substituted or unsubstituted heteroalkyl;

wherein the thiol saccharide compound comprises at least two thiol moieties.

Embodiment P20. The method of embodiment P19, wherein the thiol saccharide compound has the formula:

(I-1)

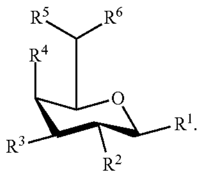

Embodiment P21. The method of embodiment P19, wherein the thiol saccharide compound has the formula:

(I-2)

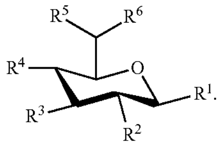

Embodiment P22. The method of embodiment P19, wherein the thiol saccharide compound has the formula:

(I-3)

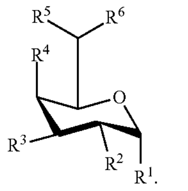

Embodiment P23. The method of embodiment P19, wherein the thiol saccharide compound has the formula:

(I-4)

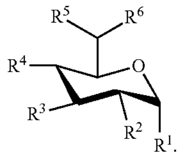

Embodiment P24. The method of one of embodiments P19 to P23, wherein $R^2$ is —$SR^{2A}$, —$OR^{2A}$, substituted or unsubstituted $C_1$-$C_{10}$ alkyl, or substituted or unsubstituted 2 to 10 membered heteroalkyl;

$R^3$ is —$SR^{3A}$, —$OR^{3A}$, substituted or unsubstituted $C_1$-$C_{10}$ alkyl, or substituted or unsubstituted 2 to 10 membered heteroalkyl;

$R^4$ is —$SR^{4A}$, —$OR^{4A}$, substituted or unsubstituted $C_1$-$C_{10}$ alkyl, or substituted or unsubstituted 2 to 10 membered heteroalkyl;

$R^5$ is hydrogen, —$SR^{5A}$, —$OR^{5A}$, substituted or unsubstituted $C_1$-$C_{10}$ alkyl, or substituted or unsubstituted 2 to 10 membered heteroalkyl; and $R^6$ is —$SR^{6A}$, —$OR^{6A}$, substituted or unsubstituted $C_1$-$C_{10}$ alkyl, or substituted or unsubstituted 2 to 10 membered heteroalkyl.

Embodiment P25. The method of one of embodiments P19 to P23, wherein $R^2$ is —$SR^{2A}$, —$OR^{2A}$, substituted or unsubstituted $C_1$-$C_{10}$ thiol-alkyl, or substituted or unsubstituted 2 to 10 membered thiol-heteroalkyl;

$R^3$ is —$SR^{3A}$, —$OR^{3A}$, substituted or unsubstituted $C_1$-$C_{10}$ thiol-alkyl, or substituted or unsubstituted 2 to 10 membered thiol-heteroalkyl;

$R^4$ is —$SR^{4A}$, —$OR^{4A}$, substituted or unsubstituted $C_1$-$C_{10}$ thiol-alkyl, or substituted or unsubstituted 2 to 10 membered thiol-heteroalkyl;

$R^5$ is hydrogen, —$SR^{5A}$, —$OR^{5A}$, substituted or unsubstituted $C_1$-$C_{10}$ thiol-alkyl, or substituted or unsubstituted 2 to 10 membered thiol-heteroalkyl; and $R^6$ is —$SR^{6A}$, —$OR^{6A}$, substituted or unsubstituted $C_1$-$C_{10}$ thiol-alkyl, or substituted or unsubstituted 2 to 10 membered thiol-heteroalkyl.

Embodiment P26. The method of one of embodiments P19 to P23, wherein $R^2$ is —$SR^{2A}$ or —$OR^{2A}$;

$R^3$ is —$SR^{3A}$ or —$OR^{3A}$;

$R^4$ is —$SR^{4A}$ or —$OR^{4A}$; and $R^6$ is —$SR^{6A}$ or —$OR^{6A}$.

Embodiment P27. The method of one of embodiments P19 to P23, wherein $R^2$ is —SH or —OH;

$R^3$ is —SH or —OH;

$R^4$ is —SH or —OH; and $R^6$ is —SH or —OH.

Embodiment P28. The method of one of embodiments P19 to P27, wherein $R^1$ is —$OR^{1A}$.

Embodiment P29. The method of one of embodiments P19 to P28, wherein $R^{1A}$ is a substituted or unsubstituted $C_1$-$C_{10}$ alkyl.

Embodiment P30. The method of one of embodiments P19 to P28, wherein $R^{1A}$ is an unsubstituted $C_1$-$C_5$ alkyl.

Embodiment P31. The method of one of embodiments P19 to P28, wherein $R^{1A}$ is a substituted or unsubstituted 2 to 10 membered heteroalkyl.

Embodiment P32. The method of one of embodiments P19 to P28, wherein $R^{1A}$ is an unsubstituted 2 to 6 membered heteroalkyl.

Embodiment P33. The method of one of embodiments P19 to P28, wherein $R^{1A}$ is

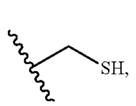 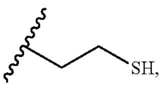 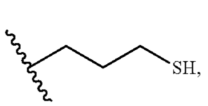

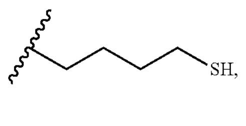 or 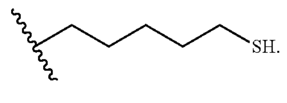

Embodiment P34. The method of one of embodiments P19 to P27, wherein $R^1$ is an unsubstituted methoxy, unsubstituted ethoxy, unsubstituted propoxy, or unsubstituted butoxy.

Embodiment P35. The method of one of embodiments P19 to P27, wherein $R^1$ is —SH.

Embodiment P36. The method of one of embodiments P19 to P35, wherein $R^5$ is hydrogen.

Embodiment P37. The method of embodiment P19, wherein the thiol saccharide compound has the formula:

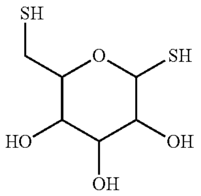

or

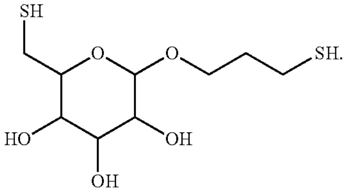

Embodiment P38. The method of embodiment P19, wherein the thiol saccharide compound has the formula:

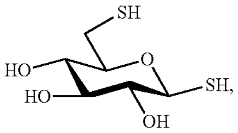

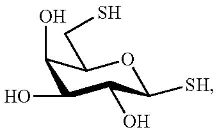

or

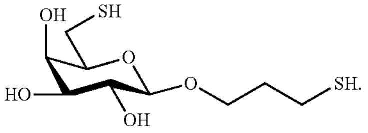

Embodiment P39. The method of embodiment P19, wherein the thiol saccharide compound has the formula:

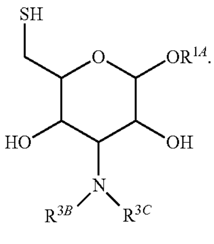

Embodiment P40. The method of embodiment P19, wherein the thiol saccharide compound has the formula:

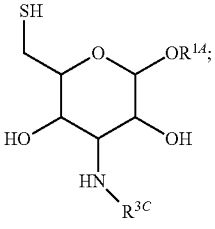

wherein $R^{3C}$ is a substituted or unsubstituted $C_1$-$C_{10}$ thiol-alkyl.

Embodiment P41. The method of embodiment P19, wherein the thiol saccharide compound has the formula:

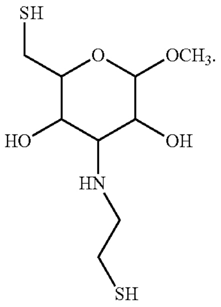 [SMILES: COC1OC(CS)C(O)C(NCCS)C1O]

Embodiment P42. The method of one of embodiments P1 to P16, wherein the thiol saccharide compound has the formula:

(V)

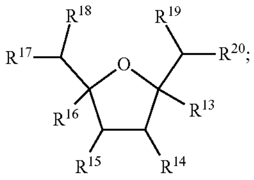

wherein $R^{13}$ is hydrogen, $—SR^{13A}$, $—OR^{13A}$, $—NR^{13B}R^{13C}$, $—NR^{13B}C(O)R^{13C}$, $—NR^{13B}C(O)OR^{13C}$, substituted or unsubstituted alkyl, or substituted or unsubstituted heteroalkyl;

$R^{14}$ is $—SR^{14A}$, $—OR^{14A}$, $—NR^{14B}R^{14C}$, $—NR^{14B}C(O)R^{14C}$, $—NR^{14B}C(O)OR^{14C}$, substituted or unsubstituted alkyl, or substituted or unsubstituted heteroalkyl;

$R^{15}$ is $—SR^{15A}$, $—OR^{15A}$, $—NR^{15B}R^{15C}$, $—NR^{15B}C(O)R^{15C}$, $—NR^{15B}C(O)OR^{15C}$, substituted or unsubstituted alkyl, or substituted or unsubstituted heteroalkyl;

$R^{16}$ is hydrogen, $—SR^{16A}$, $—OR^{16A}$, $—NR^{16B}R^{16C}$, $—NR^{16B}C(O)R^{16C}$, $—NR^{16B}C(O)OR^{16C}$, substituted or unsubstituted alkyl, or substituted or unsubstituted heteroalkyl;

$R^{17}$ is hydrogen, $—SR^{17A}$, $—OR^{17A}$, $—NR^{17B}R^{17C}$, $—NR^{17B}C(O)R^{17C}$, $—NR^{17B}C(O)OR^{17C}$, or substituted or unsubstituted alkyl, or substituted or unsubstituted heteroalkyl;

$R^{18}$ is $—SR^{18A}$, $—OR^{18A}$, $—NR^{18B}R^{18C}$, $—NR^{18B}C(O)R^{18C}$, $—NR^{18B}C(O)OR^{18C}$, substituted or unsubstituted alkyl, or substituted or unsubstituted heteroalkyl;

$R^{19}$ is hydrogen, $—SR^{19A}$, $—OR^{19A}$, $—NR^{19B}R^{19C}$, $—NR^{19B}C(O)R^{19C}$, $—NR^{19B}C(O)OR^{19C}$, substituted or unsubstituted alkyl, or substituted or unsubstituted heteroalkyl;

$R^{20}$ is $—SR^{20A}$, $—OR^{20A}$, $—NR^{20B}R^{20C}$, $—NR^{20B}C(O)R^{20C}$, $—NR^{20B}C(O)OR^{20C}$, or substituted or unsubstituted alkyl, or substituted or unsubstituted heteroalkyl; and $R^{13A}$, $R^{13B}$, $R^{13C}$, $R^{14A}$, $R^{14B}$, $R^{14C}$, $R^{15A}$, $R^{15B}$, $R^{15C}$, $R^{16A}$, $R^{16B}$, $R^{16C}$, $R^{17A}$, $R^{17B}$, $R^{17C}$, $R^{18A}$, $R^{18B}$, $R^{18C}$, $R^{19A}$, $R^{19B}$, $R^{19C}$, $R^{20A}$, $R^{20B}$, and $R^{20C}$ are each independently hydrogen, substituted or unsubstituted alkyl, or substituted or unsubstituted heteroalkyl;

wherein the thiol saccharide compound comprises at least two thiol moieties.

Embodiment P43. The method of embodiment P42, wherein the thiol saccharide compound has the formula:

(V-1)

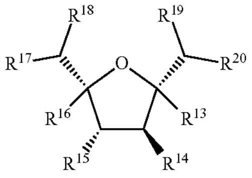

Embodiment P44. The method of embodiment P42, wherein the thiol saccharide compound has the formula:

(V-2)

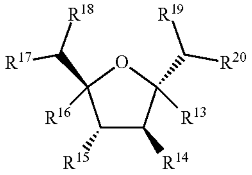

Embodiment P45. The method of one of embodiments P42 to P44, wherein $R^{13}$ is hydrogen, $-SR^{13A}$, $-OR^{13A}$, substituted or unsubstituted $C_1$-$C_{10}$ alkyl, or substituted or unsubstituted 2 to 10 membered heteroalkyl;

$R^{14}$ is $-SR^{14A}$, $-OR^{14A}$, substituted or unsubstituted $C_1$-$C_{10}$ thiol-alkyl, or substituted or unsubstituted 2 to 10 membered thiol-heteroalkyl;

$R^{15}$ is $-SR^{15A}$, $-OR^{15A}$, substituted or unsubstituted $C_1$-$C_{10}$ thiol-alkyl, or substituted or unsubstituted 2 to 10 membered thiol-heteroalkyl;

$R^{16}$ is hydrogen, $-SR^{16A}$, $-OR^{16A}$, substituted or unsubstituted $C_1$-$C_{10}$ thiol-alkyl, or substituted or unsubstituted 2 to 10 membered thiol-heteroalkyl;

$R^{17}$ is hydrogen, $-SR^{17A}$, $-OR^{17A}$, substituted or unsubstituted $C_1$-$C_{10}$ thiol-alkyl, or substituted or unsubstituted 2 to 10 membered thiol-heteroalkyl;

$R^{18}$ is $-SR^{18A}$, $-OR^{18A}$, substituted or unsubstituted $C_1$-$C_{10}$ thiol-alkyl, or substituted or unsubstituted 2 to 10 membered thiol-heteroalkyl;

$R^{19}$ is hydrogen, $-SR^{19A}$, $-OR^{19A}$, substituted or unsubstituted $C_1$-$C_{10}$ thiol-alkyl, or substituted or unsubstituted 2 to 10 membered thiol-heteroalkyl; and $R^{20}$ is $-SR^{20A}$, $-OR^{20A}$, substituted or unsubstituted $C_1$-$C_{10}$ thiol-alkyl, or substituted or unsubstituted 2 to 10 membered thiol-heteroalkyl.

Embodiment P46. The method of one of embodiments P42 to P44, wherein $R^{13}$ is hydrogen, $-SR^{13A}$, or $-OR^{13A}$;

$R^{14}$ is $-SR^{14A}$ or $-OR^{14A}$;

$R^{15}$ is $-SR^{15A}$ or $-OR^{15A}$;

$R^{16}$ is hydrogen, $-SR^{16A}$, or $-OR^{16A}$;

$R^{18}$ is $-SR^{18A}$ or $-OR^{18A}$; and $R^{20}$ is $-SR^{20A}$ or $-OR^{20A}$.

Embodiment P47. The method of one of embodiments P42 to P44, wherein $R^{16}$ is hydrogen.

Embodiment P48. The method of embodiment P42, wherein the thiol saccharide compound has the formula:

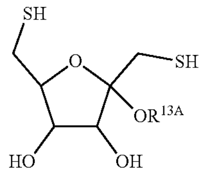

Embodiment P49. The method of embodiment P42, wherein the thiol saccharide compound has the formula:

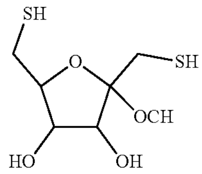

Embodiment P50. The method of one of embodiments P1 to P16, wherein the thiol saccharide compound has the formula:

(VI)

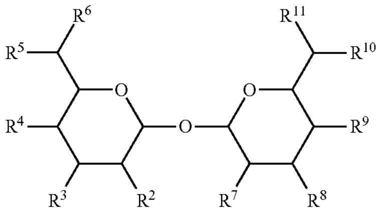

or (VII)

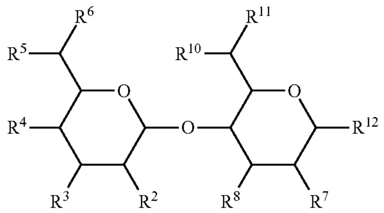

;

wherein $R^2$ is $-SR^{2A}$, $-OR^{2A}$, $-NR^{2B}R^{2C}$, $-NR^{2B}C(O)R^{2C}$, $-NR^{2B}C(O)OR^{2C}$, substituted or unsubstituted alkyl, or substituted or unsubstituted heteroalkyl;

$R^3$ is $-SR^{3A}$, $-OR^{3A}$, $-NR^{3B}R^{3C}$, $-NR^{3B}C(O)R^{3C}$, $-NR^{3B}C(O)OR^{3C}$, substituted or unsubstituted alkyl, or substituted or unsubstituted heteroalkyl;

$R^4$ is $-SR^{4A}$, $-SC(O)R^{4A}$, $-OR^{4A}$, $-NR^{4B}R^{4C}$, $-NR^{4B}C(O)R^{4C}$, $-NR^{4B}C(O)OR^{4C}$, substituted or unsubstituted alkyl, or substituted or unsubstituted heteroalkyl;

$R^5$ is hydrogen, $-SR^{5A}$, $-SC(O)R^{5A}$, $-OR^{5A}$, $-NR^{5B}R^{5C}$, $-NR^{5B}C(O)R^{5C}$, $-NR^{5B}C(O)OR^{5C}$, or substituted or unsubstituted alkyl, or substituted or unsubstituted heteroalkyl;

$R^6$ is hydrogen, $-SR^{6A}$, $-OR^{6A}$, $-NR^{6B}R^{6C}$, $-NR^{6B}C(O)R^{6C}$, $-NR^{6B}C(O)OR^{6C}$, substituted or unsubstituted alkyl, or substituted or unsubstituted heteroalkyl;

$R^7$ is $-SR^{7A}$, $-OR^{7A}$, $-NR^{7B}R^{7C}$, $-NR^{7B}C(O)R^{7C}$, $-NR^{7B}C(O)OR^{7C}$, substituted or unsubstituted alkyl, or substituted or unsubstituted heteroalkyl;

$R^8$ is —$SR^{8A}$, —$OR^{8A}$, —$NR^{8B}R^{8C}$, —$NR^{8B}C(O)R^{8C}$, —$NR^{8B}C(O)OR^{8C}$, substituted or unsubstituted alkyl, or substituted or unsubstituted heteroalkyl;

$R^9$ is —$SR^{9A}$, —$SC(O)R^{9A}$, —$OR^{9A}$, —$NR^{9B}R^{9C}$, —$NR^{9B}C(O)R^{9C}$, —$NR^{9B}C(O)OR^{9C}$, substituted or unsubstituted alkyl, or substituted or unsubstituted heteroalkyl;

$R^{10}$ is hydrogen, —$SR^{10A}$, —$SC(O)R^{10A}$, —$OR^{10A}$, —$NR^{10B}R^{10C}$, —$NR^{10B}C(O)R^{10C}$, —$NR^{10B}C(O)OR^{10C}$, substituted or unsubstituted alkyl, or substituted or unsubstituted heteroalkyl;

$R^{11}$ is hydrogen, —$SR^{11A}$, —$OR^{11A}$, —$NR^{11B}R^{11C}$, —$NR^{11B}C(O)R^{11C}$, —$NR^{11B}C(O)OR^{11C}$, substituted or unsubstituted alkyl, or substituted or unsubstituted heteroalkyl;

$R^{12}$ is —$SR^{12A}$, —$OR^{12A}$, —$NR^{12B}R^{12C}$, —$NR^{12B}C(O)R^{12C}$, —$NR^{12B}C(O)OR^{12C}$, substituted or unsubstituted alkyl, or substituted or unsubstituted heteroalkyl; and $R^{2A}$, $R^{2B}$, $R^{2C}$, $R^{3A}$, $R^{3B}$, $R^{3C}$, $R^{4A}$, $R^{4B}$, $R^{4C}$, $R^{5A}$, $R^{5B}$, $R^{5C}$, $R^{6A}$, $R^{6B}$, $R^{6C}$, $R^{7A}$, $R^{7B}$, $R^{7C}$, $R^{8A}$, $R^{8B}$, $R^{8C}$, $R^{9A}$, $R^{9B}$, $R^{9C}$, $R^{10A}$, $R^{10B}$, $R^{10C}$, $R^{11A}$, $R^{11B}$, $R^{11C}$, $R^{12A}$, $R^{12B}$, and $R^{12C}$ are each independently hydrogen, substituted or unsubstituted alkyl, or substituted or unsubstituted heteroalkyl;

wherein the thiol saccharide compound comprises at least two thiol moieties.

Embodiment P51. The method of embodiment P50, wherein the thiol saccharide compound has the formula:

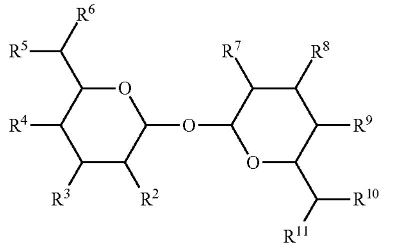

Embodiment P52. The method of embodiment P50, wherein the thiol saccharide compound has the formula:

(VII)

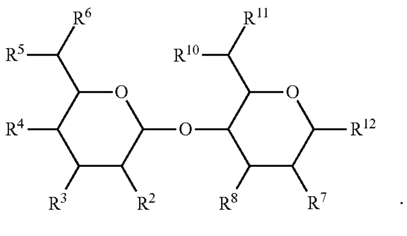

Embodiment P53. The method of embodiment P50, wherein the thiol saccharide compound has the formula:

(VI-1)

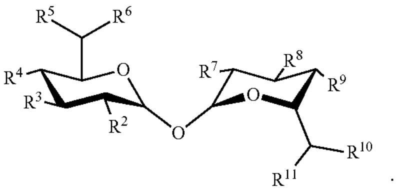

Embodiment P54. The method of embodiment P50, wherein the thiol saccharide compound has the formula:

(VII-1)

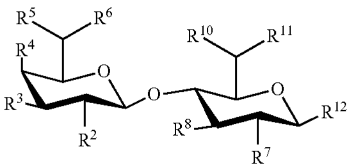

, (VII-2)

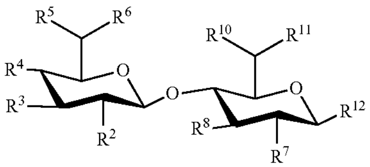

, (VII-3)

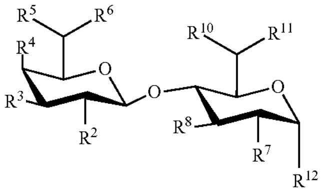

, or (VII-4)

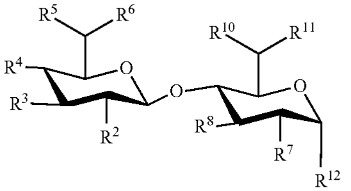

Embodiment P55. The method of embodiment P50, wherein $R^2$ is —$SR^{2A}$, —$OR^{2A}$, substituted or unsubstituted $C_1$-$C_{10}$ alkyl, or substituted or unsubstituted 2 to 10 membered heteroalkyl;

$R^3$ is —$SR^{3A}$, —$OR^{3A}$, substituted or unsubstituted $C_1$-$C_{10}$ alkyl, or substituted or unsubstituted 2 to 10 membered heteroalkyl;

$R^4$ is —$SR^{4A}$, —$OR^{4A}$, substituted or unsubstituted $C_1$-$C_{10}$ alkyl, or substituted or unsubstituted 2 to 10 membered heteroalkyl;

$R^5$ is hydrogen, —$SR^{5A}$, —$OR^{5A}$, substituted or unsubstituted $C_1$-$C_{10}$ alkyl, or substituted or unsubstituted 2 to 10 membered heteroalkyl;

$R^6$ is —$SR^{6A}$, —$OR^{6A}$, substituted or unsubstituted $C_1$-$C_{10}$ alkyl, or substituted or unsubstituted 2 to 10 membered heteroalkyl;

$R^7$ is —$SR^{7A}$, —$OR^{7A}$, substituted or unsubstituted $C_1$-$C_{10}$ alkyl, or substituted or unsubstituted 2 to 10 membered heteroalkyl;

$R^8$ is —$SR^{8A}$, —$OR^{8A}$, substituted or unsubstituted $C_1$-$C_{10}$ alkyl, or substituted or unsubstituted 2 to 10 membered heteroalkyl;

$R^9$ is —$SR^{9A}$, —$OR^{9A}$, substituted or unsubstituted $C_1$-$C_{10}$ alkyl, or substituted or unsubstituted 2 to 10 membered heteroalkyl;

$R^{10}$ is hydrogen, —$SR^{10A}$, —$OR^{10A}$, substituted or unsubstituted $C_1$-$C_{10}$ alkyl, or substituted or unsubstituted 2 to 10 membered heteroalkyl;

$R^{11}$ is —$SR^{11A}$, —$OR^{11A}$, substituted or unsubstituted $C_1$-$C_{10}$ alkyl, or substituted or unsubstituted 2 to 10 membered heteroalkyl; and $R^{12}$ is —$SR^{12A}$, —$OR^{12A}$, substituted or unsubstituted $C_1$-$C_{10}$ alkyl, or substituted or unsubstituted 2 to 10 membered heteroalkyl.

Embodiment P56. The method of embodiment P50, wherein $R^2$ is —$SR^{2A}$, —$OR^{2A}$, substituted or unsubstituted $C_1$-$C_{10}$ thiol-alkyl, or substituted or unsubstituted 2 to 10 membered thiol-heteroalkyl;

$R^3$ is —$SR^{3A}$, —$OR^{3A}$, substituted or unsubstituted $C_1$-$C_{10}$ thiol-alkyl, or substituted or unsubstituted 2 to 10 membered thiol-heteroalkyl;

$R^4$ is —$SR^{4A}$, —$OR^{4A}$, substituted or unsubstituted $C_1$-$C_{10}$ thiol-alkyl, or substituted or unsubstituted 2 to 10 membered thiol-heteroalkyl;

$R^5$ is hydrogen, —$SR^{5A}$, —$OR^{5A}$, substituted or unsubstituted $C_1$-$C_{10}$ thiol-alkyl, or substituted or unsubstituted 2 to 10 membered thiol-heteroalkyl;

$R^6$ is —$SR^{6A}$, —$OR^{6A}$, substituted or unsubstituted $C_1$-$C_{10}$ thiol-alkyl, or substituted or unsubstituted 2 to 10 membered thiol-heteroalkyl;

$R^7$ is —$SR^{7A}$, —$OR^{7A}$, substituted or unsubstituted $C_1$-$C_{10}$ thiol-alkyl, or substituted or unsubstituted 2 to 10 membered thiol-heteroalkyl;

$R^8$ is —$SR^{8A}$, —$OR^{8A}$, substituted or unsubstituted $C_1$-$C_{10}$ thiol-alkyl, or substituted or unsubstituted 2 to 10 membered thiol-heteroalkyl;

$R^9$ is —$SR^{9A}$, —$OR^{9A}$, substituted or unsubstituted $C_1$-$C_{10}$ thiol-alkyl, or substituted or unsubstituted 2 to 10 membered thiol-heteroalkyl;

$R^{10}$ is hydrogen, —$SR^{10A}$, —$OR^{10A}$, substituted or unsubstituted $C_1$-$C_{10}$ thiol-alkyl, or substituted or unsubstituted 2 to 10 membered thiol-heteroalkyl;

$R^{11}$ is —$SR^{11A}$, —$OR^{11A}$, substituted or unsubstituted $C_1$-$C_{10}$ thiol-alkyl, or substituted or unsubstituted 2 to 10 membered thiol-heteroalkyl; and $R^{12}$ is —$SR^{12A}$, —$OR^{12A}$, substituted or unsubstituted $C_1$-$C_{10}$ thiol-alkyl, or substituted or unsubstituted 2 to 10 membered thiol-heteroalkyl.

Embodiment P57. The method of embodiment P50, wherein $R^2$ is —$SR^{2A}$ or —$OR^{2A}$;

$R^3$ is —$SR^{3A}$ or —$OR^{3A}$;

$R^4$ is —$SR^{4A}$ or —$OR^{4A}$;

$R^6$ is —$SR^{6A}$ or —$OR^{6A}$;

$R^7$ is —$SR^{7A}$ or —$OR^{7A}$;

$R^8$ is —$SR^{8A}$ or $OR^{8A}$;

$R^9$ is —$SR^{9A}$ or —$OR^{9A}$; and $R^{11}$ is —$SR^{11A}$ or —$OR^{11A}$.

Embodiment P58. The method of embodiment P50, wherein $R^2$ is —SH or —OH;

$R^3$ is —SH or —OH;

$R^4$ is —SH or —OH;

$R^6$ is —SH or —OH;

$R^7$ is —SH or —OH;

$R^8$ is —SH or —OH;

$R^9$ is —SH or —OH; and $R^{11}$ is —SH or —OH.

Embodiment P59. The method of one of embodiments P50 to P58, wherein $R^5$ is hydrogen.

Embodiment P60. The method of one of embodiments P50 to P59, wherein $R^{10}$ is hydrogen.

Embodiment P61. The method of one of embodiments P50 to P60, wherein $R^{12}$ is —$OR^{12A}$.

Embodiment P62. The method of one of embodiments P50 to P61, wherein $R^{12A}$ is a substituted or unsubstituted $C_1$-$C_{10}$ alkyl.

Embodiment P63. The method of one of embodiments P50 to P61, wherein $R^{12A}$ is an unsubstituted $C_1$-$C_5$ alkyl.

Embodiment P64. The method of one of embodiments P50 to P61, wherein $R^{12A}$ is a substituted or unsubstituted 2 to 10 membered heteroalkyl.

Embodiment P65. The method of one of embodiments P50 to P61, wherein $R^{12A}$ is an unsubstituted 2 to 6 membered heteroalkyl.

Embodiment P66. The method of one of embodiments P50 to P60, wherein $R^{12}$ is unsubstituted methoxy, unsubstituted ethoxy, unsubstituted propoxy, or unsubstituted butoxy.

Embodiment P67. The method of one of embodiments P50 to P60, wherein $R^{12}$ is —SH.

Embodiment P68. The method of embodiment P50, wherein the thiol saccharide compound has the formula:

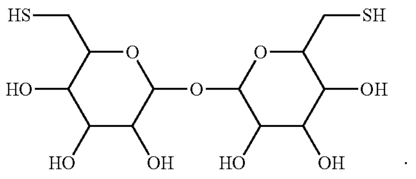 [SMILES: OC1C(CS)OC(OC2OC(CS)C(O)C(O)C2O)C(O)C1O]

Embodiment P69. The method of embodiment P50, wherein the thiol saccharide compound has the formula:

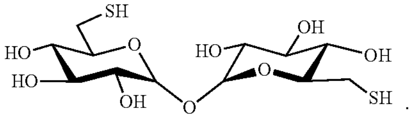

Embodiment P70. The method of embodiment P50, wherein the thiol saccharide compound has the formula:

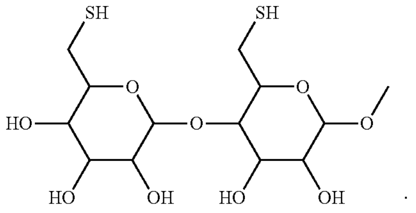 [SMILES: COC1OC(CS)C(OC2OC(CS)C(O)C(O)C2O)C(O)C1O]

Embodiment P71. The method of embodiment P50, wherein the thiol saccharide compound has the formula:

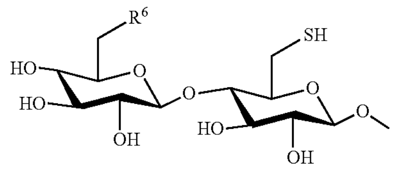

Embodiment P72. The method of embodiment P50, wherein the thiol saccharide compound has the formula:

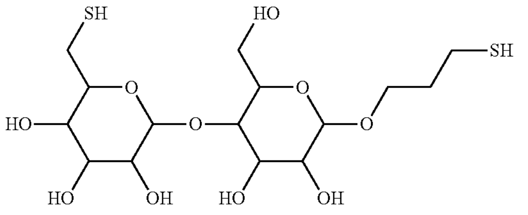

Embodiment P73. The method of embodiment P50, wherein the thiol saccharide compound has the formula:

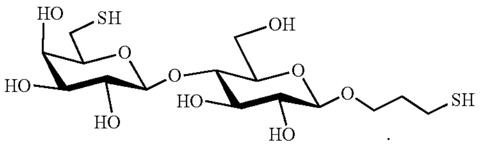

Embodiment P74. The method of one of embodiments P1 to P16, wherein the thiol saccharide compound has the formula:

(VIII)

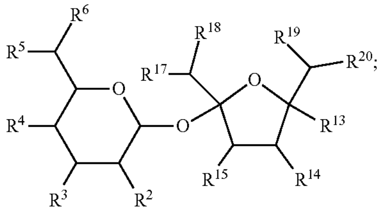

wherein $R^2$ is —$SR^{2A}$, —$OR^{2A}$, —$NR^{2B}R^{2C}$, —$NR^{2B}C(O)R^{2C}$, —$NR^{2B}C(O)OR^{2C}$, substituted or unsubstituted alkyl, or substituted or unsubstituted heteroalkyl;

$R^3$ is —$SR^{3A}$, —$OR^{3A}$, —$NR^{3B}R^{3C}$, —$NR^{3B}C(O)R^{3C}$, —$NR^{3B}C(O)OR^{3C}$, substituted or unsubstituted alkyl, or substituted or unsubstituted heteroalkyl;

$R^4$ is —$SR^{4A}$, —$SC(O)R^{4A}$, —$OR^{4A}$, —$NR^{4B}R^{4C}$, —$NR^{4B}C(O)R^{4C}$, —$NR^{4B}C(O)OR^{4C}$, substituted or unsubstituted alkyl, or substituted or unsubstituted heteroalkyl;

$R^5$ is hydrogen, —$SR^{5A}$, —$SC(O)R^{5A}$, —$OR^{5A}$, —$NR^{5B}R^{5C}$, —$NR^{5B}C(O)R^{5C}$, —$NR^{5B}C(O)OR^{5C}$, or substituted or unsubstituted alkyl, or substituted or unsubstituted heteroalkyl;

$R^6$ is hydrogen, —$SR^{6A}$, —$OR^{6A}$, —$NR^{6B}R^{6C}$, —$NR^{6B}C(O)R^{6C}$, —$NR^{6B}C(O)OR^{6C}$, substituted or unsubstituted alkyl, or substituted or unsubstituted heteroalkyl;

$R^{13}$ is hydrogen, —$SR^{13A}$, —$OR^{13A}$, —$NR^{13B}R^{13C}$, —$NR^{13B}C(O)R^{13C}$, —$NR^{13B}C(O)OR^{13C}$, substituted or unsubstituted alkyl, or substituted or unsubstituted heteroalkyl;

$R^{14}$ is —$SR^{14A}$, —$OR^{14A}$, —$NR^{14B}R^{14C}$, —$NR^{14B}C(O)R^{14C}$, —$NR^{14B}C(O)OR^{14C}$, substituted or unsubstituted alkyl, or substituted or unsubstituted heteroalkyl;

$R^{15}$ is —$SR^{15A}$, —$OR^{15A}$, —$NR^{15B}R^{15C}$, —$NR^{15C}C(O)R^{15C}$, —$NR^{15B}C(O)OR^{15C}$, substituted or unsubstituted alkyl, or substituted or unsubstituted heteroalkyl;

$R^{17}$ is hydrogen, —$SR^{17A}$, —$OR^{17A}$, —$NR^{17B}R^{17C}$, —$NR^{17B}C(O)R^{17C}$, —$NR^{17B}C(O)OR^{17C}$, or substituted or unsubstituted alkyl, or substituted or unsubstituted heteroalkyl;

$R^{18}$ is —$SR^{18A}$, —$OR^{18A}$, —$NR^{18B}R^{18C}$, —$NR^{18B}C(O)R^{18C}$, —$NR^{18B}(O)OR^{18C}$, substituted or unsubstituted alkyl, or substituted or unsubstituted heteroalkyl;

$R^{19}$ is hydrogen, —$SR^{19A}$, —$OR^{19A}$, —$NR^{19B}R^{19C}$, —$NR^{19B}C(O)R^{19C}$, —$NR^{19B}C(O)OR^{19C}$, substituted or unsubstituted alkyl, or substituted or unsubstituted heteroalkyl;

$R^{20}$ is —$SR^{20A}$, —$OR^{20A}$, —$NR^{20B}R^{20C}$, —$NR^{20B}C(O)R^{20C}$, —$NR^{20B}C(O)OR^{20C}$, or substituted or unsubstituted alkyl, or substituted or unsubstituted heteroalkyl; and $R^{2A}$, $R^{2B}$, $R^{2C}$, $R^{3A}$, $R^{3B}$, $R^{3C}$, $R^{4A}$, $R^{4B}$, $R^{4C}$, $R^{5A}$, $R^{5B}$, $R^{5C}$, $R^{6A}$, $R^{6B}$, $R^{6C}$, $R^{13A}$, $R^{13B}$, $R^{13C}$, $R^{14A}$, $R^{14B}$, $R^{14C}$, $R^{15A}$, $R^{15B}$, $R^{15C}$, $R^{17A}$, $R^{17B}$, $R^{17C}$, $R^{18A}$, $R^{18B}$, $R^{18C}$, $R^{19A}$, $R^{19B}$, $R^{19C}$, $R^{20A}$, $R^{20B}$, and $R^{20C}$ are each independently hydrogen, substituted or unsubstituted alkyl, or substituted or unsubstituted heteroalkyl;

wherein the thiol saccharide compound comprises at least two thiol moieties.

Embodiment P75. The method of embodiment P74, wherein $R^2$ is —$SR^{2A}$, —$OR^{2A}$, substituted or unsubstituted $C_1$-$C_{10}$ thiol-alkyl, or substituted or unsubstituted 2 to 10 membered thiol-heteroalkyl;

$R^3$ is —$SR^{3A}$, —$OR^{3A}$, substituted or unsubstituted $C_1$-$C_{10}$ thiol-alkyl, or substituted or unsubstituted 2 to 10 membered thiol-heteroalkyl;

$R^4$ is —$SR^{4A}$, —$OR^{4A}$, substituted or unsubstituted $C_1$-$C_{10}$ thiol-alkyl, or substituted or unsubstituted 2 to 10 membered thiol-heteroalkyl;

$R^5$ is hydrogen, —$SR^{5A}$, —$OR^{5A}$, substituted or unsubstituted $C_1$-$C_{10}$ thiol-alkyl, or substituted or unsubstituted 2 to 10 membered thiol-heteroalkyl;

$R^6$ is —$SR^{6A}$, —$OR^{6A}$, substituted or unsubstituted $C_1$-$C_{10}$ thiol-alkyl, or substituted or unsubstituted 2 to 10 membered thiol-heteroalkyl;

$R^{13}$ is hydrogen, —$SR^{13A}$, —$OR^{13A}$, substituted or unsubstituted $C_1$-$C_{10}$ thiol-alkyl, or substituted or unsubstituted 2 to 10 membered thiol-heteroalkyl;

$R^{14}$ is —$SR^{14A}$, —$OR^{14A}$, substituted or unsubstituted $C_1$-$C_{10}$ thiol-alkyl, or substituted or unsubstituted 2 to 10 membered thiol-heteroalkyl;

$R^{15}$ is —$SR^{15A}$, —$OR^{15A}$, substituted or unsubstituted $C_1$-$C_{10}$ thiol-alkyl, or substituted or unsubstituted 2 to 10 membered thiol-heteroalkyl;

$R^{17}$ is hydrogen, —$SR^{17A}$, —$OR^{17A}$, substituted or unsubstituted $C_1$-$C_{10}$ thiol-alkyl, or substituted or unsubstituted 2 to 10 membered thiol-heteroalkyl;

$R^{18}$ is —$SR^{18A}$, —$OR^{18A}$, substituted or unsubstituted $C_1$-$C_{10}$ thiol-alkyl, or substituted or unsubstituted 2 to 10 membered thiol-heteroalkyl;

$R^{19}$ is hydrogen, —$SR^{19A}$, —$OR^{19A}$, substituted or unsubstituted $C_1$-$C_{10}$ thiol-alkyl, or substituted or unsubstituted 2 to 10 membered thiol-heteroalkyl; and $R^{20}$ is —$SR^{20A}$, —$OR^{20A}$, substituted or unsubstituted $C_1$-$C_{10}$ thiol-alkyl, or substituted or unsubstituted 2 to 10 membered thiol-heteroalkyl.

Embodiment P76. The method of embodiment P74, wherein $R^2$ is —$SR^{2A}$ or —$OR^{2A}$;

$R^3$ is —$SR^{3A}$ or —$OR^{3A}$;

$R^4$ is —$SR^{4A}$ or —$OR^{4A}$;

$R^6$ is —$SR^{6A}$ or —$OR^{6A}$;

$R^{13}$ is hydrogen, —$SR^{13A}$ or —$OR^{13A}$;

$R^{14}$ is —$SR^{14A}$ or —$OR^{14A}$;

$R^{15}$ is —$SR^{15A}$ or —$OR^{15A}$;

$R^{18}$ is —$SR^{18A}$ or —$OR^{18A}$; and $R^{20}$ is —$SR^{20A}$ or —$OR^{20A}$.

Embodiment P77. The method of one of embodiments P1 to P16, wherein the thiol saccharide compound has the formula:

(IX)

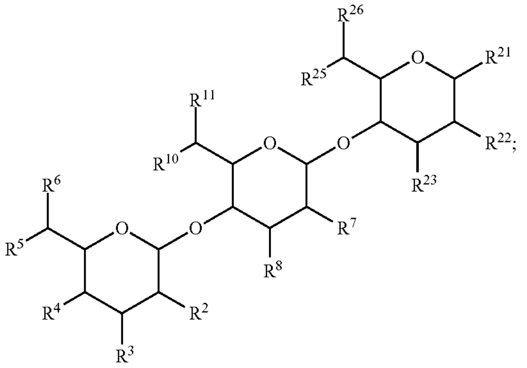

wherein $R^2$ is —$SR^{2A}$, —$OR^{2A}$, —$NR^{2B}R^{2C}$, —$NR^{2B}C(O)R^{2C}$, —$NR^{2B}C(O)OR^{2C}$, substituted or unsubstituted alkyl, or substituted or unsubstituted heteroalkyl;

$R^3$ is —$SR^{3A}$, —$OR^{3A}$, —$NR^{3B}R^{3C}$, —$NR^{3B}C(O)R^{3C}$, —$NR^{3B}C(O)OR^{3C}$, substituted or unsubstituted alkyl, or substituted or unsubstituted heteroalkyl;

$R^4$ is —$SR^{4A}$, —$SC(O)R^{4A}$, —$OR^{4A}$, —$NR^{4B}R^{4C}$, —$NR^{4B}C(O)R^{4C}$, —$NR^{4B}C(O)OR^{4C}$, substituted or unsubstituted alkyl, or substituted or unsubstituted heteroalkyl;

$R^5$ is hydrogen, —$SR^{5A}$, —$SC(O)R^{5A}$, —$OR^{5A}$, —$NR^{5B}R^{5C}$, —$NR^{5B}C(O)R^{5C}$, —$NR^{5B}C(O)OR^{5C}$, or substituted or unsubstituted alkyl, or substituted or unsubstituted heteroalkyl;

$R^6$ is hydrogen, —$SR^{6A}$, —$OR^{6A}$, —$NR^{6B}R^{6C}$, —$NR^{6B}C(O)R^{6C}$, —$NR^{6B}C(O)OR^{6C}$, substituted or unsubstituted alkyl, or substituted or unsubstituted heteroalkyl;

$R^7$ is —$SR^{7A}$, —$OR^{7A}$, —$NR^{7B}R^{7C}$, —$NR^{7B}C(O)R^{7C}$, —$NR^{7B}C(O)OR^{7C}$, substituted or unsubstituted alkyl, or substituted or unsubstituted heteroalkyl;

$R^8$ is —$SR^{8A}$, —$OR^{8A}$, —$NR^{8B}R^{8C}$, —$NR^{8B}C(O)R^{8C}$, —$NR^{8B}C(O)OR^{8C}$, substituted or unsubstituted alkyl, or substituted or unsubstituted heteroalkyl;

$R^{10}$ is hydrogen, —$SR^{10A}$, —$SC(O)R^{10A}$, —$OR^{10A}$, —$NR^{10B}R^{10C}$, —$NR^{10B}C(O)R^{10C}$, —$NR^{10B}C(O)OR^{10C}$, substituted or unsubstituted alkyl, or substituted or unsubstituted heteroalkyl;

$R^{11}$ is hydrogen, —$SR^{11A}$, —$OR^{11A}$, —$NR^{11B}R^{11C}$, —$NR^{11B}C(O)R^{11C}$, —$NR^{11B}C(O)OR^{11C}$, substituted or unsubstituted alkyl, or substituted or unsubstituted heteroalkyl;

$R^{21}$ is —$SR^{21A}$, —$OR^{21A}$, —$NR^{21B}R^{21C}$, —$NR^{21B}C(O)R^{21C}$, —$NR^{21B}C(O)OR^{21C}$, substituted or unsubstituted alkyl, or substituted or unsubstituted heteroalkyl;

$R^{22}$ is —$SR^{22A}$, —$OR^{22A}$, —$NR^{22B}R^{22C}$, —$NR^{22B}C(O)R^{22C}$, —$NR^{22B}C(O)OR^{22C}$, substituted or unsubstituted alkyl, or substituted or unsubstituted heteroalkyl;

$R^{23}$ is —$SR^{23A}$, —$OR^{23A}$, —$NR^{23B}BR^{23C}$, —$NR^{23B}C(O)R^{23C}$, —$NR^{23B}C(O)OR^{23C}$, substituted or unsubstituted alkyl, or substituted or unsubstituted heteroalkyl;

$R^{25}$ is hydrogen, —$SR^{25A}$, —$SC(O)R^{25A}$, —$OR^{25A}$, —$NR^{25B}R^{25C}$, —$NR^{25B}C(O)R^{25C}$, —$NR^{25B}C(O)OR^{25C}$, or substituted or unsubstituted alkyl, or substituted or unsubstituted heteroalkyl;

$R^{26}$ is hydrogen, —$SR^{26A}$, —$OR^{26A}$, —$NR^{26B}R^{26C}$, —$NR^{26B}C(O)R^{26C}$, —$NR^{26B}C(O)OR^{26C}$, or substituted or unsubstituted alkyl, or substituted or unsubstituted heteroalkyl; and $R^{2A}$, $R^{2B}$, $R^{2C}$, $R^{3A}$, $R^{3B}$, $R^{3C}$, $R^{4A}$, $R^{4B}$, $R^{4C}$, $R^{5A}$, $R^{5B}$, $R^{5C}$, $R^{6A}$, $R^{6B}$, $R^{6C}$, $R^{7A}$, $R^{7B}$, $R^{7C}$, $R^{8A}$, $R^{8B}$, $R^{8C}$, $R^{10A}$, $R^{10B}$, $R^{10C}$, $R^{11A}$, $R^{11B}$, $R^{11C}$, $R^{21A}$, $R^{21B}$, $R^{21C}$, $R^{22A}$, $R^{22B}$, $R^{22C}$, $R^{23A}$, $R^{23B}$, $R^{23C}$, $R^{25A}$, $R^{25B}$, $R^{25C}$, $R^{26A}$, $R^{26B}$, and $R^{26C}$ are each independently hydrogen, substituted or unsubstituted alkyl, or substituted or unsubstituted heteroalkyl.

Embodiment P78. The method of embodiment P77, wherein $R^2$ is —$SR^{2A}$, —$OR^{2A}$, substituted or unsubstituted $C_1$-$C_{10}$ thiol-alkyl, or substituted or unsubstituted 2 to 10 membered thiol-heteroalkyl;

$R^3$ is —$SR^{3A}$, —$OR^{3A}$, substituted or unsubstituted $C_1$-$C_{10}$ thiol-alkyl, or substituted or unsubstituted 2 to 10 membered thiol-heteroalkyl;

$R^4$ is —$SR^{4A}$, —$OR^{4A}$, substituted or unsubstituted $C_1$-$C_{10}$ thiol-alkyl, or substituted or unsubstituted 2 to 10 membered thiol-heteroalkyl;

$R^5$ is hydrogen, —$SR^{5A}$, —$OR^{5A}$, substituted or unsubstituted $C_1$-$C_{10}$ thiol-alkyl, or substituted or unsubstituted 2 to 10 membered thiol-heteroalkyl;

$R^6$ is —$SR^{6A}$, —$OR^{6A}$, substituted or unsubstituted $C_1$-$C_{10}$ thiol-alkyl, or substituted or unsubstituted 2 to 10 membered thiol-heteroalkyl;

$R^7$ is —$SR^{7A}$, —$OR^{7A}$, substituted or unsubstituted $C_1$-$C_{10}$ thiol-alkyl, or substituted or unsubstituted 2 to 10 membered thiol-heteroalkyl;

$R^8$ is —$SR^{8A}$, —$OR^{8A}$, substituted or unsubstituted $C_1$-$C_{10}$ thiol-alkyl, or substituted or unsubstituted 2 to 10 membered thiol-heteroalkyl;

$R^{10}$ is hydrogen, —$SR^{10A}$, —$OR^{10A}$, substituted or unsubstituted $C_1$-$C_{10}$ thiol-alkyl, or substituted or unsubstituted 2 to 10 membered thiol-heteroalkyl;

$R^{11}$ is —$SR^{11A}$, —$OR^{11A}$, substituted or unsubstituted $C_1$-$C_{10}$ thiol-alkyl, or substituted or unsubstituted 2 to 10 membered thiol-heteroalkyl;

$R^{21}$ is —$SR^{21A}$, —$OR^{21A}$, substituted or unsubstituted $C_1$-$C_{10}$ thiol-alkyl, or substituted or unsubstituted 2 to 10 membered thiol-heteroalkyl;

$R^{22}$ is —$SR^{22A}$, —$OR^{22A}$, substituted or unsubstituted $C_1$-$C_{10}$ thiol-alkyl, or substituted or unsubstituted 2 to 10 membered thiol-heteroalkyl;

$R^{23}$ is —$SR^{23A}$, —$OR^{23A}$, substituted or unsubstituted $C_1$-$C_{10}$ thiol-alkyl, or substituted or unsubstituted 2 to 10 membered thiol-heteroalkyl;

$R^{25}$ is hydrogen, —$SR^{25A}$, —$OR^{25A}$, substituted or unsubstituted $C_1$-$C_{10}$ thiol-alkyl, or substituted or unsubstituted 2 to 10 membered thiol-heteroalkyl; and $R^{26}$ is —$SR^{26A}$, —$OR^{26A}$, substituted or unsubstituted $C_1$-$C_{10}$ thiol-alkyl, or substituted or unsubstituted 2 to 10 membered thiol-heteroalkyl.

Embodiment P79. The method of embodiment P77, wherein $R^2$ is —$SR^{2A}$ or —$OR^{2A}$;

$R^3$ is —$SR^{3A}$ or —$OR^{3A}$;

$R^4$ is —$SR^{4A}$ or —$OR^{4A}$;

$R^6$ is —$SR^{6A}$ or —$OR^{6A}$;

$R^7$ is —$SR^{7A}$ or —$OR^{7A}$;

$R^8$ is —$SR^{8A}$ or —$OR^{8A}$;

$R^{11}$ is —$SR^{11A}$ or —$OR^{11A}$;

$R^{21}$ is —$SR^{21A}$ or —$OR^{21A}$;

$R^{22}$ is —$SR^{22A}$ or —$OR^{22A}$;

$R^{23}$ is —$SR^{23A}$ or —$OR^{23A}$; and $R^{26}$ is —$SR^{26A}$ or —$OR^{26A}$.

Embodiment P80. The method of one of embodiments P1 to P16, wherein the thiol saccharide compound comprises two thiol moieties.

Embodiment P81. A thiol saccharide compound for use in a method of any one of embodiments P1 to P80.

Embodiment P82. A pharmaceutical composition comprising a pharmaceutically acceptable excipient and a thiol saccharide compound, or a pharmaceutically acceptable salt thereof.

Embodiment P83. The pharmaceutical composition of embodiment P82 for use in a method of any one of embodiments P1 to P80.

V. Additional Embodiments

Embodiment 1. A method of treating a coronavirus infection in a subject in need thereof, the method comprising administering to the subject in need thereof an effective amount of a thiol saccharide compound, or a pharmaceutically acceptable salt thereof.

Embodiment 2. The method of embodiment 1, wherein the coronavirus infection is a SARS-CoV-2 infection.

Embodiment 3. The method of one of embodiments 1 to 2, wherein the subject in need thereof has or is suspected of having COVID-19.

Embodiment 4. The method of one of embodiments 1 to 3, further comprising reducing inflammation, wherein the inflammation is in the lung.

Embodiment 5. The method of one of embodiments 1 to 4, wherein the effective amount of the thiol saccharide compound is administered within 48 to 96 hours of the onset of one or more symptoms of the coronavirus infection.

Embodiment 6. The method of embodiment 5, wherein the effective amount of the thiol saccharide compound is administered within 72 hours of the onset of the one or more symptoms.

Embodiment 7. The method of embodiment 5, wherein the effective amount of the thiol saccharide compound is administered within 48 hours of the onset of the one or more symptoms.

Embodiment 8. The method of one of embodiments 1 to 7, wherein the effective amount of the thiol saccharide compound is effective to reduce viral load in the subject in need thereof, optionally wherein the viral load is reduced in the lung.

Embodiment 9. The method of one of embodiments 1 to 8, wherein the thiol saccharide compound is administered by pulmonary delivery.

Embodiment 10. The method of embodiment 9, wherein the thiol saccharide compound is administered as a liquid aerosol or a dry powder.

Embodiment 11. The method of one of embodiments 1 to 8, wherein the thiol saccharide compound is administered orally.

Embodiment 12. The method of embodiment 11, wherein the thiol saccharide compound is administered as a lozenge.

Embodiment 13. The method of one of embodiments 1 to 8, wherein the thiol saccharide compound is administered as a nasal spray.

Embodiment 14. The method of one of embodiments 1 to 8, wherein the thiol saccharide compound is administered intravenously.

Embodiment 15. The method of one of embodiments 1 to 14, wherein the subject in need thereof is not hospitalized.

Embodiment 16. The method of one of embodiments 1 to 14, wherein the subject in need thereof is hospitalized.

Embodiment 17. The method of one of embodiments 1 to 14, wherein the subject in need thereof is in an intensive care unit.

Embodiment 18. The method of one of embodiments 1 to 17, wherein the thiol saccharide compound is a thiol monosaccharide compound, a thiol disaccharide compound, or a thiol trisaccharide compound.

Embodiment 19. The method of one of embodiments 1 to 17, wherein the thiol saccharide compound comprises D-glucopyranose, D-galactopyranose, D-mannopyranose, D-glucopyranoside, D-galactopyranoside, or D-mannopyranoside moieties.

Embodiment 20. The method of one of embodiments 1 to 17, wherein the thiol saccharide compound has the formula:

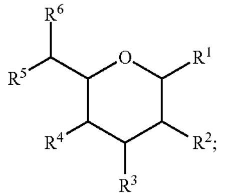

(I)

wherein $R^1$ is —$SR^{1A}$, —$OR^{1A}$, —$NR^{1B}R^{1C}$, —$NR^{1B}C(O)R^{1C}$, —$NR^{1B}C(O)OR^{1C}$, substituted or unsubstituted alkyl, or substituted or unsubstituted heteroalkyl;

$R^2$ is —$SR^{2A}$, —$OR^{2A}$, —$NR^{2B}R^{2C}$, —$NR^{2B}C(O)R^{2C}$, —$NR^{2B}C(O)OR^{2C}$, substituted or unsubstituted alkyl, or substituted or unsubstituted heteroalkyl;

$R^3$ is —$SR^{3A}$, —$OR^{3A}$, —$NR^{3B}R^{3C}$, —$NR^{3B}C(O)R^{3C}$, —$NR^{3B}C(O)OR^{3C}$, substituted or unsubstituted alkyl, or substituted or unsubstituted heteroalkyl;

$R^4$ is —$SR^{4A}$, —$SC(O)R^{4A}$, —$OR^{4A}$, —$NR^{4B}R^{4C}$, —$NR^{4B}C(O)R^{4C}$, —$NR^{4B}C(O)OR^{4C}$, substituted or unsubstituted alkyl, or substituted or unsubstituted heteroalkyl;

$R^5$ is hydrogen, —$SR^{5A}$, —$SC(O)R^{5A}$, —$OR^{5A}$, —$NR^{5B}R^{5C}$, —$NR^{5B}C(O)R^{5C}$, —$NR^{5B}C(O)OR^{5C}$, or substituted or unsubstituted alkyl, or substituted or unsubstituted heteroalkyl;

$R^6$ is hydrogen, —$SR^{6A}$, —$OR^{6A}$, —$NR^{6B}R^{6C}$, —$NR^{6B}C(O)R^{6C}$, —$NR^{6B}C(O)OR^{6C}$, substituted or unsubstituted alkyl, or substituted or unsubstituted heteroalkyl; and $R^{1A}$, $R^{1B}$, $R^{1C}$, $R^{2A}$, $R^{2B}$, $R^{2C}$, $R^{3A}$, $R^{3B}$, $R^{3C}$, $R^{4A}$, $R^{4B}$, $R^{4C}$, $R^{5A}$, $R^{5B}$, $R^{5C}$, $R^{6A}$, $R^{6B}$, and $R^{6C}$ are each independently hydrogen, substituted or unsubstituted alkyl, or substituted or unsubstituted heteroalkyl;

wherein the thiol saccharide compound comprises at least two thiol moieties.

Embodiment 21. The method of embodiment 20, wherein the thiol saccharide compound has the formula:

(I-1)

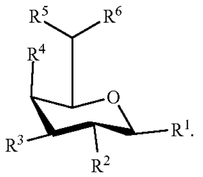

Embodiment 22. The method of embodiment 20, wherein the thiol saccharide compound has the formula:

(I-2)

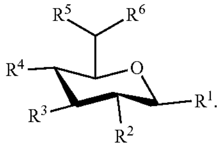

Embodiment 23. The method of embodiment 20, wherein the thiol saccharide compound has the formula:

(I-3)

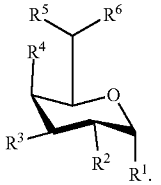

Embodiment 24. The method of embodiment 20, wherein the thiol saccharide compound has the formula:

(I-4)

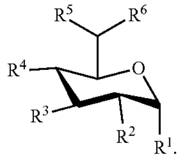

Embodiment 25. The method of one of embodiments 20 to 24, wherein $R^2$ is —$SR^{2A}$, —$OR^{2A}$, substituted or unsubstituted $C_1$-$C_{10}$ alkyl, or substituted or unsubstituted 2 to 10 membered heteroalkyl;

$R^3$ is —$SR^{3A}$, —$OR^{3A}$, substituted or unsubstituted $C_1$-$C_{10}$ alkyl, or substituted or unsubstituted 2 to 10 membered heteroalkyl;

$R^4$ is —$SR^{4A}$, —$OR^{4A}$, substituted or unsubstituted $C_1$-$C_{10}$ alkyl, or substituted or unsubstituted 2 to 10 membered heteroalkyl;

$R^5$ is hydrogen, —$SR^{5A}$, —$OR^{5A}$, substituted or unsubstituted $C_1$-$C_{10}$ alkyl, or substituted or unsubstituted 2 to 10 membered heteroalkyl; and $R^6$ is —$SR^{6A}$, —$OR^{6A}$, substituted or unsubstituted $C_1$-$C_{10}$ alkyl, or substituted or unsubstituted 2 to 10 membered heteroalkyl.

Embodiment 26. The method of one of embodiments 20 to 24, wherein $R^2$ is —$SR^{2A}$, —$OR^{2A}$, substituted or unsubstituted $C_1$-$C_{10}$ thiol-alkyl, or substituted or unsubstituted 2 to 10 membered thiol-heteroalkyl;

$R^3$ is —$SR^{3A}$, —$OR^{3A}$, substituted or unsubstituted $C_1$-$C_{10}$ thiol-alkyl, or substituted or unsubstituted 2 to 10 membered thiol-heteroalkyl;

$R^4$ is —$SR^{4A}$, —$OR^{4A}$, substituted or unsubstituted $C_1$-$C_{10}$ thiol-alkyl, or substituted or unsubstituted 2 to 10 membered thiol-heteroalkyl;

$R^5$ is hydrogen, —$SR^{5A}$, —$OR^{5A}$, substituted or unsubstituted $C_1$-$C_{10}$ thiol-alkyl, or substituted or unsubstituted 2 to 10 membered thiol-heteroalkyl; and $R^6$ is —$SR^{6A}$, —$OR^{6A}$, substituted or unsubstituted $C_1$-$C_{10}$ thiol-alkyl, or substituted or unsubstituted 2 to 10 membered thiol-heteroalkyl.

Embodiment 27. The method of one of embodiments 20 to 24, wherein $R^2$ is —$SR^{2A}$ or —$OR^{2A}$;

$R^3$ is —$SR^{3A}$ or —$OR^{3A}$;

$R^4$ is —$SR^{4A}$ or —$OR^{4A}$; and $R^6$ is —$SR^{6A}$ or —$OR^{6A}$.

Embodiment 28. The method of one of embodiments 20 to 24, wherein $R^2$ is —SH or —OH;

$R^3$ is —SH or —OH;

$R^4$ is —SH or —OH; and $R^6$ is —SH or —OH.

Embodiment 29. The method of one of embodiments 20 to 28, wherein $R^1$ is —$OR^{1A}$.

Embodiment 30. The method of one of embodiments 20 to 29, wherein $R^{1A}$ is a substituted or unsubstituted $C_1$-$C_{10}$ alkyl.

Embodiment 31. The method of one of embodiments 20 to 29, wherein $R^{1A}$ is an unsubstituted $C_1$-$C_5$ alkyl.

Embodiment 32. The method of one of embodiments 20 to 29, wherein $R^{1A}$ is a substituted or unsubstituted 2 to 10 membered heteroalkyl.

Embodiment 33. The method of one of embodiments 20 to 29, wherein $R^{1A}$ is an unsubstituted 2 to 6 membered heteroalkyl.

Embodiment 34. The method of one of embodiments 20 to 29, wherein $R^{1A}$ is

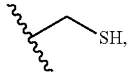,
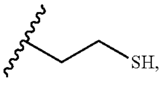,
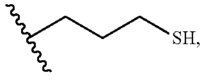,
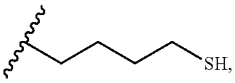, or
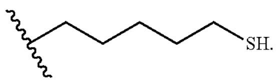.

Embodiment 35. The method of one of embodiments 20 to 28, wherein $R^1$ is an unsubstituted methoxy, unsubstituted ethoxy, unsubstituted propoxy, or unsubstituted butoxy.

Embodiment 36. The method of one of embodiments 20 to 28, wherein $R^1$ is —SH.

Embodiment 37. The method of one of embodiments 20 to 36, wherein $R^5$ is hydrogen.

Embodiment 38. The method of embodiment 20, wherein the thiol saccharide compound has the formula:

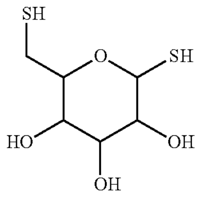

or

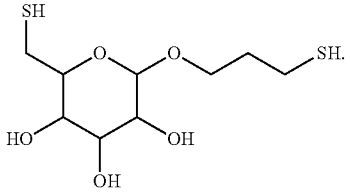

Embodiment 39. The method of embodiment 20, wherein the thiol saccharide compound has the formula:

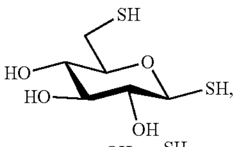

,

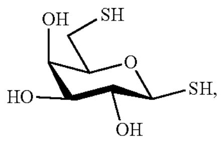

, or

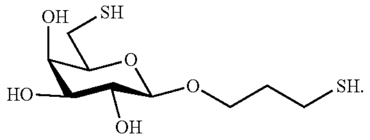

Embodiment 40. The method of embodiment 20, wherein the thiol saccharide compound has the formula:

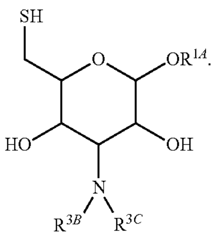

Embodiment 41. The method of embodiment 20, wherein the thiol saccharide compound has the formula:

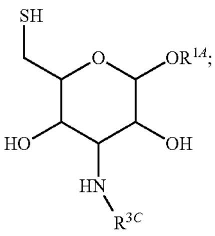

wherein $R^{3C}$ is a substituted or unsubstituted $C_1$-$C_{10}$ thiol-alkyl.

Embodiment 42. The method of embodiment 20, wherein the thiol saccharide compound has the formula:

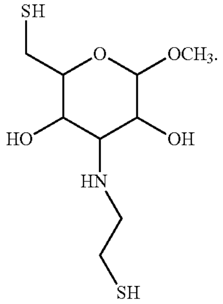 [SMILES: COC1OC(CS)C(O)C(NCCS)C1O]

Embodiment 43. The method of one of embodiments 1 to 17, wherein the thiol saccharide compound has the formula:

(V)

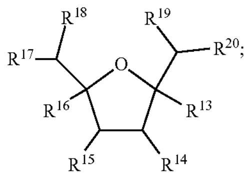

wherein $R^{13}$ is hydrogen, —$SR^{13A}$, —$OR^{13A}$, —$NR^{13B}R^{13C}$, —$NR^{13B}C(O)R^{13C}$, —$NR^{13B}C(O)OR^{13C}$, substituted or unsubstituted alkyl, or substituted or unsubstituted heteroalkyl;

$R^{14}$ is —$SR^{14A}$, —$OR^{14A}$, —$NR^{14B}R^{14C}$, —$NR^{14B}C(O)R^{14C}$, —$NR^{14B}C(O)OR^{14C}$, substituted or unsubstituted alkyl, or substituted or unsubstituted heteroalkyl;

$R^{15}$ is —$SR^{15A}$, —$OR^{15A}$, —$NR^{15B}R^{15C}$, —$NR^{15B}C(O)R^{15C}$, —$NR^{15B}C(O)OR^{15C}c$, substituted or unsubstituted alkyl, or substituted or unsubstituted heteroalkyl;

$R^{16}$ is hydrogen, —$SR^{16A}$, —$OR^{16A}$, —$NR^{16B}R^{16C}$, —$NR^{16B}C(O)R^{16C}$, —$NR^{16B}C(O)OR^{16C}$, substituted or unsubstituted alkyl, or substituted or unsubstituted heteroalkyl;

$R^{17}$ is hydrogen, —$SR^{17A}$, —$OR^{17A}$, —$NR^{17B}R^{17C}$, —$NR^{17B}C(O)R^{17C}$, —$NR^{17B}C(O)OR^{17C}$, or substituted or unsubstituted alkyl, or substituted or unsubstituted heteroalkyl;

$R^{18}$ is —$SR^{18A}$, —$OR^{18A}$, —$NR^{18B}R^{18C}$, —$NR^{18B}C(O)R^{18C}$, —$NR^{18B}C(O)OR^{18C}$, substituted or unsubstituted alkyl, or substituted or unsubstituted heteroalkyl;

$R^{19}$ is hydrogen, —$SR^{19A}$, —$OR^{19A}$, —$NR^{19B}R^{19C}$, —$NR^{19B}C(O)R^{19C}$, —$NR^{19B}C(O)OR^{19C}$, substituted or unsubstituted alkyl, or substituted or unsubstituted heteroalkyl;

$R^{20}$ is —$SR^{20A}$, —$OR^{20A}$, —$NR^{20B}R^{20C}$, —$NR^{20B}C(O)R^{20C}$, —$NR^{20B}C(O)OR^{20C}$, or substituted or unsubstituted alkyl, or substituted or unsubstituted heteroalkyl; and $R^{13A}$, $R^{13B}$, $R^{13C}$, $R^{14A}$, $R^{14B}$, $R^{14C}$, $R^{15A}$, $R^{15B}$, $R^{15C}$, $R^{16A}$, $R^{16B}$, $R^{16C}$, $R^{17A}$, $R^{17B}$, $R^{17C}$, $R^{18A}$, $R^{18B}$, $R^{18C}$, $R^{19A}$, $R^{19B}$, $R^{19C}$, $R^{20A}$, $R^{20B}$, and $R^{20C}$ are each independently hydrogen, substituted or unsubstituted alkyl, or substituted or unsubstituted heteroalkyl;

wherein the thiol saccharide compound comprises at least two thiol moieties.

Embodiment 44. The method of embodiment 43, wherein the thiol saccharide compound has the formula:

(V-1)

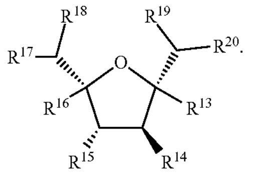

Embodiment 45. The method of embodiment 43, wherein the thiol saccharide compound has the formula:

(V-2)

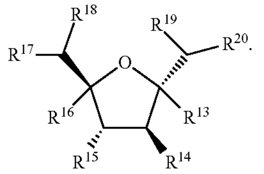

Embodiment 46. The method of one of embodiments 43 to 45, wherein $R^{13}$ is hydrogen, —$SR^{13A}$, —$OR^{13A}$, substituted or unsubstituted $C_1$-$C_{10}$ alkyl, or substituted or unsubstituted 2 to 10 membered heteroalkyl;

$R^{14}$ is —$SR^{14A}$, —$OR^{14A}$, substituted or unsubstituted $C_1$-$C_{10}$ thiol-alkyl, or substituted or unsubstituted 2 to 10 membered thiol-heteroalkyl;

$R^{15}$ is —$SR^{15A}$, —$OR^{15A}$, substituted or unsubstituted $C_1$-$C_{10}$ thiol-alkyl, or substituted or unsubstituted 2 to 10 membered thiol-heteroalkyl;

$R^{16}$ is hydrogen, —$SR^{16A}$, —$OR^{16A}$, substituted or unsubstituted $C_1$-$C_{10}$ thiol-alkyl, or substituted or unsubstituted 2 to 10 membered thiol-heteroalkyl;

$R^{17}$ is hydrogen, —$SR^{17A}$, —$OR^{17A}$, substituted or unsubstituted $C_1$-$C_{10}$ thiol-alkyl, or substituted or unsubstituted 2 to 10 membered thiol-heteroalkyl;

$R^{18}$ is —$SR^{18A}$, —$OR^{18A}$, substituted or unsubstituted $C_1$-$C_{10}$ thiol-alkyl, or substituted or unsubstituted 2 to 10 membered thiol-heteroalkyl;

$R^{19}$ is hydrogen, —$SR^{19A}$, —$OR^{19A}$, substituted or unsubstituted $C_1$-$C_{10}$ thiol-alkyl, or substituted or unsubstituted 2 to 10 membered thiol-heteroalkyl; and $R^{20}$ is —$SR^{20A}$, —$OR^{20A}$, substituted or unsubstituted $C_1$-$C_{10}$ thiol-alkyl, or substituted or unsubstituted 2 to 10 membered thiol-heteroalkyl.

Embodiment 47. The method of one of embodiments 43 to 45, wherein $R^{13}$ is hydrogen, —$SR^{13A}$, or —$OR^{13A}$;

$R^{14}$ is —$SR^{14A}$ or —$OR^{14A}$;

$R^{15}$ is —$SR^{15A}$ or —$OR^{15A}$;

$R^{16}$ is hydrogen, —$SR^{16A}$, or —$OR^{16A}$;

$R^{18}$ is —$SR^{18A}$ or —$OR^{18A}$; and $R^{20}$ is —$SR^{20A}$ or —$OR^{20A}$.

Embodiment 48. The method of one of embodiments 43 to 45, wherein $R^{16}$ is hydrogen.

Embodiment 49. The method of embodiment 43, wherein the thiol saccharide compound has the formula:

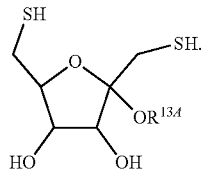

Embodiment 50. The method of embodiment 43, wherein the thiol saccharide compound has the formula:

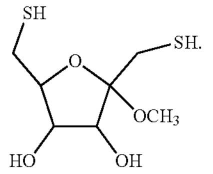

Embodiment 51. The method of one of embodiments 1 to 17, wherein the thiol saccharide compound has the formula:

(VI)

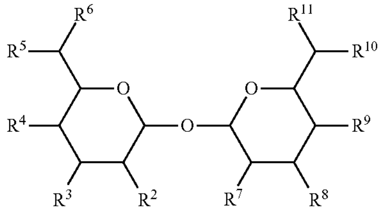

or (VII)

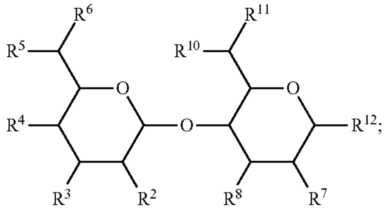

wherein $R^2$ is —$SR^{2A}$, —$OR^{2A}$, —$NR^{2B}R^{2C}$, —$NR^{2B}C(O)R^{2C}$c, —$NR^{2B}C(O)OR^{2C}$, substituted or unsubstituted alkyl, or substituted or unsubstituted heteroalkyl;

$R^3$ is —$SR^{3A}$, —$OR^{3A}$, —$NR^{3B}R^{3C}$, —$NR^{3B}C(O)R^{3C}$, —$NR^{3B}C(O)OR^{3C}$, substituted or unsubstituted alkyl, or substituted or unsubstituted heteroalkyl;

$R^4$ is —$SR^{4A}$, —$SC(O)R^{4A}$, —$OR^{4A}$, —$NR^{4B}R^{4C}$, —$NR^{4B}C(O)R^{4C}$, —$NR^{4B}C(O)OR^{4C}$, substituted or unsubstituted alkyl, or substituted or unsubstituted heteroalkyl;

$R^5$ is hydrogen, —$SR^{5A}$, —$SC(O)R^{5A}$, —$OR^{5A}$, —$NR^{5B}R^{5C}$, —$NR^{5B}C(O)R^{5C}$, —$NR^{5B}C(O)OR^{5C}$, or substituted or unsubstituted alkyl, or substituted or unsubstituted heteroalkyl;

$R^6$ is hydrogen, —$SR^{6A}$, —$OR^{6A}$, —$NR^{6B}R^{6C}$, —$NR^{6B}C(O)R^{6C}$, —$NR^{6B}C(O)OR^{6C}$, substituted or unsubstituted alkyl, or substituted or unsubstituted heteroalkyl;

$R^7$ is —$SR^{7A}$, —$OR^{7A}$, —$NR^{7B}R^{7C}$, —$NR^{7B}C(O)R^{7C}$, —$NR^{7B}C(O)OR^{7C}$, substituted or unsubstituted alkyl, or substituted or unsubstituted heteroalkyl;

$R^8$ is —$SR^{8A}$, —$OR^{8A}$, —$NR^{8B}R^{8C}$, —$NR^{8B}C(O)R^{8C}$, —$NR^{8B}C(O)OR^{8C}$, substituted or unsubstituted alkyl, or substituted or unsubstituted heteroalkyl;

$R^9$ is —$SR^{9A}$, —$SC(O)R^{9A}$, —$OR^{9A}$, —$NR^{9B}R^{9C}$, —$NR^{9B}C(O)R^{9C}$, —$NR^{9B}C(O)OR^{9C}$, substituted or unsubstituted alkyl, or substituted or unsubstituted heteroalkyl;

$R^{10}$ is hydrogen, —$SR^{10A}$, —$SC(O)R^{10A}$, —$OR^{10A}$, —$NR^{10B}R^{10C}$, —$NR^{10B}C(O)R^{10C}$, —$NR^{10B}C(O)OR^{10C}$, substituted or unsubstituted alkyl, or substituted or unsubstituted heteroalkyl;

$R^{11}$ is hydrogen, —$SR^{11A}$, —$OR^{11A}$, —$NR^{11B}R^{11C}$, —$NR^{11B}C(O)R^{11C}$, —$NR^{11B}C(O)OR^{11C}$, substituted or unsubstituted alkyl, or substituted or unsubstituted heteroalkyl;

$R^{12}$ is —$SR^{12A}$, —$OR^{12A}$, —$NR^{12B}R^{12C}$, —$NR^{12B}C(O)R^{12C}$, —$NR^{12B}C(O)OR^{12C}$, substituted or unsubstituted alkyl, or substituted or unsubstituted heteroalkyl; and $R^{2A}$, $R^{2B}$, $R^{2C}$, $R^{3A}$, $R^{3B}$, $R^{3C}$, $R^{4A}$, $R^{4B}$, $R^{4C}$, $R^{5A}$, $R^{5B}$, $R^{5C}$, $R^{6A}$, $R^{6B}$, $R^{6C}$, $R^{7A}$, $R^{7B}$, $R^{7C}$, $R^{8A}$, $R^{8B}$, $R^{8C}$, $R^{9A}$, $R^{9B}$, $R^{9C}$, $R^{10A}$, $R^{10B}$, $R^{10C}$, $R^{11A}$, $R^{11B}$, $R^{11C}$, $R^{12A}$, $R^{12B}$, and $R^{12C}$ are each independently hydrogen, substituted or unsubstituted alkyl, or substituted or unsubstituted heteroalkyl;

wherein the thiol saccharide compound comprises at least two thiol moieties.

Embodiment 52. The method of embodiment 51, wherein the thiol saccharide compound has the formula:

(VI)

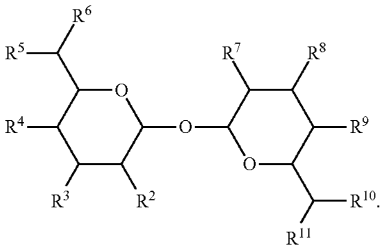

Embodiment 53. The method of embodiment 51, wherein the thiol saccharide compound has the formula:

(VII)

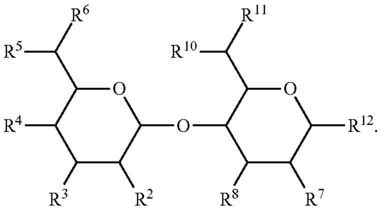

Embodiment 54. The method of embodiment 51, wherein the thiol saccharide compound has the formula:

(VI-1)

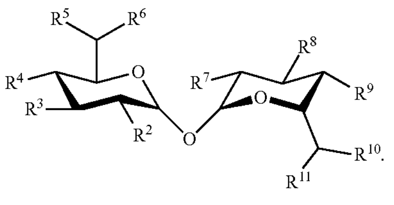

Embodiment 55. The method of embodiment 51, wherein the thiol saccharide compound has the formula:

(VII-1)

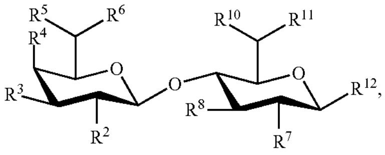

(VII-2)

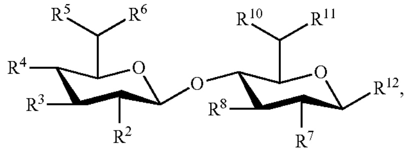

(VII-3)

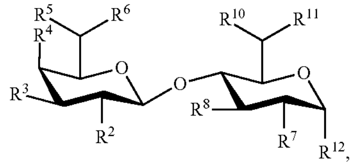

or (VII-4)

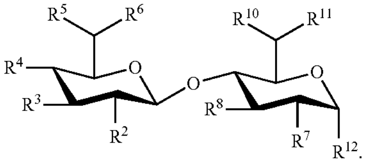

Embodiment 56. The method of embodiment 51, wherein $R^2$ is —$SR^{2A}$, —$OR^{2A}$, substituted or unsubstituted $C_1$-$C_{10}$ alkyl, or substituted or unsubstituted 2 to 10 membered heteroalkyl;

$R^3$ is —$SR^{3A}$, —$OR^{3A}$, substituted or unsubstituted $C_1$-$C_{10}$ alkyl, or substituted or unsubstituted 2 to 10 membered heteroalkyl;

$R^4$ is —$SR^{4A}$, —$OR^{4A}$, substituted or unsubstituted $C_1$-$C_{10}$ alkyl, or substituted or unsubstituted 2 to 10 membered heteroalkyl;

$R^5$ is hydrogen, —$SR^{5A}$, —$OR^{5A}$, substituted or unsubstituted $C_1$-$C_{10}$ alkyl, or substituted or unsubstituted 2 to 10 membered heteroalkyl;

$R^6$ is —$SR^{6A}$, —$OR^{6A}$, substituted or unsubstituted $C_1$-$C_{10}$ alkyl, or substituted or unsubstituted 2 to 10 membered heteroalkyl;

$R^7$ is —$SR^{7A}$, —$OR^{7A}$, substituted or unsubstituted $C_1$-$C_{10}$ alkyl, or substituted or unsubstituted 2 to 10 membered heteroalkyl;

$R^8$ is —$SR^{8A}$, —$OR^{8A}$, substituted or unsubstituted $C_1$-$C_{10}$ alkyl, or substituted or unsubstituted 2 to 10 membered heteroalkyl;

$R^9$ is —$SR^{9A}$, —$OR^{9A}$, substituted or unsubstituted $C_1$-$C_{10}$ alkyl, or substituted or unsubstituted 2 to 10 membered heteroalkyl;

$R^{10}$ is hydrogen, —$SR^{10A}$, —$OR^{10A}$, substituted or unsubstituted $C_1$-$C_{10}$ alkyl, or substituted or unsubstituted 2 to 10 membered heteroalkyl;

$R^{11}$ is —$SR^{11A}$, —$OR^{11A}$, substituted or unsubstituted $C_1$-$C_{10}$ alkyl, or substituted or unsubstituted 2 to 10 membered heteroalkyl; and $R^{12}$ is —$SR^{12A}$, —$OR^{12A}$, substituted or unsubstituted $C_1$-$C_{10}$ alkyl, or substituted or unsubstituted 2 to 10 membered heteroalkyl.

Embodiment 57. The method of embodiment 51, wherein $R^2$ is —$SR^{2A}$, —$OR^{2A}$, substituted or unsubstituted $C_1$-$C_{10}$ thiol-alkyl, or substituted or unsubstituted 2 to 10 membered thiol-heteroalkyl;

$R^3$ is —$SR^{3A}$, —$OR^{3A}$, substituted or unsubstituted $C_1$-$C_{10}$ thiol-alkyl, or substituted or unsubstituted 2 to 10 membered thiol-heteroalkyl;

R is —$SR^{4A}$, —$OR^{4A}$, substituted or unsubstituted $C_1$-$C_{10}$ thiol-alkyl, or substituted or unsubstituted 2 to 10 membered thiol-heteroalkyl;

$R^5$ is hydrogen, —$SR^{5A}$, —$OR^{5A}$, substituted or unsubstituted $C_1$-$C_{10}$ thiol-alkyl, or substituted or unsubstituted 2 to 10 membered thiol-heteroalkyl;

$R^6$ is —$SR^{6A}$, —$OR^{6A}$, substituted or unsubstituted $C_1$-$C_{10}$ thiol-alkyl, or substituted or unsubstituted 2 to 10 membered thiol-heteroalkyl;

$R^7$ is —$SR^{7A}$, —$OR^{7A}$, substituted or unsubstituted $C_1$-$C_{10}$ thiol-alkyl, or substituted or unsubstituted 2 to 10 membered thiol-heteroalkyl;

$R^8$ is —$SR^{8A}$, —$OR^{8A}$, substituted or unsubstituted $C_1$-$C_{10}$ thiol-alkyl, or substituted or unsubstituted 2 to 10 membered thiol-heteroalkyl;

$R^9$ is —$SR^{9A}$, —$OR^{9A}$, substituted or unsubstituted $C_1$-$C_{10}$ thiol-alkyl, or substituted or unsubstituted 2 to 10 membered thiol-heteroalkyl;

$R^{10}$ is hydrogen, —$SR^{10A}$, —$OR^{10A}$, substituted or unsubstituted $C_1$-$C_{10}$ thiol-alkyl, or substituted or unsubstituted 2 to 10 membered thiol-heteroalkyl;

$R^{11}$ is —$SR^{11A}$, —$OR^{11A}$, substituted or unsubstituted $C_1$-$C_{10}$ thiol-alkyl, or substituted or unsubstituted 2 to 10 membered thiol-heteroalkyl; and $R^{12}$ is —$SR^{12A}$, —$OR^{12A}$, substituted or unsubstituted $C_1$-$C_{10}$ thiol-alkyl, or substituted or unsubstituted 2 to 10 membered thiol-heteroalkyl.

Embodiment 58. The method of embodiment 51, wherein $R^2$ is —$SR^{2A}$ or —$OR^{2A}$;

$R^3$ is —$SR^{3A}$ or —$OR^{3A}$;

R is —$SR^{4A}$ or —$OR^{4A}$;

$R^6$ is —$SR^{6A}$ or —$OR^{6A}$;

$R^7$ is —$SR^{7A}$ or —$OR^{7A}$;

$R^8$ is —$SR^{8A}$ or —$OR^{8A}$;

$R^9$ is —$SR^{9A}$ or —$OR^{9A}$; and $R^{11}$ is —$SR^{11A}$ or —$OR^{11A}$.

Embodiment 59. The method of embodiment 51, wherein $R^2$ is —SH or —OH;

$R^3$ is —SH or —OH;

$R^4$ is —SH or —OH;

$R^6$ is —SH or —OH;

$R^7$ is —SH or —OH;

$R^8$ is —SH or —OH;

$R^9$ is —SH or —OH; and $R^{11}$ is —SH or —OH.

Embodiment 60. The method of one of embodiments 51 to 59, wherein $R^5$ is hydrogen.

Embodiment 61. The method of one of embodiments 51 to 60, wherein $R^{10}$ is hydrogen.

Embodiment 62. The method of one of embodiments 51 to 61, wherein $R^{12}$ is —$OR^{12A}$.

Embodiment 63. The method of one of embodiments 51 to 62, wherein $R^{12A}$ is a substituted or unsubstituted $C_1$-$C_{10}$ alkyl.

Embodiment 64. The method of one of embodiments 51 to 62, wherein $R^{12A}$ is an unsubstituted $C_1$-$C_5$ alkyl.

Embodiment 65. The method of one of embodiments 51 to 62, wherein $R^{12A}$ is a substituted or unsubstituted 2 to 10 membered heteroalkyl.

Embodiment 66. The method of one of embodiments 51 to 62, wherein $R^{12A}$ is an unsubstituted 2 to 6 membered heteroalkyl.

Embodiment 67. The method of one of embodiments 51 to 61, wherein $R^{12}$ is unsubstituted methoxy, unsubstituted ethoxy, unsubstituted propoxy, or unsubstituted butoxy.

Embodiment 68. The method of one of embodiments 51 to 61, wherein $R^{12}$ is —SH.

Embodiment 69. The method of embodiment 51, wherein the thiol saccharide compound has the formula:

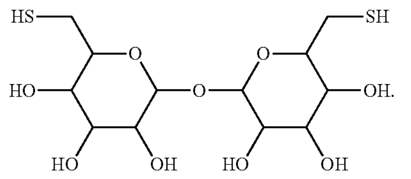 [SMILES: OC1C(CS)OC(OC2OC(CS)C(O)C(O)C2O)C(O)C1O]

Embodiment 70. The method of embodiment 51, wherein the thiol saccharide compound has the formula:

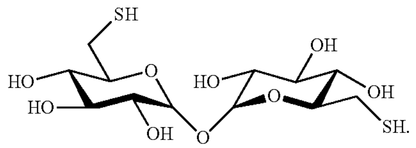

Embodiment 71. The method of embodiment 51, wherein the thiol saccharide compound has the formula:

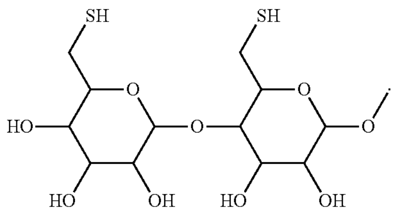

Embodiment 72. The method of embodiment 51, wherein the thiol saccharide compound has the formula:

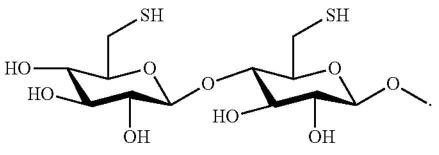

Embodiment 73. The method of embodiment 51, wherein the thiol saccharide compound has the formula:

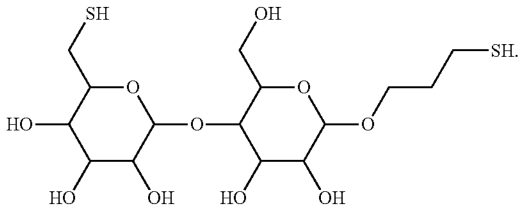 [SMILES: OCC1OC(OCCCS)C(O)C(O)C1OC1OC(CS)C(O)C(O)C1O]

Embodiment 74. The method of embodiment 51, wherein the thiol saccharide compound has the formula:

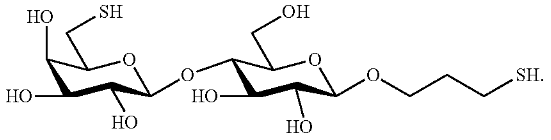

Embodiment 75. The method of one of embodiments 1 to 17, wherein the thiol saccharide compound has the formula:

(VIII)

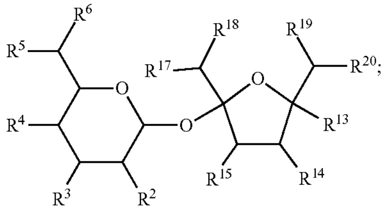

wherein $R^2$ is —$SR^{2A}$, —$OR^{2A}$, —$NR^{2B}R^{2C}$, —$NR^{2B}C(O)R^{2C}$, —$NR^{2B}C(O)OR^{2C}$, substituted or unsubstituted alkyl, or substituted or unsubstituted heteroalkyl;

$R^3$ is —$SR^{3A}$, —$OR^{3A}$, —$NR^{3B}R^{3C}$, —$NR^{3B}C(O)R^{3C}$, —$NR^{3B}C(O)OR^{3C}$, substituted or unsubstituted alkyl, or substituted or unsubstituted heteroalkyl;

$R^4$ is —$SR^{A}$, —$SC(O)R^{4A}$, —$OR^{4A}$, —$NR^{4B}R^{5C}$, —$NR^{4B}C(O)R^{4C}$, —$NR^{4B}C(O)OR^{4C}$, substituted or unsubstituted alkyl, or substituted or unsubstituted heteroalkyl;

$R^5$ is hydrogen, —$SR^{5A}$, —$SC(O)R^{5A}$, —$OR^{5A}$, —$NR^{5B}R^{5C}$, —$NR^{5B}C(O)R^{5C}$, —$NR^{5B}C(O)OR^{5C}$, or substituted or unsubstituted alkyl, or substituted or unsubstituted heteroalkyl;

$R^6$ is hydrogen, —$SR^{6A}$, —$OR^{6A}$, —$NR^{6B}R^{6C}$, —$NR^{6B}C(O)R^{6C}$, —$NR^{6B}$ $C(O)OR^{6C}$, substituted or unsubstituted alkyl, or substituted or unsubstituted heteroalkyl;

$R^{13}$ is hydrogen, —$SR^{13A}$, —$OR^{13A}$, —$NR^{13B}R^{13C}$, —$NR^{13B}C(O)R^{13C}$, —$NR^{13B}C(O)OR^{13C}$, substituted or unsubstituted alkyl, or substituted or unsubstituted heteroalkyl;

$R^{14}$ is —$SR^{14A}$, —$OR^{14A}$, —$NR^{14B}R^{14C}$, —$NR^{14B}C(O)R^{14C}$, —$NR^{14B}C(O)OR^{14C}$, substituted or unsubstituted alkyl, or substituted or unsubstituted heteroalkyl;

$R^{15}$ is —$SR^{15A}$, —$OR^{15A}$, —$NR^{15B}R^{15C}$, —$NR^{15B}C(O)R^{15C}$, —$NR^{15B}C(O)OR^{15C}$, substituted or unsubstituted alkyl, or substituted or unsubstituted heteroalkyl;

$R^{17}$ is hydrogen, —$SR^{17A}$, —$OR^{17A}$, —$NR^{17B}R^{15C}$, —$NR^{17B}C(O)R^{17C}$, —$NR^{17B}C(O)OR^{17C}$, or substituted or unsubstituted alkyl, or substituted or unsubstituted heteroalkyl;

$R^{18}$ is —$SR^{18A}$, —$OR^{18A}$, —$NR^{18B}R^{18C}$, —$NR^{18B}C(O)R^{18C}$, —$NR^{18B}C(O)OR^{18C}$, substituted or unsubstituted alkyl, or substituted or unsubstituted heteroalkyl;

$R^{19}$ is hydrogen, —$SR^{19A}$, —$OR^{19A}$, —$NR^{19B}R^{19C}$, —$NR^{19B}C(O)R^{19C}$, —$NR^{19B}C(O)OR^{19C}$c, substituted or unsubstituted alkyl, or substituted or unsubstituted heteroalkyl;

$R^{20}$ is —$SR^{20A}$, —$OR^{20A}$, —$NR^{20B}R^{20C}$, —$NR^{20B}C(O)R^{20C}$, —$NR^{20B}C(O)OR^{20C}$, or substituted or unsubstituted alkyl, or substituted or unsubstituted heteroalkyl; and $R^{2A}$, $R^{2B}$, $R^{2C}$, $R^{3A}$, $R^{3B}$, $R^{3C}$, $R^{4A}$, $R^{4B}$, $R^{4C}$, $R^{5A}$, $R^{5B}$, $R^{5C}$, $R^{6A}$, $R^{6B}$, $R^{6C}$, $R^{13A}$, $R^{13B}$, $R^{13C}$, $R^{14A}$, $R^{14B}$, $R^{14C}$, $R^{15A}$, $R^{15B}$, $R^{15C}$, $R^{17A}$, $R^{17B}$, $R^{17C}$, $R^{18A}$, $R^{18B}$, $R^{18C}$, $R^{19A}$, $R^{19B}$, $R^{19C}$, $R^{20A}$, $R^{20B}$, and $R^{20C}$ are each independently hydrogen, substituted or unsubstituted alkyl, or substituted or unsubstituted heteroalkyl;

wherein the thiol saccharide compound comprises at least two thiol moieties.

Embodiment 76. The method of embodiment 75, wherein $R^2$ is —$SR^{2A}$, —$OR^{2A}$, substituted or unsubstituted $C_1$-$C_{10}$ thiol-alkyl, or substituted or unsubstituted 2 to 10 membered thiol-heteroalkyl;

$R^3$ is —$SR^{3A}$, —$OR^{3A}$, substituted or unsubstituted $C_1$-$C_{10}$ thiol-alkyl, or substituted or unsubstituted 2 to 10 membered thiol-heteroalkyl;

$R^4$ is —$SR^{4A}$, —$OR^{4A}$, substituted or unsubstituted $C_1$-$C_{10}$ thiol-alkyl, or substituted or unsubstituted 2 to 10 membered thiol-heteroalkyl;

$R^5$ is hydrogen, —$SR^{5A}$, —$OR^{5A}$, substituted or unsubstituted $C_1$-$C_{10}$ thiol-alkyl, or substituted or unsubstituted 2 to 10 membered thiol-heteroalkyl;

$R^6$ is —$SR^{6A}$, —$OR^{6A}$, substituted or unsubstituted $C_1$-$C_{10}$ thiol-alkyl, or substituted or unsubstituted 2 to 10 membered thiol-heteroalkyl;

$R^{13}$ is hydrogen, —$SR^{13A}$, —$OR^{13A}$, substituted or unsubstituted $C_1$-$C_{10}$ thiol-alkyl, or substituted or unsubstituted 2 to 10 membered thiol-heteroalkyl;

$R^{14}$ is —$SR^{14A}$, —$OR^{14A}$, substituted or unsubstituted $C_1$-$C_{10}$ thiol-alkyl, or substituted or unsubstituted 2 to 10 membered thiol-heteroalkyl;

$R^{15}$ is —$SR^{15A}$, —$OR^{15A}$, substituted or unsubstituted $C_1$-$C_{10}$ thiol-alkyl, or substituted or unsubstituted 2 to 10 membered thiol-heteroalkyl;

$R^{17}$ is hydrogen, —$SR^{17A}$, —$OR^{17A}$, substituted or unsubstituted $C_1$-$C_{10}$ thiol-alkyl, or substituted or unsubstituted 2 to 10 membered thiol-heteroalkyl;

$R^{18}$ is —$SR^{18A}$, —$OR^{18A}$, substituted or unsubstituted $C_1$-$C_{10}$ thiol-alkyl, or substituted or unsubstituted 2 to 10 membered thiol-heteroalkyl;

$R^{19}$ is hydrogen, —$SR^{19A}$, —$OR^{19A}$, substituted or unsubstituted $C_1$-$C_{10}$ thiol-alkyl, or substituted or unsubstituted 2 to 10 membered thiol-heteroalkyl; and $R^{20}$ is —$SR^{20A}$, —$OR^{20A}$, substituted or unsubstituted $C_1$-$C_{10}$ thiol-alkyl, or substituted or unsubstituted 2 to 10 membered thiol-heteroalkyl.

Embodiment 77. The method of embodiment 75, wherein $R^2$ is —$SR^{2A}$ or —$OR^{2A}$;

$R^3$ is —$SR^{3A}$ or —$OR^{3A}$;

$R^4$ is —$SR^{4A}$ or —$OR^{4A}$;

$R^6$ is —$SR^{6A}$ or —$OR^{6A}$;

$R^{13}$ is hydrogen, —$SR^{13A}$ or —$OR^{13A}$;

$R^{14}$ is —$SR^{14A}$ or —$OR^{14A}$;

$R^{15}$ is —$SR^{15A}$ or —$OR^{15A}$;

$R^{18}$ is —$SR^{18A}$ or —$OR^{18A}$; and $R^{20}$ is —$SR^{20A}$ or —$OR^{20A}$.

Embodiment 78. The method of one of embodiments 1 to 17, wherein the thiol saccharide compound has the formula:

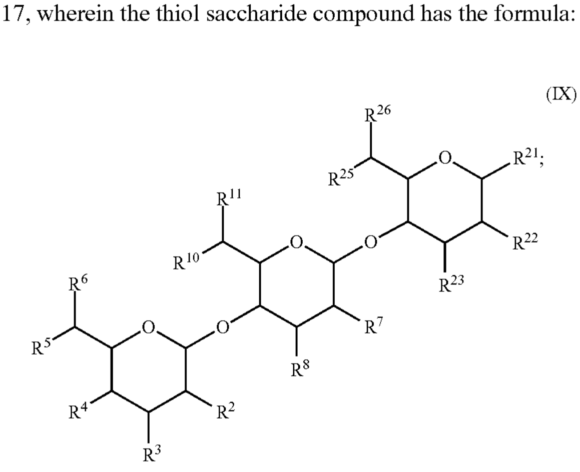

(IX)

wherein $R^2$ is —$SR^{2A}$, —$OR^{2A}$, —$NR^{2B}R^{2C}$, —$NR^{2B}C(O)R^{2C}$, —$NR^{2B}C(O)OR^{2C}$, substituted or unsubstituted alkyl, or substituted or unsubstituted heteroalkyl;

$R^3$ is —$SR^{3A}$, —$OR^{3A}$, —$NR^{3B}R^{3C}$, —$NR^{3B}C(O)R^{3C}$, —$NR^{3B}C(O)OR^{3C}$, substituted or unsubstituted alkyl, or substituted or unsubstituted heteroalkyl;

$R^4$ is —$SR^{4A}$, —$SC(O)R^{4A}$, —$OR^{4A}$, —$NR^{4B}R^{4C}$, —$NR^{4B}C(O)R^{4C}$, —$NR^{4B}C(O)OR^{4C}$, substituted or unsubstituted alkyl, or substituted or unsubstituted heteroalkyl;

$R^5$ is hydrogen, —$SR^{5A}$, —$SC(O)R^{5A}$, —$OR^{5A}$, —$NR^{5B}R^{5C}$, —$NR^{5B}C(O)R^{5C}$, —$NR^{5B}C(O)OR^{5C}$, or substituted or unsubstituted alkyl, or substituted or unsubstituted heteroalkyl;

$R^6$ is hydrogen, —$SR^{6A}$, —$OR^{6A}$, —$NR^{5B}R^{6C}$, —$NR^{6B}C(O)R^{6C}$, —$NR^{6B}C(O)OR^{6C}$, substituted or unsubstituted alkyl, or substituted or unsubstituted heteroalkyl;

$R^7$ is —$SR^{7A}$, —$OR^{7A}$, —$NR^{7B}R^{7C}$, —$NR^{7B}C(O)R^{7C}$, —$NR^{7B}C(O)OR^{7C}$, substituted or unsubstituted alkyl, or substituted or unsubstituted heteroalkyl;

$R^8$ is —$SR^{8A}$, —$OR^{8A}$, —$NR^{8B}R^{8C}$, —$NR^{8B}C(O)R^{8C}$, —$NR^{8B}C(O)OR^{8C}$, substituted or unsubstituted alkyl, or substituted or unsubstituted heteroalkyl;

$R^{10}$ is hydrogen, —$SR^{10A}$, —$SC(O)R^{10A}$, $OR^{10A}$, —$NR^{10B}R^{10A}$, —$NR^{10B}C(O)R^{10C}$, —$NR^{10B}C(O)OR^{10C}$, substituted or unsubstituted alkyl, or substituted or unsubstituted heteroalkyl;

$R^{11}$ is hydrogen, —$SR^{11A}$, —$OR^{11A}$, —$NR^{11B}R^{11C}$, —$NR^{11B}C(O)R^{11C}$, —$NR^{11B}C(O)OR^{11C}$, substituted or unsubstituted alkyl, or substituted or unsubstituted heteroalkyl;

$R^{21}$ is —$SR^{21A}$, —$OR^{21A}$, —$NR^{21B}R^{21C}$, —$NR^{21B}C(O)R^{21C}$, —$NR^{21B}C(O)OR^{21C}$c, substituted or unsubstituted alkyl, or substituted or unsubstituted heteroalkyl;

$R^{22}$ is —$SR^{22A}$, —$OR^{22A}$, —$NR^{22B}R^{22C}$, —$NR^{22B}C(O)R^{22C}$, —$NR^{22B}C(O)OR^{22C}$, substituted or unsubstituted alkyl, or substituted or unsubstituted heteroalkyl;

$R^{23}$ is —$SR^{23A}$, —$OR^{23A}$, —$NR^{23B}R^{23C}$, —$NR^{23B}C(O)R^{23C}$, —$NR^{23B}C(O)OR^{23C}$, substituted or unsubstituted alkyl, or substituted or unsubstituted heteroalkyl;

$R^{25}$ is hydrogen, —$SR^{25A}$, —$SC(O)R^{25A}$, —$OR^{26A}$, —$NR^{25B}R^{25C}$, —$NR^{25B}C(O)R^{25C}$, —$NR^{25B}C(O)OR^{25C}$, or substituted or unsubstituted alkyl, or substituted or unsubstituted heteroalkyl;

$R^{26}$ is hydrogen, —$SR^{26A}$, —$OR^{26A}$, —$NR^{26B}R^{26C}$, —$NR^{26B}C(O)R^{26C}$, —$NR^{26B}C(O)OR^{26C}$, or substituted or unsubstituted alkyl, or substituted or unsubstituted heteroalkyl; and $R^{2A}$, $R^{2B}$, $R^{2C}$, $R^{3A}$, $R^{3B}$, $R^{3C}$, $R^{4A}$, $R^{4B}$, $R^{4C}$, $R^{5A}$, $R^{5B}$, $R^{5C}$, $R^{6A}$, $R^{6B}$, $R^{6C}$, $R^{7A}$, $R^{7B}$, $R^{7C}$, $R^{8A}$, $R^{8B}$, $R^{8C}$, $R^{10A}$, $R^{10B}$, $R^{10C}$, $R^{11A}$, $R^{11B}$, $R^{11C}$, $R^{21A}$, $R^{21B}$, $R^{21C}$, $R^{22A}$, $R^{22B}$, $R^{22C}$, $R^{23A}$, $R^{23B}$, $R^{23C}$, $R^{25A}$, $R^{25B}$, $R^{25C}$, $R^{26A}$, $R^{26B}$, and $R^{26C}$ are each independently hydrogen, substituted or unsubstituted alkyl, or substituted or unsubstituted heteroalkyl.

Embodiment 79. The method of embodiment 78, wherein $R^2$ is —$SR^{2A}$, —$OR^{2A}$, substituted or unsubstituted $C_1$-$C_{10}$ thiol-alkyl, or substituted or unsubstituted 2 to 10 membered thiol-heteroalkyl;

$R^3$ is —$SR^{3A}$, —$OR^{3A}$, substituted or unsubstituted $C_1$-$C_{10}$ thiol-alkyl, or substituted or unsubstituted 2 to 10 membered thiol-heteroalkyl;

$R^4$ is —$SR^{4A}$, —$OR^{4A}$, substituted or unsubstituted $C_1$-$C_{10}$ thiol-alkyl, or substituted or unsubstituted 2 to 10 membered thiol-heteroalkyl;

$R^5$ is hydrogen, —$SR^{5A}$, —$OR^{5A}$, substituted or unsubstituted $C_1$-$C_{10}$ thiol-alkyl, or substituted or unsubstituted 2 to 10 membered thiol-heteroalkyl;

$R^6$ is —$SR^{6A}$, —$OR^{6A}$, substituted or unsubstituted $C_1$-$C_{10}$ thiol-alkyl, or substituted or unsubstituted 2 to 10 membered thiol-heteroalkyl;

$R^7$ is —$SR^{7A}$, —$OR^{7A}$, substituted or unsubstituted $C_1$-$C_{10}$ thiol-alkyl, or substituted or unsubstituted 2 to 10 membered thiol-heteroalkyl;

$R^8$ is —$SR^{8A}$, —$OR^{8A}$, substituted or unsubstituted $C_1$-$C_{10}$ thiol-alkyl, or substituted or unsubstituted 2 to 10 membered thiol-heteroalkyl;

$R^{10}$ is hydrogen, —$SR^{10A}$, —$OR^{10A}$, substituted or unsubstituted $C_1$-$C_{10}$ thiol-alkyl, or substituted or unsubstituted 2 to 10 membered thiol-heteroalkyl;

$R^{11}$ is —$SR^{11A}$, —$OR^{11A}$, substituted or unsubstituted $C_1$-$C_{10}$ thiol-alkyl, or substituted or unsubstituted 2 to 10 membered thiol-heteroalkyl;

$R^{21}$ is —$SR^{21A}$, —$OR^{21A}$, substituted or unsubstituted $C_1$-$C_{10}$ thiol-alkyl, or substituted or unsubstituted 2 to 10 membered thiol-heteroalkyl;

$R^{22}$ is —$SR^{22A}$, —$OR^{22A}$, substituted or unsubstituted $C_1$-$C_{10}$ thiol-alkyl, or substituted or unsubstituted 2 to 10 membered thiol-heteroalkyl;

$R^{23}$ is —$SR^{23A}$, —$OR^{23A}$, substituted or unsubstituted $C_1$-$C_{10}$ thiol-alkyl, or substituted or unsubstituted 2 to 10 membered thiol-heteroalkyl;

$R^{25}$ is hydrogen, —$SR^{25A}$, —$OR^{25A}$, substituted or unsubstituted $C_1$-$C_{10}$ thiol-alkyl, or substituted or unsubstituted 2 to 10 membered thiol-heteroalkyl; and $R^{26}$ is —$SR^{26A}$, —$OR^{26A}$, substituted or unsubstituted $C_1$-$C_{10}$ thiol-alkyl, or substituted or unsubstituted 2 to 10 membered thiol-heteroalkyl.

Embodiment 80. The method of embodiment 78, wherein $R^2$ is —$SR^{2A}$ or —$OR^{2A}$;

$R^3$ is —$SR^{3A}$ or —$OR^{3A}$;

$R^4$ is —$SR^{4A}$ or —$OR^{4A}$;

$R^6$ is —$SR^{6A}$ or —$OR^{6A}$;

$R^7$ is —$SR^{7A}$ or —$OR^{7A}$;

$R^8$ is —$SR^{8A}$ or —$OR^{8A}$;

$R^{11}$ is —$SR^{11A}$ or —$OR^{11A}$;

$R^{21}$ is —$SR^{21A}$ or —$OR^{21A}$;

$R^{22}$ is —$SR^{22A}$ or —$OR^{22A}$;

$R^{23}$ is —$SR^{23A}$ or —$OR^{23A}$; and $R^{26}$ is —$SR^{26A}$ or —$OR^{26A}$.

Embodiment 81. The method of one of embodiments 1 to 17, wherein the thiol saccharide compound comprises two thiol moieties.

Embodiment 82. A thiol saccharide compound for use in a method of any one of embodiments 1 to 81.

Embodiment 83. A pharmaceutical composition comprising a pharmaceutically acceptable excipient and a thiol saccharide compound, or a pharmaceutically acceptable salt thereof.

Embodiment 84. The pharmaceutical composition of embodiment 83 for use in a method of any one of embodiments 1 to 81.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

It is understood that the examples and embodiments described herein are for illustrative purposes only and that various modifications or changes in light thereof will be suggested to persons skilled in the art and are to be included within the spirit and purview of this application and scope of the appended claims.

Example 1: Inhibiting SARS-CoV-2 Entry by Targeting the Spike Protein

Betacoronaviruses are enveloped positive-sense, single-stranded RNA viruses that infect humans and generally cause illnesses that induce fever and respiratory symptoms. For example, the SARS-CoV-1 coronavirus strain causes Severe Acute Respiratory Syndrome (SARS), and the SARS-CoV-2 coronavirus strain causes Coronavirus Disease 2019 (COVID-19), a respiratory illness with symptoms ranging from fever and cough to potentially fatal complications including acute respiratory distress and kidney failure.

The SARS-CoV-2 spike (S) protein (SARS-2-S) is an envelope glycoprotein trimer that binds angiotensin converting enzyme 2 (ACE2) as an entry receptor. Recently it has been shown that IFNα drives ACE2 expression in primary human nasal epithelial cells. In this manner, SARS-CoV-2 exploits interferon-driven upregulation of ACE2, normally a tissue-protective mediator during lung injury, to enhance infection. A strategy to preventing such infection is to block binding of SARS-CoV-2 to ACE2.

The S1 domain of SARS-2-S includes a receptor binding domain (RBD) that mediates the initial high affinity interaction of SARS-CoV-2 with the ACE2 receptor. In the homologous SARS-CoV-1 Spike protein (SARS-1-S), the S1 RBD was previously shown to block S protein-mediated infection more efficiently than the full-length S1 domain. Further, abolishing disulfide bonds formed by cysteine residues in the SARS-1-S RBD was shown to disrupt viral binding to ACE2 (Wong, S. K. et al. A 193-Amino Acid Fragment of the SARS Coronavirus S Protein Efficiently Binds Angiotensin-converting Enzyme 2. *J Biol. Chem.* 2004, 279:3197). Thus, conserved cysteine residues in the SARS-2-S RBD may similarly be essential for SARS-2-S associating with ACE2. Without wishing to be bound by any theory, cleavage of disulfide bonds in the SARS-2-S protein could alter the native conformation of the RBD and disable SARS-2-S binding to ACE2.

Figure 1B:
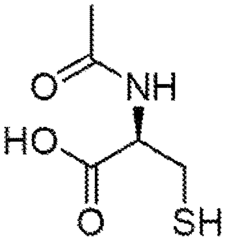
Figure 1B:
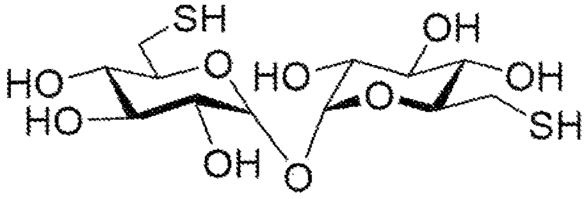

6,6'-Dithiotrehalose (also referred to herein as "MUC", "MUC-031", or "TS21"; structure shown in FIG. 1B), is a dithiol substituted trehalose that potently cleaves disulfides and also has multiple other attractive drug attributes, including solubility, stability, and favorable aerosol characteristics. Another compound, N-acetyl-L-cysteine (NAC; structure shown in FIG. 1B), has previously been shown to reduce disulfide bonds in mucoproteins. Thus, MUC and NAC were screened for inhibiting SARS-2-S binding to ACE2 using a plate-based binding assay. Recombinantly expressed RBD of SARS-2-S was first immobilized to a surface. Immobilized protein was incubated in either MUC or NAC; drug was then washed off. Biotinylated ACE2 was added and allowed to bind to surface-immobilized SARS-2-S. Detection of ACE2 binding was achieved by addition of streptavidin-modified horseradish peroxidase (HRP), followed by a colorimetric substrate for the HRP enzyme. As illustrated in FIG. 1A, both compounds MUC and NAC inhibited binding of ACE2 to SARS-2-S, though MUC showed stronger potency in inhibiting ACE2 binding compared to NAC. Notably, the inhibition of binding to ACE2 occurs even when MUC is washed out of the reaction mixture, demonstrating that binding inhibition persists following drug contact.

Figure 2:
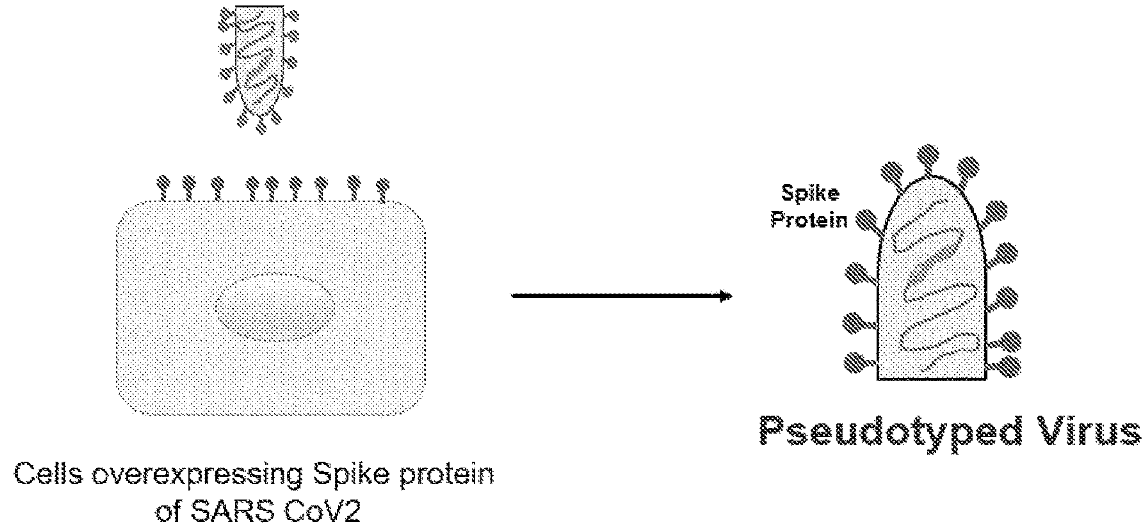
FIG. 2. Schematic depicting generation of a vesicular stomatitus virus (VSV) pseudotype. The VSV pseudotype (VSV-S) includes the gene encoding luciferase and bears the SARS-CoV-2 spike protein (SARS-2-S) on its viral envelope.

MUC and NAC were then tested for their ability to inhibit entry of a SARS-CoV-2 pseudovirus using a cell culture-based assay. The vesicular stomatitis virus (VSV) is promiscuous as to the membrane protein that may be incorporated into its envelope, and thus, VSV may readily form pseudotypes with heterologous membrane proteins. (Whitt, M. A. Generation of VSV Pseudotypes Using Recombinant AG-VSV for Studies on Virus Entry, Identification of Entry Inhibitors, and Immune Responses to Vaccines. *J Virol Methods.* 2010, 169(2):365). A VSV in which the glycoprotein (G) gene was deleted (VSV-AG) was used to produce the VSV pseudotype. The VSV glycoprotein gene was replaced with the gene encoding luciferase (VSV-AG-Luciferase), enabling detection. As illustrated in FIG. 2, VSV-AG-Luciferase budding from a host cell expressing SARS-2-S resulted in the acquisition of the envelope including the lipid bilayer derived from the host cell plasma membrane, generating a VSV pseudotype bearing the SARS-2-S protein (VSV-S).

Figure 3:
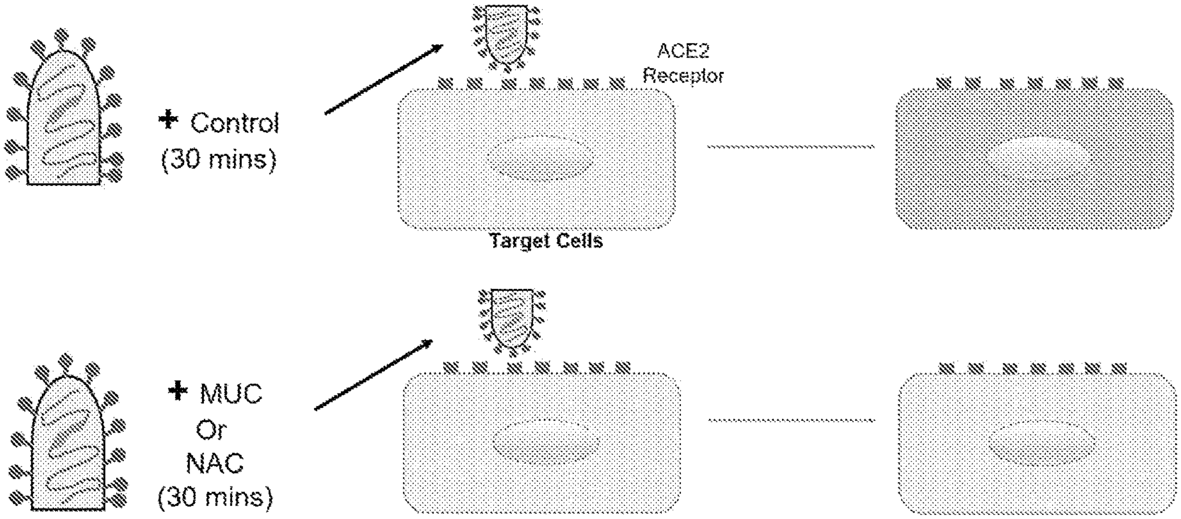
FIG. 3. Schematic illustrating VSV-S entering target cells in the absence of an inhibitor compound (top panel) and inhibition of VSV-S cellular entry when incubated with MUC or NAC (bottom panel).
Figure 4:
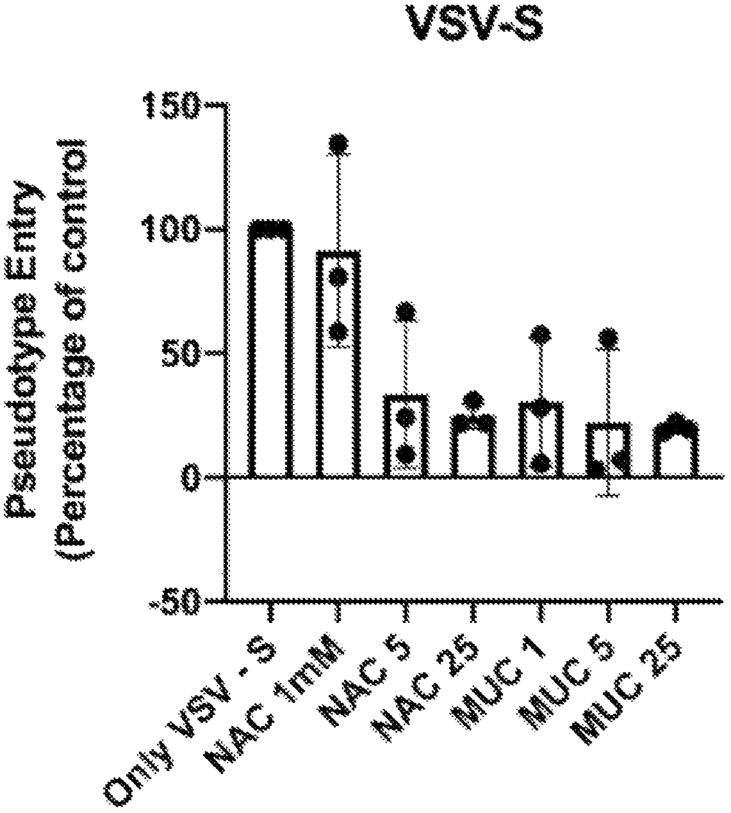
FIG. 4. Bar graph showing VSV-S is inhibited from entering ACE2 expressing cells when treated with MUC or NAC.

Calu-3 cells were used to determine if MUC inhibits SARS-CoV-2 infection of lung epithelial cells in a cell culture. The cells were incubated with VSV-S for 30 minutes in the presence of either 1 mM MUC, 5 mM MUC, 25 mM MUC, 1 mM NAC, 5 mM NAC, 25 mM NAC, or no compound (control). As shown in FIG. 3, VSV-S readily entered Calu-3 cells in the control group, while both MUC and NAC inhibited VSV-S cellular entry. Experiments were also conducted with a 2-hour incubation time. All three concentrations of MUC resulted in potent inhibition of VSV-S entry, while only 5 and 25 mM of NAC resulted in significant cell entry inhibition, as illustrated in FIG. 4. These results demonstrate MUC is more effective than NAC for inhibiting viral entry.

In additional cell culture experiments using the VSV-S pseudovirus, epithelial cells are pre-incubated with interferons to upregulate ACE2. Additional cell types to test include airway epithelial cells and type 2 alveolar cells.

Example 2: Treatment of COVID-19 with MUC Using Animal Models

An animal model of COVID-19 is used to determine efficacy of aerosolized MUC in treating COVID-19. It has been shown that Syrian hamsters are susceptible to lung infection with SARS-CoV-2, and infected animals develop high lung viral load, marked cytokine activation and diffuse pneumonia within the first week of virus challenge. Challenged index hamsters consistently infect naïve contact hamsters housed within the same cage, resulting in similar pathology.

Syrian hamsters are administered aerosolized MUC for up to 7 days following infection with SARS-CoV-2. Outcomes will include viral load (copy number/mL) and infectious titer (plaque/TCID50) for characterization of virus, and clinical signs (weight and respiratory rate) and lung histopathology for characterization of COVID-19 outcomes.

Example 3: Treatment of COVID-19

A subject having COVID-19 and presenting either mild, moderate, or severe disease conditions is treated with a thiosaccharide compound of the present disclosure as shown in Table 1. Mild severity may be characterized by the subject's confirmed COVID-19 diagnosis, and symptoms that do not require hospitalization. Moderate severity may be characterized by hospitalization of the subject, medical care required for the subject's COVID-19 symptoms, or when the subject has an $SpO_2$ of at least 94%. Severe conditions may be characterized by hospitalization of the subject, or when the subject either has an $SpO_2$ of less than 94% or requires supplemental oxygen, either with or without mechanical ventilation.

TABLE 1

Use of different formulation types of thiosaccharide compounds for treatment of COVID-19.

| Formulation type | Disease Severity | Setting | Rationale |
|---|---|---|---|
| Oral | Moderate and Severe | Out-patient and in-patient | Systemic delivery to target viral pneumonia; Simplest route of administration (for non-sedated patients); Avoids aerosol spread that is a concern to healthcare workers. (1) |
| I.V. | Moderate and Severe | In-patient | Systemic delivery to target viral pneumonia; Avoids aerosol spread that is a concern to healthcare workers. (1) |
| Inhaled-liquid aerosol | Mild | Out-patient | Deliverable by hand held nebulizer and the aerosolized drug will have anti-viral effects in the oropharynx and the lungs. Mucolytic mechanism will assist with mucus clearance. |
| | Moderate/ Severe | In-patient | Delivery by hand held nebulizer (non-intubated patients) or by an in-line nebulizer (e.g., Aerogen solo) that is coupled to mechanical ventilator circuits (intubated patients). High local doses in the lung provide both anti-viral and mucolytic effect; May be limited to negative pressure isolation rooms to avoid aerosol spread to healthcare workers. (1) |
| Inhaled-dry power | Mild | Out-patient | Targets virus in the oropharynx and lungs. Mucolytic mechanism will assist with mucus clearance. |
| | Moderate/ Severe | In-patient | Limited to non-sedated patients; Limits aerosol spread to healthcare workers (as compared to inhaled liquid aerosol delivery by nebulizer). |
| Lozenge | Mild | Out-patient | Targets virus in the throat (2), preventing spread into the lungs. Most effective early from onset of symptoms or confirmed diagnosis. |
| Nasal spray | Mild | Out-patient | Targets virus in the nasopharynx (2), preventing spread into the lungs. Most effective early from onset of symptoms or confirmed diagnosis. |

References: 1. Tran et al., PLOS One (2012), doi.org/10.1371/journal.pone.0035797. 2. Wölfel et al, Nature 2020 DOI: 10.1038/941586-020-2196-x: Reference demonstrates high viral load and replication in upper respiratory tract and throat.

Example 4: Antiviral and Anti-Inflammatory Effects of Thiol Drugs in COVID19

Coronavirus disease 2019 (COVID-19) is caused by the severe acute respiratory syndrome coronavirus 2 (SARS-CoV-2). The SARS-CoV-2 spike protein is an envelope glycoprotein that binds angiotensin converting enzyme 2 (ACE2) as an entry receptor. Treatments that prevent viral entry are needed because entry inhibitors prevent cell infection and interrupt active infection. We considered the possibility that thiol-based drugs could cleave cystine bridges in the SARS-CoV-2 spike protein (SARS-2-S) and disrupt the native binding interface required for interaction with ACE2. We show that thiol drugs decrease binding of SARS-CoV-S to ACE2 to decrease the entry efficiency of SARS-CoV-2 and decrease viral titers in the lung. We also show that thiol drugs can limit SARS-CoV-2 lung inflammation without decreasing SARS-CoV-2 viral infection. Our findings reveal that thiol drugs can improve COVID-19-related lung disease through either antiviral or anti-inflammatory mechanisms and provide strong rationale for further testing the efficacy of these drugs in clinical trials.

The capacity of enveloped viruses such as SARS-CoV-2 to infect host cells often depends on a precise thiol/disulfide balance in their surface glycoprotein complexes. All identified SARS-CoV-2 variants have conserved cystines in their receptor binding domains (RBDs) of the spike protein, but it was unknown if these cystines were critical to maintaining a native binding interface to ACE2 and if disruption of these cystines by thiol-based drugs is a viable therapeutic strategy against the virus. Using a receptor binding assay, and pseudovirus and live virus cell infection assays, we showed that multiple thiol-based drugs, including cysteamine (approved) and a novel thiol-saccharide drug ("MUC-31", in preclinical development), decreased binding of SARS-CoV-2 spike protein to its receptor to decrease the entry efficiency of SARS-CoV-2 spike pseudotyped virus and inhibit live virus infection. Moreover, in SARS-CoV-2-infected hamsters, aerosol delivery of MUC-31 directly to the lung, at a dose which achieves millimolar local concentrations decreased SARS-CoV-2 virus copy number and lung inflammation, whereas intraperitoneal delivery of cysteamine, at a dose which achieves micromolar concentrations or less in the lung did not decrease virus copy number but did decrease lung inflammation. Our findings show that thiol-based drugs have both antiviral and anti-inflammatory effects in COVID-19-related lung disease and that direct anti-viral effects can be achieved by aerosol delivery to the lung.

SARS-CoV-2 causes COVID-19, a multidimensional disease characterized predominantly by pneumonia that can progress to respiratory failure and death[1,2]. The envelope glycoproteins of SARS-CoV-2 include a spike glycoprotein trimer (SARS-2-S) that binds a cell surface protease (angiotensin converting enzyme 2 [ACE2]) as an entry receptor[3]. The viral envelopes of so-called type I enveloped viruses, including coronaviruses, retroviruses, and filoviruses, exhibit similar structural and mechanistic strategies for viral entry[4]. Among these viruses, the capacity of their envelope glycoproteins to mediate fusion of virus to host cell membranes often depends on a precise thiol/disulfide balance in the viral surface glycoprotein complex[5-8]. Natural and specific thiol/disulfide rearrangements in this complex can trigger conformational changes that promote virus entry[9-11], but removal of disulfide bridges by chemical reduction or by replacement of cysteines by mutagenesis can also disrupt viral binding to prevent infection. For example, chemical reduction of the S1 domain of SARS-CoV decreases its binding to ACE2 and inhibits transduction of Vero E6 cells by SARS-CoV pseudovirions, and site-directed mutagenesis replacing cystine forming cysteines with alanines in the SARS-COV spike (hereafter SARS-1-S) RBD prevents binding of ACE2[6]. In addition, molecular dynamics simulations reveal that the binding affinity of SARS-2-S RBD for ACE2 is significantly impaired when all of the disulfide bonds of both ACE2 and SARS-2-S are reduced to thiol groups[12]. Multiple drugs have at least one functional thiol group and can reduce cystines to cysteines, but it is not known if thiol drugs can disrupt cystines in SARS-2-S to inhibit binding to ACE2 or virus entry into cells, and if they can do so at doses that are deliverable safely in vivo.

Figure 5A:
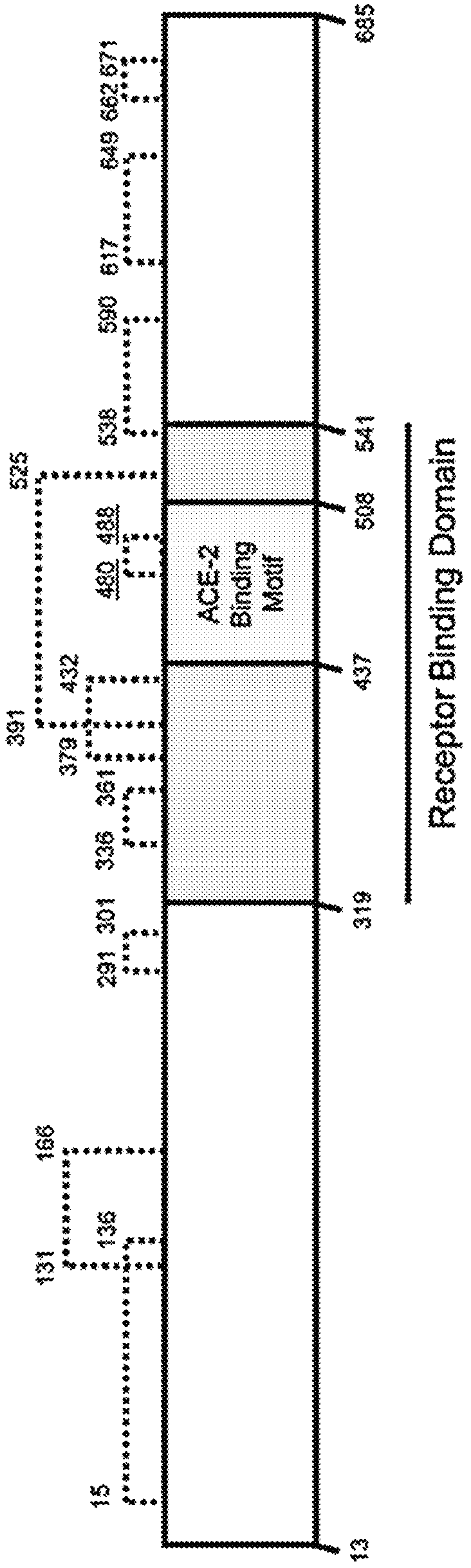
FIGS. 5A-5D. Cystine mapping and conservation of cystines in beta coronavirus RBD.
Figure 5B:
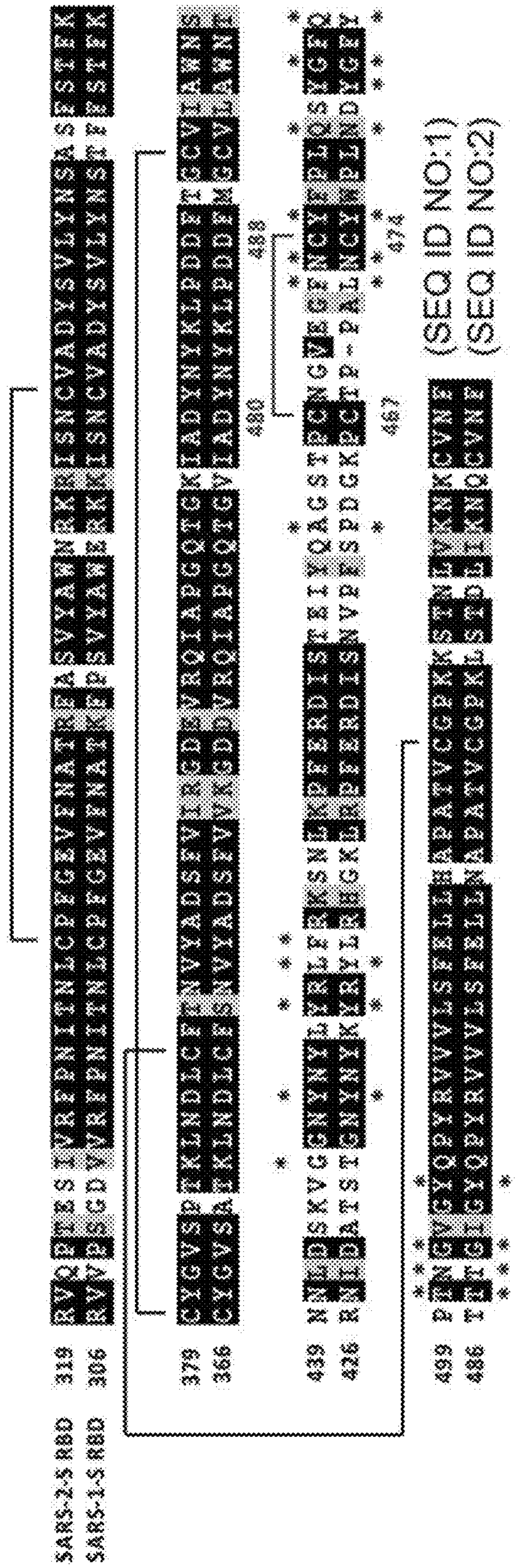
Figures 5C, 5D:
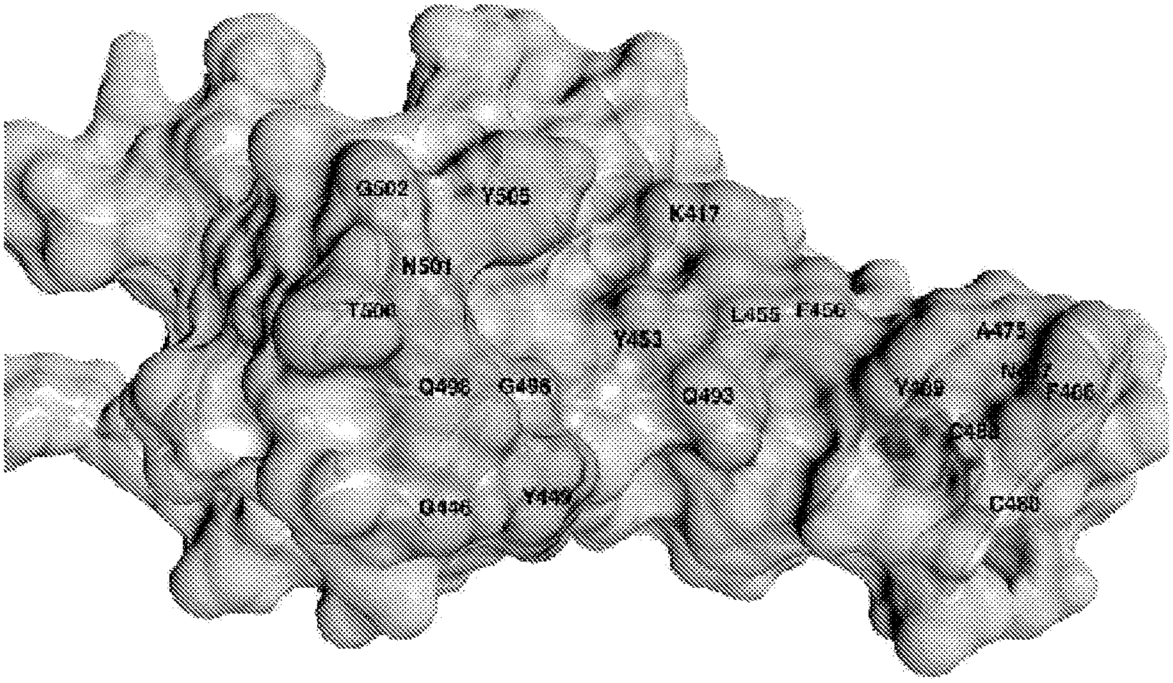

To address this question we used published data[17,18] to build a cystine bridge map of the S1 domain of SARS-2-S, and we compared the amino acid alignment of the receptor binding domains (RBDs) in SARS-2-S and SARS-1-S. We noted 10 cystine bridges in the SARS-2-S1 domain (FIG. 5A) and 4 conserved cystines between SARS-1-S and SARS-2-S RBD (FIG. 5B). The conserved Cys467-Cys474 in SARS-1-S and Cys480-Cys488 in SARS-2-S constrain the ACE2 binding domains, and previous studies with SARS-1-S RBD have shown that mutagenesis of either homologous cysteine leads to loss of ACE-2 binding[6]. To further explore if Cys480-Cys488 in SARS-2-S might be vulnerable to chemical cleavage, we used protein modeling software to render the SARS-2-S RBD based on PDB entry 6M0J (FIG. 5C). This rendering shows that Cys480-Cys488 is very near the RBD surface (FIG. 5C) and could be accessible to cleavage by thiol-based drugs. Apart from Cys480-Cys488 cystine, cleavage of the other six cystines in the RBD could also allosterically modify the binding interface in ways that decrease binding to ACE2. Studies in SARS-CoV have shown that cysteine residues flanking the S2 domain—including Cys822 and Cys833—mediate membrane fusion of SARS CoV (Madu et al., Virology, 2009 Oct. 25; 393(2):265-71). Amino acid alignment of the spike protein of SARS-CoV and SARS-CoV2 shows that these cysteine residues are conserved in the spike protein of SARS-CoV2 (Cys 840 and Cys 851), which raises the possibility that thiol-based drugs could inhibit membrane fusion in addition to inhibitory effects on receptor binding. Recognizing that multiple variants of SARS CoV2 show sequence variations, including in the RBD, we generated a consensus RBD sequence to highlight and annotate differences among the variants' amino acid sequences (FIG. 5D). As shown in FIG. 5D, the RBD of the UK variant (B1.1.7) has an N501Y mutation ($RBDN^{N501Y}$), the RBD of the Brazilian variant (P1) has an E484K mutation ($RBD^{E484K}$), the RBD of the California variant has an E484K mutation ($RBD^{L452R}$), and the RBD of the South African variant (B1.351) has K417N, E484K, and $N_{501}Y$ mutations ($RBD^{K417N, E484K, N501Y}$). All of these variants have the four cystine bridges present in the original SARS-CoV2 RBD, and all have the Cys480-Cys488 that is conserved between SARS-CoV and SARS-CoV2 (FIG. 5D).

Figure 6A:
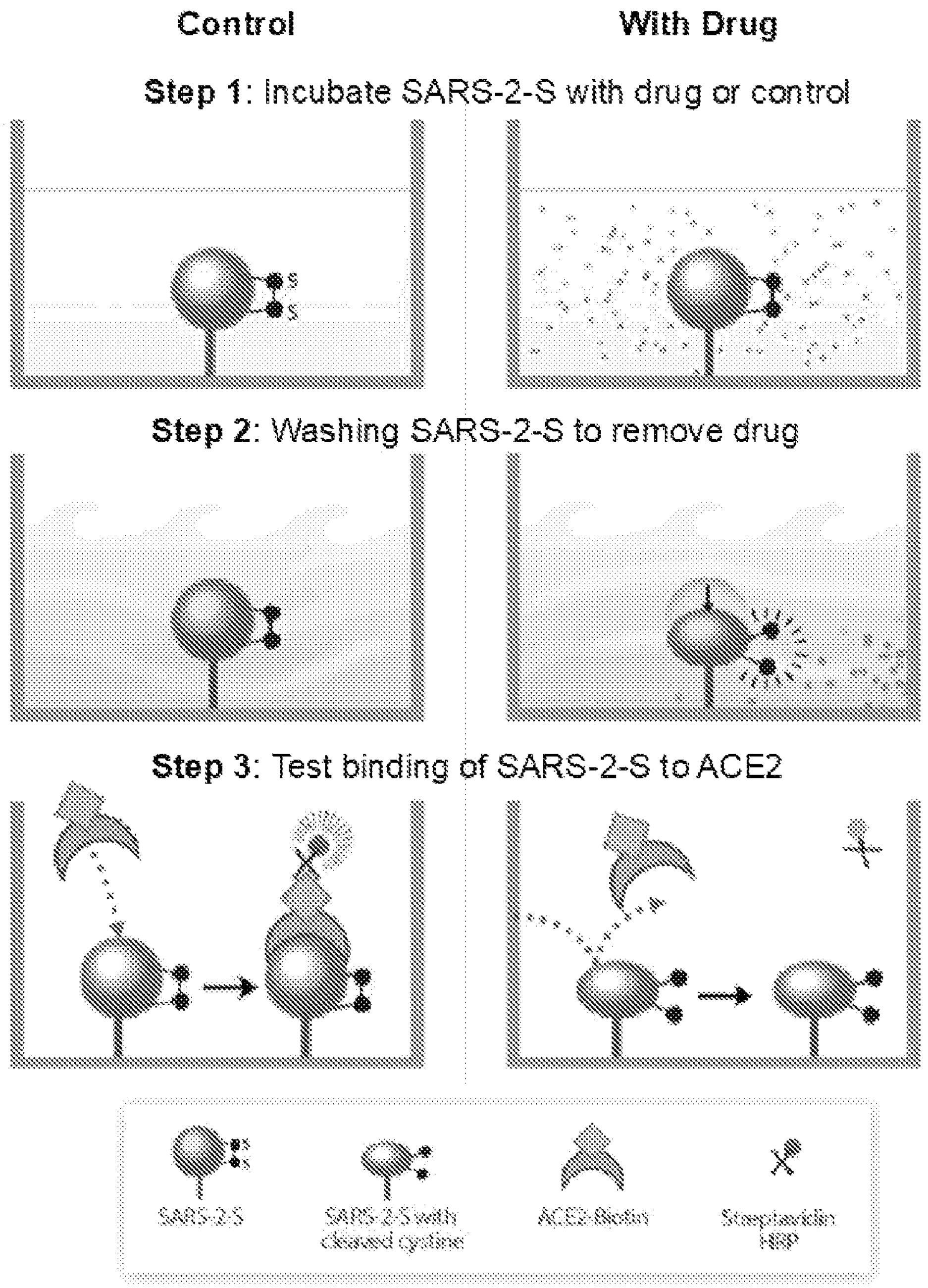
FIGS. 6A-6J. Binding of SARS-CoV-2 RBD to ACE2 is inhibited by thiol-based drugs.
Figure 6B:
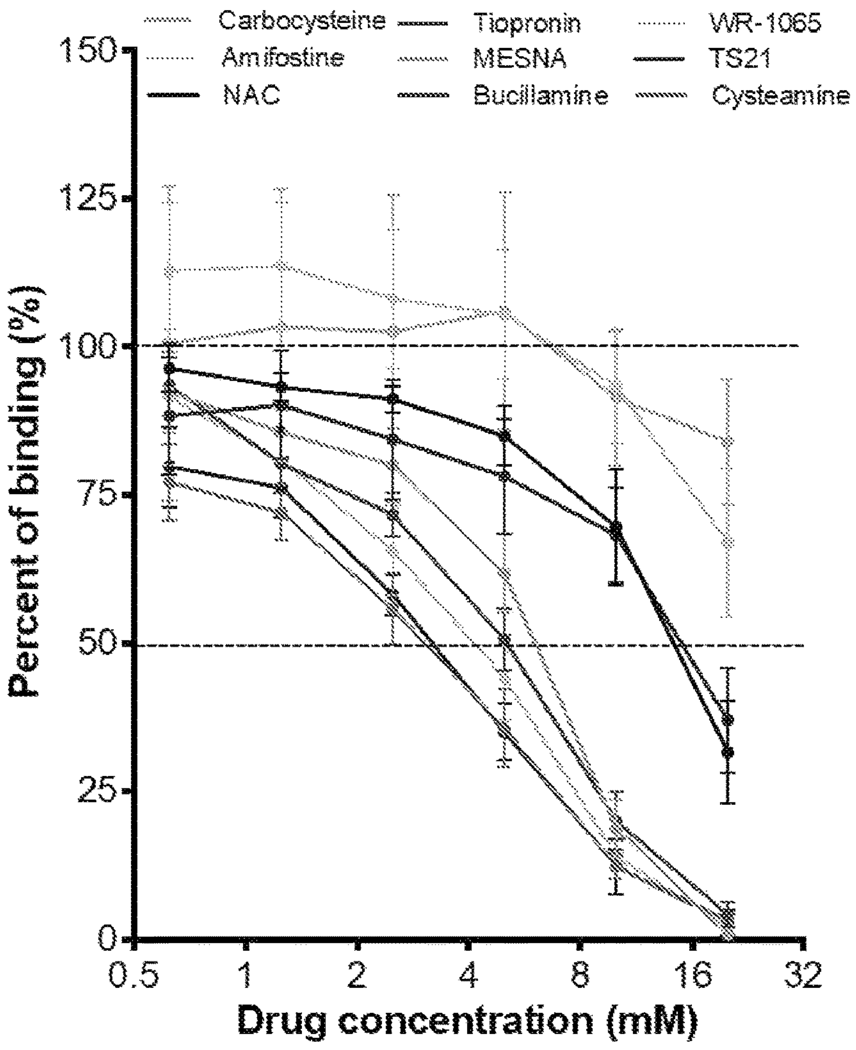
Figure 6C:
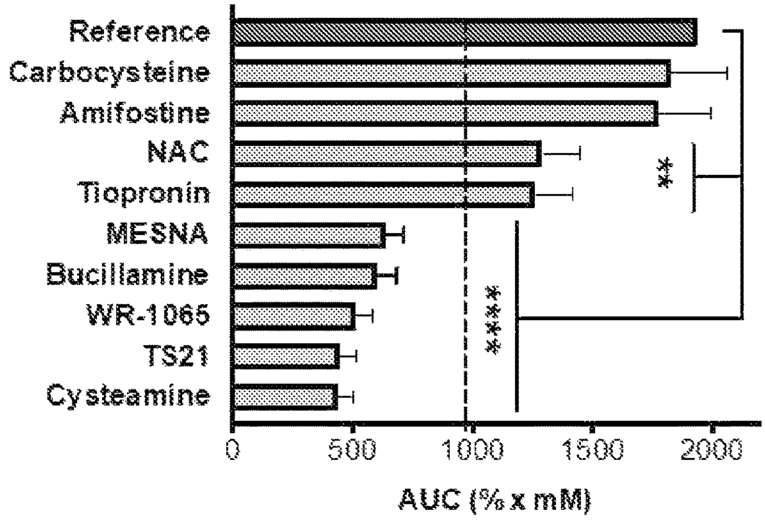
Figure 6D:
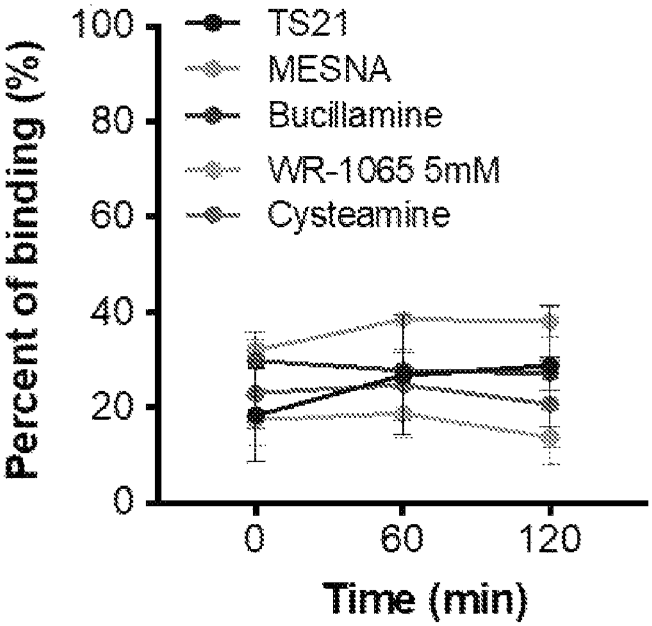
Figure 6E:
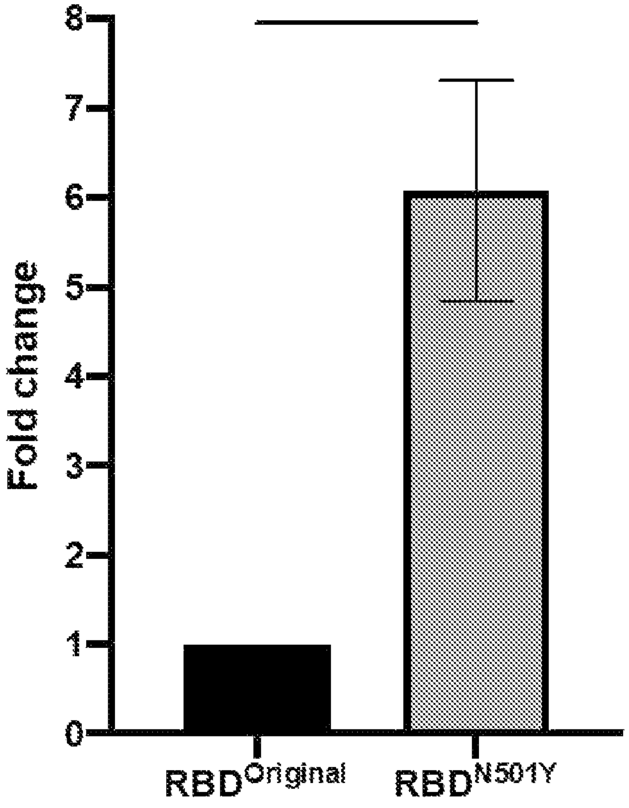
Figure 6F:
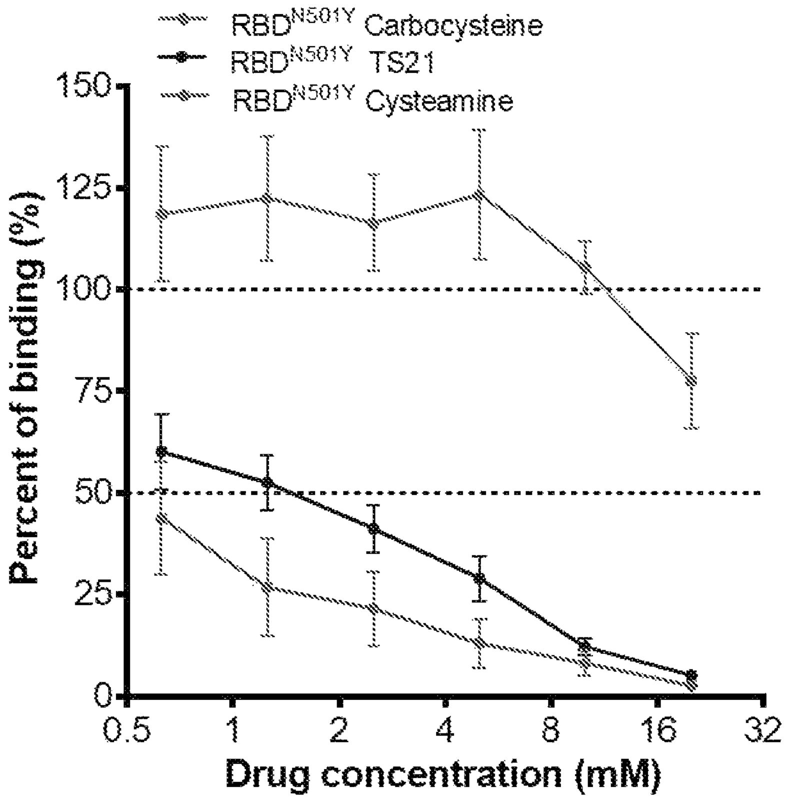
Figure 6G:
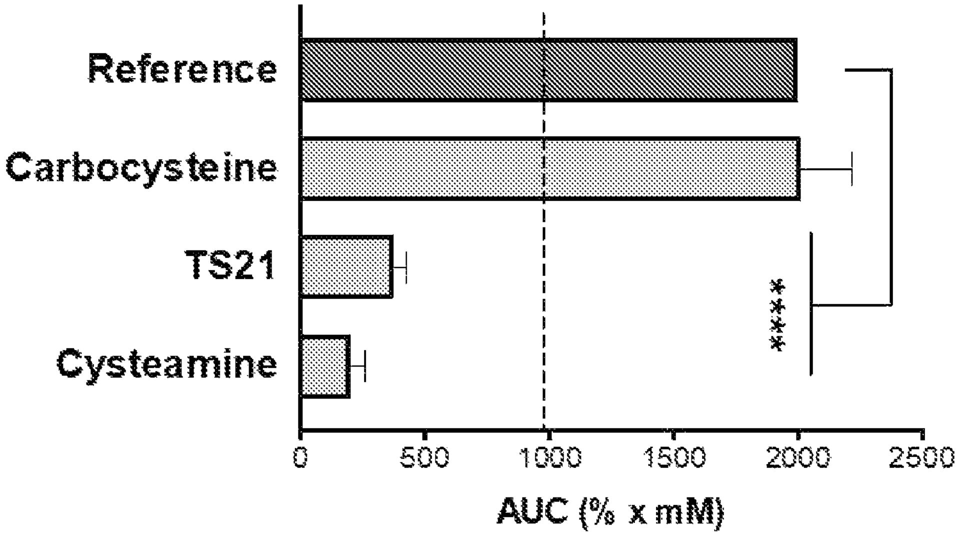
Figure 6H:
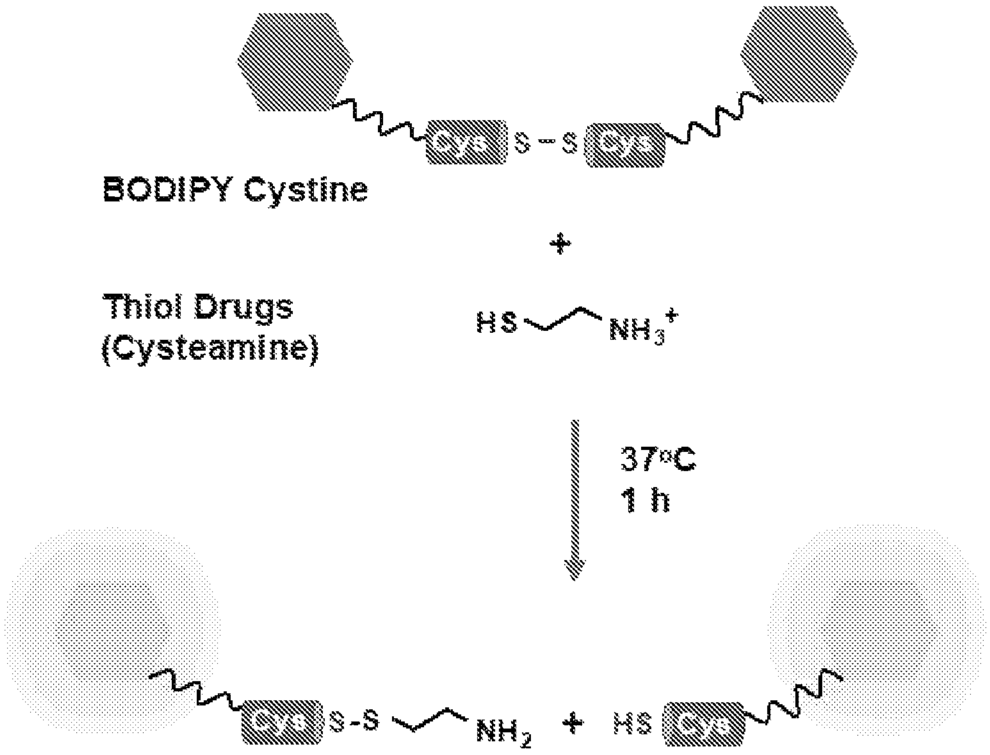
Figure 6I:
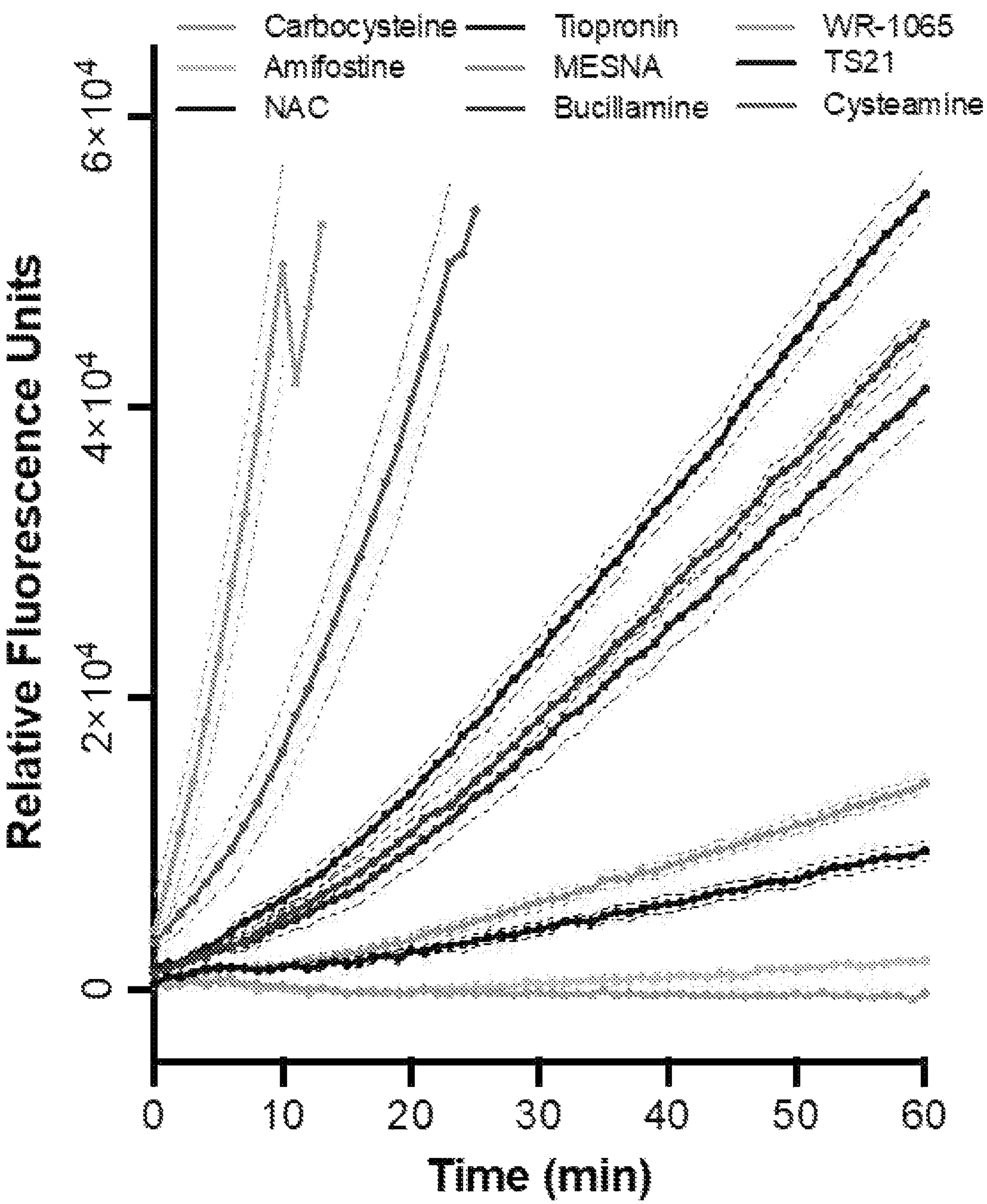
Figure 6J:
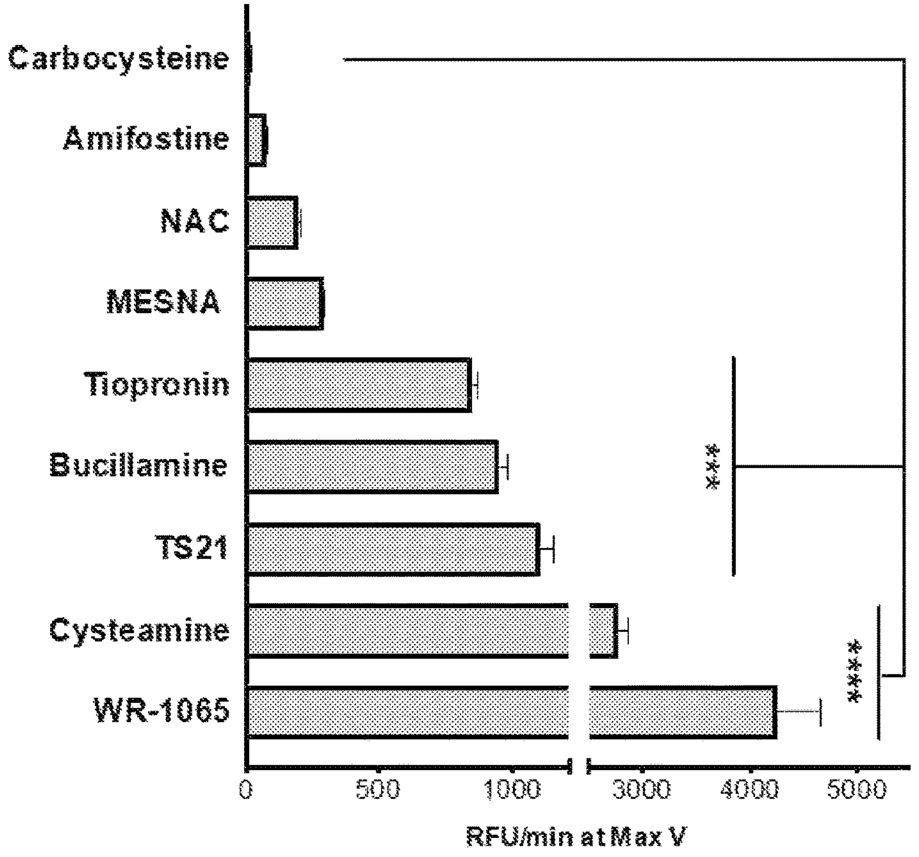

To test if thiol drugs can cleave cystines in the RBD of SARS-2-S to disrupt binding to ACE2, we exposed the RBD of the original SARS-CoV isolates ($RBD^{original}$) to eight existing thiol drugs and quantified ACE2 binding affinity in a plate-based binding assay. We also tested an investigational thiol saccharide drug (MUC-31) in this system, because of the potential advantages of thiol-saccharides as drugs for inhaled delivery[16]. Carbocysteine and amifostine were included as negative controls because carbocysteine is a sulfur containing drug lacking a free thiol warhead and amifostine is a phosphorothiolate prodrug whose dephosphorylated metabolite (WR-1065) is the active drug metabolite. The ACE2-SARS-2-S RBD binding assay was optimized by modifying a commercially available kit. $RBD^{original}$ was covalently coupled to plates functionalized with primary amine-reactive maleic anhydride, and ACE2 binding was then quantified after exposure of $RBD^{original}$ to drugs for 60 minutes (FIG. 6A). We found that all of the thiol drugs inhibited binding of $RBD^{original}$ to ACE2 in a dose dependent manner. 2-Mercaptoethane sulfonate, sodium salt (MESNA), bucillamine, cysteamine, WR-1065, and MUC-31 had strong inhibitory effects (FIGS. 6B-6C). We also measured binding of $RBD^{original}$ to ACE2 at one and two hours post exposure and wash to MESNA, bucillamine, cysteamine, MUC-31 and WR-1065 and found that binding inhibition was retained for two hours after drug removal (FIG. 6D). Next, we tested if cysteamine and MUC-31 inhibit binding of $RBD^{N501Y}$ to ACE2. $RBD^{N501Y}$ bound more strongly than $RBD^{original}$ to ACE2 (FIG. 6E) confirming recent reports [19,20,21], and cysteamine and MUC-31 potently inhibited this binding of $RBDN^{N501Y}$ (FIG. 6F). To determine if the variable effects of thiol drugs on RBD binding relates to their cystine cleaving potency, we leveraged the BODIPY FL L-cystine reagent which fluoresces when thiol-specific exchange leads to mixed disulfide formation (FIG. 6H). The potency of the thiol drugs in the BODIPY assay mirrored the potency order seen in the RBD-ACE2 binding assay (FIGS. 6I-6J) suggesting that cystine cleaving potency could explain the drug potency differences in the binding assay.

Figure 7A:
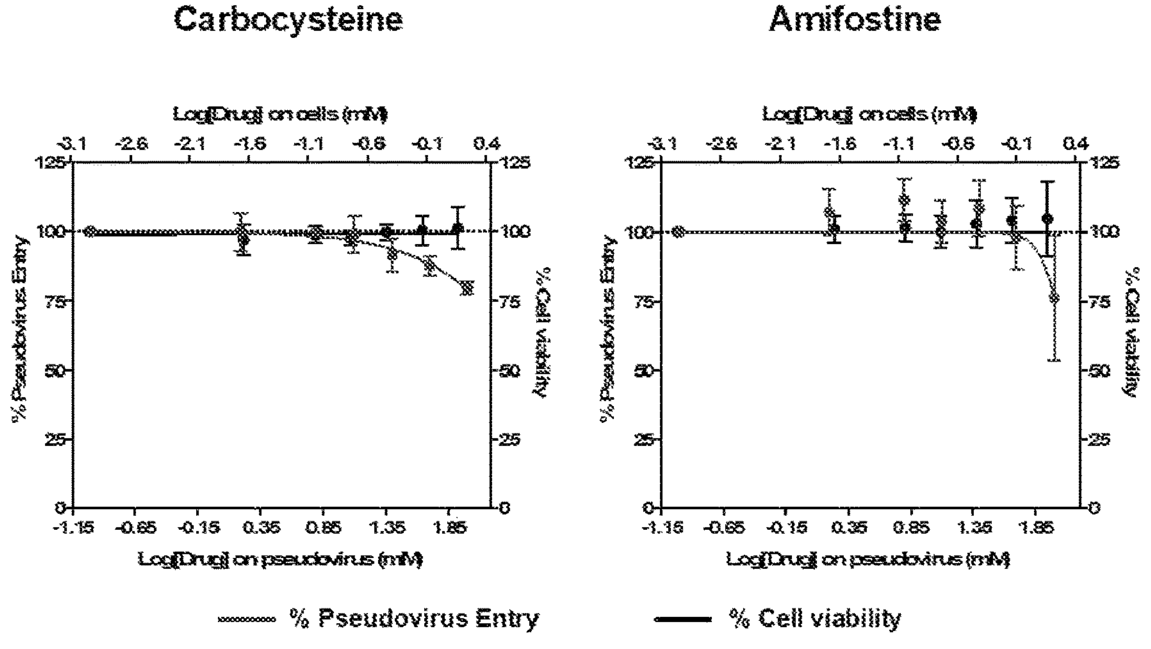
FIGS. 7A-7E. Entry of SARS-CoV-2 pseudoviruses into 293T-ACE2-TMPRSS2 cells is inhibited by thiol-based drugs. Pseudovirus (PV) entry efficiency, quantified by luciferase activity, when the pseudoviruses were exposed to thiol-based drugs prior to cell transduction (n=3-4). The effects of drugs on 293T-ACE2-TMPRSS2 cell viability was quantified using Cell Titer Glo 2.0 with lower drug dose exposures, reflecting 66-fold dilution of drugs when pseudovirus/drug mixture was incubated with cells (n=3). X-axes are scaled to log 10—the lower X-axis refers to concentration of drugs on the pseudovirus and the upper X-axis refers to equivalent concentration of drugs on the cells. The left Y-axis refers to PV entry efficiency and the right Y-axis refers to cell viability. Percentage changes are with respect to no drug control which is set as 100%. $IC_{50}$ of the drugs was determined using the non-linear regression fitting with a variable slope. Data are mean SD. In each graph, the most downward-trending plot corresponds to pseudovirus entry.
Figure 7B:
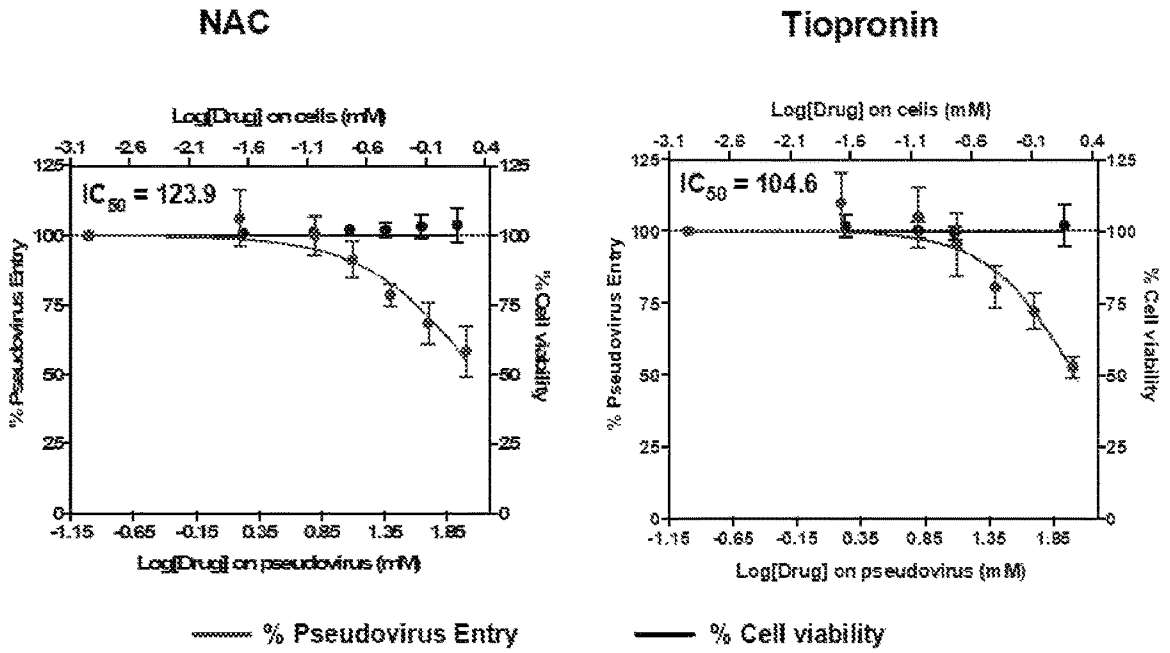
Figure 7C:
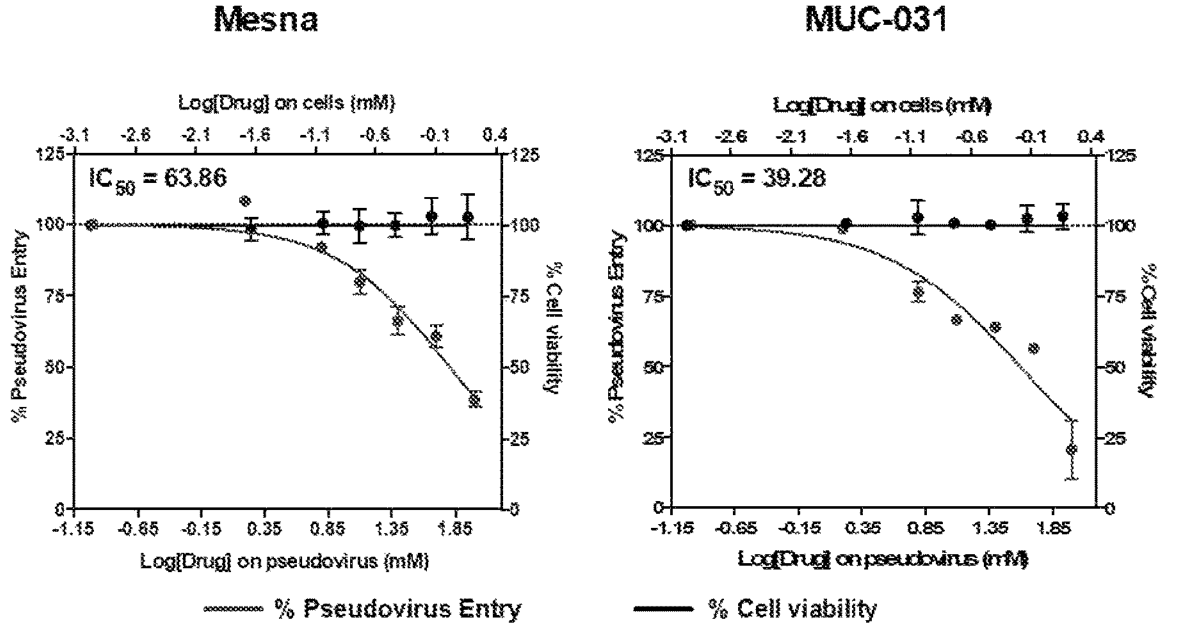
Figure 7D:
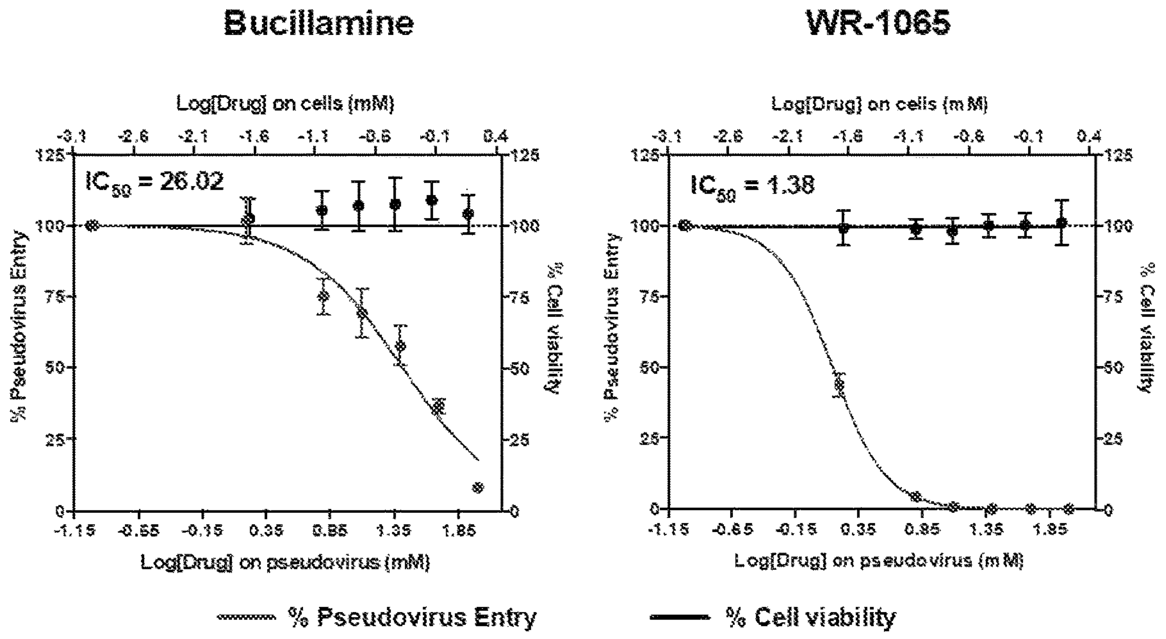
Figure 7E:
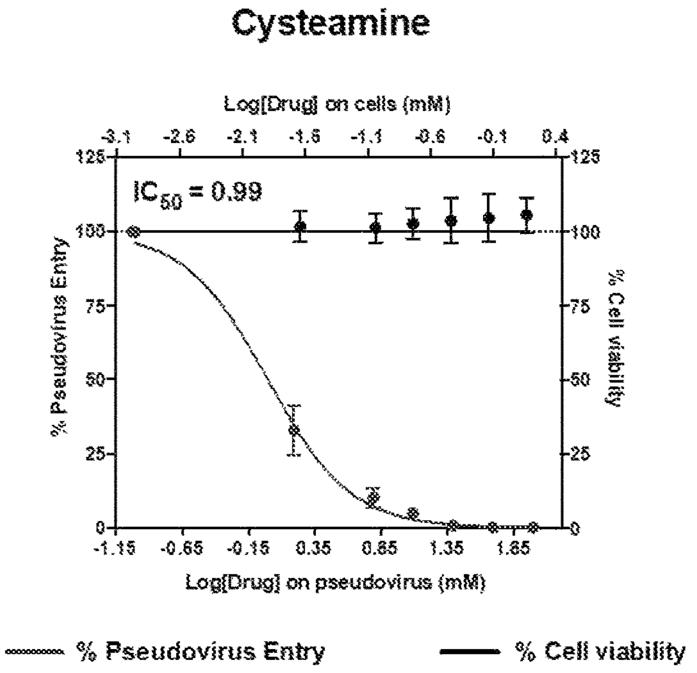
Figure 9A:
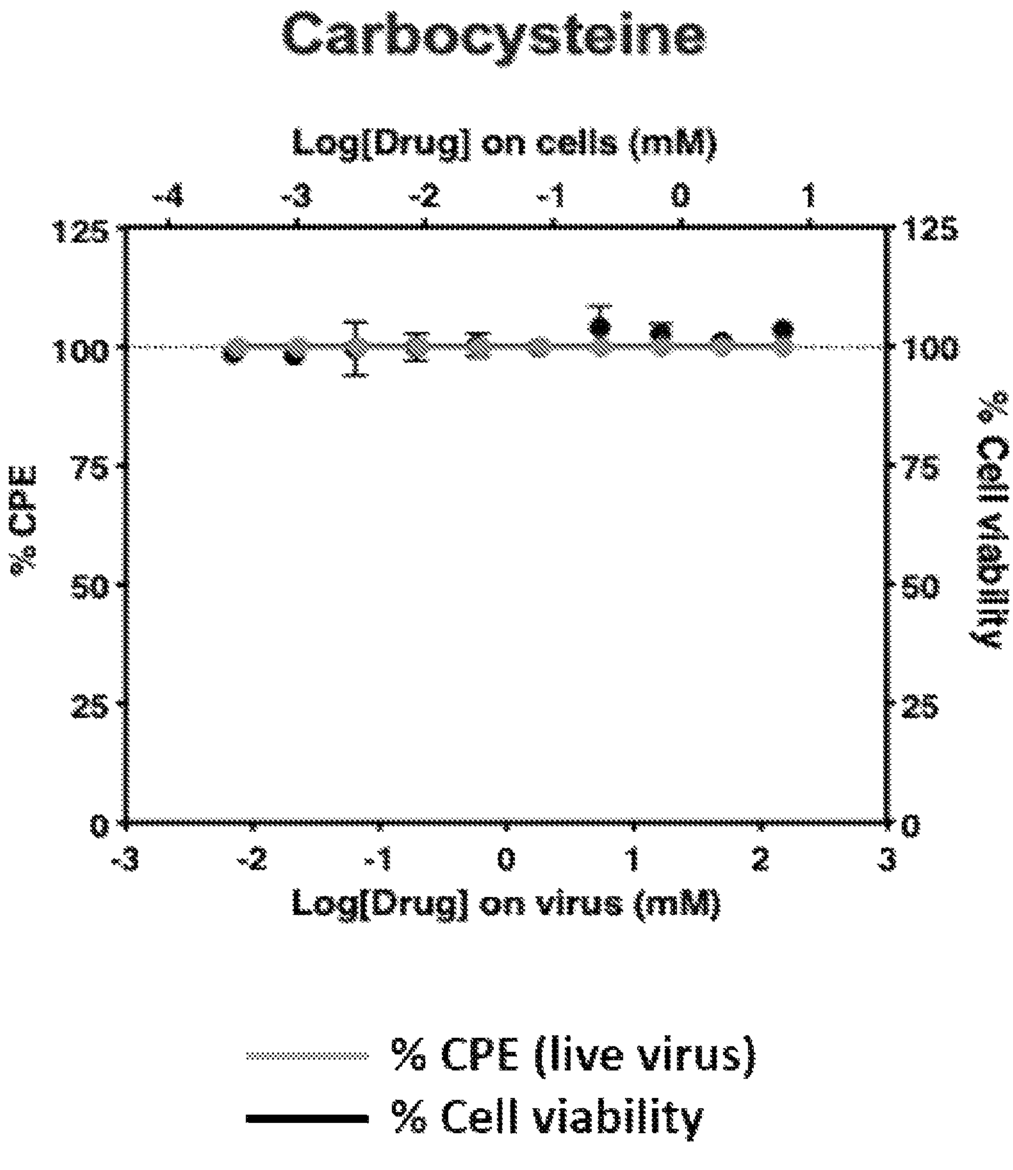
FIGS. 9A-9C. Thiol-based drugs inhibit SARS-CoV-2 virus infectivity in VeroE6 cells. Cytopathic effects (CPE) quantified by visual inspection when virus is exposed to drugs prior to infection in Vero E6-TMPRSS2 cells (n=3). The effects of drugs on Vero E6 cell viability was quantified with exposure of cell to lower drug doses, reflecting the 24-fold dilution of drugs when virus/drug mixture was incubated with cells (n=3). Percentage changes are with respect to no drug control which is set as 100%. $IC_{50}$ of the drugs was determined using the non-linear regression fitting with a variable slope. Data are mean SD.
Figure 9B:
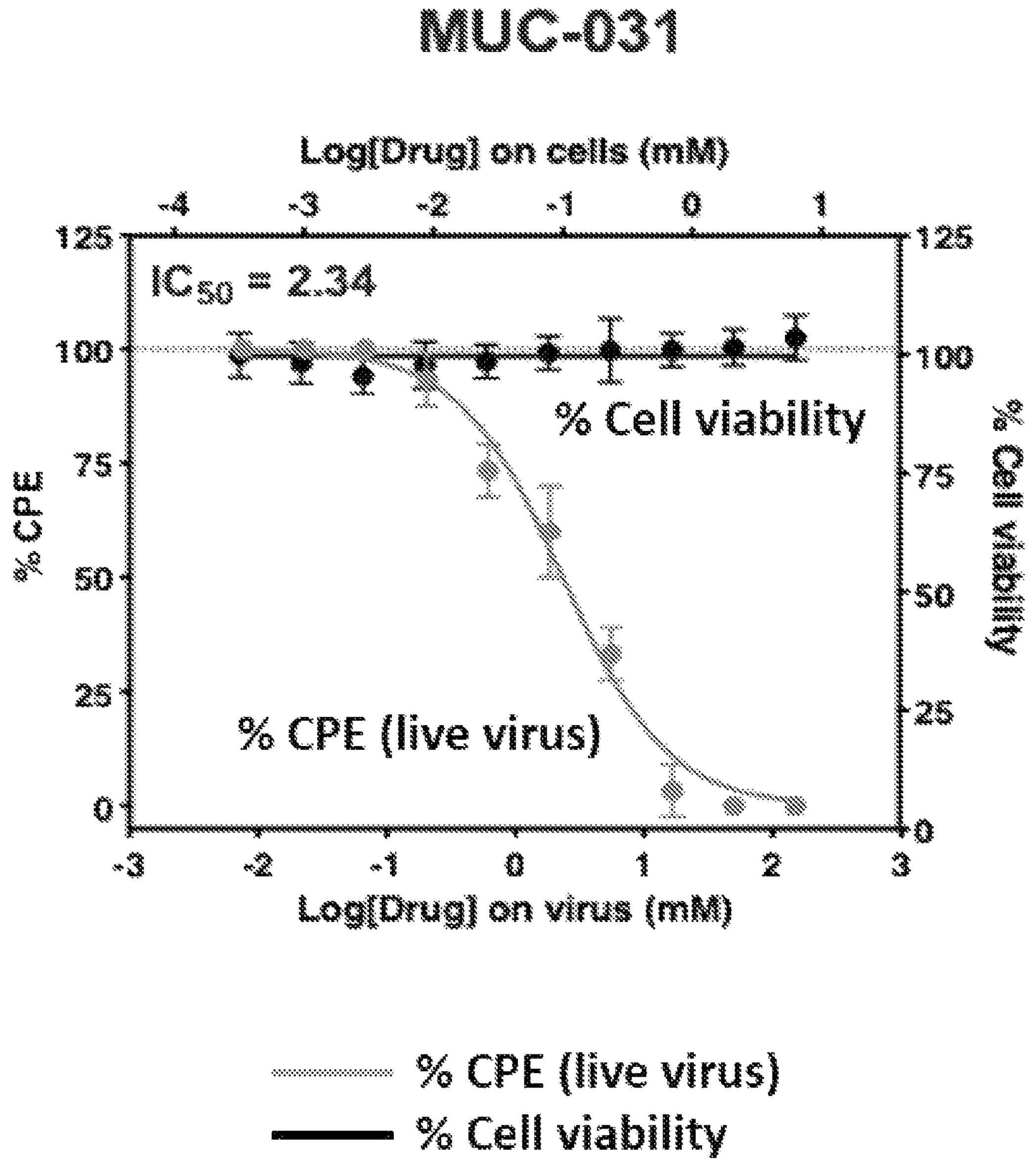
Figure 9C:
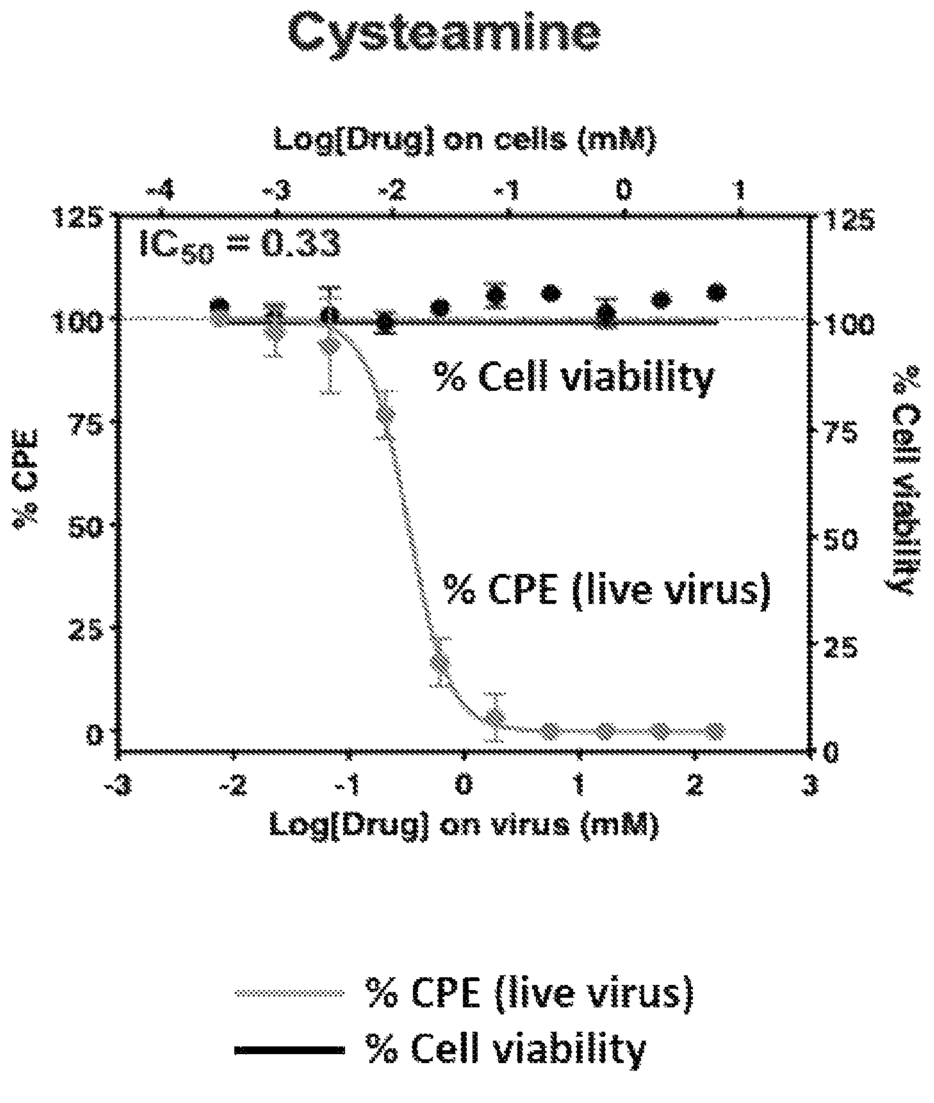

To test if thiol drugs can inhibit SARS-COV2 entry into cells, we first tested drug efficacy in pseudovirus and live virus assays. The pseudovirus particles carry SARS-2-S on the surface and enclose a viral genome of recombinant vesicular stomatitis virus (VSV) with a deleted glycoprotein (rVSV-AG) and an insertion of the firefly luciferase gene. In these experiments, we first exposed pseudovirus particles to thiol-based drugs and then quantified cell entry efficiency in human embryonic kidney cells (HEK293T) stably transfected to express huACE2 and transmembrane protease, serine 2 (TMPRSS2, a priming serine protease for SARS-CoV-2 [3]) (293T-ACE2-TMRPRSS2 cells). None of the drugs significantly affected cell viability, and pretreatment of SARS-2-S pseudovirus with carbocysteine and amifostine did not inhibit viral cell entry (FIG. 7A). In contrast, pretreatment of SARS-2-S pseudovirus with all of the thiol-based drugs significantly decreased viral entry in a dose dependent manner (FIGS. 7B-7D). The thiol drugs had only small and inconsistent effects on pseudovirus cell entry when the 293T-ACE2-TMPRSS2 cells were first pretreated with thiol drugs and then infected with untreated SARS-2-S pseudovirus. To confirm that these data with pseudovirus particles extend to live virus, we tested the effects of a subset of the drugs (cysteamine, MUC-31, and carbocysteine as negative control) on SARS-CoV-2 infection of Vero E6 cells (FIGS. 9A-9C). We found that cytopathic effects in virus-infected cells was significantly inhibited by all of these drugs, and that inhibition was minimal when the VERO E6 cells were first pretreated with thiol drugs and then infected with untreated SARS-CoV2. Taken together, these data demonstrate that thiol-based drugs inhibit SARS-COV2 entry into cells.

To determine if thiol-based drugs inhibit SARS-COV2 infection in vivo, we tested two drugs in the Syrian hamster model of COVID-19[22-25]. Since millimolar drug concentrations of the thiol drugs were most effective in the pseudovirus and live virus assays, we hypothesized that pulmonary delivery of the drug by aerosol will most reliably result in these concentrations in the airways. MUC-31 was selected for in vivo testing by aerosol administration because it is formulated for aerosol delivery. The lung deposited dose of 0.5 mg/kg was calculated to result in millimolar concentrations in the airways and lungs.

Figure 8A:
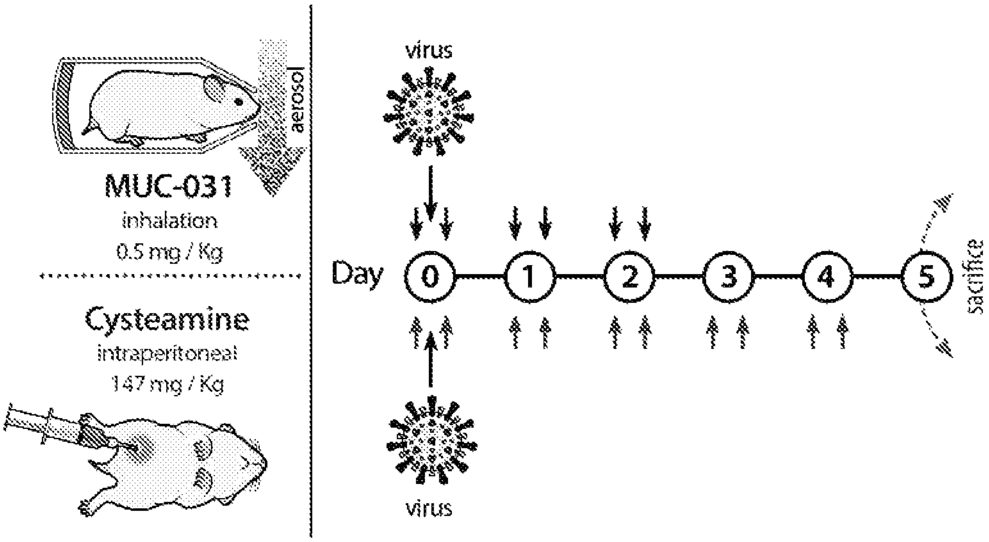
FIGS. 8A-8H. Effects of TS21 and cysteamine on a Syrian hamster model of SARS CoV2 infection.
Figure 8B:
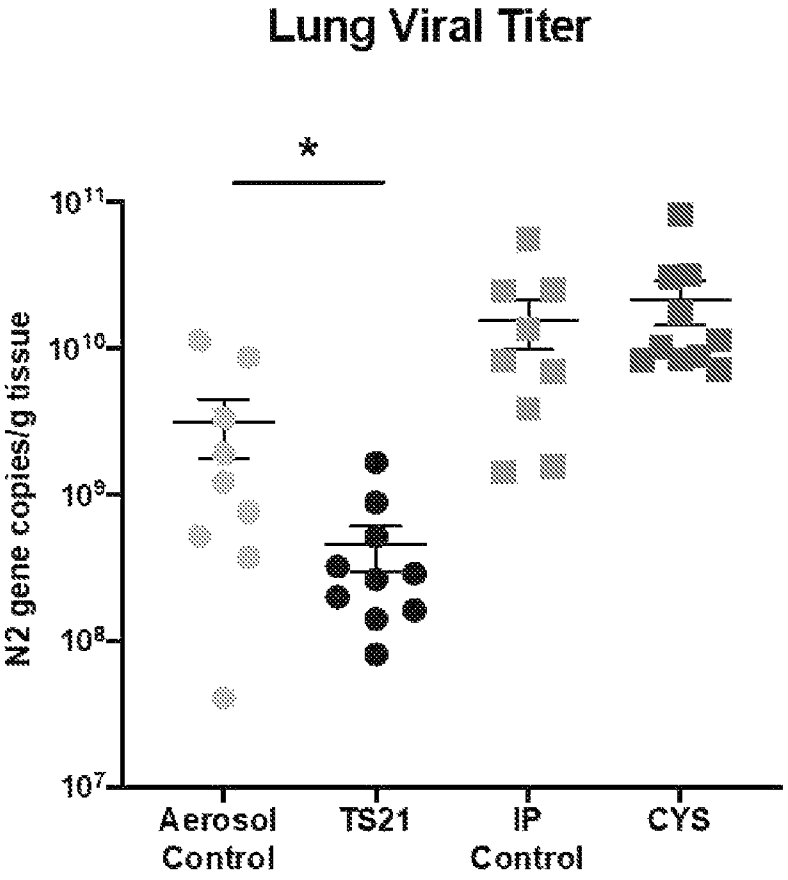
Figure 8C:
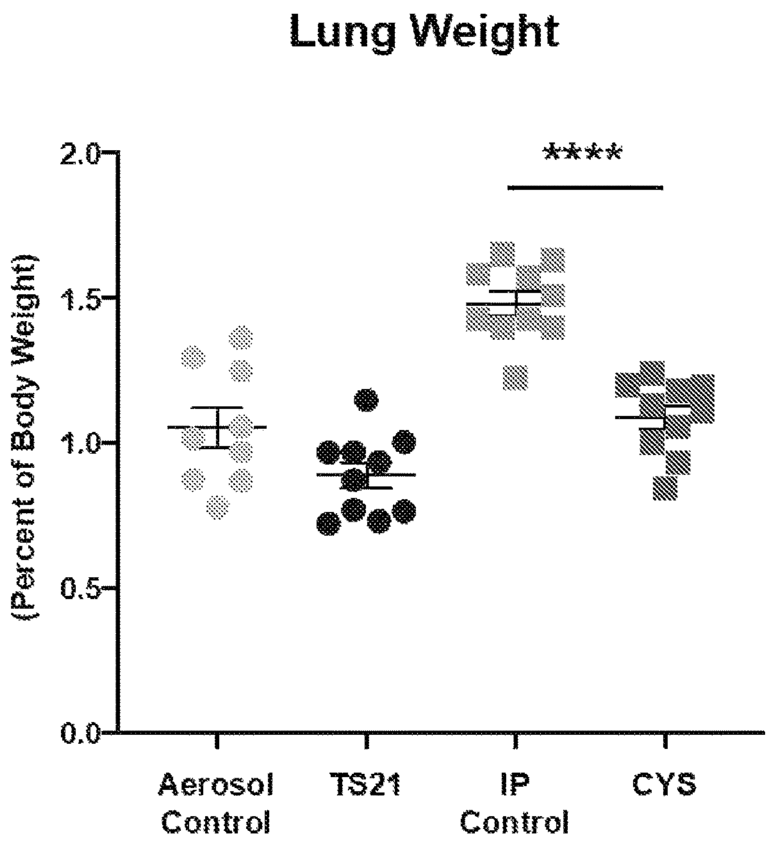
Figure 8D:
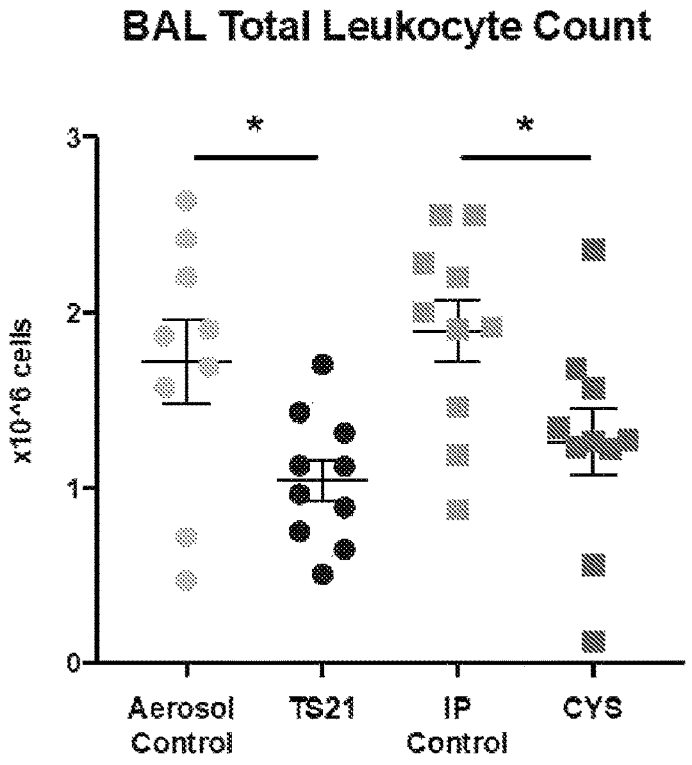
Figure 8E:
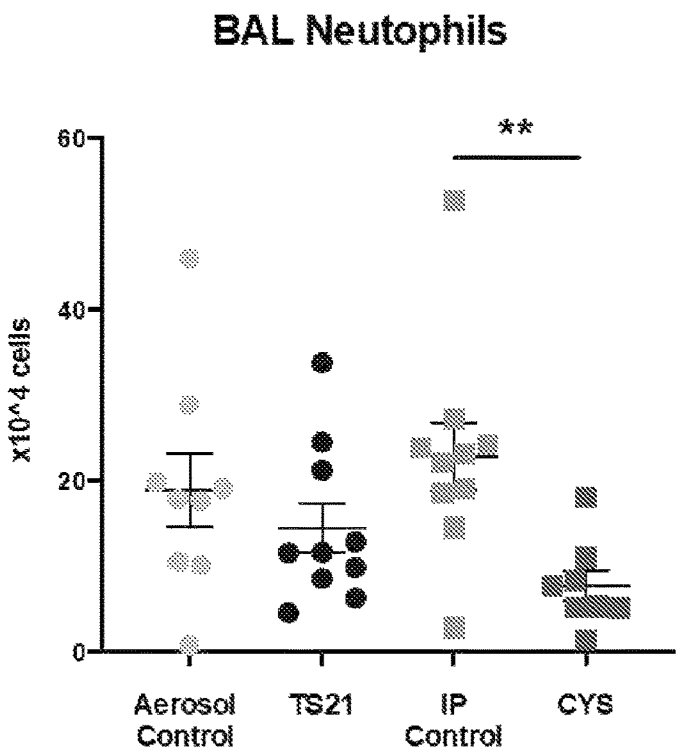
Figure 8F:
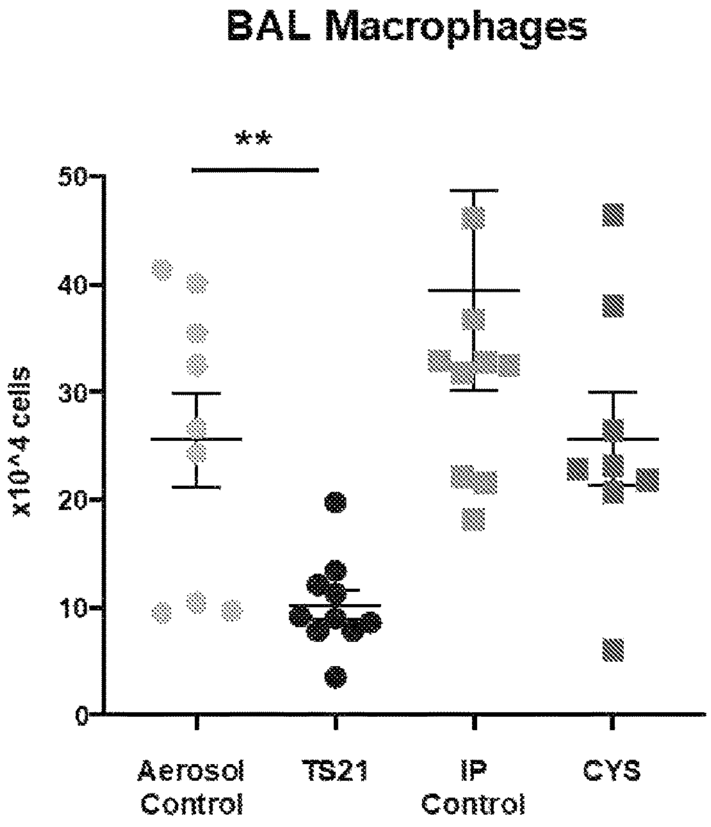
Figure 8G:
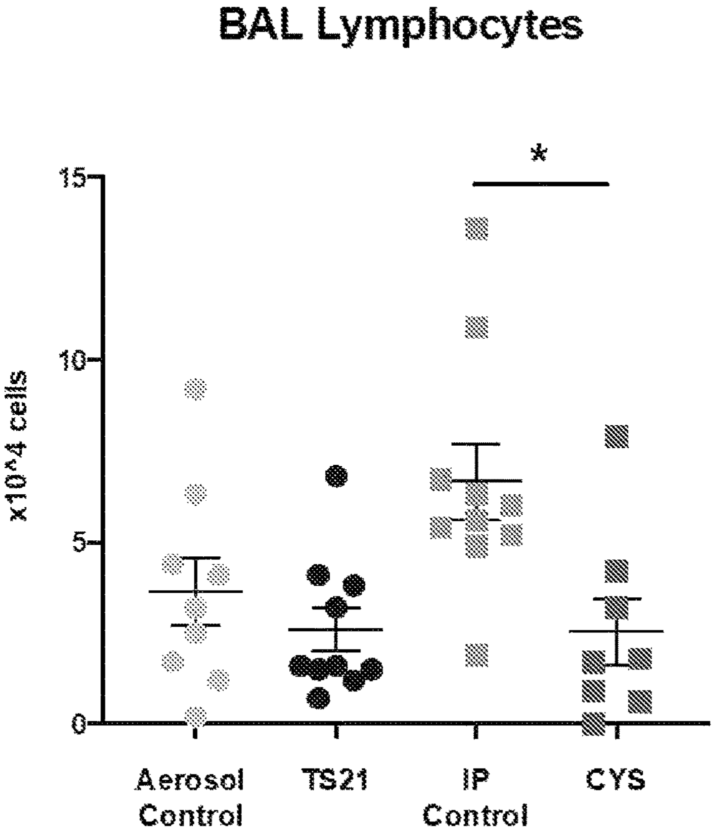
Figure 8H:
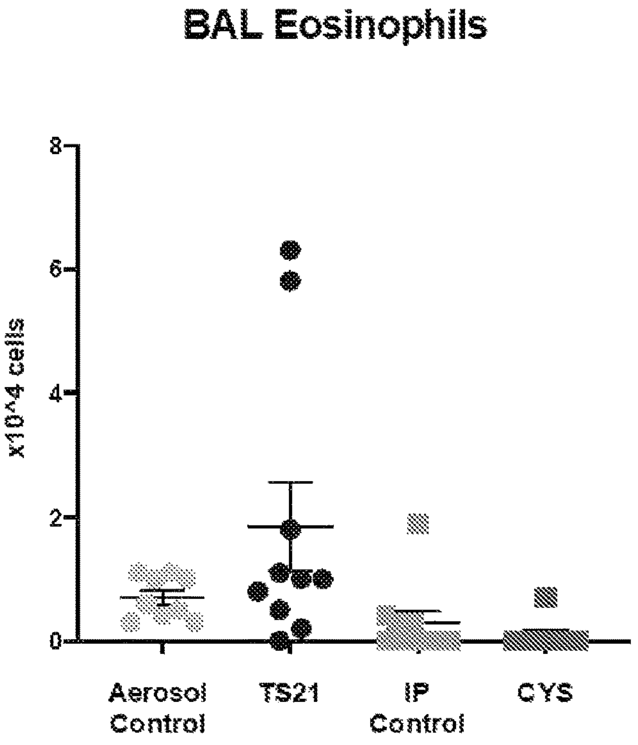

Cysteamine was selected for in vivo testing because it was the most potent thiol drug in the in vitro assays, but it is not formulated for aerosol delivery and so was given by intraperitoneal (IP) injection. A high dose of 100 mg/Kg of cysteamine free base was selected because cysteamine is used in high doses clinically (2 g per day)[26,27] but even this high IP dose is not likely to achieve millimolar concentration in the airways and lungs. Our expectation therefore was that aerosolized MUC-31 would be more effective than IP cysteamine in these hamster experiments. The in vivo protocol is schematized in FIG. 8A and shows that the first dose of both drugs was given 2 hours prior to intranasal viral inoculation of SARS CoV2 (1E+05 $TCID_{50}$/animal). Cysteamine-treated animals were dosed for 5 days and MUC-31-treated animals were dosed for three days (the initial plan to dose MUC-31 for five days was modified when initial experiments indicated that SARS-CoV2 infected animals would have difficulty tolerating twice daily 20 minute tube confinements for 5 days). MUC-31-treated animals had significantly lower SARS-CoV2 viral titers in their lungs, but the cysteamine-treated animals did not (FIG. 8A-8B). Despite this difference in viral titer results, both MUC-31 and cysteamine decreased the severity of SARS-CoV2 lung inflammation. Specifically, the lung weights in MUC-31- and cysteamine-treated hamsters were lower than in control groups with cysteamine's effects being larger, possibly because of the extra 2 days of treatment (FIG. 8C-8D). In addition, the total leukocyte counts in the bronchoalveolar lavage (BAL) fluid were lower than control in both MUC-31- and cysteamine-treated animals (FIG. SE), effects driven by decreases in macrophages in MUC-31-treated hamsters and in neutrophils and lymphocytes in cysteamine-treated hamsters (FIG. 8F). Furthermore, interleukin-6 levels in lung lavage were lower than control in both MUC-31- and cysteamine-treated animals (FIG. 8F).

Our study shows that thiol drugs decrease binding of SARS-CoV-2 spike protein to its receptor to decrease the entry efficiency of SARS-CoV-2 and that an aerosolized thiol drug (MUC-31) decreases SARS-CoV-2 viral titers in the lung to limit SARS-COV-2-associated lung inflammation. The antiviral efficacy of MUC-31 in vivo can be attributed to aerosol administration which allows millimolar drug concentrations in the airways and lungs. MUC-31 is an investigational drug not yet approved for human use, but N-acetyl cysteine (NAC) and MESNA are approved thiol drugs that are administered by aerosol. Our data indicate that MESNA is more attractive than NAC as a candidate COVID-19 drug, because it has superior antiviral efficacy in vitro. Surprisingly, cysteamine—delivered IP—has anti-inflammatory effects in the lungs of SARS-CoV-2 infected hamsters, even though it does not decrease SARS-COV-2 viral titers in the lung. The anti-inflammatory effect of cysteamine is plausibly explained by the general anti-oxidant properties of thiol drugs to scavenge reactive oxygen species (ROS) and limit ROS-mediated inflammatory cascades. Some thiol drugs in their disulfide linked dimer form, including cysteamine, also inhibit transglutaminase. Thus, the beneficial effects of thiol drugs on COVID-19-related lung disease result from both antiviral and anti-inflammatory mechanisms, but the anti-viral effects were most pronounced at millimolar concentrations in the airways and lungs whereas the anti-inflammatory effect can be achieved at micromolar concentrations or less. Multiple thiol drugs can be administered by oral and intravenous routes, but amifostine (a prodrug whose dephosphorylated metabolite is WR-1065) and cysteamine have potency profiles that make them particularly attractive for repurposing as treatments for COVID-19. Finally, because the anti-viral effect of thiol drugs relates to cystines in the spike protein that are conserved among known SARS-CoV-2 variants, it is unlikely that these variants will escape the thiol drug effect. The anti-inflammatory effects of thiol drugs should operate in lung inflammation caused by all SARS-CoV-2 variants as well. Our work provides rationale for clinical studies of thiol drugs administered by inhaled or systemic routes to combat COVID-19.

Materials and Methods

Cells, Plasmids and Virus

HEK293T/clone17 (CRL-11268) and Vero E6 (CRL-1586) cells were cultured in Dulbecco's Modified Eagle's Medium (DMEM) supplemented with 10% fetal bovine serum and 1% penicillin/streptomycin (Thermo Fischer Scientific). The cells were obtained from ATCC and incubated at 37° C. and 5% $CO_2$. MEXi 293E cells (IBA Lifesciences) were cultured in MEXi culture medium (IBA Lifesciences) at 37° C., 5% $CO_2$ and 125 RPM as described by the manufacturer. The codon-optimized SARS-CoV-2 spike gene was subcloned from pCG SARS-CoV-2 Spike (provided courtesy of Stefan Pölhmann[3]) into the EBNA-1 dependent expression vector pTT5 for high-level expression in MEXi 293E cells. To boost cell surface expression of SARS-CoV-2 spike for efficient pseudotyping VSV, the C-terminal 21 amino acid containing the ER-retrieval signal (KxHxx) of spike was deleted. Plasmids for engineering lentiviral ACE2 and TMPRSS2 expression constructs: pLKO5d.SFFV.dCas9-KRAB.P2A.BSD (a gift from Dirk Heckl, Addgene plasmid) and pDUAL CLDN (GFP) (a gift from Joe Grove, Addgene plasmid). SARS-CoV-2, isolate USA-WA1/2020 (NR-52281) was obtained from BEI resources and passaged in Vero E6 cells. Confluent Vero E6 cells grown in T175 flasks were infected with SARS-CoV-2 and the culture supernatant was collected when widespread cytopathic effect (CPE) was observed. After filtration through 0.45 μm filters, the virus containing culture supernatant was stored at −80° C. in small aliquots.

Thiol-Based Drugs and Thiol Content Determination

N-acetylcysteine (NAC) and MESNA were the pharmaceutical formulations, with NAC manufactured by American Reagent INC at 200 mg/ml and MESNA by Baxter at 100 mg/ml USP. Cysteamine (MilliporeSigma), amifostine (MilliporeSigma), WR-1065 (MilliporeSigma) and penicillamine (MP Biomedicals) were lyophilized powders that were solubilized as 500 mM concentrated stocks in water. Cysteamine and WR-2065 were at pH 5. Amifostine was at pH 7 which was adjusted to pH 5. To ensure that amifostine does not auto-dephosphorylate to WR-1065, it was made fresh before the experiment each time. Bucillamine (MilliporeSigma) and tiopronin (Spectrum Chemicals) were lyophilized powders that were solubilized as 500 mM concentrated stocks in equimolar NaOH to increase the solubility, and the pH was adjusted to pH 5. Carbocysteine (MilliporeSigma) and succimer (MilliporeSigma) were solubilized as 250 mM concentrated stocks in 500 mM NaOH to increase solubility with pH adjusted to pH 5. Free thiol content, and thus concentration of an active drug, was measured before every experiment using Ellman's Reagent, 5,5'-dithio-bis-(2-nitrobenzoic acid) (DTNB) (Abcam), with the molar extinction coefficient of 14,150 $M^{-1}cm^{-1}$ at 412 nm[30]. Active drug concentration measured by DTNB was within 85 to 99% of nominal drug concentration. The stocks were stored at −20° C. and discarded if the thiol content went below 85%. Drug concentrations reported in plate-binding and viral entry assays are based on active drug concentration in stock.

Structure Rendering and Analysis

Space filling images and receptor distance calculations were performed using indicated PDB entries with UCSF Chimera, developed by the Resource for Biocomputing, Visualization, and Informatics at the University of California, San Francisco, with support from NIH P41-GM1-03311 [31].

RBD to ACE2 Plate Based Binding Assay

Wells of amine-reactive maleic anhydride-derivatized plates (Thermo Scientific) were washed with PBS+0.05% Tween-20, and coated overnight with 1 μg/ml recombinant SARS-CoV-2 Receptor binding domain (aa 319-537; ACRO Biosystems). The following day, the plates were washed and blocked with 2% BSA for 1 hour at 37° C. Wells were then incubated with drugs at concentrations ranging from 0 to 20 mM diluted in PBS for an hour at 37° C. Negative controls included wells with no RBD or no ACE2. After washing, biotinylated soluble recombinant ACE2 (ACRO Biosystems) was added at 0.06 μg/ml and incubated at 37° C. for 60 minutes. After washing, streptavidin-HRP at 0.1 μg/ml (ACRO Biosystems) was added to wells for an hour at 37° C. The plates were washed and incubated with TMB (Sera Care). The reaction was stopped with 0.5 M hydrochloric acid stop solution and absorbance was read at 450 nm on a Biotek plate reader. Absorbance readings, after subtracting from negative control wells, were transformed to percent binding, with the wells containing no drug set as 100 percent binding.

To measure the stability of binding of cysteamine, WR-1065, Mesna and bucillamine, wells were incubated with either drugs at 5 mM for 1 hour, followed by three washes. ACE2 was then added to the wells either immediately, after 60 minutes, or after 120 minutes. Wells waiting for ACE2 were filled with dilution buffer. This was followed by the same steps to assess ACE2 binding as described above. For all binding assays, 4-6 independent experiments were carried out for all drugs, with 2 replicates in each.

To measure the difference in binding of the SARS CoV2 RBD variants, the plate was coated overnight with 1 ug/ml of the respective RBDs. Then the plate was blocked, followed by incubation with varying concentrations of biotinylated ACE2 ranging from 60 ng/ml to 0.7 ng/ml for 1 hour. Finally, the plates were incubated with streptavidin-HRP and developed using TMB. The fold change in the absorbance was assessed for each variant, relative to the original RBD.

BODIPY FL L-Cystine Cleaving Assay

BODIPY FL L-cystine (Thermo Fischer scientific) was reconstituted to a final stock concentration of 1 mM with methanol. In a black Maxi Sorp 96-well flat-bottomed plate (Nunc), 10 uM of BODIPY reagent was added onto 25 uM of the thiol-based drugs and the change in fluorescence was kinetically measured, at 1 minute intervals, for an hour at 37° C. Fluorescence reads, after subtracting the no drug control reads, were plotted against time. The maximum slope (Max V) for all the thiol-based drugs from this plot was measured and represented as relative fluorescence units/min (RFU/min) to assess the cystine cleaving ability of the drugs. The experiment was repeated three times.

Production of Pseudoviruses

Pseudoviruses bearing SARS-2-S were generated using recombinant VSVΔG-luciferase-based viruses, which lack glycoprotein (G) gene and instead code for reporter gene firefly luciferase. Briefly, MEXi cells were transfected with SARS-CoV-2 Spike expression plasmid (pTT5 SARS-CoV-2 SΔ21), using PEI as described by the manufacturer. Mock transfection served as the 'no glycoprotein' control. At 2-3 days post-transfection, the cells were inoculated with VSVG/VSVΔG-luc at a multiplicity of infection (MOI) of 0.3. After 6 hours of incubation, the cells were washed twice with PBS by centrifugation and resuspended in culture medium containing 1% I1 anti-VSV-G hybridoma supernatant (ATCC CRL-2700). At 24 hours post-infection, the culture supernatant was collected by centrifugation and filtered through a 0.45-μm syringe filter to clear off cellular debris. The supernatant containing viral particles was aliquoted and stored at −80° C. until further use.

Establishment of HEK293T Cells Stably Expressing ACE2 and TMPRSS2 (293T-ACE2-TMPRSS2)

Engineering of Lentiviral ACE2 and TMPRSS2 Expression Constructs

ACE2 and TMPRSS2 were cloned into separate lentiviral expression constructs. ACE2 was cloned into pLKO5d.SFFV.dCas9-KRAB.P2A.BSD (a gift from Dirk Heckl, Addgene plasmid) by replacing dCAS9-KRAB with new unique enzyme restriction sites (SpeI and NheI) and subsequently inserting the ACE2 gene sequence into the expression construct downstream of the SFFV promoter based on restriction enzyme cloning. TMPRSS2 was cloned into pDUAL CLDN (GFP) (a gift from Joe Grove, Addgene plasmid). GFP was exchanged with a puromycin cassette using enzyme restriction sites MluI and XhoI to enable antibiotic selection in cell culture. TMPRSS2 was inserted into the expression construct immediately downstream of the SFFV promoter following the addition of unique enzyme restriction sites (SrfI and SalI). All cloning steps were confirmed by Sanger sequencing.

Production of Lentiviral Particles

Lentiviral particles for delivery of lentiviral ACE2 and TMPRSS2 vectors were produced using a polyethylenimine (PEI; Polysciences, Inc) transfection protocol. Briefly, HEK293T cells were transfected with three plasmids: lentiviral ACE2 or TMPRSS2 constructs, psPAX2, and VSVg, at a ratio of 4:3:1 and a final DNA amount of 1.5 μg prepared in Opti-MEM (ThermoFisher). PEI was added at a ratio of 3:1 PEI:DNA (4.5 μg PEI). The transfection mix was vortexed and incubated for 15 min at RT and added to the cells. 16 h post transfection, transfection medium was replaced with standard culture medium, and cells were cultured for another 24 h. Cell supernatants containing the newly produced viral particles were then collected 48 h post transfection. Supernatants were centrifuged at 4° C. and subsequently filtered using 0.22 μm vacuum filter units (MilliporeSigma). The supernatants were then aliquoted and stored at −80° C.

Establishment of Cells Stably Expressing ACE2 and TMPRSS2 (293T-ACE2-TMPRSS2)

To establish HEK293T cells stably expressing ACE2 and TMPRSS2 (293T-ACE2-TMPRSS2 cells), $0.4\times10^6$ cells were seeded in 12-well plates. The following day, cells were transduced with lentiviral particles containing the ACE2 vector by adding 500 μl of lentiviral particles and 500 μl culture medium per well. 48 h post transduction, medium was replaced with blastidicin (BSD; InvivoGen) selection medium at a final concentration of 10 mg/ml BSD. After 5 days of selection, cells were transferred to 75 $cm^2$ cell culture flasks for further expansion of cells stably expressing ACE2. The process was then repeated to further transduce cells with TMPRSS2 lentiviral particles and cells were cultured in antibiotic selection medium containing 10 μg/ml BSD and 1 μg/ml Puromycin 48 h post transduction. The expression of ACE2 and TMPRSS2 was confirmed by Western Blot and compared to nontransduced cells.

Pseudovirus Transduction Experiments

293T-ACE2-TMPRSS2 cells were plated in black 96-well tissue culture treated plates (Greiner Bio-one) 18 hours before the experiment. Two experimental strategies of pseudovirus pre-treatment and cell pre-treatment were followed. For pseudovirus pre-treatment, the pseudoviruses were pre-incubated with different concentrations (1.56-100 mM) of the thiol-based drugs for 2 hours at 37° C., followed by 66-fold dilution with standard culture media. The cells were then transduced with these pre-treated virions for 2 hours at 37° C. After the incubation, the virions were removed and cells were cultured in standard culture medium. For cell re-treatment, the 293T-ACE2-TMPRSS2 cells were incubated with the different drug concentration (0.02-1.5 mM) for 2 hours at 37° C., 5% $CO_2$. These concentrations reflect the 66-fold dilution of drugs when virus/drug mix was incubated with the cells in the pseudovirus pre-treatment experiment. After incubation, the media was removed and the cells were transduced with untreated pseudoviruses for 2 hours at 37° C. After the incubation, the virions were removed and the cells were cultured in standard culture medium.

For both experimental conditions, at 18 hours post-transduction, the cells were lysed and luciferase activity was measured using Promega luciferase assay system and Biotek Synergy H1 plate reader. Data was normalized to the viral particles without any viral envelope protein. For each experiment, luciferase reads of no drug control group was set as 100% and the relative transduction efficiencies in the presence of thiol-based drugs were calculated. Three-four independent experiments were carried out for each PV pretreatment and cell pretreatment strategies, with 12 replicates in each for all the drug doses.

SARS-CoV-2 Quantification

Titers of SARS-CoV-2 was measured by $TCID_{50}$ using Vero E6 cells. Viruses were 10-fold serially diluted in DMEM with 1% FBS prior to addition to cell monolayer in 96-well-plate. For each dilution, viruses were added to 10 replicate wells at 100 μl per well.

After two hours of infection, cells were washed and cultured with fresh DMEM medium containing 1% FBS at 37° C. with 5% $CO_2$. Clear CPE was observed two days later. 50% endpoints were calculated with Reed and Muench method[32].

Inhibition of SARS-CoV-2 Infection

SARS-CoV-2 of $1.2\times10^4$ $TCID_{50}$/ml was incubated with 2-fold serially diluted thiol-based drugs at 37° C. for 2 hrs. Virus-drug mixtures were diluted 12-fold before addition to Vero E6 cell monolayer in 96-well-plate. For each drug concentration, virus-drug mixtures were added to 10 replicate wells at 100 μl per well. The final titer of virus added to cells was $1\times10^3$ $TCID_{50}$/ml (100 $TCID_{50}$ per 100 ul per well in 96-well-plate). After two hours of infection, virus-drug inoculum was replaced with fresh DMEM medium containing 1% FBS. Clear CPE developed after two days of incubation at 37° C. with 5% $CO_2$. The experiment was repeated thrice. Wells with clear CPE were counted positive and percentage of positive wells for each concentration of tested drugs were plotted. The effect of thiol-based drugs on Vero E6 cells during the two hours of SARS-CoV-2 infection was evaluated by addition of 8.33 mM or 0.52 mM of each drug and 100 $TCID_{50}$ SARS-CoV-2 simultaneously to Vero E6 cell monolayer in 96-well-plate. After two hours of infection, cells were washed and then cultured with fresh DMEM medium containing 1% FBS at 37° C. with 5% $CO_2$. Clear CPE developed two days post infection.

Quantification of Cell Viability

The cell viability was quantified using CellTiter-Glo2.0 assay (Promega) which measures cellular ATP content, indicating the metabolically active cells. For all cell viability experiments, the experimental protocol was the same as the main experiment except for the step of pseudovirus/live virus infection. For cell viability measurement corresponding to pseudovirus experiment, 293T-ACE-TMPRSS2 cells were seeded in 96 well black plates 18 hours prior to the experiment. The cells were then incubated with different concentrations (0.02-1.5 mM) of the thiol-based drugs for 2 hours at 37° C., followed by removal of the drugs and incubation of cells with standard culture medium for 18 hours. The experiment was carried out thrice with 5-6 replicates for each drug. These concentrations reflect the 66-fold dilution of drugs when pseudovirus/drug mix was incubated with the cells in the pseudovirus pretreatment setting. For the cell viability measurement corresponding to the live virus experiment, Vero E6 cells were incubated with different concentrations of the drugs (0.03-8.33 mM) in 1% FBS for 2 days. These concentrations reflect the 12-fold dilution of drugs when virus/drug mix was incubated with the cells in the live virus infection setting. The cell viability experiment on Vero E6 cells was carried out thrice with 6 replicates for each drug. For both cell viability experiments, post the respective incubations, the plates and their contents were equilibrated at room temperature for 30 minutes before addition of equal volumes of CellTiter Glo2.0 reagent. Afterwards, the contents were mixed on a plate shaker to induce cell lysis. The plates were then incubated at room temperature for 10 minutes followed by measurement of luminescence using Biotek plate reader. Luciferase reads of control-treated cells was set as 100% and the relative viability of cells incubated in the presence of thiol-based drugs was calculated.

Syrian Hamster Model of COVID-19

The efficacy of two thiol-based drugs, MUC-31 and cysteamine, was tested in a Syrian hamster model of SARS CoV2 infection. All the antiviral studies were performed in animal biosafety level 3 (ABSL3) facility at the Lovelace Respiratory Research Institute, Albuquerque, New Mexico. All work was conducted under protocols approved by the Institutional Animal Care and Use Committee (IACUC). A total of 40 Syrian hamsters (*Mesocricetus auratus*), with a target age of 6-10 weeks old and a target weight of 130-160 g, were on the study. The animals were divided into 4 groups. Groups 1 and 2 included animals receiving aerosol delivery/to be exposed to nose-only inhalation of the vehicle (20 mM citrate, pH 4.5±0.2, and 38.5 mM NaCl), and MUC-31 (0.48 mg/Kg lung deposition dose) respectively. Groups 3 and 4 included animals receiving intraperitoneal dosing of the vehicle (water) and cysteamine hydrochloride (147 mg/kg; MilliporeSigma). The animals were dosed twice daily starting on Day 0, as showing in FIG. 8A. The first dose was administered 2 hours prior to the viral inoculation. All animals were inoculated intranasally with SARS CoV2 (isolate USA-WA1/2020) at $1\times10^5$ $TCID_{50}$/animal. Animals in group 3 and 4 received 2× daily dosing on Days 0-4. Animals in groups 1 and 2 received 2× daily dosing on Days 0-2. Animals in all groups were sacrificed on Day 5. Efficacy of the drugs was determined by measuring viral load by RT-qPCR and lung inflammation, as measured by lung weight gain and total and differential cell counts in the bronchoalveolar lavage fluid.

Aerosol Exposure for MUC-031

Vehicle solution used as control in the aerosol study was 20 mM sodium citrate, pH 4.5 with 38.5 mM NaCl. MUC-031 was formulated at 11 mg/mL in vehicle. Two separate chambers were used for vehicle and MUC-031 exposures. Aerosols were generated using one Aerogen Solo vibrating mesh nebulizer with nominal forced air dilution of 8.5±0.5 L/min. Animals were exposed for 20 minutes twice a day (to both active and vehicle control formulations). Prior to animal exposures, aerosol trials were conducted to establish the relationship between nebulization times and deposited dose. Aerosol concentration was measured at the breathing zone of the exposure system by collection of the aerosol onto 47-mm glass fiber filters (GE Whatman GF/A membrane filters). Filter samples were collected throughout all exposures at a nominal flowrate of 0.3 L/min. After drying and weighing the filters, total aerosol concentration (AC, mg/L) was measured gravimetrically: AC (mg/L)=Δ(Filter Weight)/(Exposure time (min)×Flowrate (L/min)). During trials, the deposited material from filters was then extracted into 0.1% TFA/$H_2O$. MUC-031 in extract solution was quantified chromatographically, using a previously established HPLC method at Lovelace. Thus, a relationship could be established between total aerosol concentration and MUC-031 aerosol concentration. That relationship was used to monitor exposure inside BSL3 facility and to subsequently determine pulmonary deposited doses during in vivo exposures (described in Alexander et al). The average mass median aerodynamic diameter (MMAD) of the MUC-031 exposure atmosphere was 2.60 μm (measured with Mercer-style cascade impactor) and is considered to be within respirable range for rodents (Kuehl et al). Aerosol exposures resulted in average pulmonary deposited dose of MUC-031 of 0.48 mg/kg per exposure, close to the target dose of 0.5 mg/kg.

Viral Titers Using RT-qPCR

Lung samples were homogenized in Trizol using a TissueLyser and centrifuged at 4000×g for 5 minutes. From the supernatants, RNA was isolated using the QIAGEN RNeasy Kit, according to the manufacturer's instructions. SARS-CoV-2 viral RNA was quantified by a qPCR assay targeting the SARS CoV-2 nucleocapsid phosphoprotein gene (N gene). Genome copies per g equivalents were calculated from a standard curve generated from RNA standards of known copy concentration. All samples were run in triplicate. The SARS CoV-2 N gene primers and probe sequences are as follows:

```
SARS CoV-2 Forward:
                                        (SEQ ID NO: 3)
5' TTACAAACATTGGCCGCAAA 3'

SARS CoV-2 Reverse:
                                        (SEQ ID NO: 4)
5' GCGCGACATTCCGAAGAA 3'

SARS CoV-2 Probe:
                                        (SEQ ID NO: 5)
6FAM-ACAATTTGCCCCCAGCGCTTCAG-BHQ-1
```

Amplification and detection was performed using a suitable real-time thermal cycler under the following cycling conditions: 50° C. for 5 minutes, 95° C. for 20 seconds and 40 cycles of 95° C. for 3 seconds, and 60° C. for 30 seconds.

Bronchoalveolar Lavage (BAL) Collection and Processing

BAL was performed after the collection of whole lung weight. The left lobe was clamped off and the right lung lobes were lavaged with sterile saline. Half of the BAL collected was UV irradiated for sterilization out of the ABSL3 and used for differential analysis. This aliquot was centrifuged at 1000 g, 2-8° C., ≥10 minutes. The supernatant will be collected and frozen at −80° C. for subsequent measurement of inflammatory mediators using ELISA. The cell pellet was resuspended in the appropriate amount of resuspension buffer, and red blood cell lysis buffer was used on samples as necessary. The total cell count was counted using a Nexcelom automated cell counter. A total of 50,000 cells per slide were used to prepare microscope slides by cytocentrifugation. The cells on slides were fixed and stained using Modified Wright's or Wright-Giemsa Stain. Differential counts on at least 200 nucleated cells per slide were conducted using morphological criteria to classify cells into neutrophils, macrophages, lymphocytes and eosinophils.

The remaining lavage return volume from each animal was centrifuged at 1000 g, 2-8° C., ≥10 minutes, the pellet was treated with 1000 uL of TRI-reagent and stored at −80° C. for RNA isolation and RT-PCR analysis.

Statistical Analysis

For analyzing the statistical significance of difference in loss of binding for each drug area under the curve (AUC) was plotted and ordinary one-way ANOVA followed by Dunnett's post hoc analysis was performed. To assess the difference in binding of $RBD^{N501Y}$ and $RBD^{original}$, fold change of absorbance was plotted and analyzed using two tailed, unpaired t-test. Data are presented as mean±SEM [*p≤0.05, p≤0.01, p≤0.005, ***p≤0.0001]. $IC_{50}$ of the drugs in pseudovirus transduction and live virus experiments was determined using the non-linear regression fitting with a variable slope. Data for pseudovirus and live virus experiments are plotted as mean±SD. All statistical analyses were performed using GraphPad Prism software (version 8.4.2).

TABLE 2

List of currently approved thiol-based drugs or drugs that generate a thiol-containing metabolite*

| | Compound | Structure | pKa** (thiol group) |
|---|---|---|---|
| | | Monothiol drugs | |
| 1 | N-acetylcysteine | 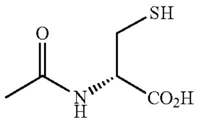 | 9.5 |
| 2 | 2-mercaptoethane sulfonate, sodium salt (MESNA) | 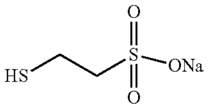 | 9.2 |
| 3 | Tiopronin | 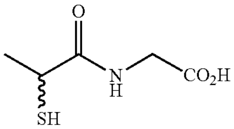 | 8.7 |
| 4 | Cysteamine | 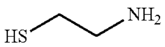 | 8.2 |
| 5 | Amifostine (parent drug) WR-1065 (active metabolite) | 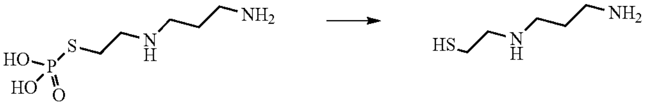 [SMILES: NCCCNCCSP(=O)(O)O ; NCCCNCCS] | 7.7 (WR-1065) |
| 6 | Erdosteine (parent drug) Met I (active metabolite) | 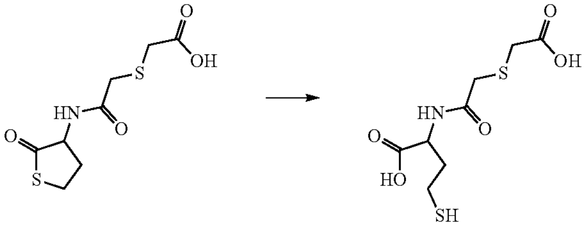 [SMILES: O=C(O)CSCC(=O)NC1CCSC1=O ; O=C(O)CSCC(=O)NC(CCS)C(=O)O] | Not available¥ |
| 7 | Penicillamine | 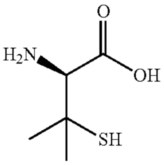 | 10.5 |
| 8 | Glutathione | 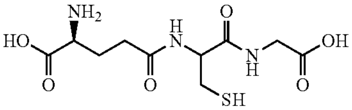 [SMILES: N[C@@H](CCC(=O)NC(CS)C(=O)NCC(=O)O)C(=O)O] | 9.2 |
| | | Dithiol drugs | |
| 9 | Bucillamine | 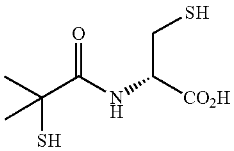 | 8.4, 10.2 |
| 10 | Dimercaptosuccinic acid (DMSA) (Succimer) | 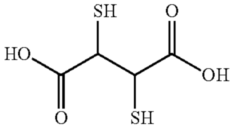 | 8.9, 10.8 |

TABLE 2-continued

List of currently approved thiol-based drugs or drugs that generate a thiol-containing metabolite*

| | Compound | Structure | pKa** (thiol group) |
|---|---|---|---|
| 11 | 2,3-Dimercaprol | 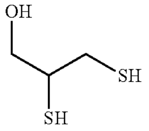 | 8.6, 10.6 |
| | | Sulfide drug (Negative Control) | |
| 12 | Carbocysteine | 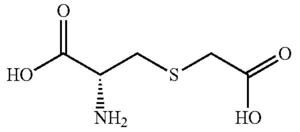 [SMILES: N[C@@H](CSCC(=O)O)C(=O)O] | |

*Not shown are three thiol containing drugs (Captopril, Zofenopril and Racecadotril) in which primary mechanisms of action is not through reactions with the thiol group
**pKa values from published literature and PubChem
¥Literature value not found;
pKa ~9-10 is anticipated based on structure

REFERENCES FOR EXAMPLE 4

1. Wiersinga, W. J., Rhodes, A., Cheng, A. C., Peacock, S. J. & Prescott, H. C. *JAMA-Journal of the American Medical Association* (2020) doi:10.1001/jama.2020.12839.
2. Zhu, N. et al. *N. Engl. J. Med.* 382, 727-733 (2020).
3. Hoffmann, M. et al. *Cell* 131, 271-280.e8 (2020).
4. Weissenhorn, W. et al. *Mol. Membr. Biol.* 16, 3-9 (1999).
5. Gallagher, T. M. *J. Virol.* 70, 4683-4690 (1996).
6. Wong, S. K., Li, W., Moore, M. J., Choe, H. & Farzan, M. *J. Biol. Chem.* 279, 3197-3201 (2004).
7. Lavillette, D. et al. *J. Biol. Chem.* 281, 9200-9204 (2006).
8. Ryser, H. J. P., Levy, E. M., Mandel, R. & DiSciullo, G. J. *Proc. Natl. Acad. Sci. U.S.A.* 91, 4559-4563 (1994).
9. Wallin, M., Ekström, M. & Garoff, H. *EMBO J.* 23, 54-65 (2004).
10. Abell, B. A. & Brown, D. T. *J. Virol.* 67, (1993).
11. Gallina, A. et al. *J. Biol. Chem.* 277, 50579-50588 (2002).
12. Hati, S. & Bhattacharyya, S. *ACS Omega* 5, 16292-16298 (2020).
13. Horowitz, R. I., Freeman, P. R. & Bruzzese, *J. Respir. Med. Case Reports* 30, (2020).
14. Akerlund, B. et al. *Eur. J. Clin. Pharmacol.* 50, 457-61 (1996).
15. Lobo-Galo, N., Terrazas-López, M., Martinez-Martinez, A. & Diaz-Sinchez, A. G. J. *Biomol. Struct Dyn.* (2020) doi:10.1080/07391102.2020.1764393.
16. Yuan, S. et al. *Sci. Transl. Med.* 7, 276ra27-276ra27 (2015).
17. Lan, J. et al. *Nature* 581, 215-220 (2020).
18. Wang, Q. et al. *Cell* 131, 894-904.e9 (2020).
19. Luan, B., Wang, H. & Huynh, T. *FEBS Lett.* 1873-3468.14076 (2021) doi:10.1002/1873-3468.14076.
20. Tian, F. et al. *bioRxiv* 2021.02.14.431117 (2021) doi:10.1101/2021.02.14.431117.
21. Ali, F., Kasry, A. & Amin, *M. Med. Drug Discov.* 10, 100086 (2021).
22. Sia, S. F. et al. *Nature* (2020) doi:10.1038/s41586-020-2342-5.
23. Roberts, A. et al. *J. Virol.* 79, 503-511 (2005).
24. Chan, J. F. W. et al. *Clin. Infect. Dis.* (2020) doi:10.1093/cid/ciaa325.
25. Imai, M. et al. *Proc. Natl. Acad. Sci. U.S.A* 117, 16587-16595 (2020).
26. Mylan Pharmaceuticals Inc. Cystagon (cysteamine bitartrate). U.S. Food and Drug Administration website www.accessdata.fda.gov/drugsatfda_docs/label/20071020392s010lbl.pdf Revised June 2007.
27. Bouaaa, N. et al. *Orphanet J. Rare Dis.* 6, 86 (2011).
28. Houk, J., Singh, R. & Whitesides, G. M. *Methods Enzymol.* 143, 129-140 (1987).
29. Nagy, P. *Antioxidants and Redox Signaling* vol. 18 1623-1641 (2013).
30. Riddles, P. W., Blakeley, R. L. & Zerner, B. *Anal. Biochem.* 94, 75-81 (1979).
31. Pettersen, E. F. et al. *J. Comput. Chem.* 25, 1605-1612 (2004).
32. Reed, L. J. & Muench, H. *Am. J. Epidemiol.* 27, 493-497 (1938).
33. Huang, S. & Pang, L. *Assay Drug Dev. Technol.* 10, 88-96 (2012).

From the disclosure it will be appreciated that, although specific embodiments of the invention have been described herein for the purposes of illustration, various modifications may be made without deviating from the spirit and scope of the invention. It should be understood that various alternatives to the embodiments of the invention described herein may be employed in practicing the invention. It is intended that the following claims define the scope of the invention and that methods and compositions within the scope of these claims and their equivalents be covered thereby.

What is claimed is:

1. A pharmaceutical composition in the form of a liquid solution, comprising water and a thiosaccharide compound having the formula:

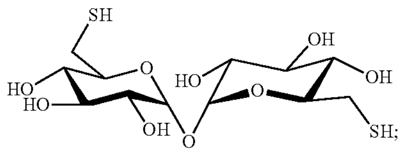

wherein said thiosaccharide compound is present at a concentration of about 30.0 mg/mL in the pharmaceutical composition.

2. The pharmaceutical composition of claim 1, further comprising sodium citrate.

3. The pharmaceutical composition of claim 1, further comprising sodium chloride.

4. The pharmaceutical composition of claim 2, further comprising sodium chloride.

5. The pharmaceutical composition of claim 1, wherein said thiosaccharide compound is present at a concentration of 30.0 mg/mL in the pharmaceutical composition.

6. The pharmaceutical composition of claim 2, wherein said thiosaccharide compound is present at a concentration of 30.0 mg/mL in the pharmaceutical composition.

7. The pharmaceutical composition of claim 3, wherein said thiosaccharide compound is present at a concentration of 30.0 mg/mL in the pharmaceutical composition.

8. The pharmaceutical composition of claim 4, wherein said thiosaccharide compound is present at a concentration of 30.0 mg/mL in the pharmaceutical composition.

9. A pharmaceutical composition in the form of a liquid solution, comprising water and a thiosaccharide compound having the formula:

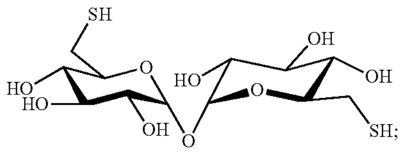

wherein said thiosaccharide compound is present at a concentration of 30.0 mg/mL or higher in the pharmaceutical composition.

10. The pharmaceutical composition of claim 9, further comprising sodium citrate.

11. The pharmaceutical composition of claim 9, further comprising sodium chloride.

12. The pharmaceutical composition of claim 10, further comprising sodium chloride.

* * * * *